US012767710B2

(12) United States Patent
Kumar et al.

(10) Patent No.: US 12,767,710 B2
(45) Date of Patent: *Oct. 20, 2026

(54) METHODS AND COMPOSITIONS FOR THE GENERATION AND USE OF HUMANIZED CONFORMATION-SPECIFIC PHOSPHORYLATED TAU ANTIBODIES

(71) Applicant: Tau Biosciences, Inc., Carlsbad, CA (US)

(72) Inventors: Shankar Kumar, Pleasanton, CA (US); Naoya Tsurushita, Palo Alto, CA (US); Michael Ahlijanian, Madison, CT (US); Martin Jefson, Stonington, CT (US)

(73) Assignee: Tau Biosciences, Inc., Carlsbad, CA (US)

( * ) Notice: Subject to any disclaimer, the term of this patent is extended or adjusted under 35 U.S.C. 154(b) by 724 days.

This patent is subject to a terminal disclaimer.

(21) Appl. No.: 18/155,230

(22) Filed: Jan. 17, 2023

(65) Prior Publication Data

US 2023/0287093 A1 Sep. 14, 2023

Related U.S. Application Data

(62) Division of application No. 16/762,141, filed as application No. PCT/US2018/059833 on Nov. 8, 2018, now Pat. No. 11,591,385.

(Continued)

(51) Int. Cl.
*C07K 16/18* (2006.01)
*A61P 25/28* (2006.01)

(Continued)

(52) U.S. Cl.
CPC .............. *C07K 16/18* (2013.01); *A61P 25/28* (2018.01); *G01N 33/533* (2013.01);

(Continued)

(58) Field of Classification Search
None
See application file for complete search history.

(56) References Cited

U.S. PATENT DOCUMENTS

2012/0148592 A1 6/2012 Imai et al.
2016/0031977 A1 2/2016 Lu et al.
2017/0244756 A1 8/2017 Bartley et al.

FOREIGN PATENT DOCUMENTS

JP 2015-521158 7/2015
JP 2016-515129 5/2016

(Continued)

OTHER PUBLICATIONS

Yoshiyama et al., Anti-Inflammatory Action of Donepezil Ameliorates Tau Pathology, Synaptic Loss, and Neurodegeneration in a Tauopathy Mouse Model. Journal of Alzheimer's Disease. 2010;22(1):295-306. (Year: 2010).*

(Continued)

*Primary Examiner* — Aurora M Fontainhas
(74) *Attorney, Agent, or Firm* — Orrick, Herrington & Sutcliffe, LLP

(57) ABSTRACT

The present disclosure relates generally to conformation-specific antibodies that can bind to and neutralize the activity of phosphorylated-Threonine 231-tau protein (pT231-tau). The antibodies of the present technology are useful in methods for treating a neurological disorder associated with elevated cis-pT231-tau protein expression in a subject in need thereof.

10 Claims, 82 Drawing Sheets

Specification includes a Sequence Listing.

Related U.S. Application Data

(60) Provisional application No. 62/583,850, filed on Nov. 9, 2017.

(51) Int. Cl.
*G01N 33/533* (2006.01)
*A61K 39/00* (2006.01)

(52) U.S. Cl.
CPC .... *A61K 2039/505* (2013.01); *C07K 2317/24* (2013.01); *C07K 2317/34* (2013.01); *C07K 2317/71* (2013.01)

(56) References Cited

FOREIGN PATENT DOCUMENTS

| | | | |
|---|---|---|---|
| WO | WO-2008/068048 | | 6/2008 |
| WO | WO-2013/151762 | A1 | 10/2013 |
| WO | WO-2014/152157 | A2 | 9/2014 |

OTHER PUBLICATIONS

Chen et al., "Enhancement and Destruction of Antibody Function by Somatic Mutation: Unequal Occurrence is Controlled by V Gene Combinatorial Associations," The EMBO Journal, 1995, 14(12):2784-2794.

International Search Report and Written Opinion issued in International Patent Application No. PCT/US2018/59833, dated Apr. 22, 2019.

Koenig et al., "Mutational landscape of antibody variable domains reveals a switch modulating the interdomain conformational dynamics and antigen binding", PNAS, 2017, vol. 114(4), pp. E486-E495.

Kohnken et al., "Detection of tau phosphorylated at threonine 231 in cerebrospinal fluid of Alzheimer's disease patients", Neuroscience Letters, May 11, 2017, vol. 287, No. 3, pp. 187-190.

Kussie et al., "A Single Engineered Amino Acid Substitution Changes Antibody Fine Specificity," Journal of Immunology, 1994, 146-152.

Lewczuk et al., "Cerebrospinal fluid and blood biomarkers for neurodegenerative dementias: An update of the Consensus of the Task Force on Biological Markers in Psychiatry of the World Federation of Societies of Biological Psychiatry", World Journal of Biological Psychiatry, 2017, vol. 19, No. 4, pp. 244-328.

Sagare et al., "Pericyte loss influences Alzheimer-like neurodegeneration in mice", Nature Communications, Dec. 1, 2013, URL:https://www.nature.com/articles/ncomms3932.

Schroeder et al., "Structure and Function of Immunoglobulins", Reference Module in Biomedical Science, Jan. 1, 2014, http://dx.doi.org/10.1016/B978-0-12-801238-3. 00112-4>.

International Preliminary Report on Patentability in International Patent Application No. PCT/US2018/059833 dated May 22, 2020.

* cited by examiner

```
1   ATG AGA TGG AGC TGT ATC ATC CTC TTC TTG GTA GCA ACA GCT ACA GGT GTC AAC TCC CAG
1   M   R   W   S   C   I   I   L   F   L   V   A   T   A   T   G   V   N   S   Q

61  GTC CAA CTG CAG CAG CCT GGG GCT GAG CTG GTG AAG CCT GGG GCT TCA GTG AAG ATG TCC
21  V   Q   L   Q   Q   P   G   A   E   L   V   K   P   G   A   S   V   K   M   S

121 TGC AAG GCT TCT GGC TAC ACC TTC ACC AGC TAC TGG ATA CAC TGG GTG AAG CAG AGG CCT
41  C   K   A   S   G   Y   T   F   T   S   Y   W   I   H   W   V   K   Q   R   P

181 GGA CAA GGC CTT GAG TGG ATC GGA GTG ATT GAT CCT TCT GAT AGT TAT ACT AGG TAC AAT
61  G   Q   G   L   E   W   I   G   V   I   D   P   S   D   S   Y   T   R   Y   N

241 CAA AAG TTC AAG GGC AAG GCC ACG TTG ACT GTA GAC ACA TCC TCC AGC ACA GCC TAC ATG
81  Q   K   F   K   G   K   A   T   L   T   V   D   T   S   S   S   T   A   Y   M

301 CAA CTC AGC AGC CTG ACA TCT GAG GAC TCT GCG GTC TAT TAC TGT ACA ACA TGG GAG GTT
101 Q   L   S   S   L   T   S   E   D   S   A   V   Y   Y   C   T   T   W   E   V

361 GAC TAC TGG GGC CAA GGC ACC ACT CTC ACA GTC TCC TCA GCC AAA ACA ACA CCC CCA TCA
121 D   Y   W   G   Q   G   T   T   L   T   V   S   S   A   K   T   T   P   P   S

421 GTC TAT CCC CTG GCC CCT   SEQ ID NO: 57
141 V   Y   P   L   A   P     SEQ ID NO: 58
```

FIG. 1

1 ATG AAG TTG CCT GTT AGG CTG TTG GTG CTG ATG TTC TGG ATT CCT GCT TCC AAC AGT GAT
M K L P V R L L V L M F W I P A S N S D

61 GTT GTG ATG ACC CAA ACT CCA CTC TCC CTG CCT GTC AGT CTT GGA GAT CAA GCC TCC ATC
21 V V M T Q T P L S L P V S L G D Q A S I

121 TCT TGC AGA TCT AGT CAG AGC CTT GTC CAC AGT GAT GGA AAC ACC TAT TTA CAT TGG TAC
41 S C R S S Q S L V H S D G N T Y L H W Y

181 CTG CAG AAG CCA GGC CAG TCT CCA AAG CTC CTG ATC TAC AAA GTT TCC AAC CGA TTT TCT
61 L Q K P G Q S P K L L I Y K V S N R F S

241 GGG GTC CCA GAC AGG TTC AGT GGC AGT GGA TCA GGG ACA GAT TTC ACA CTC AAG ATC AGC
81 G V P D R F S G S G S G T D F T L K I S

301 AGA CTG GAG GCT GAG GAT CTG GGA GTT TAT TTC TGC TCT CAA AGT ACA CAT GTT CCG TGG
101 R L E A E D L G V Y F C S Q S T H V P W

361 ACG TTC GGT GGA GGC ACC AAG CTG GAA ATC AAA CGG GCT GAT GCT GCA CCA ACT GTA TCC
121 T F G G G T K L E I K R A D A A P T V S

421 ATC TTC CCA CCA TCC AGT SEQ ID NO. 59
141 I F P P S S SEQ ID NO. 60

FIG. 2

```
                          1          2          3
               123456789 0123456789 0123456789 0123456789
PT-113 VH      QVQLQQPGA ELVKPGASVK MSCKASGYTF TSYWIHWVKQ    SEQ ID NO: 61
IGHV1S127*01   QVQLQQPGA ELVKPGASVK MSCKASGYTF TSYWMHWVKQ    SEQ ID NO: 62
                                                    *

               4          5           6          7
               0123456789 01223456789 0123456789 0123456789
                             a
PT-113 VH      RPGQGLEWIG VIDPSDSYTRY NQKFKGKATL TVDTSSSTAY    SEQ ID NO: 63
IGHV1S127*01   RPGQGLEWIG TIDPSDSYTSY NQKFKGKATL TVDTSSSTAY    SEQ ID NO: 64
                          *         *

                                         1          1
               8             9           0          1
               0122223456789 0123456789 0123456789 0123
                  abc
PT-113 VH      MQLSSLTSEDSAV YYCTTWEV-- -DYWGQGTTL TVSS    SEQ ID NO: 65
IGHV1S127*01   MQLSSLTSEDSAV YYCTR                         SEQ ID NO: 66
JH2                              *         WGQGTTV TVSS    SEQ ID NO: 67
```

FIG. 3

```
                         1          2                3
               123456789 0123456789 01234567777789 0123456789
                                            abcde
PT-113 VL      DVVMTQTPL SLPVSLGDQA SISCRSSQSLVHSDG NTYLHWYLQK  SEQ ID NO: 68
IGKV1-110*02   DVVMTQTPL SLPVSLGDQA SISCRSSQSLVHSNG NTYLHWYLQK  SEQ ID NO: 69
                                                *

               4          5          6          7
               0123456789 0123456789 0123456789 0123456789
PT-113 VL      PGQSPKLLIY KVSNRFSGVP DRFSGSGSGT DFTLKISRLE  SEQ ID NO: 70
IGKV1-110*02   PGQSPKLLIY KVSNRFSGVP DRFSGSGSGT DFTLKISRVE  SEQ ID NO: 71
                                                       *

                                     1
               8          9          0
               0123456789 0123456789 01234567
PT-113 VL      AEDLGVYFCS QSTHVPWTFG GGTKLEIK  SEQ ID NO: 72
IGKV1-110*02   AEDLGVYFC                       SEQ ID NO: 73
Jk1                                FG GGTKLEIK  SEQ ID NO: 74
```

FIG. 4

SpeI
ACTAGTACCACCATGAGATGGAGCTGTATCATCCTCTTCTTGGTGGCAACAGCTACAGGT
M R W S C I I L F L V A T A T G

GTCAACTCCCAGGTCCAACTGCAGCAGCCTGGGGCTGAGCTGGTGAAGCCTGGGGCTTCA
V N S Q V Q L Q Q P G A E L V K P G A S

GTGAAGATGTCCTGCAAGGCTTCTGGCTACACCTTCACCAGCTACTGGATTCACTGGGTC
V K M S C K A S G Y T F T S Y W I H W V

AAGCAGAGGCCTGGACAAGGCCTTGAGTGGATCGGAGTGATTGATCCTTCAGATAGTTAT
K Q R P G Q G L E W I G V I D P S D S Y

ACTAGATACAATCAAAAGTTCAAGGGCAAGGCCACATTGACTGTGGACACATCCTCCAGC
T R Y N Q K F K G K A T L T V D T S S S

ACAGCCTACATGCAGCTCAGCAGCCTGACATCTGAAGACTCTGCGGTCTATTACTGTACA
T A Y M Q L S S L T S E D S A V Y Y C T

ACCTGGGAAGTCGACTACTGGGGCCAAGGCACCACTCTCACAGTCTCCTCAGGTGAGTCC
T W E V D Y W G Q G T T L T V S S SEQ ID NO: 75

HindIII
TTAAAACCTAAGCTT SEQ ID NO: 76

FIG. 5

NheI
GCTAGCACCACCATGAAGTTGCCTGTTAGGCTGTTGGTGCTGATGTTCTGGATTCCTGCT
M K L P V R L L V L M F W I P A

TCCAACAGTGATGTTGTGATGACCCAAACTCCACTCTCCCTGCCTGTCAGTCTTGGAGAT
S N S D V V M T Q T P L S L P V S L G D

CAAGCCTCCATCTCTTGCAGATCTAGTCAGAGCCTTGTGCACAGTGATGGAAACACCTAT
Q A S I S C R S S Q S L V H S D G N T Y

CTGCATTGGTACCTGCAGAAGCCAGGCCAGTCTCCAAAGCTCCTGATCTACAAAGTTTCC
L H W Y L Q K P G Q S P K L L I Y K V S

AACCGATTTTCTGGGGTCCCAGACAGGTTCAGTGGCAGTGGATCAGGGACAGATTTCACA
N R F S G V P D R F S G S G S G T D F T

CTCAAGATCAGCAGACTGGAGGCTGAGGATCTGGGAGTTTATTTCTGCTCTCAAAGTACA
L K I S R L E A E D L G V Y F C S Q S T

CATGTTCCTTGGACGTTCGGTGGAGGCACCAAGCTGGAAATCAAACGTAAGTAGAATCCA
H V P W T F G G G T K L E I K SEQ ID NO:77

EcoRI
AAGTCGAATTC SEQ ID NO:78

FIG. 6

```
                         1          2          3
               123456789 0123456789 0123456789 0123456789
PT-113 VH      QVQLQQPGA ELVKPGASVK MSCKASGYTF TSYWIHWVRQ   SEQ ID NO:79
HuPT-113 VH1   QVQLVQSGA EVKKPGASVK VSCKASGYTF TSYWIHWVRQ   SEQ ID NO:80
HuPT-113 VH2   QVQLVQSGA EVKKPGASVK VSCKASGYTF TSYWIHWVRQ   SEQ ID NO:81
HuPT-113 VH3   QVQLVQSGA EVKKPGASVK VSCKASGYTF TSYWIHWVRQ   SEQ ID NO:82
HuPT-113 VH4   QVQLVQSGA EVKKPGASVK VSCKASGYTF TSYWIHWVRQ   SEQ ID NO:83
AF174092 VH    QVQLVQSGA EVKKPGASVK VSCKASGYTF T-----WVRQ   SEQ ID NO:84

               4          5           6          7
               0123456789 01223456789 0123456789 0123456789
                             a
PT-113 VH      RPGQGLEWIG VIDPSDSYTRY NQKFKGKATL TVDTSSSTAY   SEQ ID NO: 85
HuPT-113 VH1   APGQGLEWIG VIDPSDSYTRY NQKFKGRATL TVDTSTSTAY   SEQ ID NO: 86
HuPT-113 VH2   APGQGLEWIG VIDPSDSYTRY NQKFKGRVTL TVDTSTSTAY   SEQ ID NO: 87
HuPT-113 VH3   APGQGLEWIG VIDPSDSYTRY NQKFKGRATM TVDTSTSTAY   SEQ ID NO: 88
HuPT-113 VH4   APGQGLEWIG VIDPSDSYTRY NQKFKGRVTM TVDTSTSTAY   SEQ ID NO: 89
AF174092 VH    APGQGLEWMG ----------- ------RVTM TTDTSTSTAY   SEQ ID NO: 90

                                        1          1
               8             9          0          1
               0122223456789 0123456789 0123456789 0123
                  abc
PT-113 VH      MQLSSLTSEDSAV YYCTTWEV-- -DYWGQGTTL TVSS   SEQ ID NO: 91
HuPT-113 VH1   MELRSLRSDDTAV YYCTTWEV-- -DYWGQGTTV TVSS   SEQ ID NO: 92
HuPT-113 VH2   MELRSLRSDDTAV YYCTTWEV-- -DYWGQGTTV TVSS   SEQ ID NO: 93
HuPT-113 VH3   MELRSLRSDDTAV YYCTTWEV-- -DYWGQGTTV TVSS   SEQ ID NO: 94
HuPT-113 VH4   MELRSLRSDDTAV YYCTTWEV-- -DYWGQGTTV TVSS   SEQ ID NO: 95
AF174092 VH    MELRSLRSDDTAV YYCAR----- ---WGQGTTV TVSS   SEQ ID NO: 96
```

FIG. 8

```
                          1          2               3
                 123456789 0123456789 012345677777789 0123456789
                                             abcde
PT-113 VL        DVVMTQTPL SLPVSLGDQA SISCRSSQSLVHSDG NTYLHWYLQK  SEQ ID NO: 97
HuPT-113 VL1     DIVMTQSPL SLPVTPGEPA SISCRSSQSLVHSDG NTYLHWYLQK  SEQ ID NO: 98
M99608 VL        DIVMTQSPL SLPVTPGEPA SISC----------- -----WYLQK  SEQ ID NO: 99

                 4          5          6          7
                 0123456789 0123456789 0123456789 0123456789
PT-113 VL        PGQSPKLLIY KVSNRFSGVP DRFSGSGSGT DFTLKISRLE      SEQ ID NO: 100
HuPT-113 VL1     PGQSPQLLIY KVSNRFSGVP DRFSGSGSGT DFTLKISRVE      SEQ ID NO: 101
M99608 VL        PGQSPQLLIY -------GVP DRFSGSGSGT DFTLKISRVE      SEQ ID NO: 102

                                       1
                 8          9          0
                 0123456789 0123456789 01234567
PT-113 VL        AEDLGVYFCS QSTHVPWTFG GGTKLEIK      SEQ ID NO: 103
HuPT-113 VL1     AEDVGVYYCS QSTHVPWTFG GGTKVEIK      SEQ ID NO: 104
M99608 VL        AEDVGVYYC----------FG GGTKVEIK      SEQ ID NO: 105
```

FIG. 9

SpeI

ACTAGTACCACCATGGAATGGAGCTGTATCATCCTCTTCTTGGTGGCAACAGCTACAGGT
M E W S C I I L F L V A T A T G

GTCAACTCCCAGGTCCAACTGGTCCAGTCTGGGGCTGAAGTCAAGAAGCCTGGGGCTTCA
V N S Q V Q L V Q S G A E V K K P G A S

GTGAAAGTGTCCTGCAAGGCTTCTGGCTACACCTTCACCAGCTACTGGATTCACTGGGTC
V K V S C K A S G Y T F T S Y W I H W V

AGGCAGGCCCCTGGACAAGGCCTTGAGTGGATCGGAGTGATTGATCCTTCAGATAGTTAT
R Q A P G Q G L E W I G V I D P S D S Y

ACTAGATACAATCAAAAGTTCAAGGGCAGGGCCACATTGACTGTGGACACATCCACCAGC
T R Y N Q K F K G R A T L T V D T S T S

ACAGCCTACATGGAGCTCAGGAGCCTGAGATCTGATGACACTGCCGTCTATTACTGTACA
T A Y M E L R S L R S D D T A V Y Y C T

ACCTGGGAAGTCGACTACTGGGGCCAAGGCACCACTGTCACAGTCTCCTCAGGTGAGTCC
T W E V D Y W G Q G T T V T V S S SEQ ID NO: 106

HindIII

TTAAAACCTAAGCTT SEQ ID NO: 107

FIG. 10

```
SpeI
ACTAGTACCACCATGAGATGGAGCTGTATCATCCTCTTCTTGGTGGCAACAGCTACAGGT
            M  R  W  S  C  I  I  L  F  L  V  A  T  A  T  G

GTCAACTCCCAGGTCCAACTGGTCCAGTCTGGGGCTGAAGTCAAGAAGCCTGGGGCTTCA
 V  N  S  Q  V  Q  L  V  Q  S  G  A  E  V  K  K  P  G  A  S

GTGAAAGTGTCCTGCAAGGCTTCTGGCTACACCTTCACCAGCTACTGGATTCACTGGGTC
 V  K  V  S  C  K  A  S  G  Y  T  F  T  S  Y  W  I  H  W  V

AGGCAGGCCCCTGGACAAGGCCTTGAGTGGATCGGAGTGATTGATCCTTCAGATAGTTAT
 R  Q  A  P  G  Q  G  L  E  W  I  G  V  I  D  P  S  D  S  Y

ACTAGATACAATCAAAAGTTCAAGGGCAGGGTCACATTGACTGTGGACACATCCACCAGC
 T  R  Y  N  Q  K  F  K  G  R  V  T  L  T  V  D  T  S  T  S

ACAGCCTACATGGAGCTCAGGAGCCTGAGATCTGATGACACTGCCGTCTATTACTGTACA
 T  A  Y  M  E  L  R  S  L  R  S  D  D  T  A  V  Y  Y  C  T

ACCTGGGAAGTCGACTACTGGGGCCAAGGCACCACTGTCACAGTCTCCTCAGGTGAGTCC
 T  W  E  V  D  Y  W  G  Q  G  T  T  V  T  V  S  S  SEQ ID NO: 108

        HindIII
TTAAAACCTAAGCTT  SEQ ID NO: 109
```

FIG. 11

SpeI
ACTAGTACCACCATGGAATGGAGCTGTATCATCCTCTTCTTGGTGGCAACAGCTACAGGT
M E W S C I I L F L V A T A T G

GTCAACTCCCAGGTCCAACTGGTCCAGTCTGGGGCTGAAGTCAAGAAGCCTGGGGCTTCA
V N S Q V Q L V Q S G A E V K K P G A S

GTGAAAGTGTCCTGCAAGGCTTCTGGCTACACCTTCACCAGCTACTGGATTCACTGGGTC
V K V S C K A S G Y T F T S Y W I H W V

AGGCAGGCCCCTGGACAAGGCCTTGAGTGGATCGGAGTGATTGATCCTTCAGATAGTTAT
R Q A P G Q G L E W I G V I D P S D S Y

ACTAGATACAATCAAAAGTTCAAGGGCAGGGCCACAATGACTGTGGACACATCCACCAGC
T R Y N Q K F K G R A T M T V D T S T S

ACAGCCTACATGGAGCTCAGGAGCCTGAGATCTGATGACACTGCCGTCTATTACTGTACA
T A Y M E L R S L R S D D T A V Y Y C T

ACCTGGGAAGTCGACTACTGGGGCCAAGGCACCACTGTCACAGTCTCCTCAGGTGAGTCC
T W E V D Y W G Q G T T V T V S S SEQ ID NO: 110

HindIII
TTAAAACCTAAGCTT SEQ ID NO: 111

FIG. 12

```
SpeI
ACTAGTACCACCATGAGATGGAGCTGTATCATCCTCTTCTTGGTGGCAACAGCTACAGGT
              M  R  W  S  C  I  I  L  F  L  V  A  T  A  T  G

GTCAACTCCCAGGTCCAACTGGTCCAGTCTGGGGCTGAAGTCAAGAAGCCTGGGGCTTCA
 V  N  S  Q  V  Q  L  V  Q  S  G  A  E  V  K  K  P  G  A  S

GTGAAAGTGTCCTGCAAGGCTTCTGGCTACACCTTCACCAGCTACTGGATTCACTGGGTC
 V  K  V  S  C  K  A  S  G  Y  T  F  T  S  Y  W  I  H  W  V

AGGCAGGCCCCTGGACAAGGCCTTGAGTGGATCGGAGTGATTGATCCTTCAGATAGTTAT
 R  Q  A  P  G  Q  G  L  E  W  I  G  V  I  D  P  S  D  S  Y

ACTAGATACAATCAAAAGTTCAAGGGCAGGGTCACAATGACTGTGGACACATCCACCAGC
 T  R  Y  N  Q  K  F  K  G  R  V  T  M  T  V  D  T  S  T  S

ACAGCCTACATGGAGCTCAGGAGCCTGAGATCTGATGACACTGCCGTCTATTACTGTACA
 T  A  Y  M  E  L  R  S  L  R  S  D  D  T  A  V  Y  Y  C  T

ACCTGGGAAGTCGACTACTGGGGCCAAGGCACCACTGTCACAGTCTCCTCAGGTGAGTCC
 T  W  E  V  D  Y  W  G  Q  G  T  T  V  T  V  S  S   SEQ ID NO: 10

       HindIII
TTAAAACCTAAGCTT   SEQ ID NO: 112
```

FIG. 13

NheI
GCTAGCACCACCATGAAGTTGCCTGTTAGGCTGTTGGTGCTGATGTTCTGGATTCCTGCT
M K L P V R L L V L M F W I P A

TCCAACAGTGATATTGTGATGACCCAATCTCCACTCTCCCTGCCTGTCACTCCTGGAGAG
S N S D I V M T Q S P L S L P V T P G E

CCAGCCTCCATCTCTTGCAGATCCAGTCAGAGCCTTGTGCACAGTGATGGAAACACCTAT
P A S I S C R S S Q S L V H S D G N T Y

CTGCATTGGTACCTGCAGAAGCCAGGCCAGTCTCCACAGCTCCTGATCTACAAAGTTTCC
L H W Y L Q K P G Q S P Q L L I Y K V S

AACCGATTTTCTGGGGTCCCAGACAGGTTCAGTGGCAGTGGATCAGGGACAGATTTCACA
N R F S G V P D R F S G S G S G T D F T

CTCAAGATCAGCAGAGTGGAGGCTGAGGATGTGGGAGTTTATTACTGCTCTCAAAGTACA
L K I S R V E A E D V G V Y Y C S Q S T

CATGTTCCTTGGACGTTCGGTGGAGGCACCAAAGTCGAAATCAAACGTAAGTAGAATCCA
H V P W T F G G G T K V E I K SEQ ID NO: 113

EcoRI
AAGTCGAATTC SEQ ID NO: 114

FIG. 14

| | | |
|---|---|---|
| CMV2 | GAACCGTCAGATCGCCTGGAGACG | SEQ ID NO: 115 |
| JNT026 | TGAAAGATGAGCTGGAGGAC | SEQ ID NO: 116 |
| JNT098 | ACGTGCCAAGCATCCTCG | SEQ ID NO: 117 |

FIG. 17

ATGAAATGGAGCTGTATCATCCTCTTCTTGGTGGCAACAGCTACAGGTGTCAACTCCCAG
M K W S C I I L F L V A T A T G V N S Q
GTCCAACTGCAGCAGCCTGGGGCTGAGCTGGTGAAGCCTGGGGCTTCAGTGAAGATGTCC
V Q L Q Q P G A E L V K P G A S V K M S
TGCAAGGCTTCTGGCTACACCTTCACCAGCTACTGGATTCACTGGGTCAAGCAGAGGCCT
C K A S G Y T F T S Y W I H W V K Q R P
GGACAAGGCCTTGAGTGGATCGGAGTGATTGATCCTTCAGATAGTTATACTAGATACAAT
G Q G L E W I G V I D P S D S Y T R Y N
CAAAAGTTCAAGGGCAAGGCCACATTGACTGTGGACACATCCTCCAGCACAGCCTACATG
Q K F K G K A T L T V D T S S S T A Y M
CAGCTCAGCAGCCTGACATCTGAAGACTCTGCGGTCTATTACTGTACAACCTGGGAAGTC
Q L S S L T S E D S A V Y Y C T T W E V
GACTACTGGGGCCAAGGCACCACTCTCACAGTCTCCTCAGCCTCCACCAAGGGCCCATCG
D Y W G Q G T T L T V S S A S T K G P S
GTCTTCCCCCTGGCACCCTCCTCCAAGAGCACCTCTGGGGGCACAGCGGCCCTGGGCTGC
V F P L A P S S K S T S G G T A A L G C
CTGGTCAAGGACTACTTCCCCGAACCGGTGACGGTGTCGTGGAACTCAGGCGCCCTGACC
L V K D Y F P E P V T V S W N S G A L T
AGCGGCGTGCACACCTTCCCGGCTGTCCTACAGTCCTCAGGACTCTACTCCCTCAGCAGC
S G V H T F P A V L Q S S G L Y S L S S
GTGGTGACCGTGCCCTCCAGCAGCTTGGGCACCCAGACCTACATCTGCAACGTGAATCAC
V V T V P S S S L G T Q T Y I C N V N H
AAGCCCAGCAACACCAAGGTGGACAAGAAAGTTGAGCCCAAATCTTGTGACAAAACTCAC
K P S N T K V D K K V E P K S C D K T H
ACATGCCCACCGTGCCCAGCACCTGAACTCCTGGGGGGACCGTCAGTCTTCCTCTTCCCC
T C P P C P A P E L L G G P S V F L F P
CCAAAACCCAAGGACACCCTCATGATCTCCCGGACCCCTGAGGTCACATGCGTGGTGGTG
P K P K D T L M I S R T P E V T C V V V
GACGTGAGCCACGAAGACCCTGAGGTCAAGTTCAACTGGTACGTGGACGGCGTGGAGGTG
D V S H E D P E V K F N W Y V D G V E V
CATAATGCCAAGACAAAGCCGCGGGAGGAGCAGTACAACAGCACGTACCGTGTGGTCAGC
H N A K T K P R E E Q Y N S T Y R V V S
GTCCTCACCGTCCTGCACCAGGACTGGCTGAATGGCAAGGAGTACAAGTGCAAGGTCTCC
V L T V L H Q D W L N G K E Y K C K V S
AACAAAGCCCTCCCAGCCCCCATCGAGAAAACCATCTCCAAAGCCAAAGGGCAGCCCCGA
N K A L P A P I E K T I S K A K G Q P R
GAACCACAGGTGTACACCCTGCCCCCATCCCGGGATGAGCTGACCAAGAACCAGGTCAGC
E P Q V Y T L P P S R D E L T K N Q V S
CTGACCTGCCTGGTCAAAGGCTTCTATCCCAGCGACATCGCCGTGGAGTGGGAGAGCAAT
L T C L V K G F Y P S D I A V E W E S N
GGGCAGCCGGAGAACAACTACAAGACCACGCCTCCCGTGCTGGACTCCGACGGCTCCTTC
G Q P E N N Y K T T P P V L D S D G S F
TTCCTCTACAGCAAGCTCACCGTGGACAAGAGCAGGTGGCAGCAGGGGAACGTCTTCTCA
F L Y S K L T V D K S R W Q Q G N V F S
TGCTCCGTGATGCATGAGGCTCTGCACAACCACTACACGCAGAAGAGCCTCTCCCTGTCT
C S V M H E A L H N H Y T Q K S L S L S
CCGGGTAAATGA SEQ ID NO: 118
P G K * SEQ ID NO: 119

FIG. 18

ATGAAGTTGCCTGTTAGGCTGTTGGTGCTGATGTTCTGGATTCCTGCTTCCAACAGTGAT
M K L P V R L L V L M F W I P A S N S D
GTTGTGATGACCCAAACTCCACTCTCCCTGCCTGTCAGTCTTGGAGATCAAGCCTCCATC
V V M T Q T P L S L P V S L G D Q A S I
TCTTGCAGATCTAGTCAGAGCCTTGTGCACAGTGATGGAAACACCTATCTGCATTGGTAC
S C R S S Q S L V H S D G N T Y L H W Y
CTGCAGAAGCCAGGCCAGTCTCCAAAGCTCCTGATCTACAAAGTTTCCAACCGATTTTCT
L Q K P G Q S P K L L I Y K V S N R F S
GGGGTCCCAGACAGGTTCAGTGGCAGTGGATCAGGGACAGATTTCACACTCAAGATCAGC
G V P D R F S G S G S G T D F T L K I S
AGACTGGAGGCTGAGGATCTGGGAGTTTATTTCTGCTCTCAAAGTACACATGTTCCTTGG
R L E A E D L G V Y F C S Q S T H V P W
ACGTTCGGTGGAGGCACCAAGCTGGAAATCAAACGAACTGTGGCTGCACCATCTGTCTTC
T F G G G T K L E I K R T V A A P S V F
ATCTTCCCGCCATCTGATGAGCAGTTGAAATCTGGAACTGCCTCTGTTGTGTGCCTGCTG
I F P P S D E Q L K S G T A S V V C L L
AATAACTTCTATCCCAGAGAGGCCAAAGTACAGTGGAAGGTGGATAACGCCCTCCAATCG
N N F Y P R E A K V Q W K V D N A L Q S
GGTAACTCCCAGGAGAGTGTCACAGAGCAGGACAGCAAGGACAGCACCTACAGCCTCAGC
G N S Q E S V T E Q D S K D S T Y S L S
AGCACCCTGACGCTGAGCAAAGCAGACTACGAGAAACACAAAGTCTACGCCTGCGAAGTC
S T L T L S K A D Y E K H K V Y A C E V
ACCCATCAGGGCCTGAGCTCGCCCGTCACAAAGAGCTTCAACAGGGGAGAGTGTTAG SEQ ID NO: 120
T H Q G L S S P V T K S F N R G E C * SEQ ID NO: 121

FIG. 19

ATGAGATGGAGCTGTATCATCCTCTTCTTGGTGGCAACAGCTACAGGTGTCAACTCCCAG
M K W S C I I L F L V A T A T G V N S Q
GTCCAACTGGTCCAGTCTGGGGCTGAAGTCAAGAAGCCTGGGGCTTCAGTGAAAGTGTCC
V Q L V Q S G A E V K K P G A S V K V S
TGCAAGGCTTCTGGCTACACCTTCACCAGCTACTGGATTCACTGGGTCAGGCAGGCCCCT
C K A S G Y T F T S Y W I H W V R Q A P
GGACAAGGCCTTGAGTGGATCGGAGTGATTGATCCTTCAGATAGTTATACTAGATACAAT
G Q G L E W I G V I D P S D S Y T R Y N
CAAAAGTTCAAGGGCAGGGTCACAATGACTGTGGACACATCCACCAGCACAGCCTACATG
Q K F K G R V T M T V D T S T S T A Y M
GAGCTCAGGAGCCTGAGATCTGATGACACTGCCGTCTATTACTGTACAACCTGGGAAGTC
E L R S L R S D D T A V Y Y C T T W E V
GACTACTGGGGCCAAGGCACCACTGTCACAGTCTCCTCAGCCTCCACCAAGGGCCCATCG
D Y W G Q G T T V T V S S A S T K G P S
GTCTTCCCCCTGGCACCCTCCTCCAAGAGCACCTCTGGGGGCACAGCGGCCCTGGGCTGC
V F P L A P S S K S T S G G T A A L G C
CTGGTCAAGGACTACTTCCCCGAACCGGTGACGGTGTCGTGGAACTCAGGCGCCCTGACC
L V K D Y F P E P V T V S W N S G A L T
AGCGGCGTGCACACCTTCCCGGCTGTCCTACAGTCCTCAGGACTCTACTCCCTCAGCAGC
S G V H T F P A V L Q S S G L Y S L S S
GTGGTGACCGTGCCCTCCAGCAGCTTGGGCACCCAGACCTACATCTGCAACGTGAATCAC
V V T V P S S S L G T Q T Y I C N V N H
AAGCCCAGCAACACCAAGGTGGACAAGAAAGTTGAGCCCAAATCTTGTGACAAAACTCAC
K P S N T K V D K K V E P K S C D K T H
ACATGCCCACCGTGCCCAGCACCTGAACTCCTGGGGGGACCGTCAGTCTTCCTCTTCCCC
T C P P C P A P E L L G G P S V F L F P
CCAAAACCCAAGGACACCCTCATGATCTCCCGGACCCCTGAGGTCACATGCGTGGTGGTG
P K P K D T L M I S R T P E V T C V V V
GACGTGAGCCACGAAGACCCTGAGGTCAAGTTCAACTGGTACGTGGACGGCGTGGAGGTG
D V S H E D P E V K F N W Y V D G V E V
CATAATGCCAAGACAAAGCCGCGGGAGGAGCAGTACAACAGCACGTACCGTGTGGTCAGC
H N A K T K P R E E Q Y N S T Y R V V S
GTCCTCACCGTCCTGCACCAGGACTGGCTGAATGGCAAGGAGTACAAGTGCAAGGTCTCC
V L T V L H Q D W L N G K E Y K C K V S
AACAAAGCCCTCCCAGCCCCCATCGAGAAAACCATCTCCAAAGCCAAAGGGCAGCCCCGA
N K A L P A P I E K T I S K A K G Q P R
GAACCACAGGTGTACACCCTGCCCCCATCCCGGGATGAGCTGACCAAGAACCAGGTCAGC
E P Q V Y T L P P S R D E L T K N Q V S
CTGACCTGCCTGGTCAAAGGCTTCTATCCCAGCGACATCGCCGTGGAGTGGGAGAGCAAT
L T C L V K G F Y P S D I A V E W E S N
GGGCAGCCGGAGAACAACTACAAGACCACGCCTCCCGTGCTGGACTCCGACGGCTCCTTC
G Q P E N N Y K T T P P V L D S D G S F
TTCCTCTACAGCAAGCTCACCGTGGACAAGAGCAGGTGGCAGCAGGGGAACGTCTTCTCA
F L Y S K L T V D K S R W Q Q G N V F S
TGCTCCGTGATGCATGAGGCTCTGCACAACCACTACACGCAGAAGAGCCTCTCCCTGTCT
C S V M H E A L H N H Y T Q K S L S L S
CCGGGTAAATGA SEQ ID NO: 122
P G K * SEQ ID NO: 123

FIG. 20

ATGAAGTTGCCTGTTAGGCTGTTGGTGCTGATGTTCTGGATTCCTGCTTCCAACAGTGAT
M K L P V R L L V L M F W I P A S N S D
ATTGTGATGACCCAATCTCCACTCTCCCTGCCTGTCACTCCTGGAGAGCCAGCCTCCATC
I V M T Q S P L S L P V T P G E P A S I
TCTTGCAGATCCAGTCAGAGCATTGTGCACAGTGATGGAAACACCTATCTGCATTGGTAC
S C R S S Q S I V H S D G N T Y L H W Y
CTGCAGAAGCCAGGCCAGTCTCCACAGCTCCTGATCTACAAAGTTTCCAACCGATTTTCT
L Q K P G Q S P Q L L I Y K V S N R F S
GGGGTCCCAGACAGGTTCAGTGGCAGTGGATCAGGGACAGATTTCACACTCAAGATCAGC
G V P D R F S G S G S G T D F T L K I S
AGAGTGGAGGCTGAGGATGTGGGAGTTTATTACTGCTCTCAAAGTACACATGTTCCTTGG
R V E A E D V G V Y Y C S Q S T H V P W
ACGTTCGGTGGAGGCACCAAGGTCGAAATCAAACGAACTGTGGCTGCACCATCTGTCTTC
T F G G G T K V E I K R T V A A P S V F
ATCTTCCCGCCATCTGATGAGCAGTTGAAATCTGGAACTGCCTCTGTTGTGTGCCTGCTG
I F P P S D E Q L K S G T A S V V C L L
AATAACTTCTATCCCAGAGAGGCCAAAGTACAGTGGAAGGTGGATAACGCCCTCCAATCG
N N F Y P R E A K V Q W K V D N A L Q S
GGTAACTCCCAGGAGAGTGTCACAGAGCAGGACAGCAAGGACAGCACCTACAGCCTCAGC
G N S Q E S V T E Q D S K D S T Y S L S
AGCACCCTGACGCTGAGCAAAGCAGACTACGAGAAACACAAAGTCTACGCCTGCGAAGTC
S T L T L S K A D Y E K H K V Y A C E V
ACCCATCAGGGCCTGAGCTCGCCCGTCACAAAGAGCTTCAACAGGGGAGAGTGTTAG SEQ ID NO: 124
T H Q G L S S P V T K S F N R G E C * SEQ ID NO: 125

FIG. 21

ATGAGATGGAGCTGTATCATCCTCTTCTTGGTGGCAACAGCTACAGGTGTCAACTCCCAG
M K W S C I I L F L V A T A T G V N S Q

GTCCAACTGGTCCAGTCTGGGGCTGAAGTCAAGAAGCCTGGGGCTTCAGTGAAAGTGTCC
V Q L V Q S G A E V K K P G A S V K V S

TGCAAGGCTTCTGGCTACACCTTCACCAGCTACTGGATTCACTGGGTCAGGCAGGCCCCT
C K A S G Y T F T S Y W I H W V R Q A P

GGACAAGGCCTTGAGTGGATCGGAGTGATTGATCCTTCAGATAGTTATACTAGATACAAT
G Q G L E W I G V I D P S D S Y T R Y N

CAAAAGTTCAAGGGCAGGGTCACAATGACTGTGGACACATCCACCAGCACAGCCTACATG
Q K F K G R V T M T V D T S T S T A Y M

GAGCTCAGGAGCCTGAGATCTGATGACACTGCCGTCTATTACTGTACAACCTGGGAAGTC
E L R S L R S D D T A V Y Y C T T W E V

GACTACTGGGGCCAAGGCACCACTGTCACAGTCTCCTCAGCCTCCACCAAGGGCCCATCG
D Y W G Q G T T V T V S S A S T K G P S

GTCTTCCCCCTGGCACCCTCCTCCAAGAGCACCTCTGGGGGCACAGCGGCCCTGGGCTGC
V F P L A P S S K S T S G G T A A L G C

CTGGTCAAGGACTACTTCCCCGAACCGGTGACGGTGTCGTGGAACTCAGGCGCCCTGACC
L V K D Y F P E P V T V S W N S G A L T

AGCGGCGTGCACACCTTCCCGGCTGTCCTACAGTCCTCAGGACTCTACTCCCTCAGCAGC
S G V H T F P A V L Q S S G L Y S L S S

GTGGTGACCGTGCCCTCCAGCAGCTTGGGCACCCAGACCTACATCTGCAACGTGAATCAC
V V T V P S S S L G T Q T Y I C N V N H

AAGCCCAGCAACACCAAGGTGGACAAGAAAGTTGAGCCCAAATCTTGTGACAAAACTCAC
K P S N T K V D K K V E P K S C D K T H

ACATGCCCACCGTGCCCAGCACCTGAAGCTGCTGGAGGACCGTCAGTCTTCCTCTTCCCC
T C P P C P A P E A A G G P S V F L F P

CCAAAACCCAAGGACACCCTCATGATCTCCCGGACCCCTGAGGTCACATGCGTGGTGGTG
P K P K D T L M I S R T P E V T C V V V

GACGTGAGCCACGAAGACCCTGAGGTCAAGTTCAACTGGTACGTGGACGGCGTGGAGGTG
D V S H E D P E V K F N W Y V D G V E V

CATAATGCCAAGACAAAGCCGCGGGAGGAGCAGTACAACAGCACGTACCGTGTGGTCAGC
H N A K T K P R E E Q Y N S T Y R V V S

GTCCTCACCGTCCTGCACCAGGACTGGCTGAATGGCAAGGAGTACAAGTGCAAGGTCTCC
V L T V L H Q D W L N G K E Y K C K V S

AACAAAGCCCTCCCAGCCCCCATCGAGAAAACCATCTCCAAAGCCAAAGGGCAGCCCCGA
N K A L P A P I E K T I S K A K G Q P R

GAACCACAGGTGTACACCCTGCCCCCATCCCGGGATGAGCTGACCAAGAACCAGGTCAGC
E P Q V Y T L P P S R D E L T K N Q V S

CTGACCTGCCTGGTCAAAGGCTTCTATCCCAGCGACATCGCCGTGGAGTGGGAGAGCAAT
L T C L V K G F Y P S D I A V E W E S N

GGGCAGCCGGAGAACAACTACAAGACCACGCCTCCCGTGCTGGACTCCGACGGCTCCTTC
G Q P E N N Y K T T P P V L D S D G S F

TTCCTCTACAGCAAGCTCACCGTGGACAAGAGCAGGTGGCAGCAGGGGAACGTCTTCTCA
F L Y S K L T V D K S R W Q Q G N V F S

TGCTCCGTGATGCATGAGGCTCTGCACAACCACTACACGCAGAAGAGCCTCTCCCTGTCT
C S V M H E A L H N H Y T Q K S L S L S

CCGGGTAAATGA SEQ ID NO: 126
P G K * SEQ ID NO: 127

FIG. 22

AAGCTTGCCGCCACCATGGAATGGTCCTGGGTGTTCCTGTTCTTCCTGTCCGTGA
CCACCGGCGTGCACTCTCAGGTTCAGTTGGTTCAGTCTGGCGCCGAAGTGAAGAA
ACCTGGCGCCTCTGTGAAGGTGTCCTGCAAGGCTTCCGGCTACACCTTTACCAGC
TACTGGATCCACTGGGTCCGACAGGCTCCAGGACAAGGCCTGGAATGGATCGGC
GTGATCGACCCCTCTGACAGCTACACCCGGTACAACCAGAAATTCAAGGGCAGA
GTGACCATGACCGTGGACACCTTACCTCCACCGCCTACATGGAACTGCGGTCCC
TGAGATCTGACGACACCGCCGTGTACTACTGCACCACCTGGAAGTCGATTACTG
GGGCCAGGGCACCACAGTGACAGTGTCCTCTGCTTCCACCAAGGGACCCAGCGT
TTTCCCTCTGGCTCCATCCTCCAAGTCTACCTCTGGCGGAACAGCTGCTCTGGGCT
GCCTGGTCAAGGACTACTTTCCTGAGCCTGTGACCGTGTCCTGGAACTCTGGCGC
TCTGACATCTGGCGTGCACACATTCCCTGCTGTGCTGCAGTCCTCCGGCCTGTACT
CTCTGTCCTCTGTCGTGACCGTGCCTTCCAGCTCTCTGGGAACCCAGACCTACATC
TGCAATGTGAACCACAAGCCTTCCAACACCAAGGTGGACAAGAAGGTGGAACCC
AAGTCCTGCGACAAGACCCACACCTGTCCTCCATGTCCTGCTCCAGAAGCTGCTG
GCGGCCCTTCCGTGTTTCTGTTCCCTCCAAAGCCTAAGGACACCCTGATGATCTCT
CGGACCCCTGAAGTGACCTGCGTGGTGGTGGATGTGTCTCACGAGGACCCAGAA
GTGAAGTTCAATTGGTACGTGGACGGCGTGGAAGTGCACAACGCCAAGACCAAG
CCTAGAGAGGAACAGTACAACTCCACCTACAGAGTGGTGTCCGTGCTGACCGTG
CTGCACCAGGATTGGCTGAACGGCAAAGAGTACAAGTGCAAGGTGTCCAACAAG
GCCCTGCCTGCTCCTATCGAAAAGACCATCTCCAAGGCCAAGGGCCAGCCTAGG
GAACCCCAGGTTTACACCTTGCCTCCATCTCGGGACGAGCTGACCAAGAACCAG
GTGTCCCTGACCTGTCTCGTGAAGGGCTTCTACCCCTCCGATATCGCCGTGGAAT
GGGAGTCTAATGGCCAGCCTGAGAACAACTACAAGACAACCCCTCCTGTGCTGG
ACTCCGACGGCTCATTCTTTCTGTACTCCAAGCTGACAGTGGACAAGTCCAGATG
GCAGCAGGGCAACGTGTTCTCCTGCAGCGTGATGCACGAGGCCCTGCACAATCA
CTACACACAGAAGTCCCTGTCTCTGTCCCCTGGCAAGTGATGAATTC

SEQ ID NO:128

FIG. 27A

MEWSWVFLFFLSVTTGVHSQVQLVQSGAEVKKPGASVKVSCKASGYTFTSYWIHW
VRQAPGQGLEWIGVIDPSDSYTRYNQKFKGRVTMTVDTSTSTAYMELRSLRSDDTA
VYYCTTWEVDYWGQGTTVTVSSASTKGPSVFPLAPSSKSTSGGTAALGCLVKDYFP
EPVTVSWNSGALTSGVHTFPAVLQSSGLYSLSSVVTVPSSSLGTQTYICNVNHKPSNT
KVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIA
VEWESNGQPENNYKTTPPVLDSDGSFFLYSKLTVDKSRWQQGNVFSCSVMHEALHN
HYTQKSLSLSPGK

SEQ ID NO: 39

FIG. 27B

AAGCTTGCCGCCACCATGTCTGTGCCTACACAGGTTCTGGGACTCCTGCTGCTGT
GGCTGACCGACGCCAGATGCGACATCGTGATGACCCAGTCTCCACTGAGCCTGC
CTGTGACACCTGGCGAGCCTGCTTCCATCTCCTGCAGATCCTCTCAGTCCCTGGT
GCACTCTGACGGCAACACCTACCTGCACTGGTATCTGCAGAAGCCCGGCCAGTCT
CCTCAGCTGCTGATCTACAAGGTGTCCAACCGGTTCTCTGGCGTGCCCGACAGAT
TTTCCGGCTCTGGCTCTGGCACCGACTTCACCCTGAAGATCTCCAGAGTGGAAGC
CGAGGACGTGGGCGTGTACTACTGCTCCCAGTCTACCCATGTGCCTTGGACCTTT
GGCGGAGGCACCAAGGTGGAAATCAAGCGTACGGTGGCCGCTCCCAGCGTGTTC
ATCTTCCCCCCAAGCGACGAGCAGCTGAAGAGCGGCACCGCCAGCGTGGTGTGT
CTGCTGAACAACTTCTACCCCAGGGAGGCCAAGGTGCAGTGGAAGGTGGACAAC
GCCCTGCAGAGCGGCAACAGCCAGGAGAGCGTCACCGAGCAGGACAGCAAGGA
CTCCACCTACAGCCTGAGCAGCACCCTGACCCTGAGCAAGGCCGACTACGAGAA
GCACAAGGTGTACGCCTGTGAGGTGACCCACCAGGGCCTGTCCAGCCCCGTGAC
CAAGAGCTTCAACAGGGGCGAGTGCTGATGAATTC

SEQ ID NO: 129

FIG. 27C

MSVPTQVLGLLLLWLTDARCDIVMTQSPLSLPVTPGEPASISCRSSQSLVHSDGNTYL
HWYLQKPGQSPQLLIYKVSNRFSGVPDRFSGSGSGTDFTLKISRVEAEDVGVYYCSQ
STHVPWTFGGGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEVTHQGLSS
PVTKSFNRGEC

SEQ ID NO: 55

FIG. 27D

AAGCTTGCCGCCACCATGGAATGGTCCTGGGTGTTCCTGTTCTTCCTGTCCGTGA
CCACCGGCGTGCACTCTCAGGTTCAGTTGGTTCAGTCTGGCGCCGAAGTGAAGAA
ACCTGGCGCCTCTGTGAAGGTGTCCTGCAAGGCTTCCGGCTACACCTTTACCAGC
TACTGGATCCACTGGGTCCGACAGGCTCCAGGACAAGGCCTGGAATGGATCGGC
GTGATCGACCCCTCTGACAGCTACACCCGGTACAACCAGAAATTCAAGGGCAGA
GTGACCATGACCGTGGACACCTCTACCTCCACCGCCTACATGGAACTGCGGTCCC
TGAGATCTGACGACACCGCCGTGTACTACTGCACCACCTGGGAAGTCGATTACTG
GGGCCAGGGCACCACAGTGACAGTGTCCTCTGCTTCCACAAAGGGCCCAAGCGT
GTTCCCCCTGGCCCCCTGCTCCAGAAGCACCAGCGAGAGCACAGCCGCCCTGGG
CTGCCTGGTGAAGGACTACTTCCCCGAGCCCGTGACCGTGTCCTGGAACAGCGG
AGCCCTGACCAGCGGCGTGCACACCTTCCCCGCCGTGCTGCAGAGCAGCGGCCT
GTACAGCCTGAGCAGCGTGGTGACCGTGCCCAGCAGCAGCCTGGGCACCAAGAC
CTACACCTGTAACGTGGACCACAAGCCCAGCAACACCAAGGTGGACAAGAGGGT
GGAGAGCAAGTACGGCCCACCCTGCCCCCCCTGCCCAGCCCCCGAGTTCCTGGG
CGGACCCAGCGTGTTCCTGTTCCCCCCCAAGCCCAAGGACACCCTGATGATCAGC
AGAACCCCCGAGGTGACCTGTGTGGTGGTGGACGTGTCCCAGGAGGACCCCGAG
GTCCAGTTCAACTGGTACGTGGACGGCGTGGAGGTGCACAACGCCAAGACCAAG
CCCAGAGAGGAGCAGTTTAACAGCACCTACCGGGTGGTGTCCGTGCTGACCGTG
CTGCACCAGGACTGGCTGAACGGCAAAGAGTACAAGTGTAAGGTCTCCAACAAG
GGCCTGCCAAGCAGCATCGAAAAGACCATCAGCAAGGCCAAGGGCCAGCCTAG
AGAGCCCCAGGTCTACACCCTGCCACCCAGCCAAGAGGAGATGACCAAGAACCA
GGTGTCCCTGACCTGTCTGGTGAAGGGCTTCTACCCAAGCGACATCGCCGTGGAG
TGGGAGAGCAACGGCCAGCCCGAGAACAACTACAAGACCACCCCCCCAGTGCTG
GACAGCGACGGCAGCTTCTTCCTGTACAGCAGGCTGACCGTGGACAAGTCCAGA
TGGCAGGAGGGCAACGTCTTTAGCTGCTCCGTGATGCACGAGGCCCTGCACAAC
CACTACACCCAGAAGAGCCTGAGCCTGTCCCTGGGCTGATGAATTC

SEQ ID NO: 130

FIG. 28A

MEWSWVFLFFLSVTTGVHSQVQLVQSGAEVKKPGASVKVSCKASGYTFTSYWIHW
VRQAPGQGLEWIGVIDPSDSYTRYNQKFKGRVTMTVDTSTSTAYMELRSLRSDDTA
VYYCTTWEVDYWGQGTTVTVSSASTKGPSVFPLAPCSRSTSESTAALGCLVKDYFPE
PVTVSWNSGALTSGVHTFPAVLQSSGLYSLSSVVTVPSSSLGTKTYTCNVDHKPSNT
KVDKRVESKYGPPCPPCPAPEFLGGPSVFLFPPKPKDTLMISRTPEVTCVVVDVSQED
PEVQFNWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEALHNHYTQ
KSLSLSLG

SEQ ID NO: 40

FIG. 28B

AAGCTTGCCGCCACCATGTCTGTGCCTACACAGGTTCTGGGACTGCTGCTGCTGT
GGCTGACCGACGCCAGATGCGACATCGTGATGACCCAGTCTCCACTGAGCCTGC
CTGTGACACCTGGCGAGCCTGCTTCCATCTCCTGCAGATCCTCTCAGTCCCTGGT
GCACTCTGACGGCAACACCTACCTGCACTGGTATCTGCAGAAGCCCGGCCAGTCT
CCTCAGCTGCTGATCTACAAGGTGTCCAACCGGTTCTCTGGCGTGCCCGACAGAT
TTTCCGGCTCTGGCTCTGGCACCGACTTCACCCTGAAGATCTCCAGAGTGGAAGC
CGAGGACGTGGGCGTGTACTACTGCTCCCAGTCTACCCATGTGCCTTGGACCTTT
GGCGGAGGCACCAAGGTGGAAATCAAGCGTACGGTGGCCGCTCCCAGCGTGTTC
ATCTTCCCCCCAAGCGACGAGCAGCTGAAGAGCGGCACCGCCAGCGTGGTGTGT
CTGCTGAACAACTTCTACCCCAGGGAGGCCAAGGTGCAGTGGAAGGTGGACAAC
GCCCTGCAGAGCGGCAACAGCCAGGAGAGCGTCACCGAGCAGGACAGCAAGGA
CTCCACCTACAGCCTGAGCAGCACCCTGACCCTGAGCAAGGCCGACTACGAGAA
GCACAAGGTGTACGCCTGTGAGGTGACCCACCAGGGCCTGTCCAGCCCCGTGAC
CAAGAGCTTCAACAGGGGCGAGTGCTGATGAATTC

SEQ ID NO: 129

FIG. 28C

MSVPTQVLGLLLLWLTDARCDIVMTQSPLSLPVTPGEPASISCRSSQSLVHSDGNTYL
HWYLQKPGQSPQLLIYKVSNRFSGVPDRFSGSGSGTDFTLKISRVEAEDVGVYYCSQ
STHVPWTFGGGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEVTHQGLSS
PVTKSFNRGEC

SEQ ID NO: 55

FIG. 28D

AAGCTTGCCGCCACCATGGAATGGTCCTGGGTGTTCCTGTTCTTCCTGTCCGTGA
CCACCGGCGTGCACTCTCAGGTTCAGTTGGTTCAGTCTGGCGCCGAAGTGAAGAA
ACCTGGCGCCTCTGTGAAGGTGTCCTGCAAGGCTTCCGGCTACACCTTTACCAGC
TACTGGATCCACTGGGTCCGACAGGCTCCAGGACAAGGCCTGGAATGGATCGGC
GTGATCGACCCCTCTGACAGCTACACCCGGTACAACCAGAAATTCAAGGGCAGA
GTGACCATGACCGTGGACACCTCTACCTCCACCGCCTACATGGAACTGCGGTCCC
TGAGATCTGACGACACCGCCGTGTACTACTGCACCACCTGGGAAGTCGATTACTG
GGGCCAGGGCACCACAGTGACAGTGTCCTCTGCTTCCACAAAGGGCCCAAGCGT
GTTCCCCCTGGCCCCCAGCAGCAAGAGCACCAGCGGCGGCACAGCCGCCCTGGG
CTGCCTGGTGAAGGACTACTTCCCCGAGCCCGTGACCGTGTCCTGGAACAGCGG
AGCCCTGACCTCCGGCGTGCACACCTTCCCCGCCGTGCTGCAGAGCAGCGGCCTG
TACAGCCTGAGCAGCGTGGTGACCGTGCCCAGCAGCAGCCTGGGCACCCAGACC
TACATCTGTAACGTGAACCACAAGCCCAGCAACACCAAGGTGGACAAGAAGGTG
GAGCCCAAGAGCTGTGACAAGACCCACACCTGCCCCCCCTGCCCAGCCCCCGAG
CTGCTGGGCGGACCCAGCGTGTTCCTGTTCCCCCCCAAGCCCAAGGACACCCTGA
TGATCAGCAGAACCCCCGAGGTGACCTGTGTGGTGGTGGACGTGTCCCACGAGG
ACCCAGAGGTGAAGTTCAACTGGTACGTGGACGGCGTGGAGGTGCACAACGCCA
AGACCAAGCCCAGAGAGGAGCAGTACAACAGCACCTACAGGGTGGTGTCCGTGC
TGACCGTGCTGCACCAGGACTGGCTGAACGGCAAGGAGTACAAGTGTAAGGTGT
CCAACAAGGCCCTGCCAGCCCCAATCGAAAAGACCATCAGCAAGGCCAAGGGCC
AGCCAAGAGAGCCCCAGGTGTACACCCTGCCACCCAGCAGGGACGAGCTGACCA
AGAACCAGGTGTCCCTGACCTGTCTGGTGAAGGGCTTCTACCCAAGCGACATCGC
CGTGGAGTGGGAGAGCAACGGCCAGCCCGAGAACAACTACAAGACCACCCCCC
AGTGCTGGACAGCGACGGCAGCTTCTTCCTGTACAGCAAGCTGACCGTGGACAA
GAGCAGATGGCAGCAGGGCAACGTGTTCAGCTGCTCCGTGATGCACGAGGCCCT
GCACAACCACTACACCCAGAAGAGCCTGAGCCTGTCCCCAGGCTGATGAATTC

SEQ ID NO: 131

FIG. 29A

MRWSCIILFLVATATGVNSQVQLVQSGAEVKKPGASVKVSCKASGYTFTSYWIHWV
RQAPGQGLEWIGVIDPSDSYTRYNQKFKGRVTMTVDTSTSTAYMELRSLRSDDTAV
YYCTTWKVDYWGQGTTVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTK
VDKKVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCK
VSNKALPAPIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMHEALHNH
YTQKSLSLSPG

SEQ ID NO: 132

FIG. 29B

AAGCTTGCCGCCACCATGTCTGTGCCTACACAGGTTCTGGGACTGCTGCTGCTGT
GGCTGACCGACGCCAGATGCGACATCGTGATGACCCAGTCTCCACTGAGCCTGC
CTGTGACACCTGGCGAGCCTGCTTCCATCTCCTGCAGATCCTCTCAGTCCCTGGT
GCACTCTGACGGCAACACCTACCTGCACTGGTATCTGCAGAAGCCCGGCCAGTCT
CCTCAGCTGCTGATCTACAAGGTGTCCAACCGGTTCTCTGGCGTGCCCGACAGAT
TTTCCGGCTCTGGCTCTGGCACCGACTTCACCCTGAAGATCTCCAGAGTGGAAGC
CGAGGACGTGGGCGTGTACTACTGCTCCCAGTCTACCCATGTGCCTTGGACCTTT
GGCGGAGGCACCAAGGTGGAAATCAAGCGTACGGTGGCCGCTCCCAGCGTGTTC
ATCTTCCCCCCAAGCGACGAGCAGCTGAAGAGCGGCACCGCCAGCGTGGTGTGT
CTGCTGAACAACTTCTACCCCAGGGAGGCCAAGGTGCAGTGGAAGGTGGACAAC
GCCCTGCAGAGCGGCAACAGCCAGGAGAGCGTCACCGAGCAGGACAGCAAGGA
CTCCACCTACAGCCTGAGCAGCACCCTGACCCTGAGCAAGGCCGACTACGAGAA
GCACAAGGTGTACGCCTGTGAGGTGACCCACCAGGGCCTGTCCAGCCCCGTGAC
CAAGAGCTTCAACAGGGGCGAGTGCTGATGAATTC

SED ID NO: 129

FIG. 29C

MSVPTQVLGLLLLWLTDARCDIVMTQSPLSLPVTPGEPASISCRSSQSLVHSDGNTYL
HWYLQKPGQSPQLLIYKVSNRFSGVPDRFSGSGSGTDFTLKISRVEAEDVGVYYCSQ
STHVPWTFGGGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEVTHQGLSS
PVTKSFNRGEC

SEQ ID NO: 55

FIG. 29D

| Lane | Sample |
|---|---|
| 1 | SeeBlue Plus2 MW Ladder (10 μL) |
| 2 | HuPT-113D_IgG1-AA(455-030417-01)(non-red) |
| 3 | HuPT-113D_IgG1-AA(455-030417-01)(red) |
| 4 | HuPT-113D_IgG1-AA(455-040417-01)(non-red) |
| 5 | HuPT-113D_IgG1-AA(455-040417-01)(red) |
| 6 | HuPT-113D_IgG1-AA(455-040417-02)(non-red) |
| 7 | HuPT-113D_IgG1-AA(455-040417-02)(red) |
| 8 | HuPT-113D_IgG1-AA(455-060417-01)(non-red) |
| 9 | HuPT-113D_IgG1-AA(455-060417-01)(red) |
| 10 | $IgG_1$ control (non-reduced) |
| 11 | $IgG_1$ control (reduced) |

METHODS AND COMPOSITIONS FOR THE GENERATION AND USE OF HUMANIZED CONFORMATION-SPECIFIC PHOSPHORYLATED TAU ANTIBODIES

CROSS-REFERENCE TO RELATED APPLICATIONS

This application is a divisional of U.S. patent application Ser. No. 16/762,141 filed May 6, 2020, now U.S. Pat. No. 11,591,385 issued Feb. 28, 2023, which is a 371 (c) National Stage entry of PCT/US2018/059833, filed Nov. 8, 2018, which claims the benefit of and priority to U.S. Provisional Patent Application No. 62/583,850, filed Nov. 9, 2017, the entire disclosures of which are hereby incorporated by reference in their entireties for any and all purposes.

SEQUENCE LISTING

The instant application contains a Sequence Listing which has been filed electronically in XML format and is hereby incorporated by reference in its entirety. Said XML copy, created on Apr. 5, 2023, is named 112015-0196.xml and is 242,311 bytes in size.

FIELD OF TECHNOLOGY

The present technology relates generally to the preparation of conformation-specific antibodies that specifically bind phosphorylated-Threonine 231-tau protein (pT231-tau) and uses of the same. In particular, the present technology relates to the preparation of cis-pT231-tau neutralizing antibodies and their use in treating neurological disorders associated with elevated cis-pT231-tau protein expression.

BACKGROUND

The following description is provided to assist the understanding of the reader. None of the information provided or references cited is admitted to be prior art to the present methods.

The brains of patients with Alzheimer's disease (AD) and a number of other central nervous system disorders, such as frontotemporal dementia, Pick's disease, corticobasal degeneration, traumatic brain injury (TBI), chronic traumatic encephalopathy (CTE), and progressive supranuclear palsy, contain neurofibrillary tangles (NFTs) comprising the tau protein. This shared pathological feature has resulted in these various neurodegenerative diseases being called "tauopathies." Tau-related pathology correlates well with progressive loss of neurons and memory in AD. A very early event in tauopathy of AD is tau hyperphosphorylation notably on Ser/Thr-Pro motifs, which causes microtubule disruption and neurotoxicity. It has been found that phosphorylated Thr231-Pro motif in tau (pT231-tau) exists in the two distinct cis and trans conformations. The cis-conformation of pT231-tau protein is predominantly expressed in the brains of AD patients.

Since neuronal dysfunction occurs long before tangle formation, a major challenge is the development of immunotherapy that exclusively targets the early pathogenic events leading up to tauopathy and memory loss in AD.

SUMMARY

The present technology relates generally to conformation-specific antibodies that specifically bind and neutralize phosphorylated-Threonine 231-tau protein (pT231-tau) activity. The antibodies of the present technology are useful in methods for treating neurological disorders associated with elevated cis-pT231-tau protein expression.

In one aspect, the present technology provides an antibody comprising a heavy chain immunoglobulin variable domain sequence of SEQ ID NOs: 1-4 or 7-14, or a variant thereof having one or more conservative amino acid substitutions, and a light chain immunoglobulin variable domain sequence of SEQ ID NOs: 41, 42, or 45-48, or a variant thereof having one or more conservative amino acid substitutions. In some embodiments, the antibody is a humanized antibody.

In another aspect, the present technology provides an antigen binding fragment of the antibody, wherein the antigen binding fragment is selected from the group consisting of Fab, F(ab')2, Fab', scFv, and Fv.

In any of the above embodiments, the antibody binds to an epitope of phosphorylated-Threonine 231-tau protein comprising the amino acid sequence KVAVVRTPPKSPS (SEQ ID NO: 56). In some embodiments, the antibody specifically binds to the cis-conformation of phosphorylated-Threonine 231-tau protein (pT231-tau). In some embodiments, the antibody has an isotype selected from the group consisting of IgA1, IgA2, IgD, IgE, IgG1, IgG2, IgG3, IgG4, and IgM.

In one aspect, the present technology provides a recombinant nucleic acid sequence encoding the anti-cis-pT231-tau antibodies disclosed herein. In yet another aspect, the present technology provides a host cell or vector comprising the recombinant nucleic acid encoding the anti-cis-pT231-tau antibodies described herein.

In one aspect, the present technology provides a composition comprising an anti-cis-pT231-tau antibody and a pharmaceutically-acceptable carrier. In some embodiments, the composition comprises an anti-cis-pT231-tau antibody comprising a heavy chain immunoglobulin variable domain sequence of SEQ ID NOs: 1-4 or 7-14, or a variant thereof having one or more conservative amino acid substitutions, and optionally a light chain immunoglobulin variable domain sequence of SEQ ID NOs: 41, 42, or 45-48, or a variant thereof having one or more conservative amino acid substitutions.

In another aspect, the present technology provides a method for treating a neurological disorder associated with elevated cis-pT231-tau protein expression in a subject in need thereof, comprising administering to the subject an effective amount of an antibody comprising a heavy chain immunoglobulin variable domain sequence of SEQ ID NOs: 1-4 or 7-14, or a variant thereof having one or more conservative amino acid substitutions, wherein the antibody specifically binds to and neutralizes cis-pT231-tau protein.

In certain embodiments of the method, the antibody further comprises a light chain immunoglobulin variable domain sequence of SEQ ID NOs: 41, 42, or 45-48, or a variant thereof having one or more conservative amino acid substitutions.

In some embodiments of the method, the neurological disorder is a tauopathy, traumatic brain injury (TBI), or stroke. In a further embodiment, the tauopathy is selected from the group consisting of: progressive supranuclear palsy (PSP), chronic traumatic encephalopathy (CTE), frontotemporal dementia (FTD), frontotemporal lobar degeneration, Lytico-Bodig disease, tangle-predominant dementia, meningioangiomatosis, subacute sclerosing panencephalitis, Pick's disease, corticobasal degeneration, and Alzheimer's disease (AD).

In certain embodiments, the subject is at an early stage of said tauopathy. In one embodiment, the early stage of said tauopathy is determined by an elevated level of cis pT231-tau or an increase in cis:trans pT231-tau ratio in a sample obtained from the subject. In some embodiments, the method further comprises determining the levels of CSF t-tau, pT181-tau, Aβ42, or ApoE4 levels in the sample obtained from the subject. In certain embodiments, the sample is selected from the group consisting of urine, blood, serum, plasma, saliva, amniotic fluid, and cerebrospinal fluid (CSF).

In some embodiments, the subject has a history of repeated brain trauma.

Additionally or alternatively, in some embodiments of the method, the antibody is administered to the subject separately, sequentially or simultaneously with an additional therapeutic agent. In some embodiments, the additional therapeutic agent is one or more of donepezil, rivastigmine, galantamine, memantine, and lithium chloride.

In one aspect, the present technology provides a method for selecting a subject for treatment with the anti-cis-pT231-tau antibodies disclosed herein comprising (a) detecting an increase in the level of cis pT231-tau protein or an increase in cis:trans pT231-tau protein ratio in a sample obtained from said subject relative to that observed in a reference sample; and (b) selecting said subject for treatment with the anti-cis-pT231-tau antibodies disclosed herein. In some embodiments, the sample obtained from the subject is selected from the group consisting of: urine, blood, serum, plasma, saliva, amniotic fluid, and cerebrospinal fluid (CSF).

In certain embodiments, the reference sample is obtained from a healthy control subject.

In another aspect, the present technology provides a kit for treating a neurological disorder associated with elevated cis-pT231-tau protein expression in a subject in need thereof, comprising an antibody that specifically binds to and neutralizes cis-pT231-tau protein and instructions for use of the antibody, wherein the antibody comprises a heavy chain immunoglobulin variable domain sequence of SEQ ID NOs: 1-4 or 7-14, or a variant thereof having one or more conservative amino acid substitutions. In some embodiments of the kit, the antibody further comprises a light chain immunoglobulin variable domain sequence of SEQ ID NOs: 41, 42, or 45-48, or a variant thereof having one or more conservative amino acid substitutions.

In one aspect, the present technology provides a kit for detecting cis-pT231-tau protein in a sample comprising an antibody that specifically binds to cis-pT231-tau protein and instructions for use of the antibody, wherein the antibody comprises a heavy chain immunoglobulin variable domain sequence of SEQ ID NOs: 1-4 or 7-14, or a variant thereof having one or more conservative amino acid substitutions. In some embodiments of the kit, the antibody further comprises a light chain immunoglobulin variable domain sequence of SEQ ID NOs: 41, 42, or 45-48, or a variant thereof having one or more conservative amino acid substitutions.

In certain embodiments, the antibody is coupled to one or more detectable labels. In one embodiment, the one or more detectable labels comprise a radioactive label, a fluorescent label, or a chromogenic label.

Additionally or alternatively, in some embodiments, the kit further comprises a secondary antibody that specifically binds to the cis-pT231-tau protein antibody. In some embodiments, the secondary antibody is coupled to at least one detectable label selected from the group consisting of a radioactive label, a fluorescent label, or a chromogenic label.

BRIEF DESCRIPTION OF THE DRAWINGS

FIG. 1 shows the nucleotide and amino acid sequences of the heavy chain immunoglobulin variable (VH) domain of the murine antibody PT-113. Amino acid residues are shown in single letter code. A portion of the CH1 sequence is included in the figure.

FIG. 2 shows the nucleotide and amino acid sequences of the light chain immunoglobulin variable (VL) domain of the murine antibody PT-113. Amino acid residues are shown in single letter code. A portion of the Cκ sequence is included in the figure.

FIG. 3 shows the amino acid sequence of the mature VH domain of the mouse PT-113 antibody, aligned with that of its putative parental germline V segment IGHVIS127*01 and JH2 segment in single letter code. Residue numbers are assigned according to Kabat et al., *Sequences of Proteins of Immunological Interests*, NIH Publication No. 91-3242, U.S. Department of Health and Human Services (5th ed., 1991). The CDR sequences of the PT-113 VH domain are underlined. Asterisks indicate the differences between the PT-113 VH and IGHVIS127*01 amino acid sequences.

FIG. 4 shows the amino acid sequence of the mature VL domain of the mouse PT-113 antibody, aligned with that of its putative parental germline V segment IGKV1-110*02 and Jk1 segment in single letter code. Residue numbers are assigned according to Kabat et al. (1991). The CDR sequences of the PT-113 VL domain are underlined. Asterisks indicate the differences between the PT-113 VL and IGKV1-110*02 amino acid sequences.

FIG. 5 shows the nucleotide sequence of the synthesized mouse PT-113 VH gene flanked by SpeI and HindIII sites (underlined) along with the deduced amino acid sequence. Amino acid residues are shown in single letter code. The signal peptide sequence is in italics. The N-terminal amino acid residue (Q) of the mature VH domain is double-underlined. The CDR sequences according to the definition of Kabat et al. (1991) are underlined. The intron sequence that is contiguous to the HindIII site is in italics.

FIG. 6 shows the nucleotide sequence of the synthesized mouse PT-113 VL gene flanked by NheI and EcoRI sites (underlined) along with the deduced amino acid sequence. Amino acid residues are shown in single letter code. The signal peptide sequence is in italics. The N-terminal amino acid residue (D) of the mature VL domain is double-underlined. The CDR sequences according to the definition of Kabat et al. (1991) are underlined. The intron sequence that is contiguous to the EcoRI site is in italics.

Figure 7:
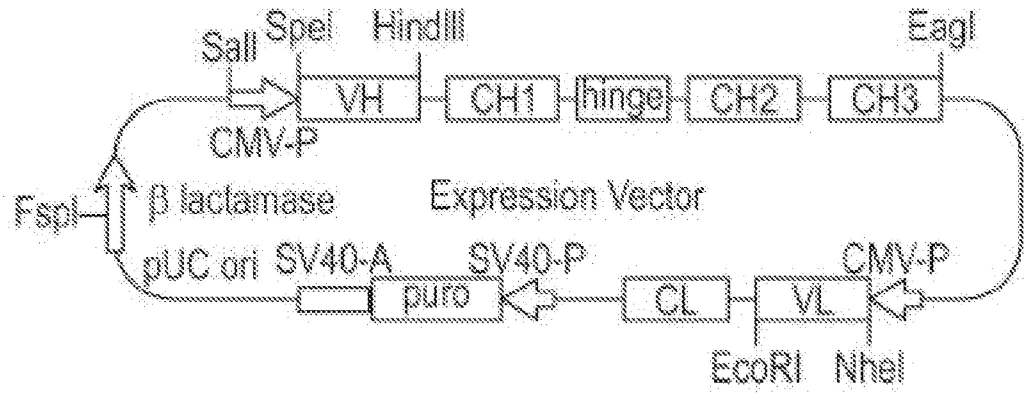
FIG. 7 shows the schematic structure of pChPT-113, pHuPT-113A, pHuPT-113B, pHuPT-113C, pHuPT-113D and pHuPT-113D-AA vectors (collectively Expression Vector). Proceeding clockwise from the SalI site, the plasmid contains the heavy chain transcription unit starting with the human cytomegalovirus (CMV) major immediate early promoter and enhancer (CMV-P) to initiate transcription of the antibody heavy chain gene. The CMV promoter is followed by the VH exon, a genomic sequence containing the human gamma-1 heavy chain constant region including the CH1, hinge, CH2 and CH3 exons with the intervening introns, and the polyadenylation site following the CH3 exon. After the heavy chain gene sequence, the light chain transcription unit begins with the CMV promoter, followed by the VL exon and a genomic sequence containing the human kappa chain constant region exon (CL) with part of the intron preceding it, and the polyadenylation site following the CL exon. The light chain gene is then followed by the SV40 early promoter (SV40-P), the puromycin N-acetyl-transferase gene (puro)

for resistance to puromycin, and a segment containing the SV40 polyadenylation site (SV40-A). Finally, the plasmid contains a part of the plasmid pUC19, comprising the bacterial origin of replication (pUC ori) and beta-lactamase gene (β lactamase). In pHuPT-113D-AA, the CH2 region carries Leu-to-Ala amino acid substitutions at positions 234 and 235 (Eu numbering of Kabat et al. (1)). Location of relevant restriction enzyme sites is shown in the figure.

FIG. 8 shows the alignment of the amino acid sequences of mouse PT-113 VH domain, four versions of humanized PT-113 VH (HuPT-113 VH1, VH2, VH3 and VH4) domains, and human acceptor AF174092 VH domain. Amino acid residues are shown in single letter code. Numbers above the sequences indicate the locations according to Kabat et al. (1991). The CDR sequences of the mouse PT-113 VH domain are underlined. CDR residues in AF174092 VH domain are omitted from the figure. The underlined residues in HuPT-113 VH1, VH2, VH3 and VH4 were predicted to play an important role for formation of the antigen binding site and the corresponding mouse residues were thus retained at these locations.

FIG. 9 shows the alignment of the amino acid sequences of mouse PT-113VL domain, humanized PT-113 VL (HuPT-113 VL1) domain and human acceptor M99608 VL domain. Amino acid residues are shown in single letter code. Numbers above the sequences indicate the positions according to Kabat et al. (1991). The CDR sequences of the mouse PT-113 VL domain are underlined. CDR residues in M99608 VL domain are omitted from the figure. No framework amino acid substitutions were needed when designing HuPT-113 VL1.

FIG. 10 shows the nucleotide sequence of the HuPT-113 VH1 gene flanked by SpeI and HindIII sites (underlined) along with the deduced amino acid sequence. Amino acid residues are shown in single letter code. The signal peptide sequence is in italics. The N-terminal amino acid residue (Q) of the mature VH domain is double-underlined. The CDR sequences according to the definition of Kabat et al. (1991) are underlined. The intron sequence that is contiguous to the HindIII site is in italics.

FIG. 11 shows the nucleotide sequence of the HuPT-113 VH2 gene flanked by SpeI and HindIII sites (underlined) along with the deduced amino acid sequence. Amino acid residues are shown in single letter code. The signal peptide sequence is in italics. The N-terminal amino acid residue (Q) of the mature VH domain is double-underlined. The CDR sequences according to the definition of Kabat et al. (1991) are underlined. The intron sequence that is contiguous to the HindIII site is in italics.

FIG. 12 shows the nucleotide sequence of the HuPT-113 VH3 gene flanked by SpeI and HindIII sites (underlined) along with the deduced amino acid sequence. Amino acid residues are shown in single letter code. The signal peptide sequence is in italics. The N-terminal amino acid residue (Q) of the mature VH domain is double-underlined. The CDR sequences according to the definition of Kabat et al. (1991) are underlined. The intron sequence that is contiguous to the HindIII site is in italics.

FIG. 13 shows the nucleotide sequence of the HuPT-113 VH4 gene flanked by SpeI and HindIII sites (underlined) along with the deduced amino acid sequence. Amino acid residues are shown in single letter code. The signal peptide sequence is in italics. The N-terminal amino acid residue (Q) of the mature VH domain is double-underlined. The CDR sequences according to the definition of Kabat et al. (1991) are underlined. The intron sequence that is contiguous to the HindIII site is in italics.

FIG. 14 shows the nucleotide sequence of the HuPT-113 VL1 gene flanked by NheI and EcoRI sites (underlined) along with the deduced amino acid sequence. Amino acid residues are shown in single letter code. The signal peptide sequence is in italics. The N-terminal amino acid residue (D) of the mature VL domain is double-underlined. The CDR sequences according to the definition of Kabat et al. (1991) are underlined. The intron sequence that is contiguous to the EcoRI site is in italics.

Figure 15:
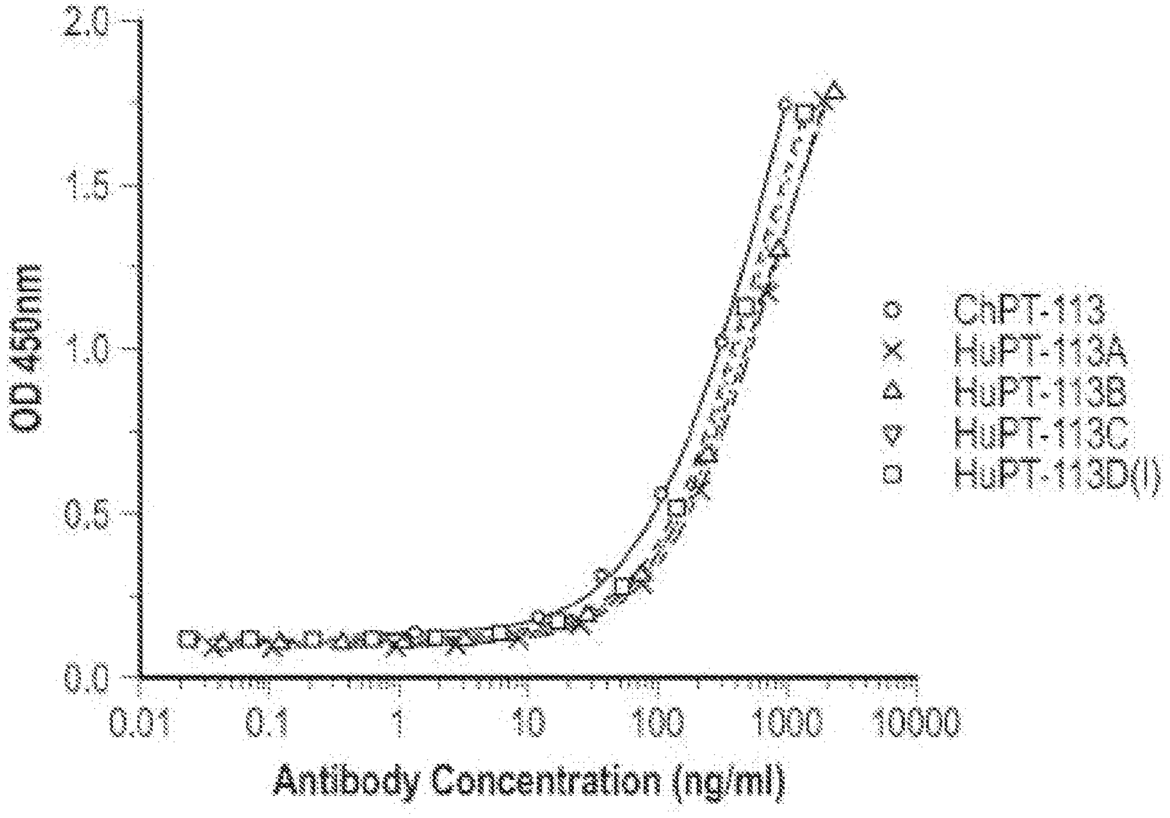

FIG. 15 shows the binding of transiently expressed ChPT-113, HuPT-113A, HuPT-113B, HuPT-113C and HuPT-113D IgG1 (I) antibodies to the pT231-Dmp Tau peptide disclosed herein.

Figure 16:
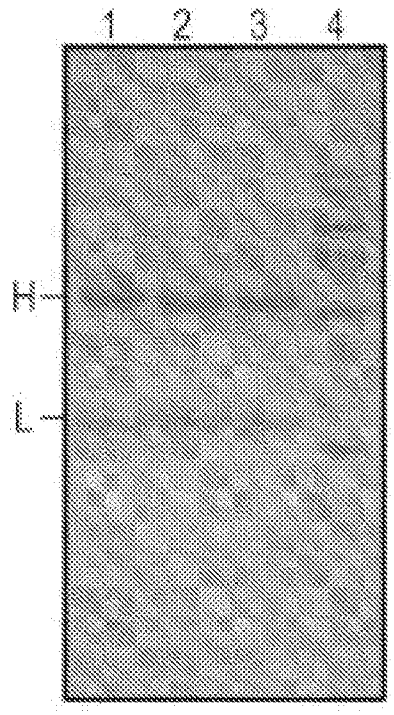

FIG. 16 shows the SDS PAGE analysis of ChPT-113 IgG1, HuPT-113D IgG1 (I) and HuPT-113D IgG1-AA (I) antibodies. Antibodies (5 μg each) were run on a 4-12% SDS PAGE gel in MES Buffer (Thermo Fisher Scientific) under reducing conditions. PageRuler Prestained Protein Ladder (Thermo Fisher Scientific) was used as molecular weight standards (Lane 4). Lane 1, ChPT-113 IgG1; lane 2, HuPT-113D IgG1 (I); lane 3, HuPT-113D IgG1-AA (I). H and L denote the heavy and light chains of each tested antibody, respectively.

FIG. 17 shows the sequences of oligonucleotides used for PCR amplification and sequencing of ChPT-113 IgG1, HuPT-113D IgG1 (I) and HuPT-113D IgG1-AA (I) heavy and light chain cDNA.

FIG. 18 shows the nucleotide sequence of the coding region (variable and constant regions) of the gamma-1 heavy chain encoded by the pChPT-113 construct. Amino acid residues are shown in single letter code. A termination codon is denoted by "•".

FIG. 19 shows the nucleotide sequence of the coding region (variable and constant regions) of the kappa light chain encoded by the pChPT-113 construct. Amino acid residues are shown in single letter code. A termination codon is denoted by "•".

FIG. 20 shows the nucleotide sequence of the coding region (variable and constant regions) of the gamma-1 heavy chain encoded by the pHuPT-113D construct. Amino acid residues are shown in single letter code. A termination codon is denoted by "•".

FIG. 21 shows the nucleotide sequence of the coding region (variable and constant regions) of the kappa light chain encoded by the pHuPT-113D and pHuPT-113D-AA constructs. Amino acid residues are shown in single letter code. A termination codon is denoted by "•".

FIG. 22 shows the nucleotide sequence of the coding region (variable and constant regions) of the gamma-1 heavy chain encoded by the pHuPT-113D-AA construct. Amino acid residues are shown in single letter code. A termination codon is denoted by "•".

Figure 23:
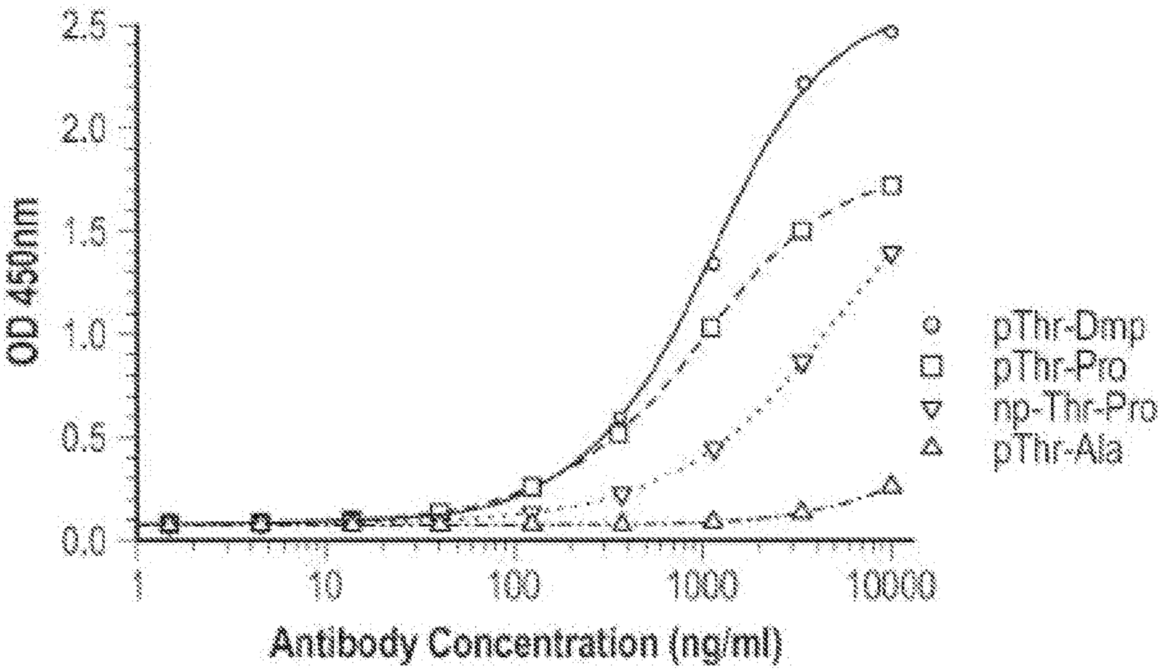

FIG. 23 shows the ELISA analysis of the binding of mouse PT-113 IgG2b antibody to four different Tau peptides.

Figure 24:
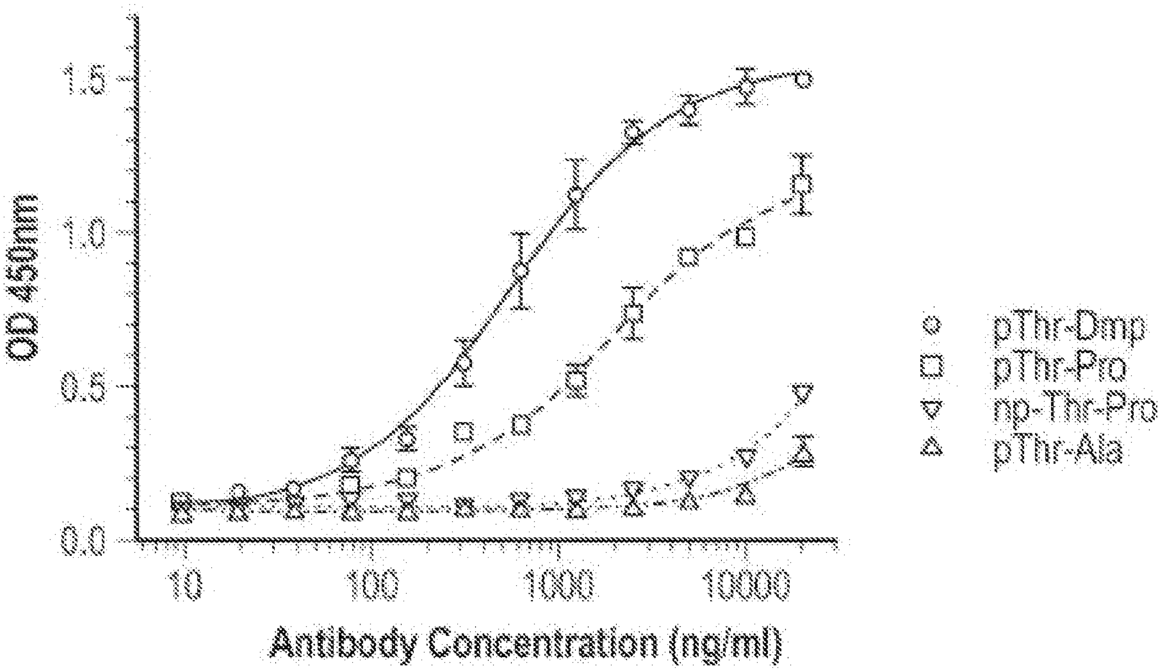

FIG. 24 shows the ELISA analysis of the binding of ChPT-113 IgG1 antibody to four different Tau peptides.

Figure 25:
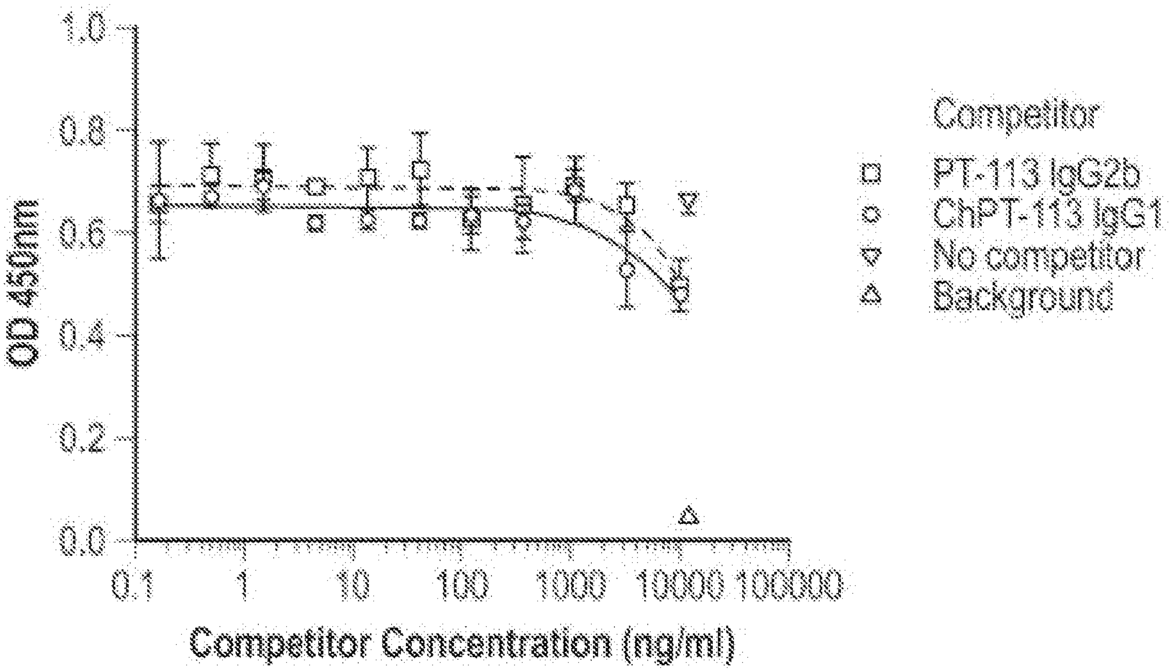

FIG. 25 shows the binding of (i) biotinylated mouse PT-113 IgG2b and (ii) ChPT-113 IgG1 antibodies to the pThr231-Dmp Tau peptide in the presence of different concentrations of a competitor antibody.

Figure 26A:
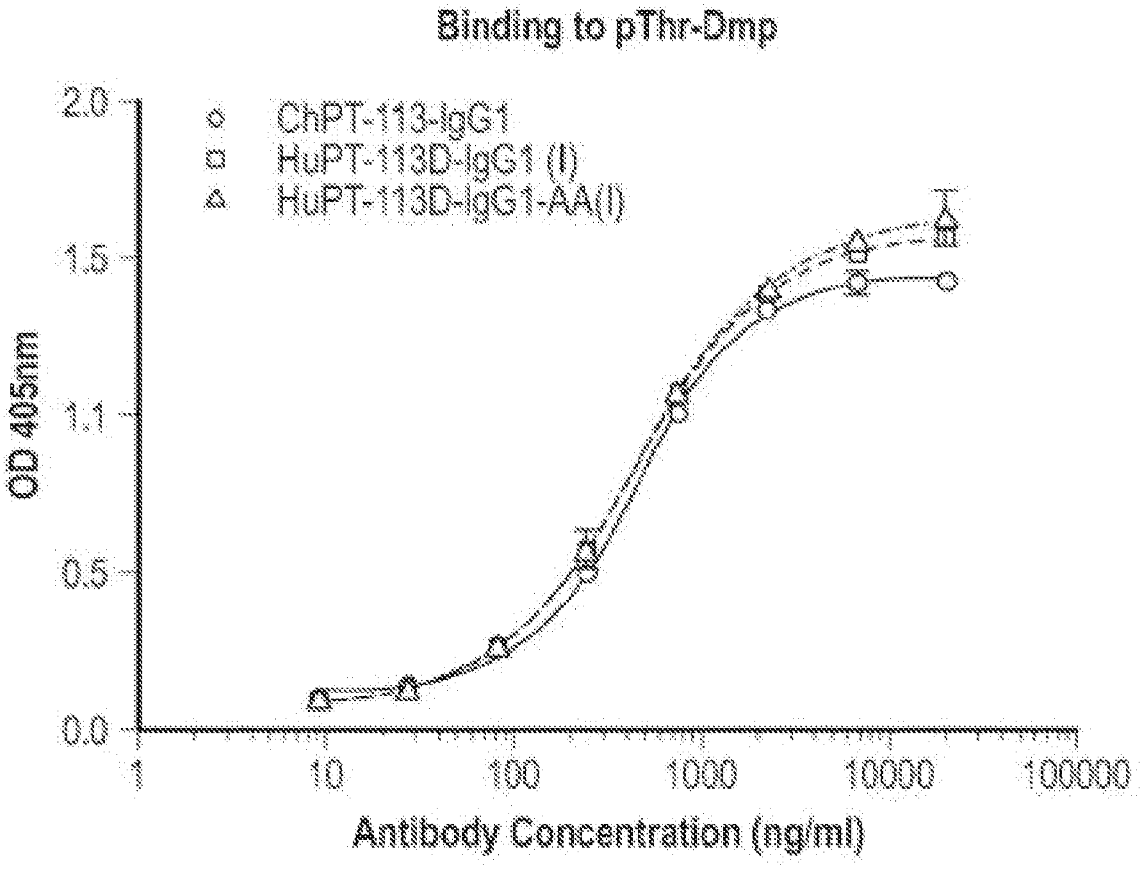
Figure 26B:
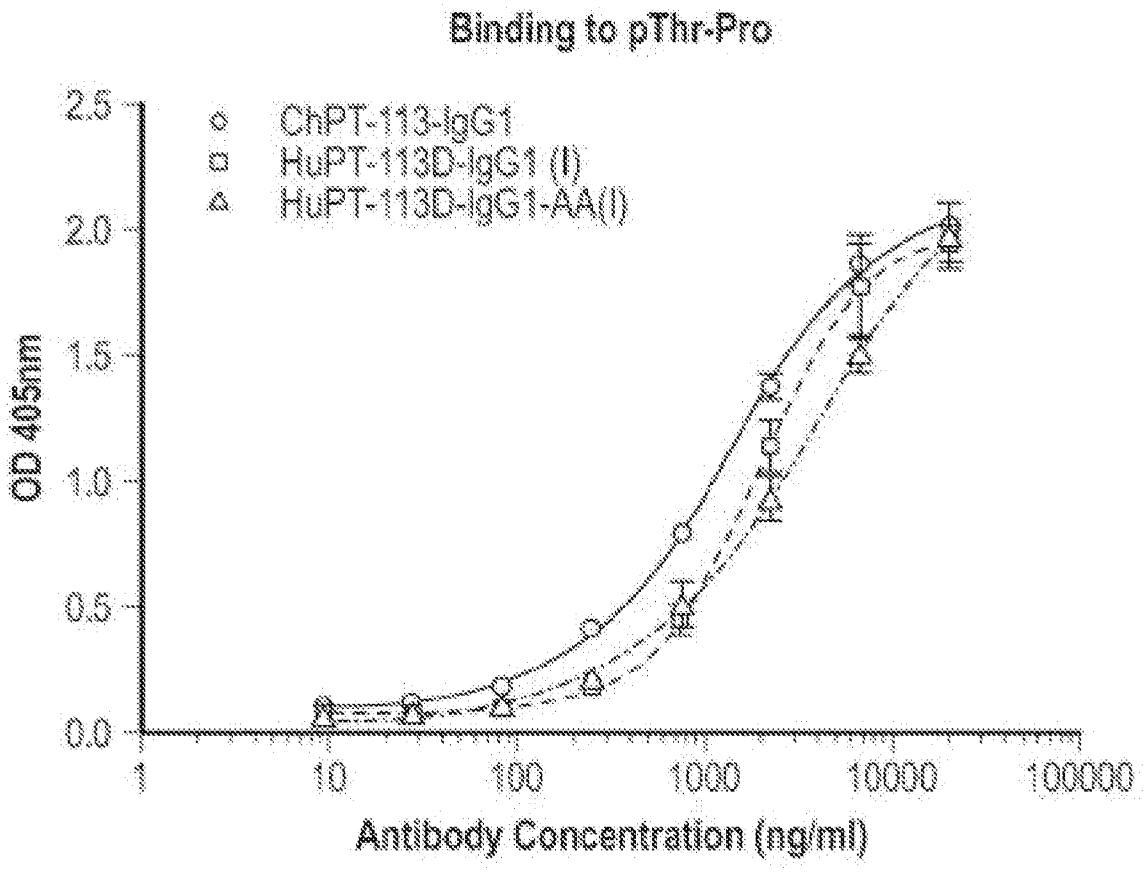
Figure 26C:
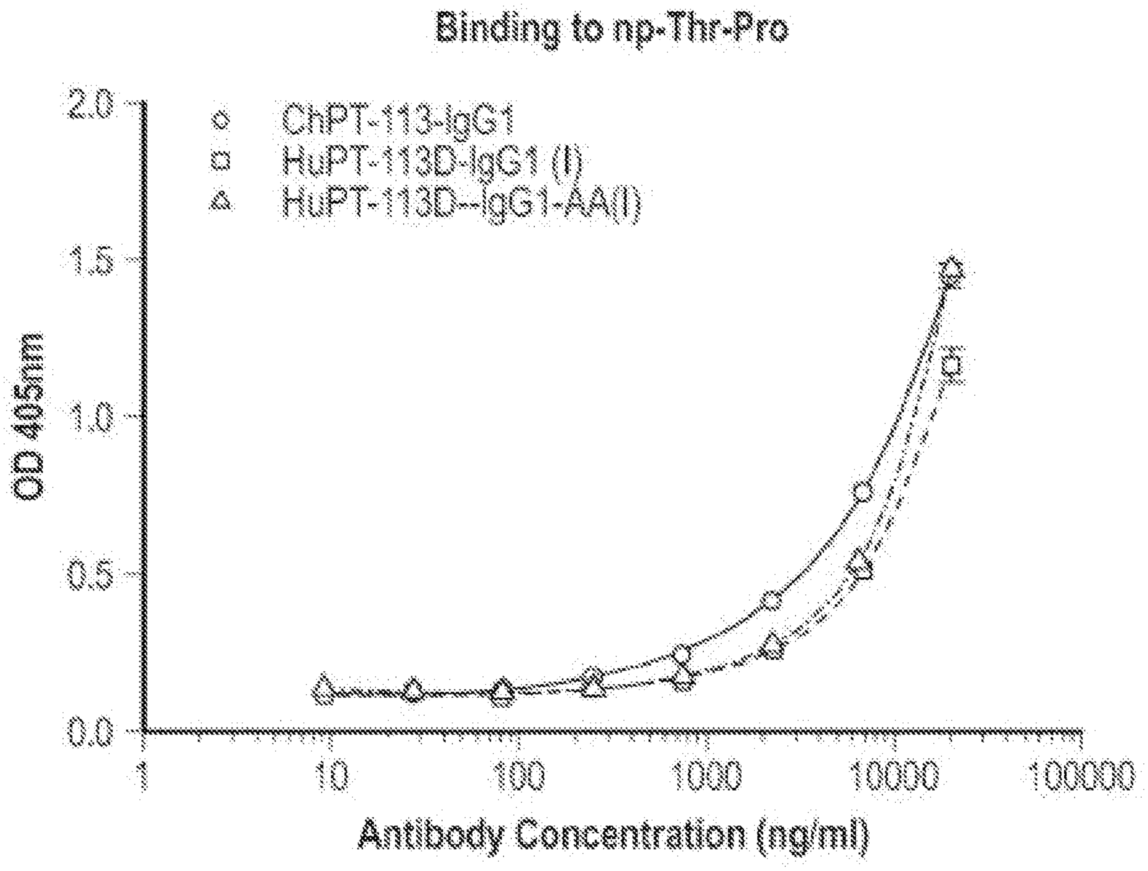
Figure 26D:
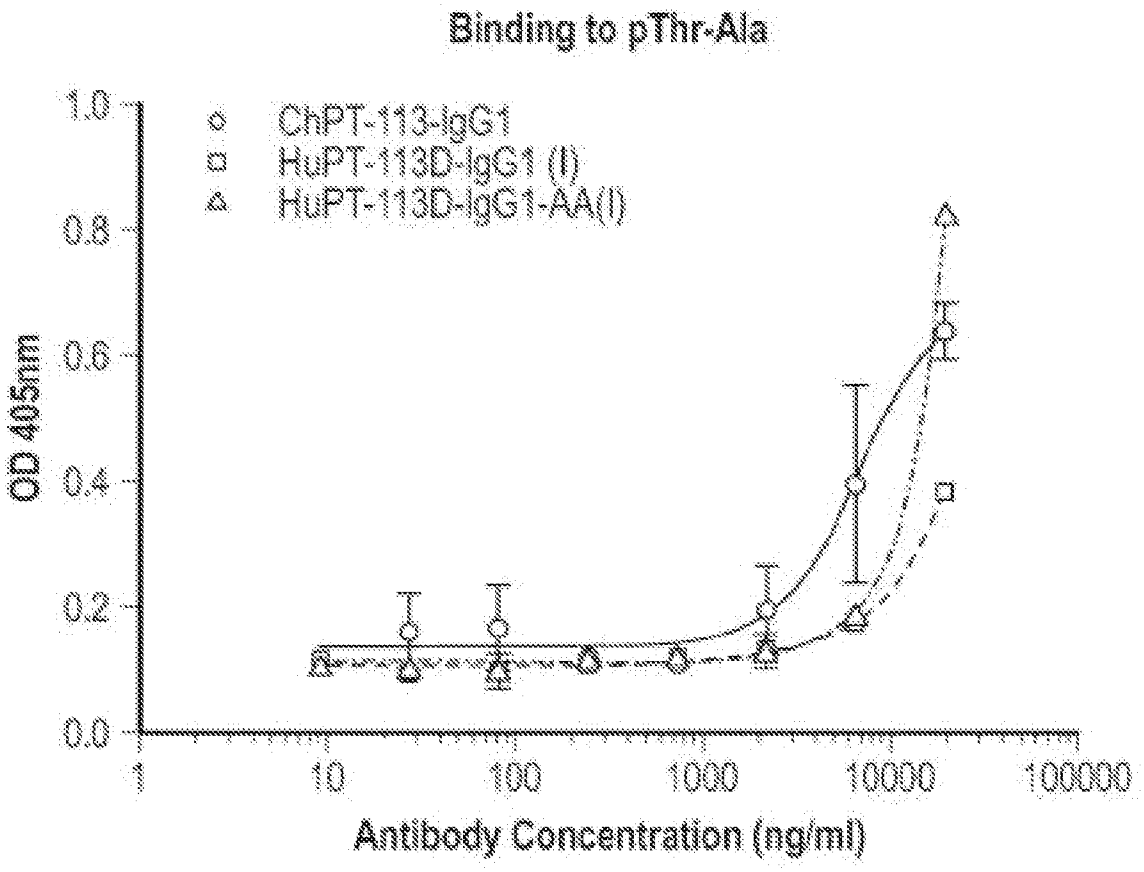

FIG. 26A shows the ELISA analysis of the binding of ChPT-113 IgG1, HuPT-113D IgG1 (I) and HuPT-113D IgG1-AA (I) antibodies to pThr231-Dmp Tau peptide. FIG. 26B shows the ELISA analysis of the binding of ChPT-113 IgG1, HuPT-113D IgG1 (I) and HuPT-113D IgG1-AA (I) antibodies to pThr231-Pro Tau peptide. FIG. 26C shows the ELISA analysis of the binding of ChPT-113 IgG1, HuPT- 113D IgG1 (I) and HuPT-113D IgG1-AA (I) antibodies to np-Thr231-Pro Tau peptide. FIG. 26D shows the ELISA analysis of the binding of ChPT-113 IgG1, HuPT-113D IgG1 (I) and HuPT-113D IgG1-AA (I) antibodies to pThr231-Ala Tau peptides.

FIG. 27A shows the nucleotide sequence for the variable heavy chain of the HuPT-113D IgG1-AA (II) construct (SEQ ID NO: 128).

FIG. 27B shows the amino acid sequence (SEQ ID NO: 39) encoded by SEQ ID NO: 128.

FIG. 27C shows the nucleotide sequence of the kappa light chain of the HuPT-113D IgG1-AA (II) construct (SEQ ID NO: 129).

FIG. 27D shows the amino acid sequence (SEQ ID NO: 55) encoded by SEQ ID NO: 129.

FIG. 28A shows the nucleotide sequence of the variable heavy chain of the HuPT-113D IgG4 (II) construct (SEQ ID NO:130).

FIG. 28B shows the amino acid sequence (SEQ ID NO: 40) encoded by SEQ ID NO: 130.

FIG. 28C shows the nucleotide sequence of the kappa light chain of the HuPT-113D IgG4 (II) construct (SEQ ID NO:129).

FIG. 28D shows the amino acid sequence (SEQ ID NO: 55) encoded by SEQ ID NO: 129.

FIG. 29A shows the nucleotide sequence of the variable heavy chain of the HuPT-113D IgG1 (II) construct (SEQ ID NO:131).

FIG. 29B shows the amino acid sequence (SEQ ID NO: 132) encoded by SEQ ID NO: 131.

FIG. 29C shows the nucleotide sequence of the kappa light chain of the HuPT-113D IgG1 (II) construct (SEQ ID NO: 129).

FIG. 29D shows the amino acid sequence (SEQ ID NO: 55) encoded by SEQ ID NO: 129.

Figure 30A:
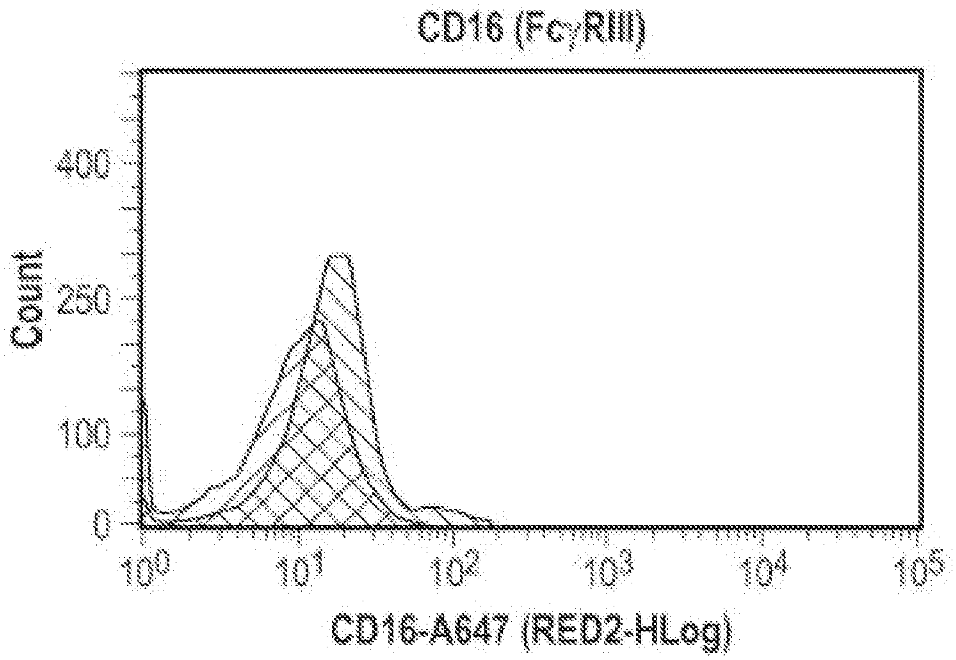

FIG. 30A is a histogram plot showing the staining for CD16 in THP-1 cells. Unstained cells in red and anti-CD16 antibody stained cells in blue.

Figure 30B:
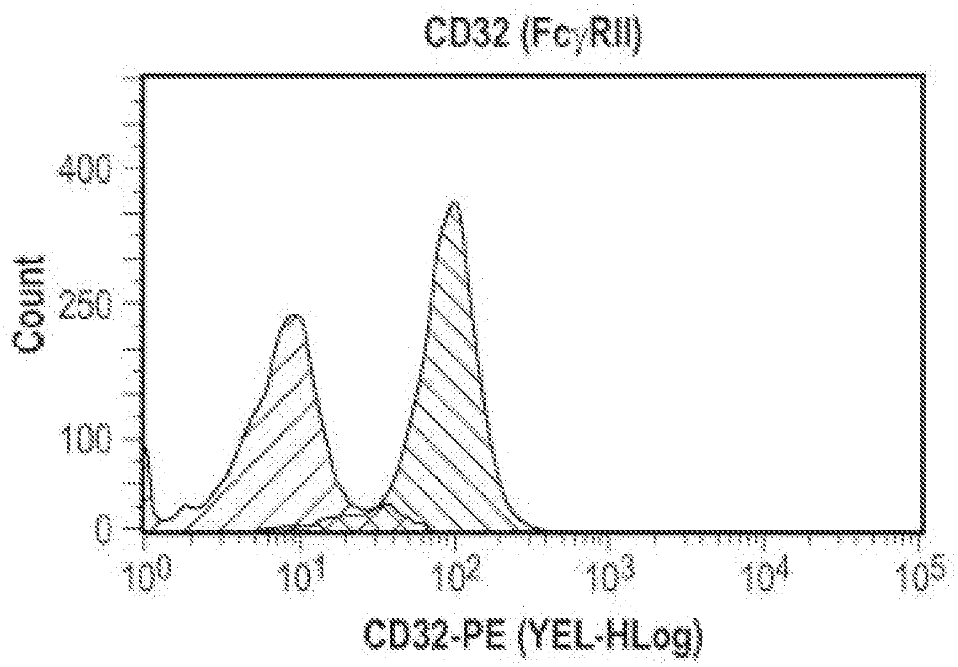

FIG. 30B is a histogram plot showing the staining for CD32 in THP-1 cells. Unstained cells in red and anti-CD32 antibody stained cells in blue.

Figure 30C:
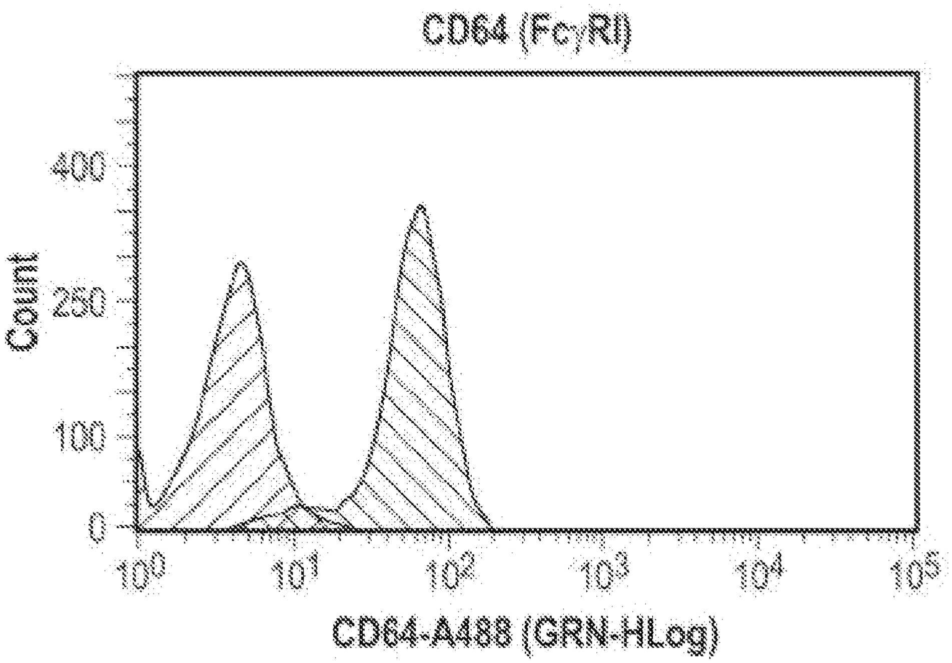

FIG. 30C is a histogram plot showing the staining for CD64 in THP-1 cells. Unstained cells in red and anti-CD64 antibody stained cells in blue.

Figure 31A:
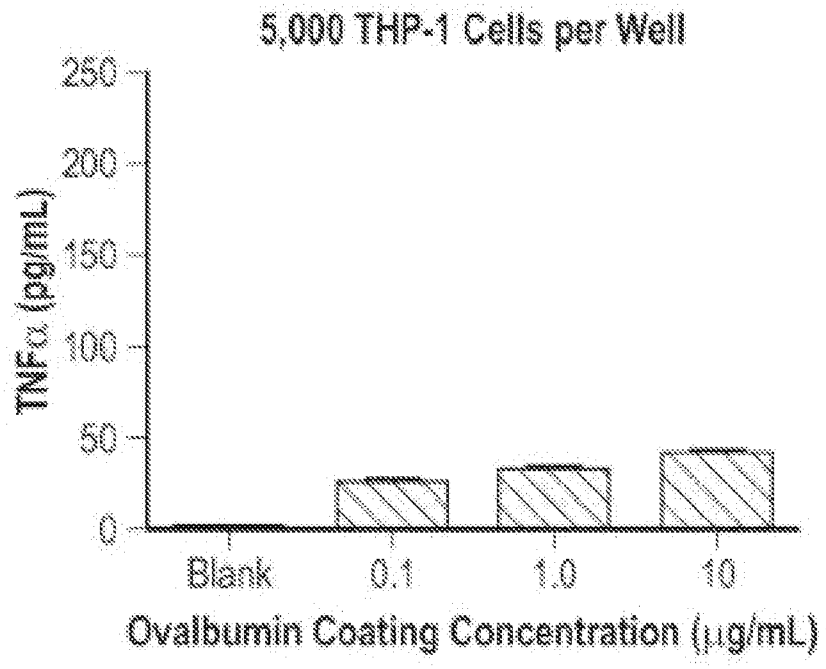

FIG. 31A is a graphing showing the impact of the Ovalbumin immune complex (IC) coating density and cell number (5,000 cells per well) on the activation of THP-1 cells as measure by TNFα secretion. The ovalbumin IC included a rabbit polyclonal anti-Ovalbumin antibody.

Figure 31B:
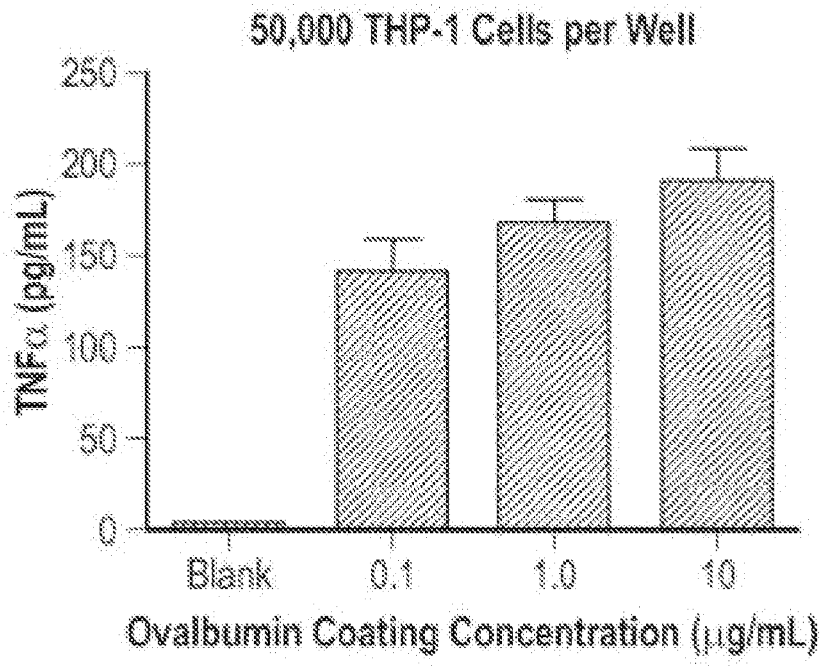

FIG. 31B is a graphing showing the impact of the Ovalbumin immune complex (IC) coating density and cell number (50,000 cells per well) on the activation of THP-1 cells as measure by TNFα secretion. The ovalbumin IC included a rabbit polyclonal anti-Ovalbumin antibody.

Figure 31C:
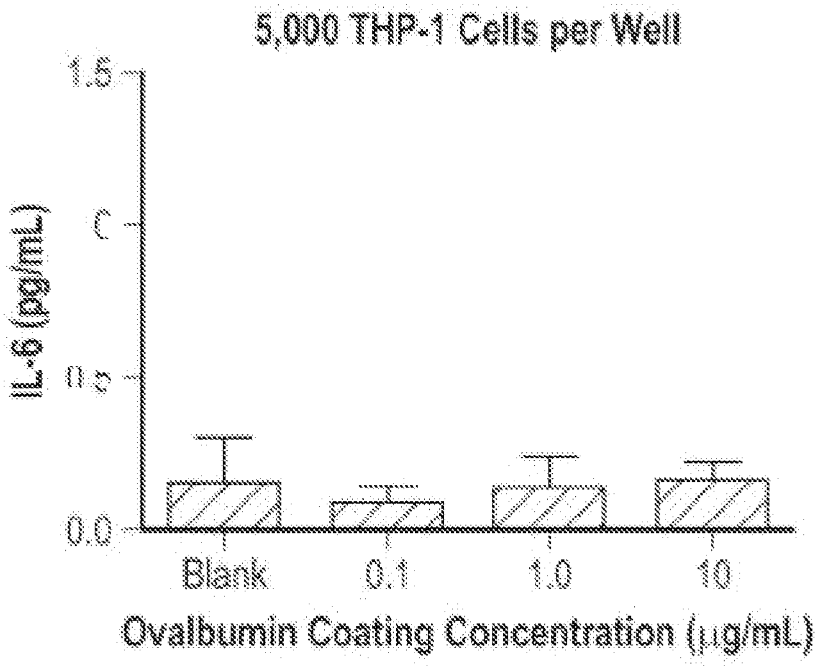

FIG. 31C is a graphing showing the impact of the Ovalbumin immune complex (IC) coating density and cell number (5,000 cells per well) on the activation of THP-1 cells as measure by IL-6 secretion. The ovalbumin IC included a rabbit polyclonal anti-Ovalbumin antibody.

Figure 31D:
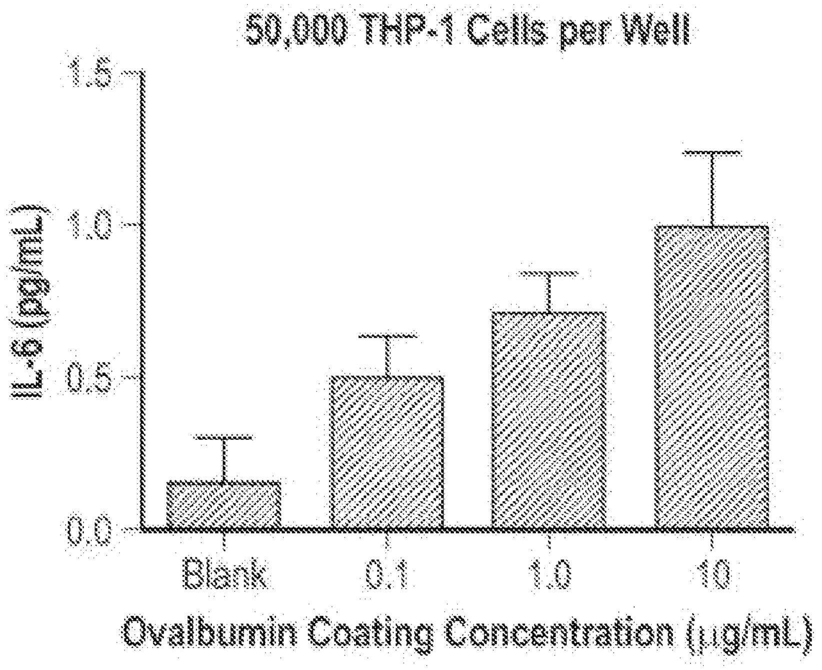

FIG. 31D is a graphing showing the impact of the Ovalbumin immune complex (IC) coating density and cell number (50,000 cells per well) on the activation of THP-1 cells as measure by IL-6 secretion. The ovalbumin IC included a rabbit polyclonal anti-Ovalbumin antibody.

Figure 32A:
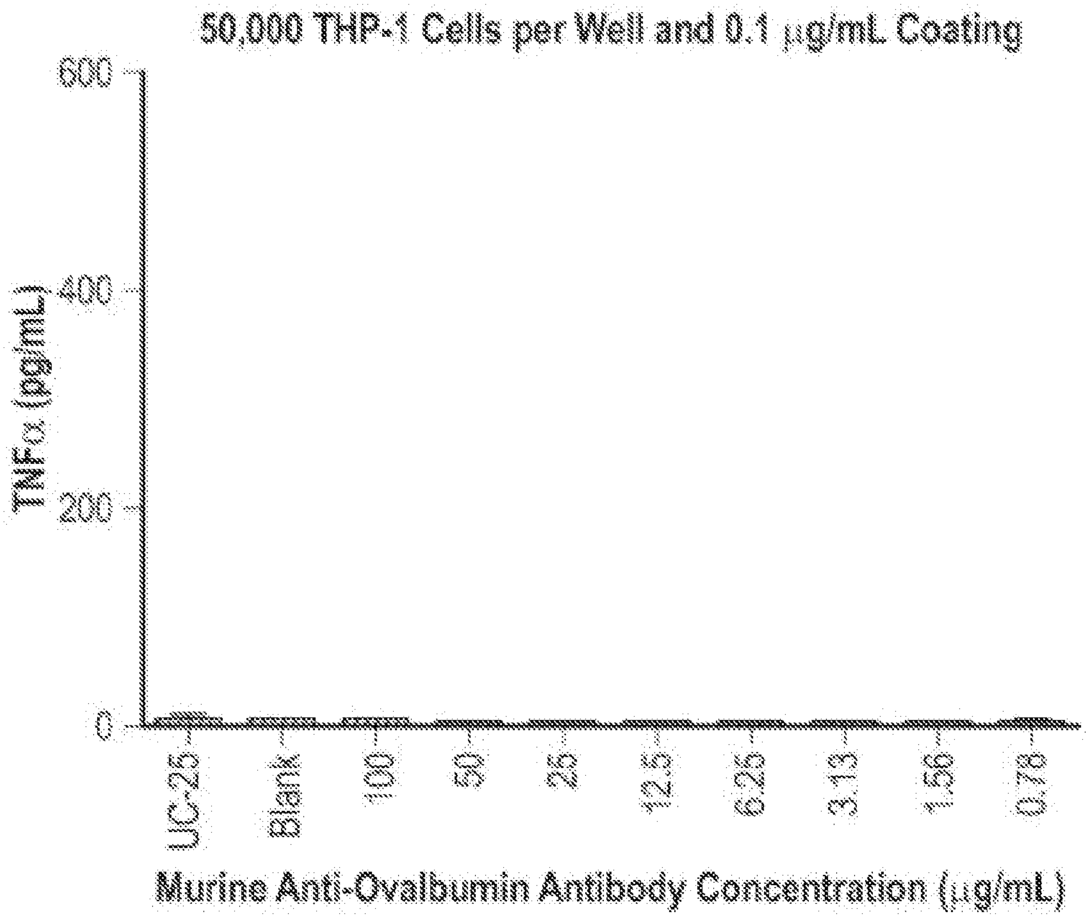

FIG. 32A is a graphing showing the impact of the Ovalbumin immune complex (IC) coating density (0.1 μg/ml coating) and cell number (50,000 cells per well) on the activation of THP-1 cells as measure by TNFα secretion. The ovalbumin IC included a murine monoclonal anti-Ovalbumin antibody.

Figure 32B:
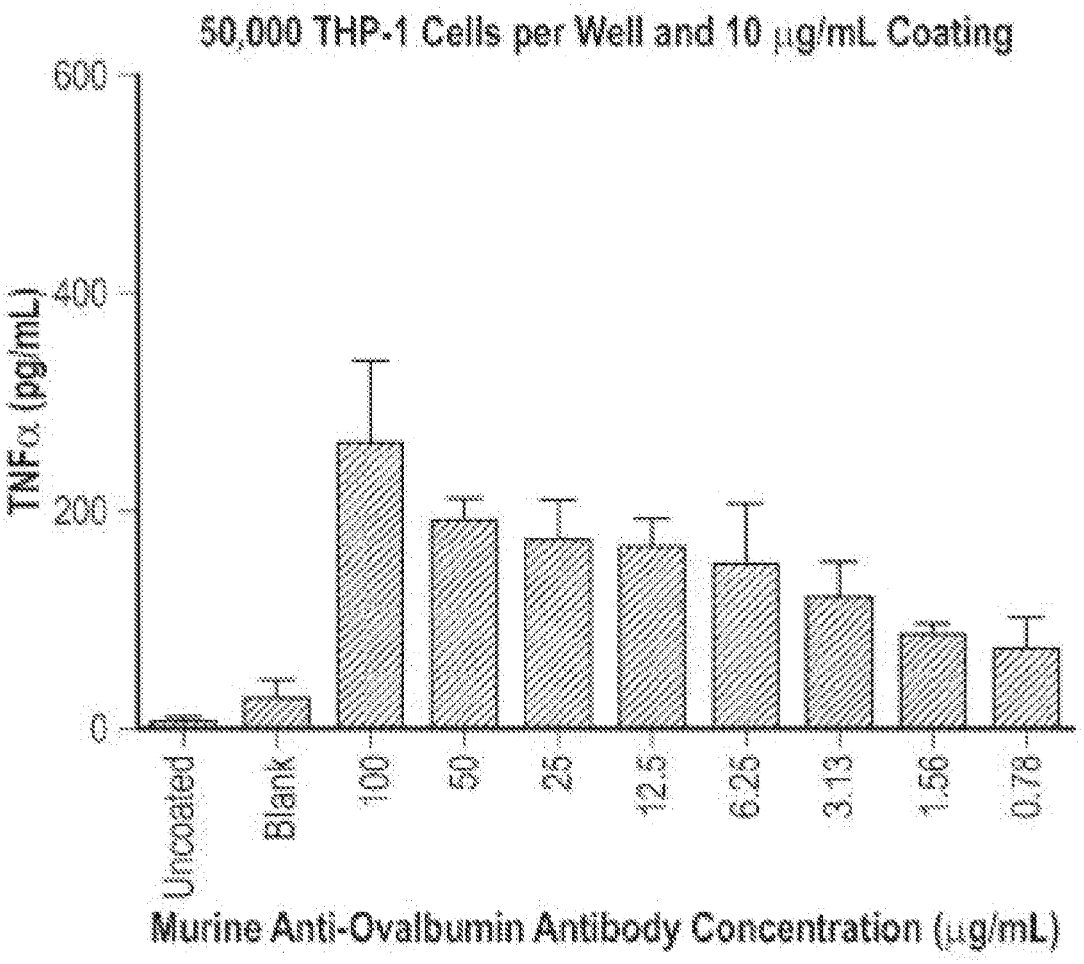

FIG. 32B is a graphing showing the impact of the Ovalbumin immune complex (IC) coating density (10 μg/ml coating) and cell number (50,000 cells per well) on the activation of THP-1 cells as measure by TNFα secretion. The ovalbumin IC included a murine monoclonal anti-Ovalbumin antibody.

Figure 32C:
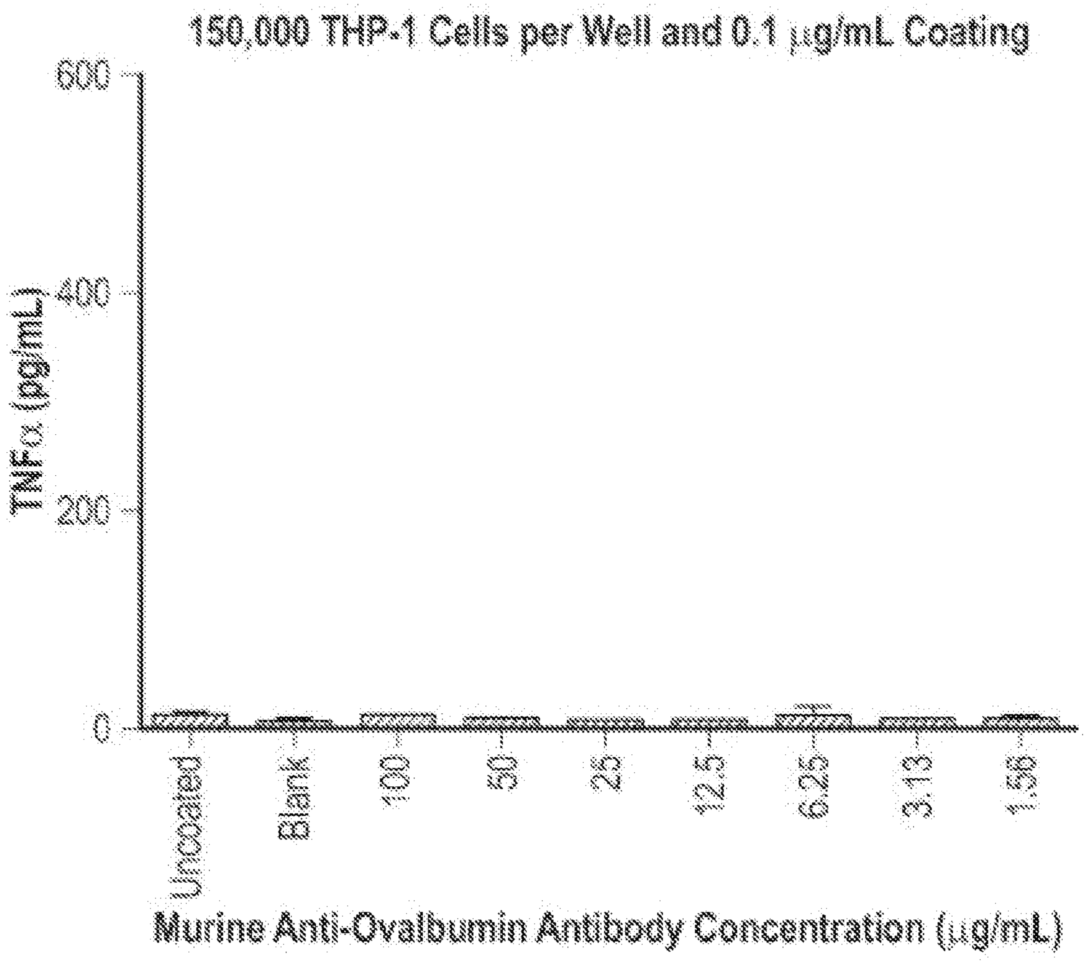

FIG. 32C is a graphing showing the impact of the Ovalbumin immune complex (IC) coating density (0.1 μg/ml coating) and cell number (150,000 cells per well) on the activation of THP-1 cells as measure by TNFα secretion. The ovalbumin IC included a murine monoclonal anti-Ovalbumin antibody.

Figure 32D:
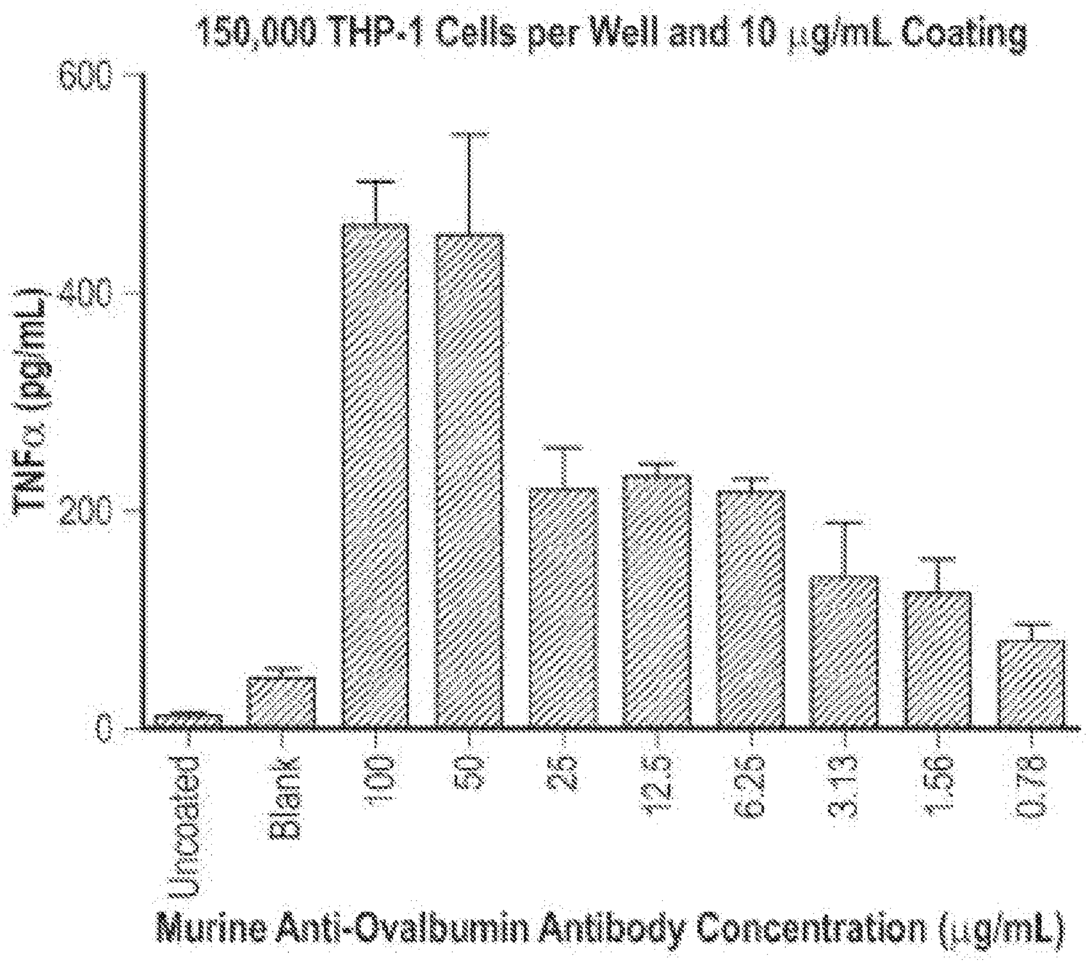

FIG. 32D is a graphing showing the impact of the Ovalbumin immune complex (IC) coating density (10 μg/ml coating) and cell number (150,000 cells per well) on the activation of THP-1 cells as measure by TNFα secretion. The ovalbumin IC included a murine monoclonal anti-Ovalbumin antibody.

Figure 33A:
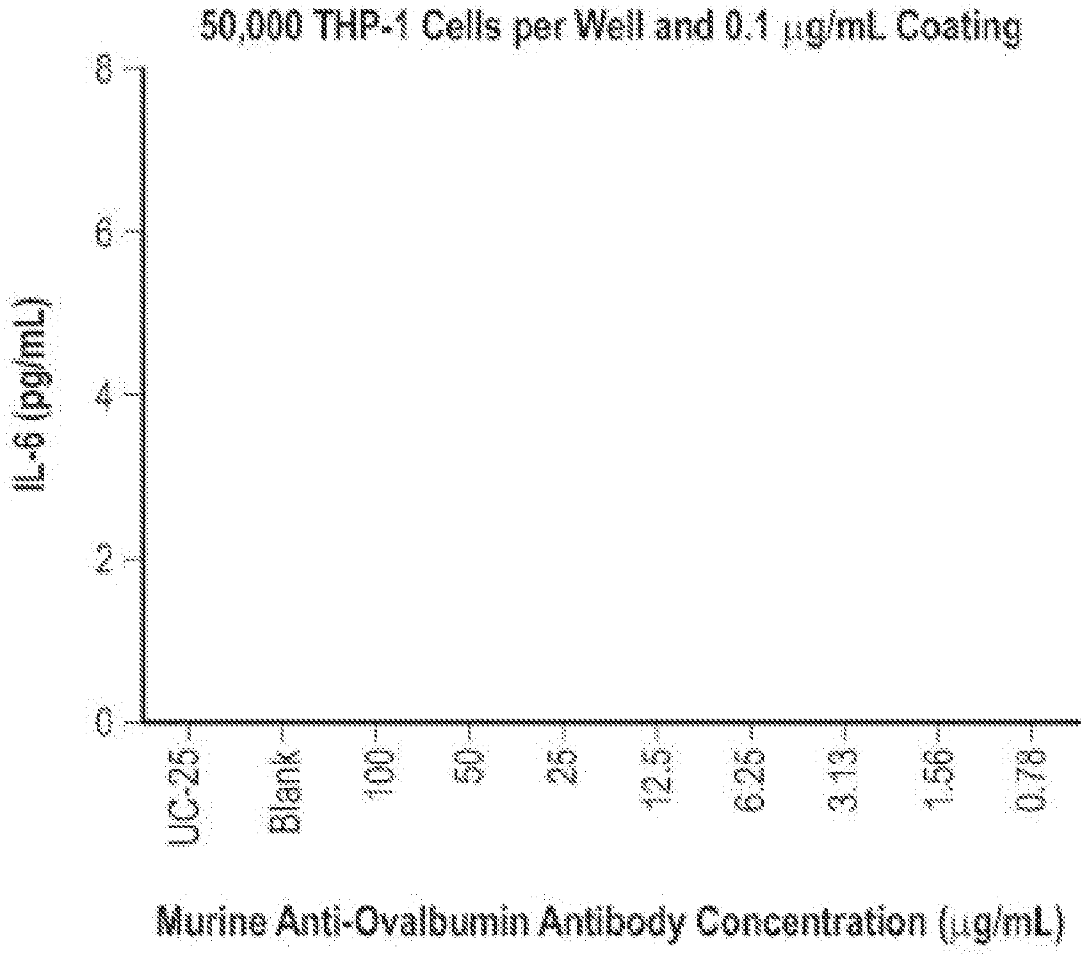

FIG. 33A is a graphing showing the impact of the Ovalbumin immune complex (IC) coating density (0.1 mg/ml coating) and cell number (50,000 cells per well) on the activation of THP-1 cells as measure by IL-6 secretion. The ovalbumin IC included a murine monoclonal anti-Ovalbumin antibody.

Figure 33B:
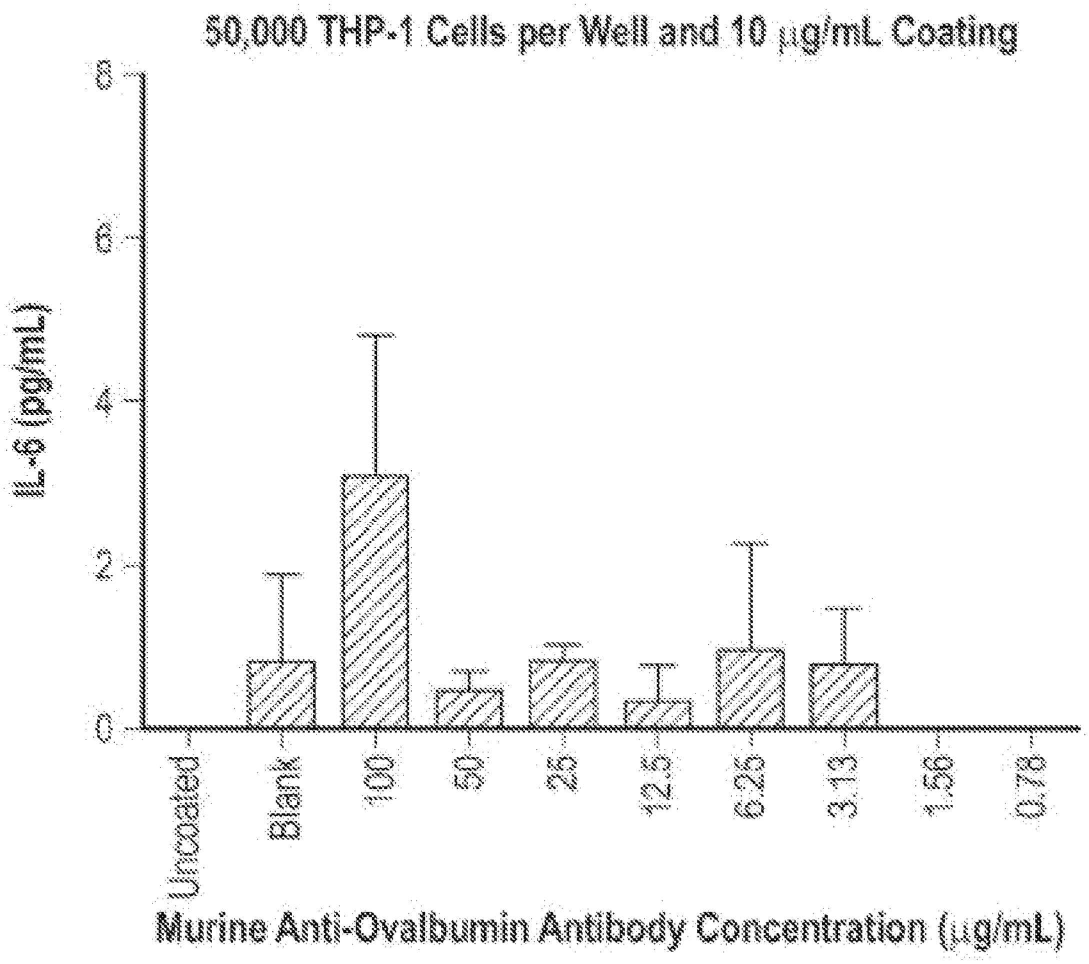

FIG. 33B is a graphing showing the impact of the Ovalbumin immune complex (IC) coating density (10 μg/ml coating) and cell number (50,000 cells per well) on the activation of THP-1 cells as measure by IL-6 secretion. The ovalbumin IC included a murine monoclonal anti-Ovalbumin antibody.

Figure 33C:
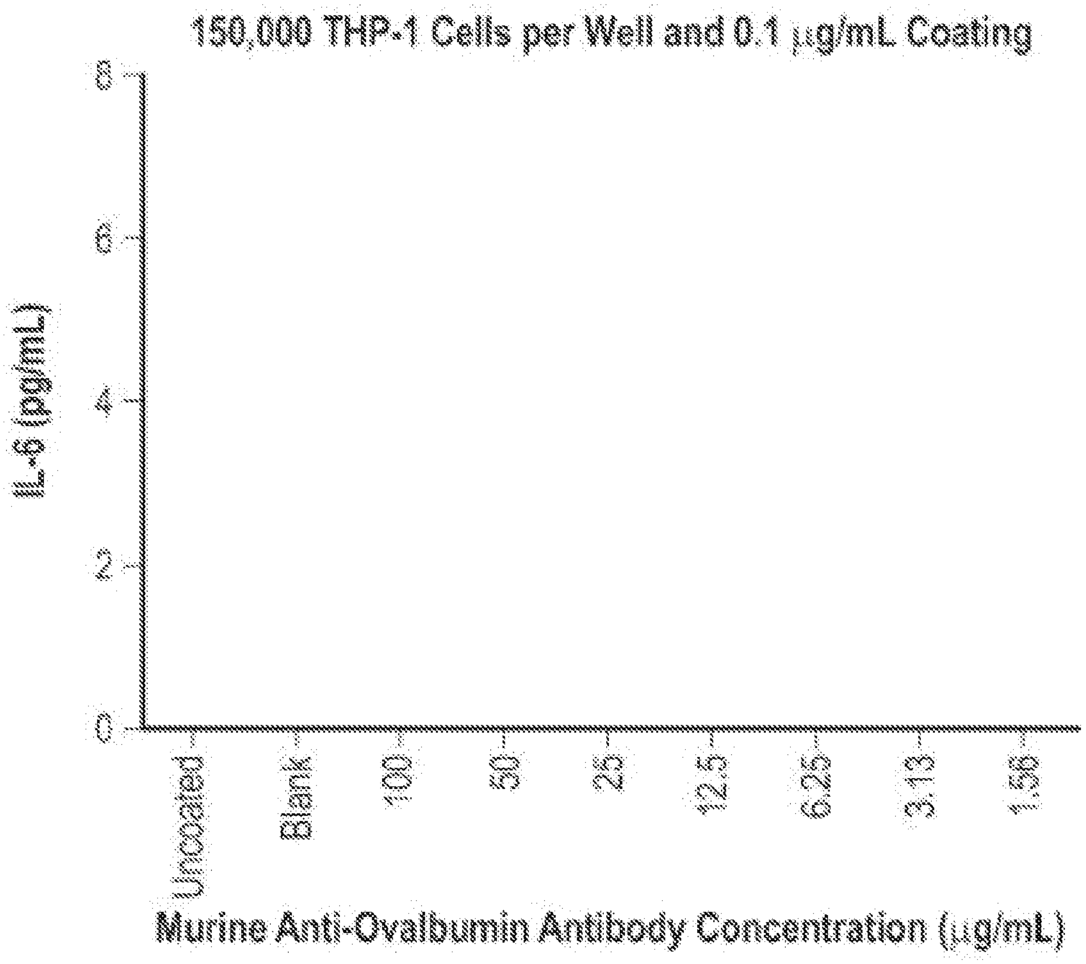

FIG. 33C is a graphing showing the impact of the Ovalbumin immune complex (IC) coating density (0.1 μg/ml coating) and cell number (150,000 cells per well) on the activation of THP-1 cells as measure by IL-6 secretion. The ovalbumin IC included a murine monoclonal anti-Ovalbumin antibody.

Figure 33D:
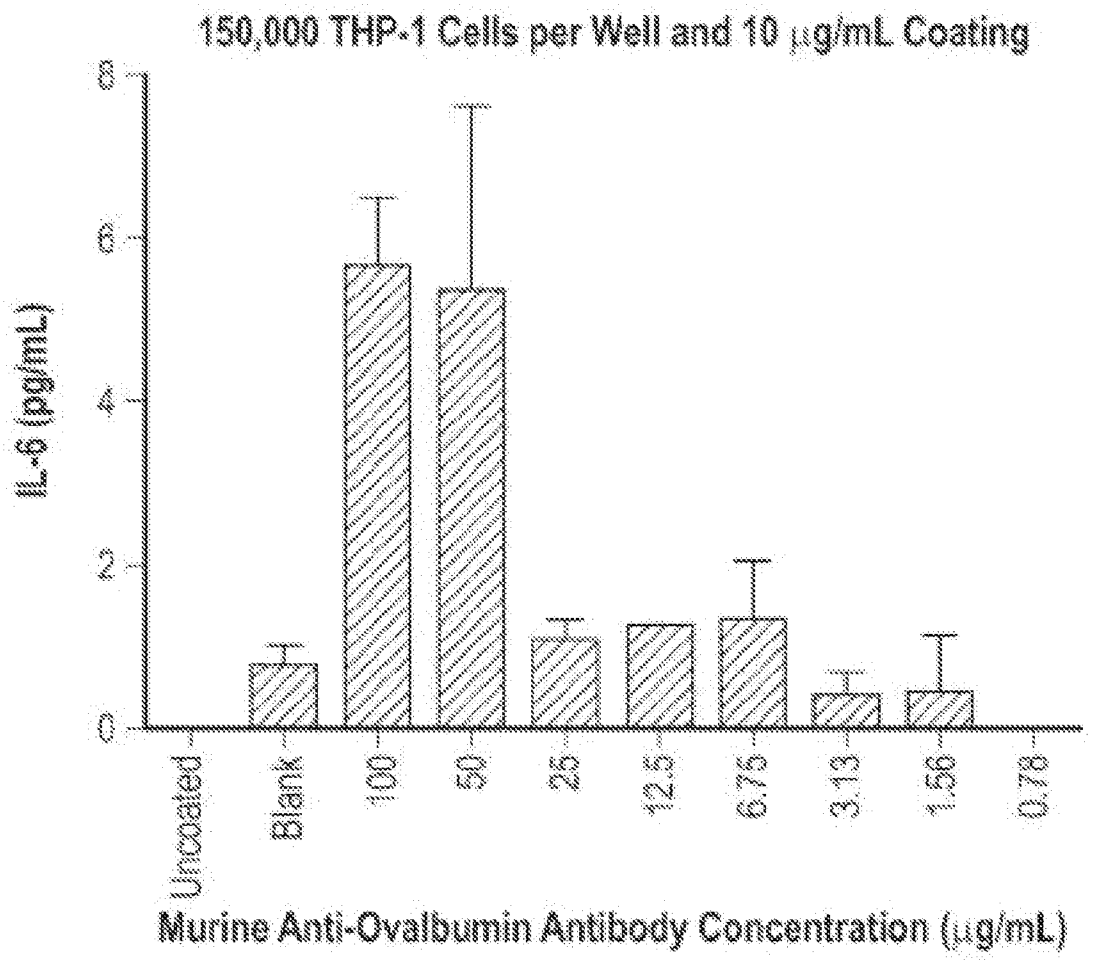

FIG. 33D is a graphing showing the impact of the Ovalbumin immune complex (IC) coating density (10 μg/ml coating) and cell number (150,000 cells per well) on the activation of THP-1 cells as measure by IL-6 secretion. The ovalbumin IC included a murine monoclonal anti-Ovalbumin antibody.

Figure 34A:
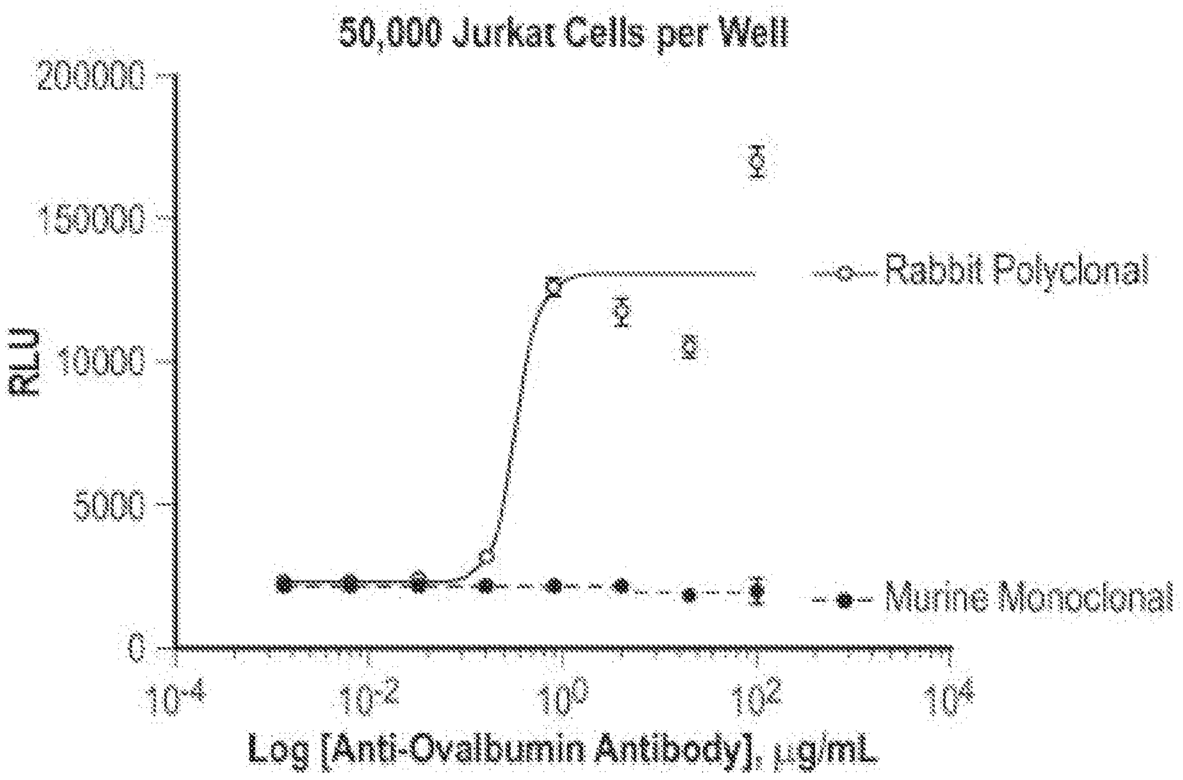

FIG. 34A is a graphing showing the impact of the Ovalbumin IC concentration and number of Jurkat cells (50,00 cells per well) on the activation of the FcR. The Ovalbumin IC was generated with Ovalbumin-coated wells (10 μg/mL) and a range of concentrations of both rabbit polyclonal and murine monoclonal anti-Ovalbumin antibodies.

Figure 34B:
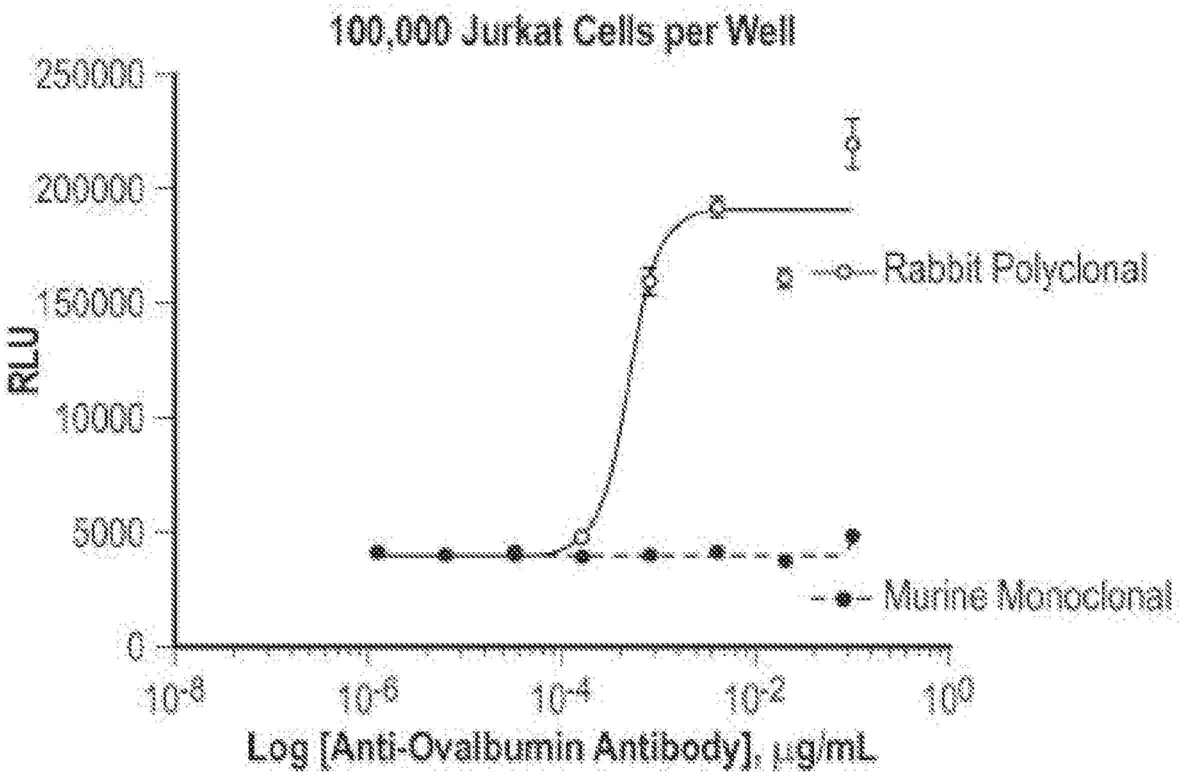

FIG. 34B is a graphing showing the impact of the Ovalbumin IC concentration and number of Jurkat cells (100,00 cells per well) on the activation of the FcR. The Ovalbumin IC was generated with Ovalbumin-coated wells (10 μg/mL) and a range of concentrations of both rabbit polyclonal and murine monoclonal anti-Ovalbumin antibodies.

Figure 35:
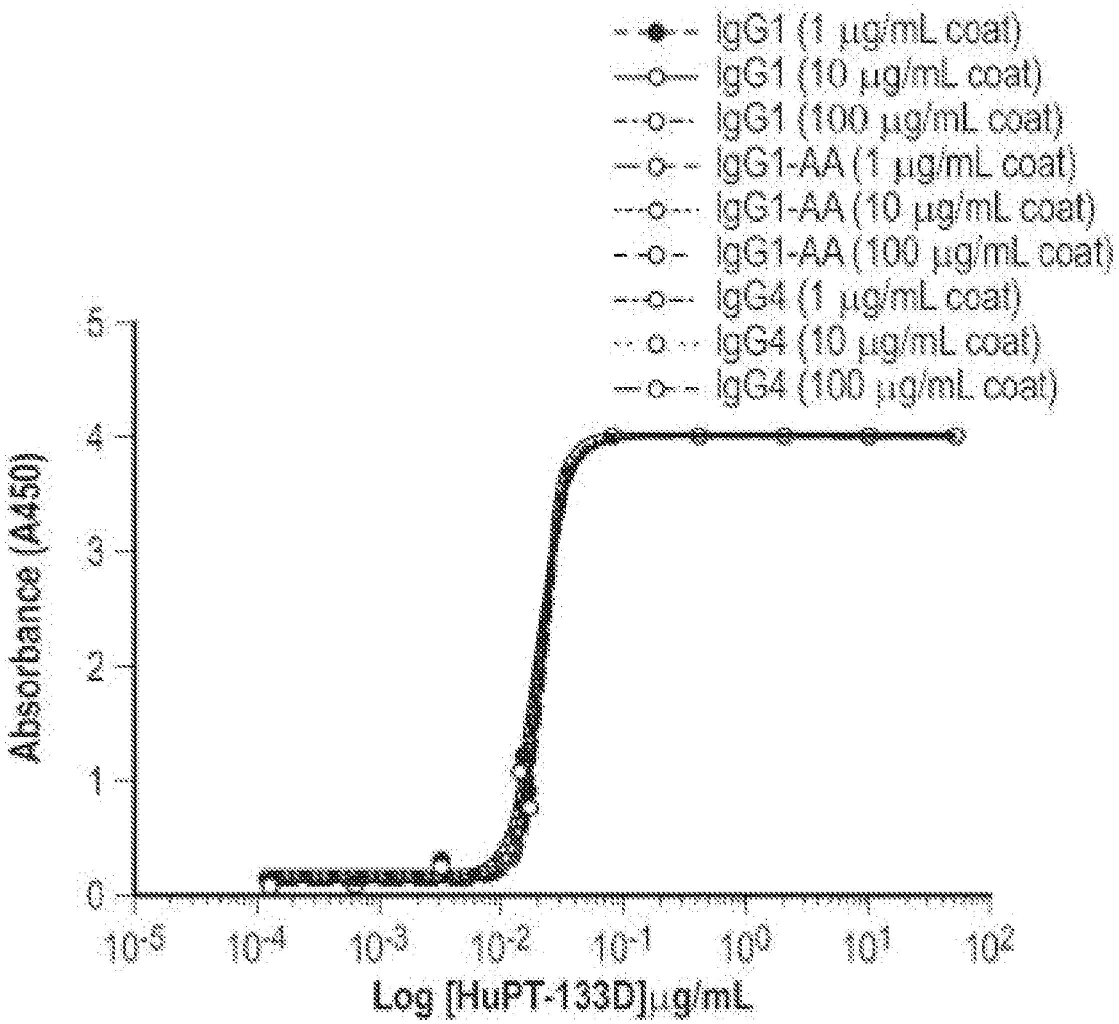

FIG. 35 is a graphing showing the binding curves for each antibody (HuPT-113D IgG1-AA (II) (IgG1-AA), HuPT-113D IgG4 (II) (IgG4), and HuPT-113D IgG1 (II) (IgG1)) at each pThr-Dmp peptide coating concentration (1 μg/ml, 10 μg/ml, and 100 μg/ml).

Figure 36A:
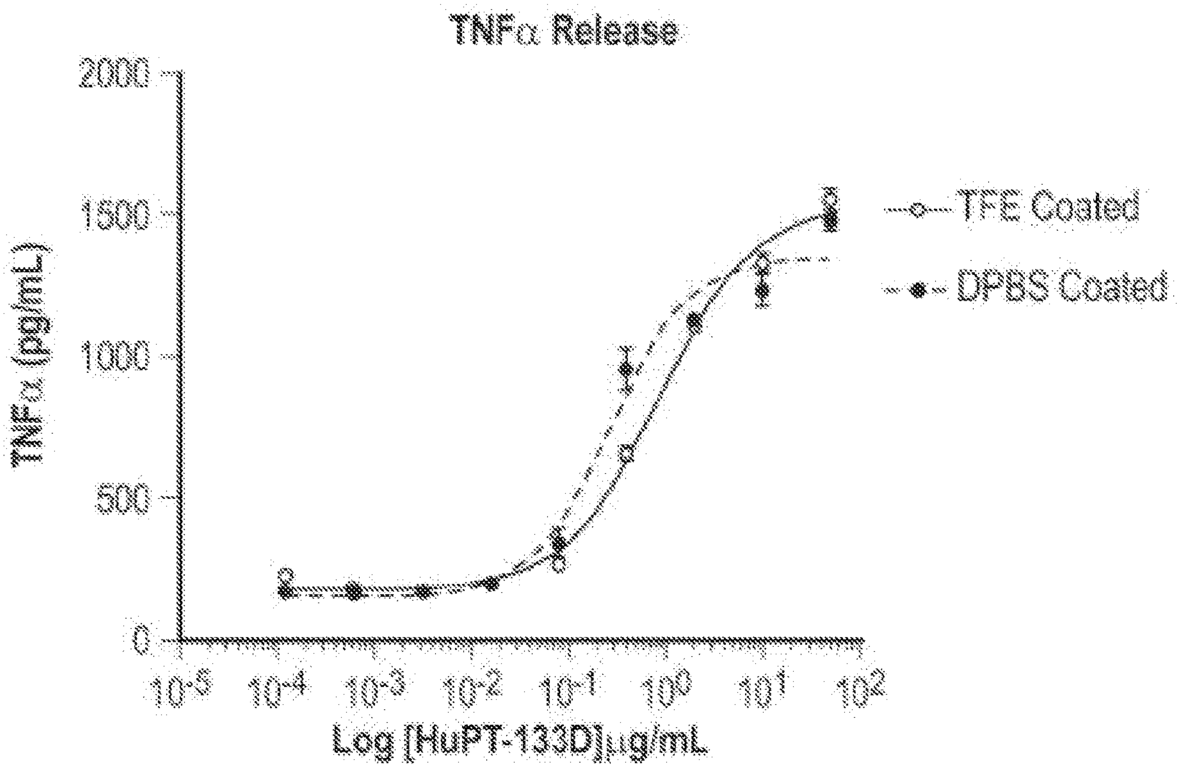

FIG. 36A is a graph showing the secretion of TNFα in THP-1 cells in response to pThr-Dmp peptide diluted in 2,2,2-trifluoroethanol (TFE) or DPBS.

Figure 36B:
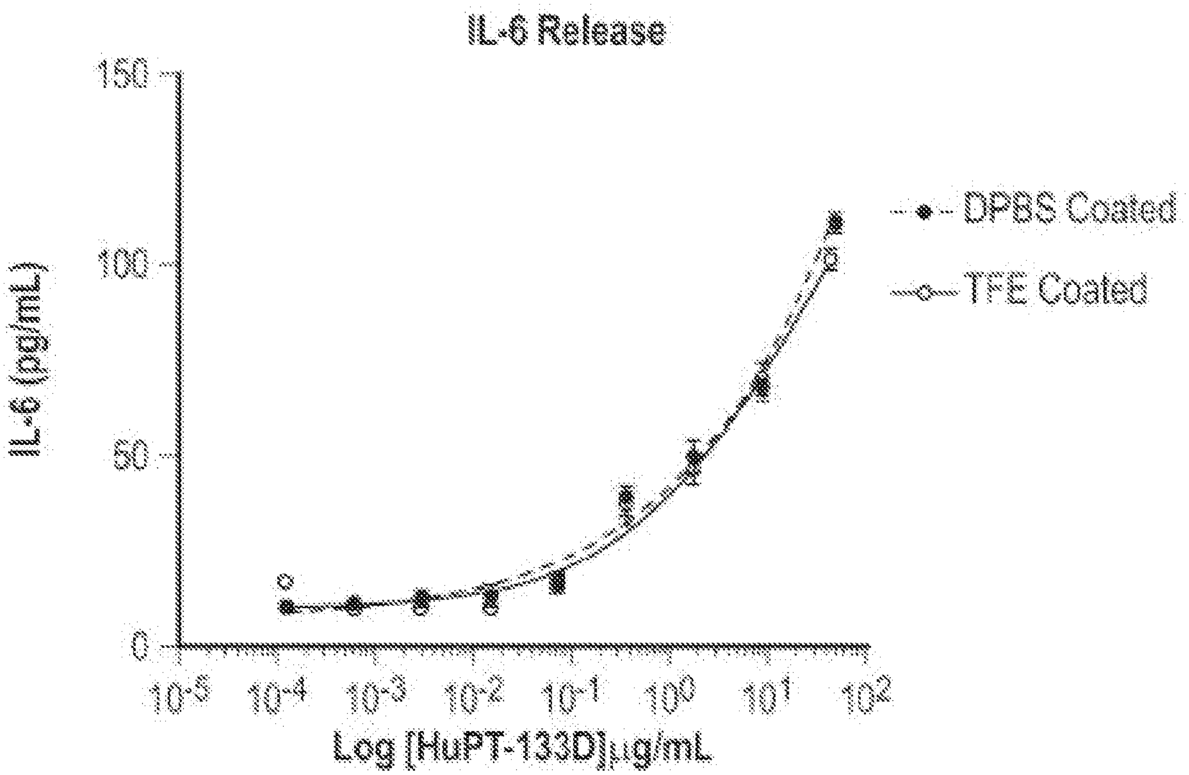

FIG. 36B is a graph showing the secretion of IL-6 in THP-1 cells in response to pThr-Dmp peptide diluted in 2,2,2-trifluoroethanol (TFE) or DPBS.

Figure 37:
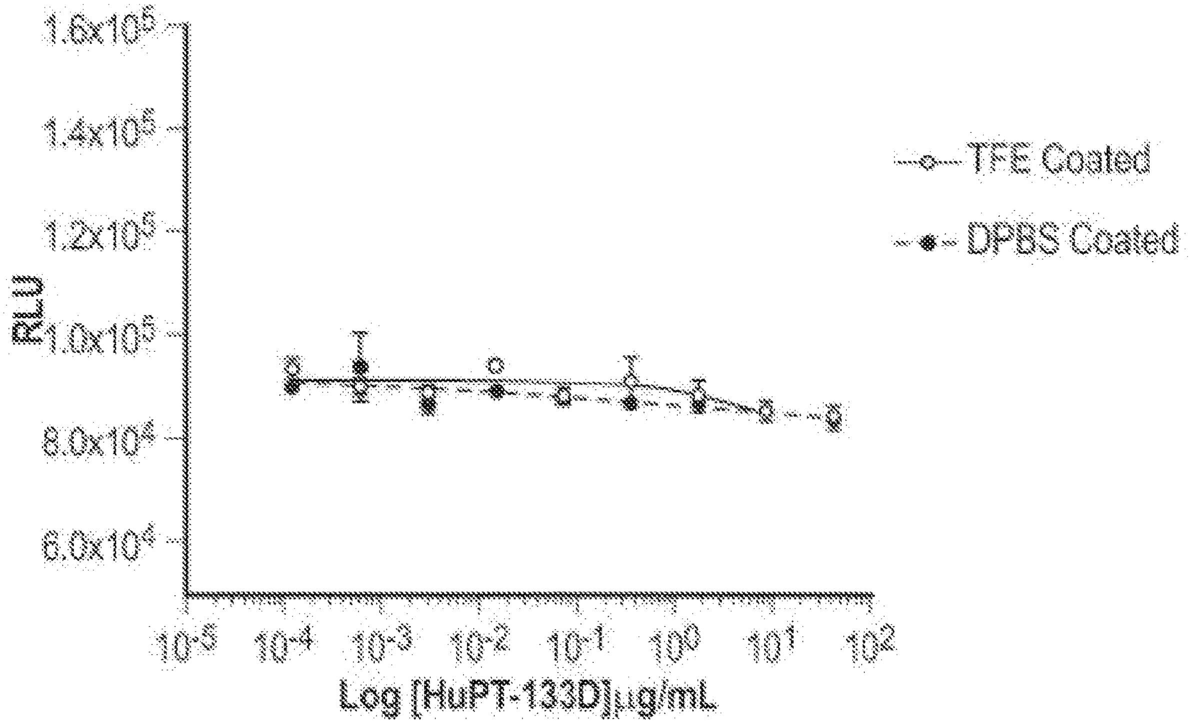

FIG. 37 is a graph showing the levels of FcγRIIIa activation in Jurkat cells coated with pThr-Dmp peptide that was diluted in either 2,2,2-trifluoroethanol (TFE) or DPBS to 1 μg/ml.

Figure 38A:
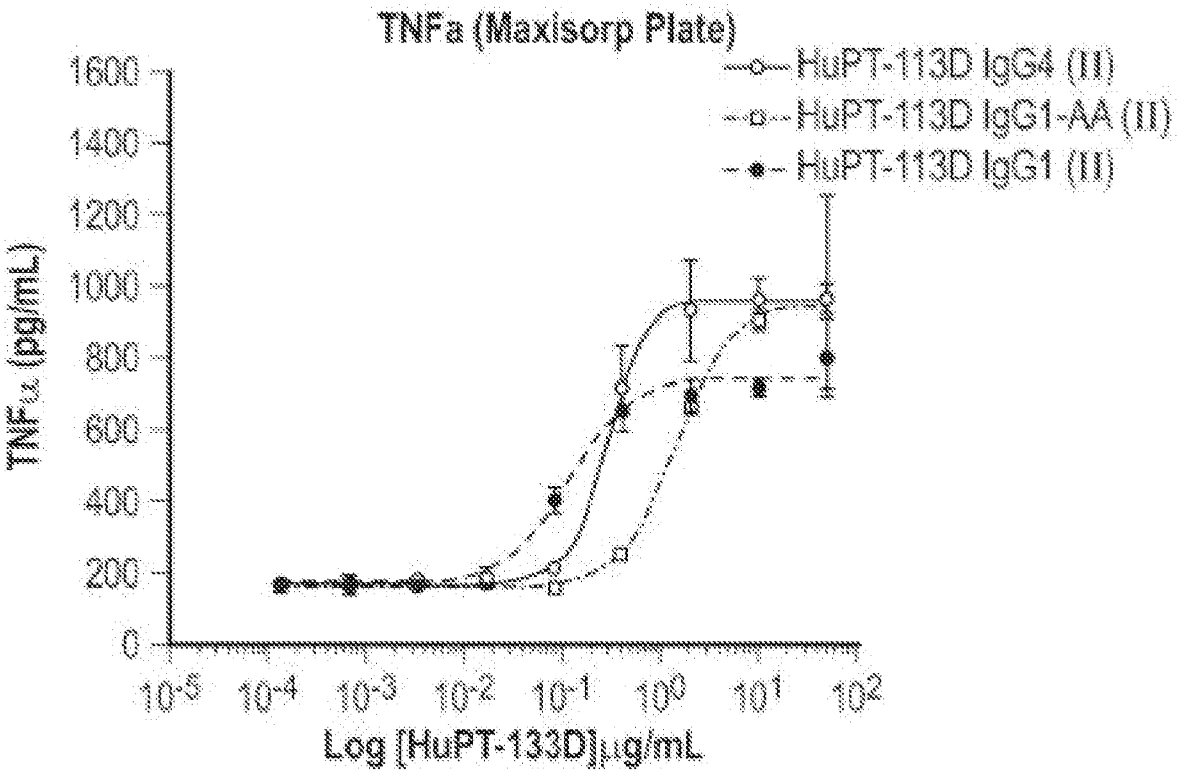

FIG. 38A is a graph showing the induction of TNFα release from THP-1 cells that were contacted with a native pThr-Dmp peptide IC and each HuPT-113D antibody (HuPT-113D IgG1 (II) (IgG1; blue), HuPT-113D IgG-AA (II) (IgG-AA; red), or HuPT-113D IgG4 (II) (IgG4; green)).

Figure 38B:
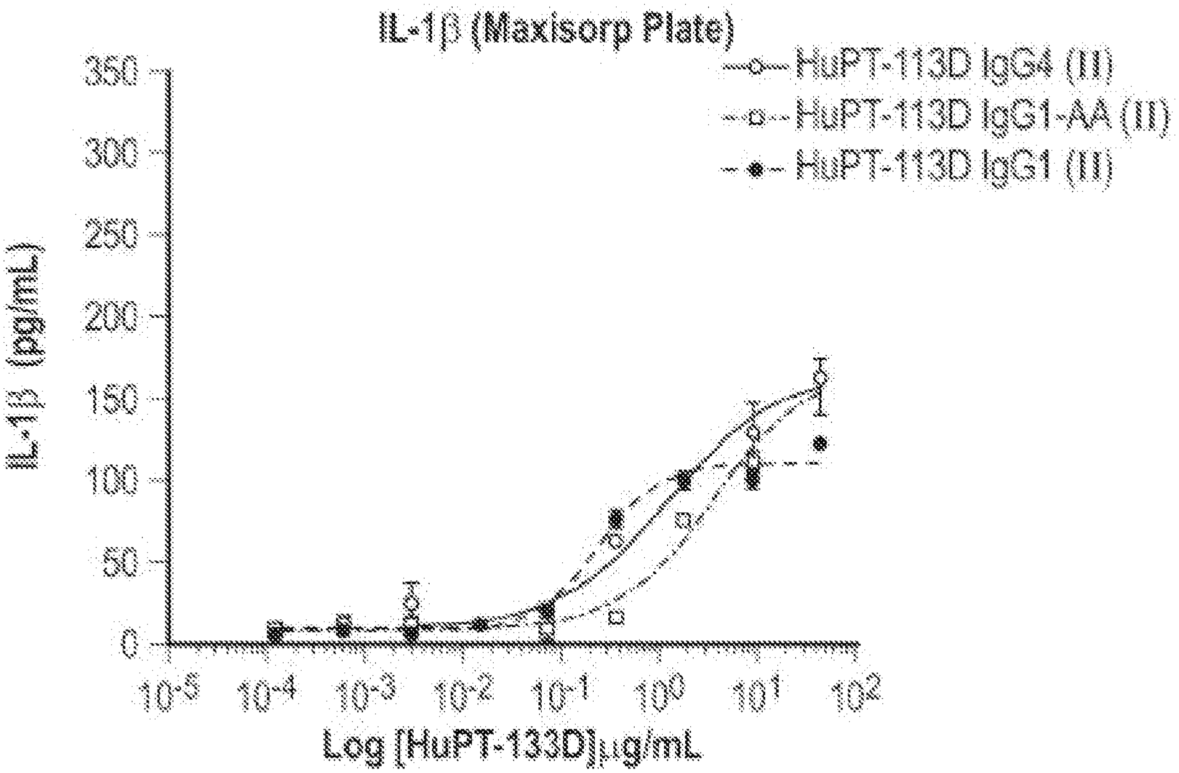

FIG. 38B is a graph showing the induction of IL-1B release from THP-1 cells that were contacted with a native pThr-Dmp peptide IC and each HuPT-113D antibody (HuPT-113D IgG1 (II) (IgG1; blue), HuPT-113D IgG-AA (II) (IgG-AA; red), or HuPT-113D IgG4 (II) (IgG4; green)).

Figure 38C:
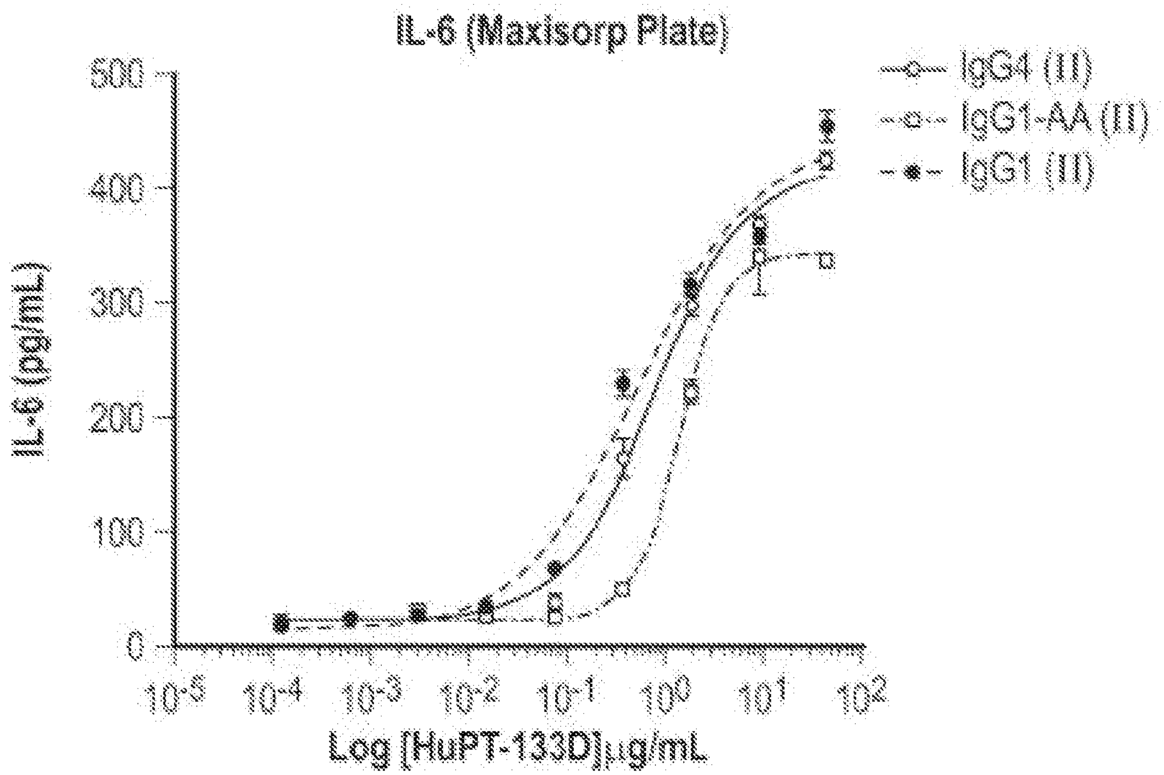

FIG. 38C is a graph showing the induction of IL-6 release from THP-1 cells that were contacted with a native pThr-Dmp peptide IC and each HuPT-113D antibody (HuPT-113D IgG1 (II) (IgG1; blue), HuPT-113D IgG-AA (II) (IgG-AA; red), or HuPT-113D IgG4 (II) (IgG4; green)).

Figure 38D:
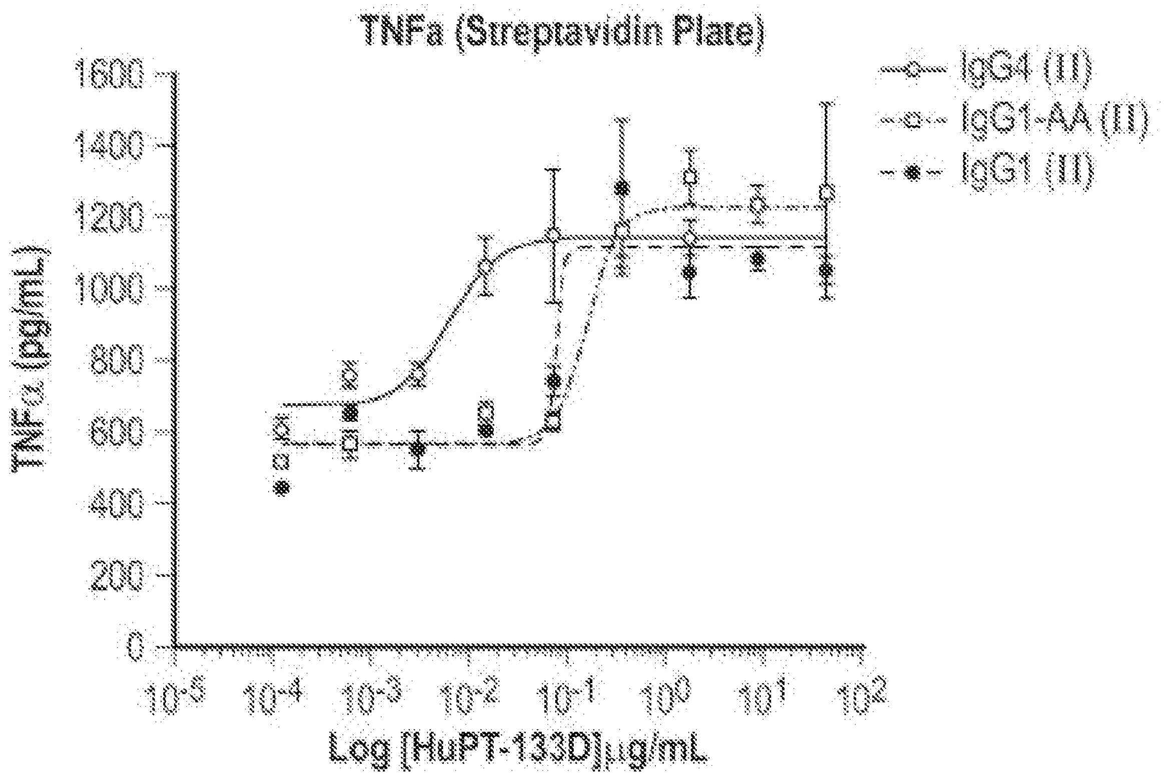

FIG. 38D is a graph showing the induction of TNFα release from THP-1 cells that were contacted with a biotinylated pThr-Dmp peptide IC and each HuPT-113D antibody (HuPT-113D IgG1 (II) (IgG1; blue), HuPT-113D IgG-AA (II) (IgG-AA; red), or HuPT-113D IgG4 (II) (IgG4; green)).

Figure 38E:
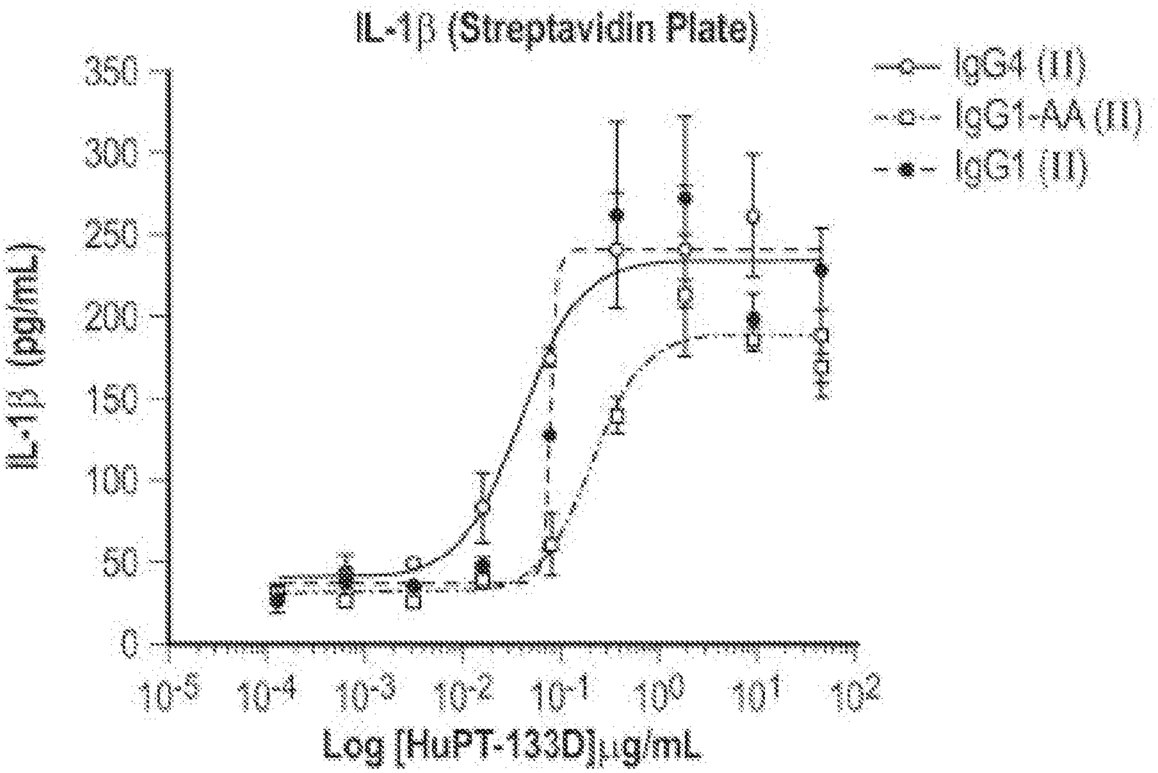

FIG. 38E is a graph showing the induction of IL-1B release from THP-1 cells that were contacted with a biotinylated pThr-Dmp peptide IC and each HuPT-113D antibody (HuPT-113D IgG1 (II) (IgG1; blue), HuPT-113D IgG-AA (II) (IgG-AA; red), or HuPT-113D IgG4 (II) (IgG4; green)).

Figure 38F:
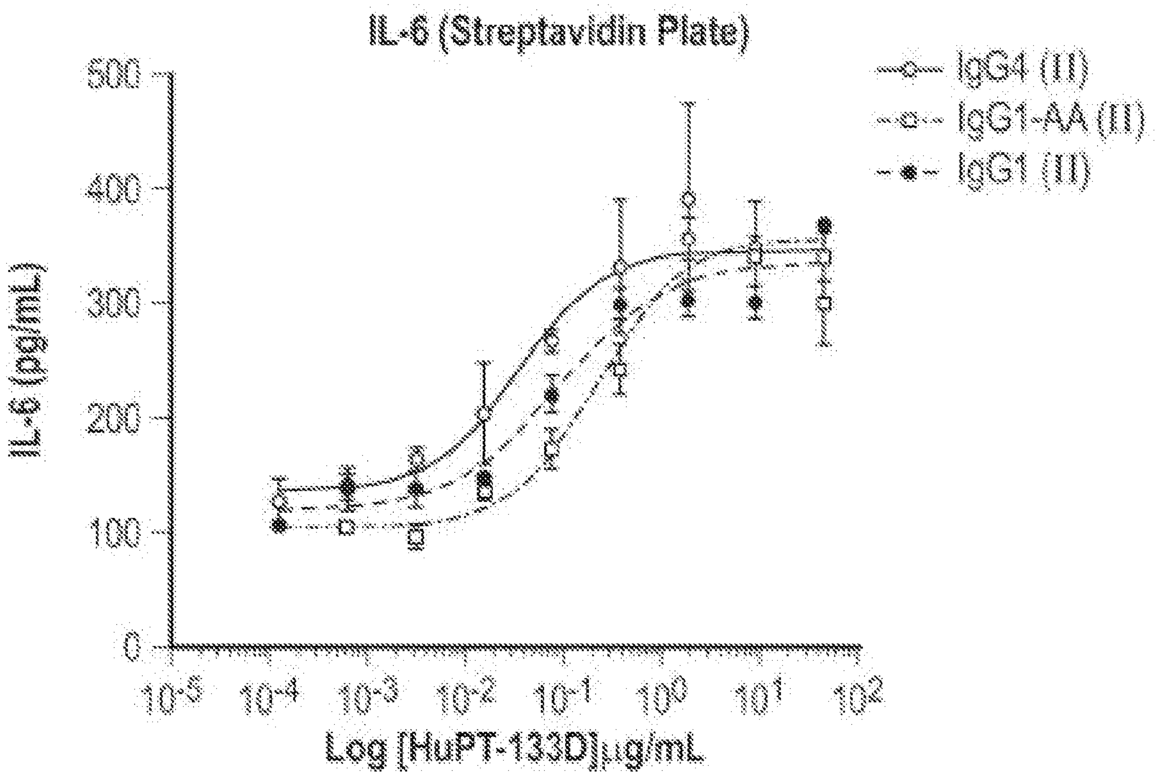

FIG. 38F is a graph showing the induction of IL-6 release from THP-1 cells that were contacted with a biotinylated pThr-Dmp peptide IC and each HuPT-113D antibody (HuPT-113D IgG1 (II) (IgG1; blue), HuPT-113D IgG-AA (II) (IgG-AA; red), or HuPT-113D IgG4 (II) (IgG4; green)).

Figure 39:
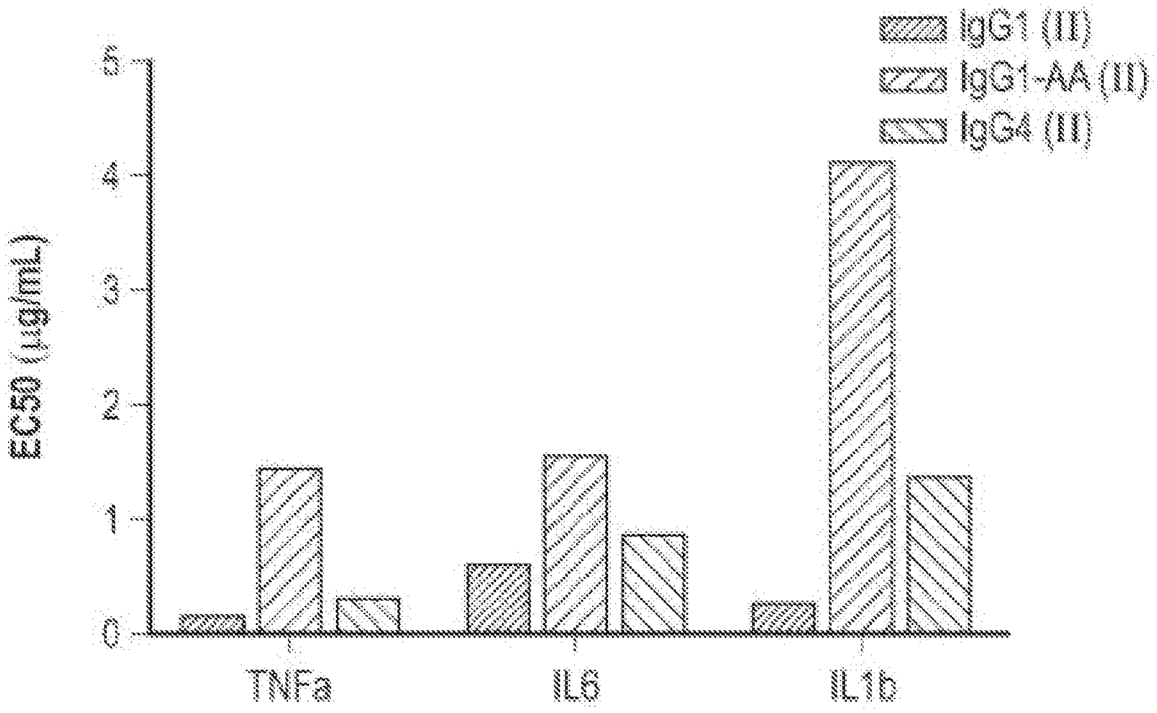

FIG. 39 is graph showing the EC50 values from FIGS. 38A-C for HuPT-113D IgG1 (II) (IgG1; blue), HuPT-113D IgG-AA (II) (IgG-AA; red), and HuPT-113D IgG4 (II) (IgG4; green).

Figure 40:
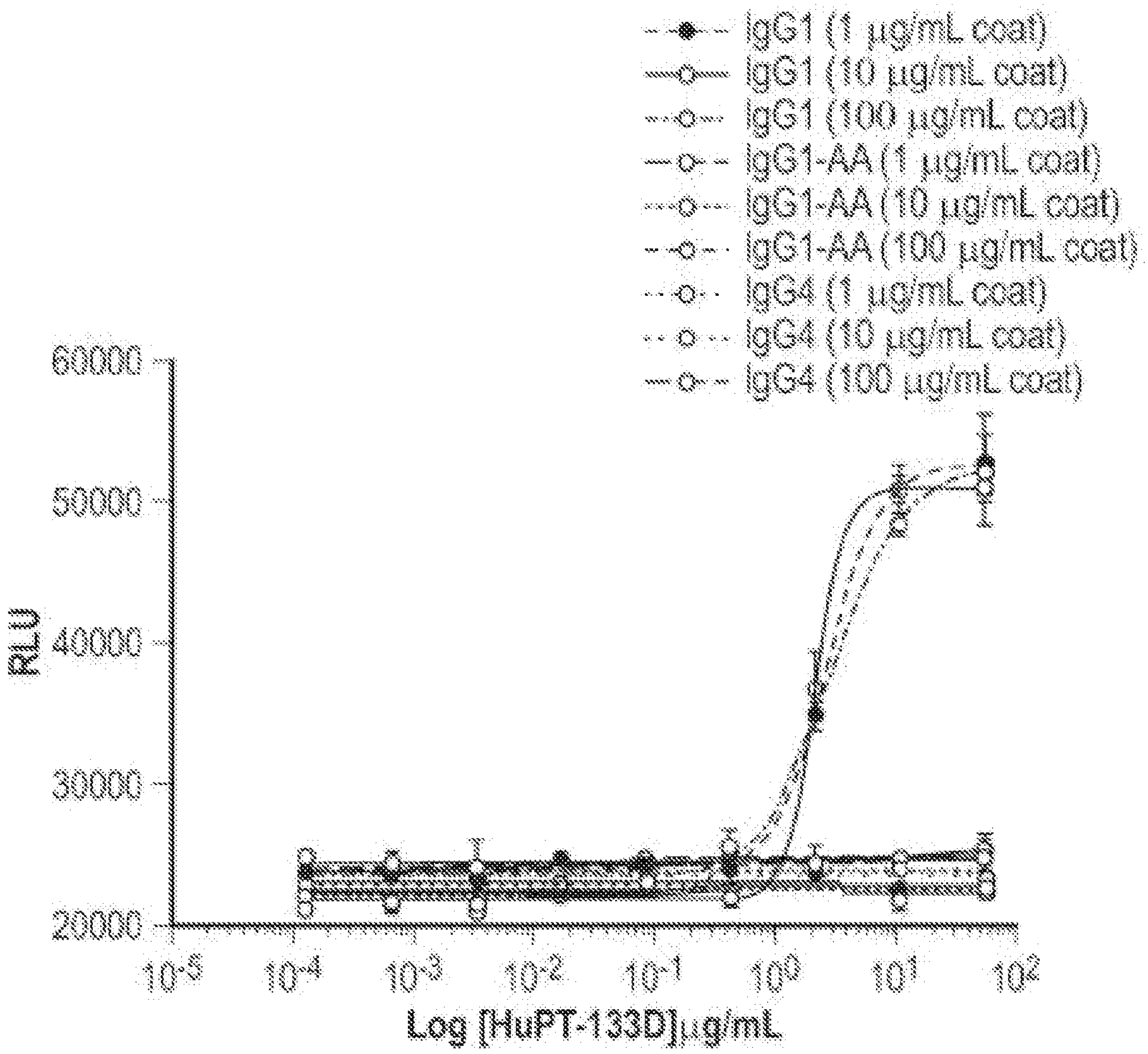

FIG. 40 is a graph showing the activation of the FcγRIIIa in Jurkat cells treated with HuPT-113D IgG1 (II) (IgG1), HuPT-113D IgG-AA (II) (IgG-AA), or HuPT-113D IgG4 (II) (IgG4). The wells were coated with a native pThr-Dmp peptide IC at 1, 10, or 100 μg/ml coat.

Figure 41A:
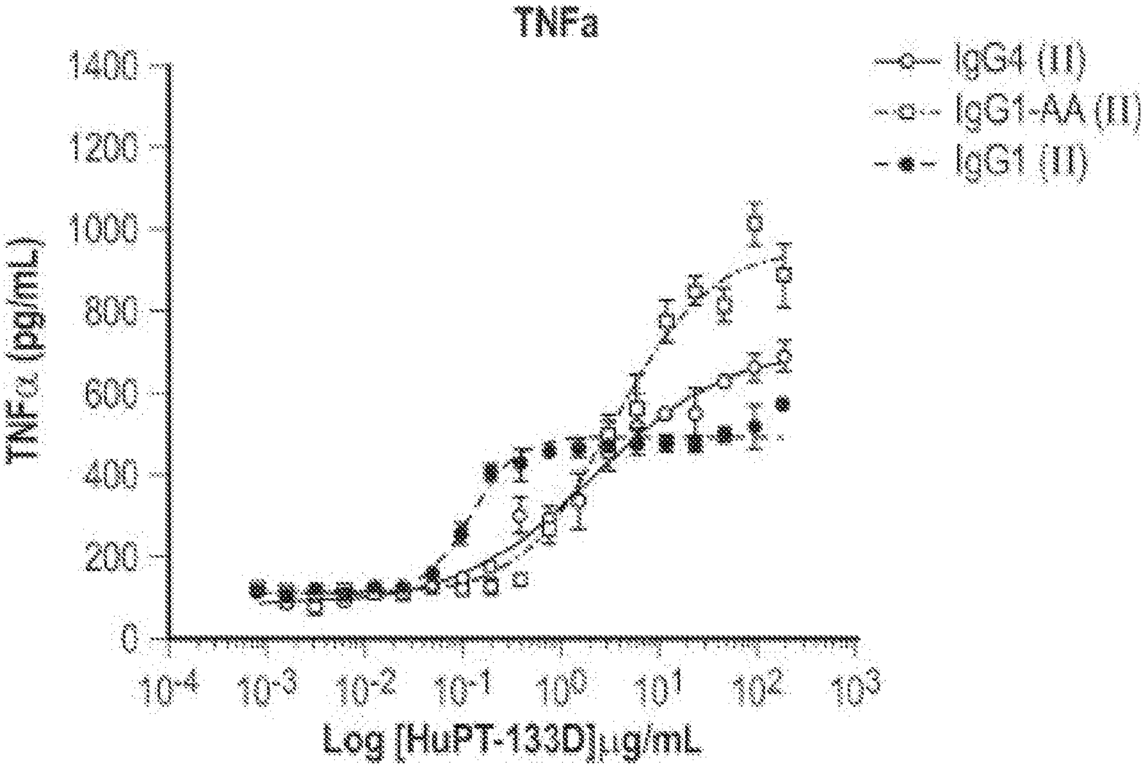

FIG. 41A is a graph showing the induction of TNFα release from THP-1 cells that were contacted with a native pThr-Dmp peptide IC and each HuPT-113D antibody (HuPT-113D IgG1 (II) (IgG1; blue), HuPT-113D IgG-AA (II) (IgG-AA; red), or HuPT-113D IgG4 (II) (IgG4; green)).

Figure 41B:
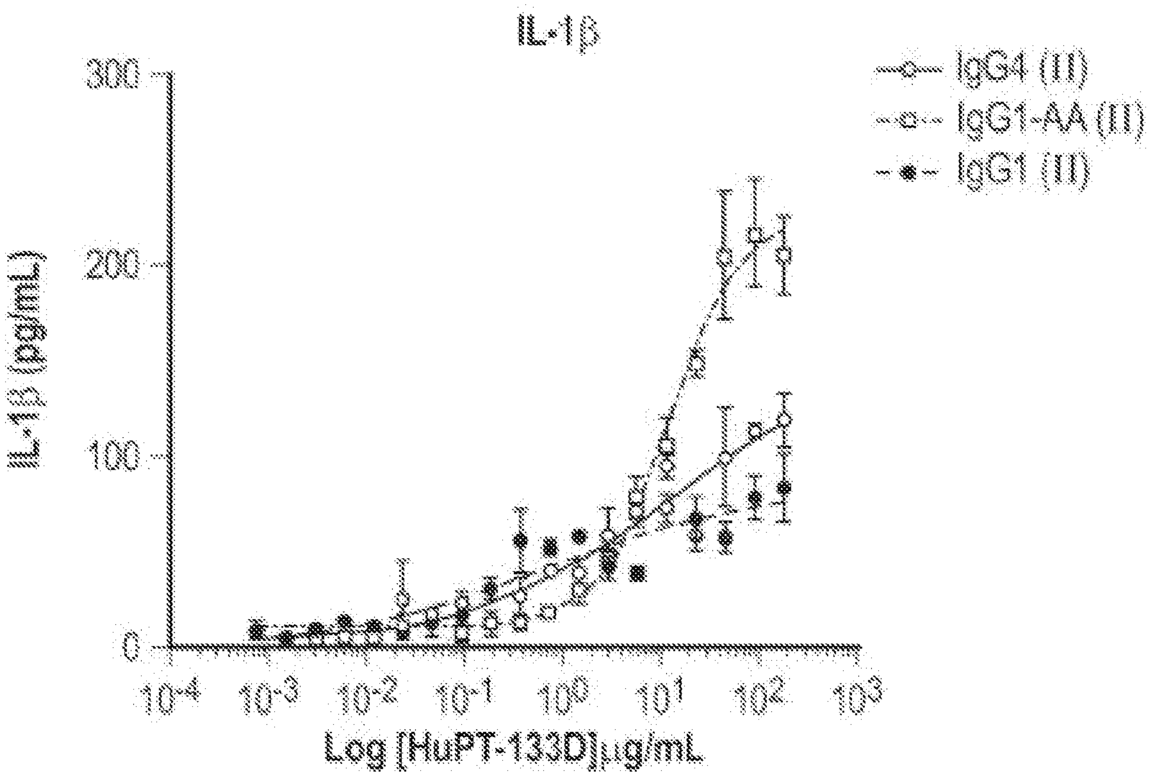

FIG. 41B is a graph showing the induction of IL-1B release from THP-1 cells that were contacted with a native pThr-Dmp peptide IC and each HuPT-113D antibody (HuPT-113D IgG1 (II) (IgG1; blue), HuPT-113D IgG-AA (II) (IgG-AA; red), or HuPT-113D IgG4 (II) (IgG4; green)).

Figure 41C:
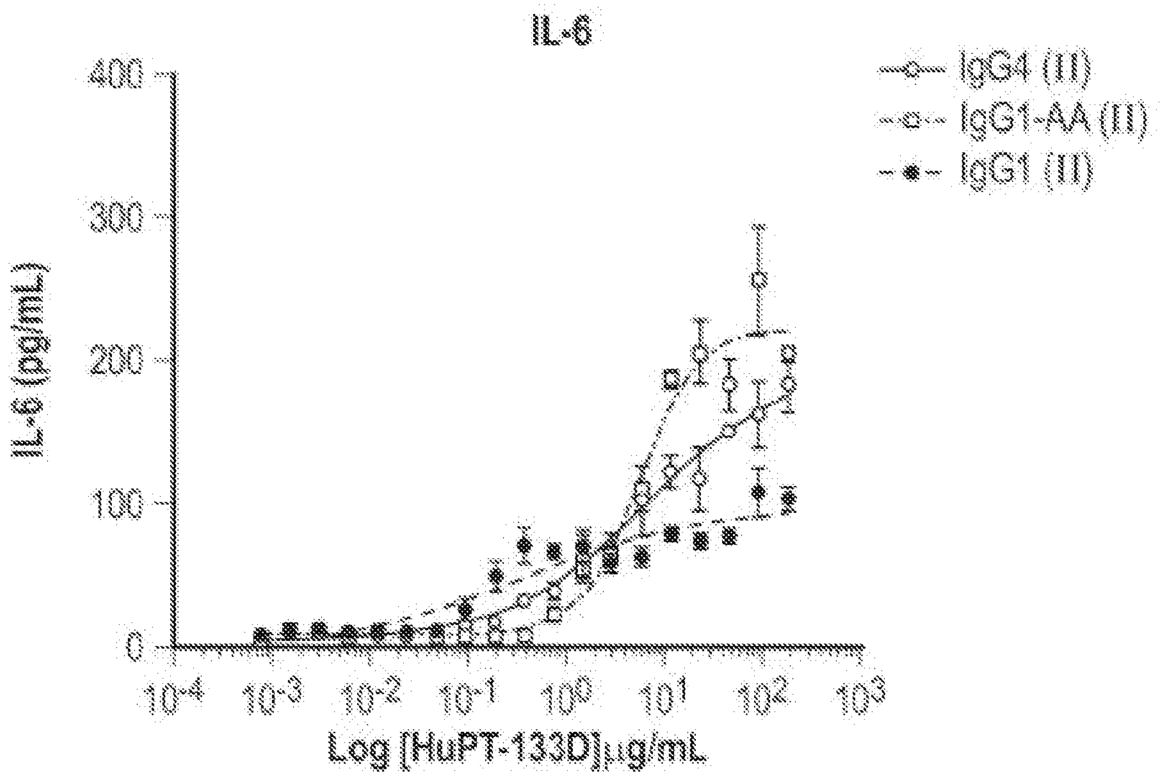

FIG. 41C is a graph showing the induction of IL-6 release from THP-1 cells that were contacted with a native pThr-Dmp peptide IC and each HuPT-113D antibody (HuPT-113D IgG1 (II) (IgG1; blue), HuPT-113D IgG-AA (II) (IgG-AA; red), or HuPT-113D IgG4 (II) (IgG4; green)).

Figure 42:
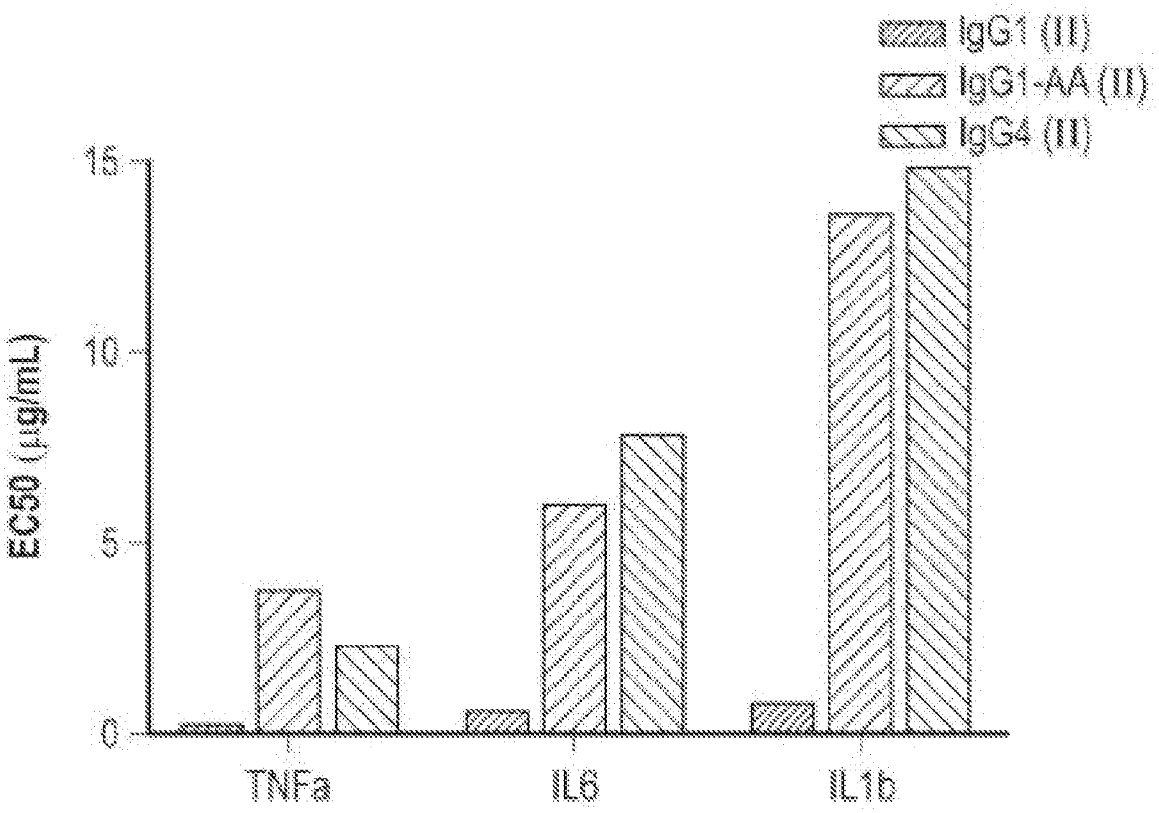

FIG. 42 is graph showing the EC50 values from FIGS. 41A-C for HuPT-113D IgG1 (II) (IgG1; blue), HuPT-113D IgG-AA (II) (IgG-AA; red), and HuPT-113D IgG4 (II) (IgG4; green)).

Figure 43:
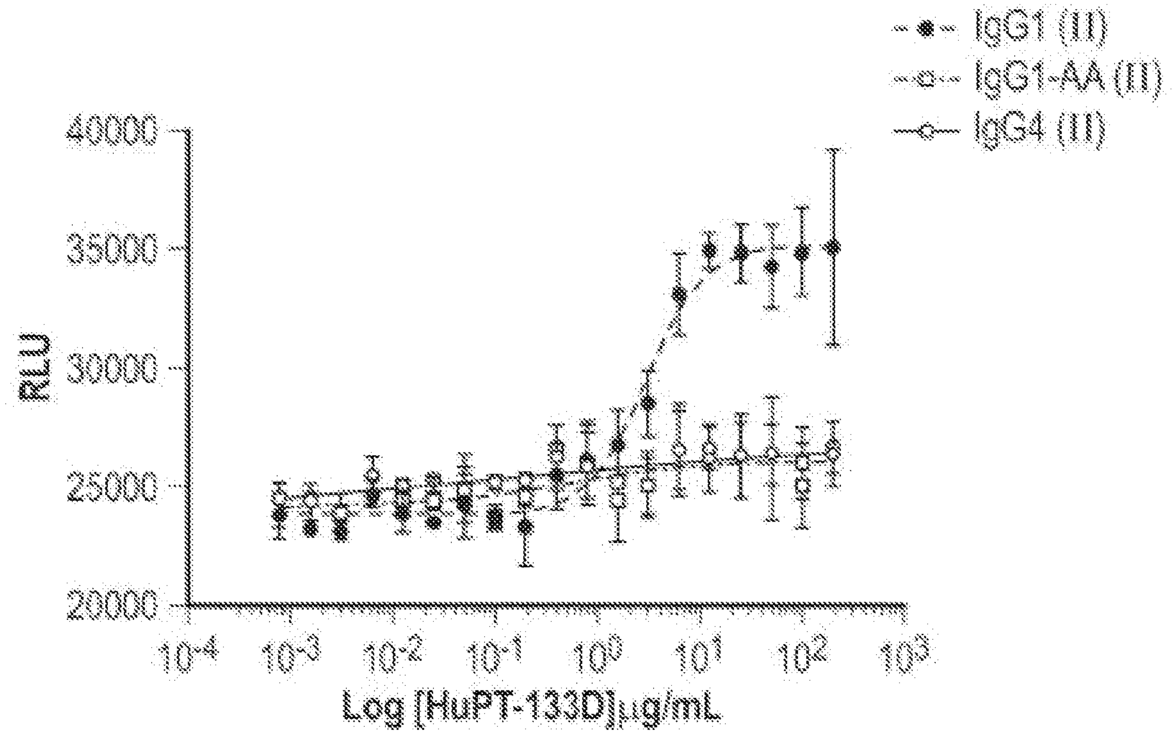

FIG. 43 is a graph showing the activation of the FcγRIIIa in Jurkat cells treated with HuPT-113D IgG1 (II) (IgG1), HuPT-113D IgG-AA (II) (IgG-AA), or HuPT-113D IgG4 (II) (IgG4).

Figure 44A:
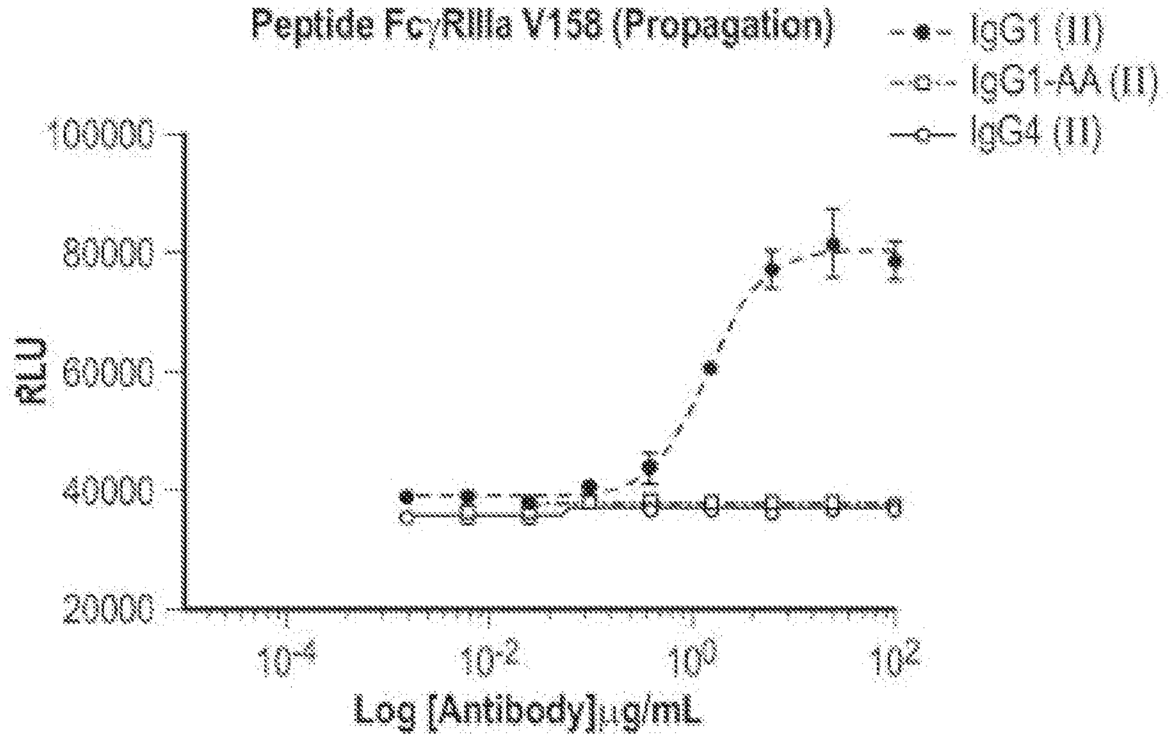

FIG. 44A is a graph showing the activation of the FcγRIIIa V158 in Jurkat cells treated with HuPT-113D IgG1 (II) (IgG1), HuPT-113D IgG-AA (II) (IgG-AA), or HuPT-113D IgG4 (II) (IgG4). The wells were coated with a native pThr-Dmp peptide IC in TFE at 1 μg/ml coat. Propagation cells were used.

Figure 44B:
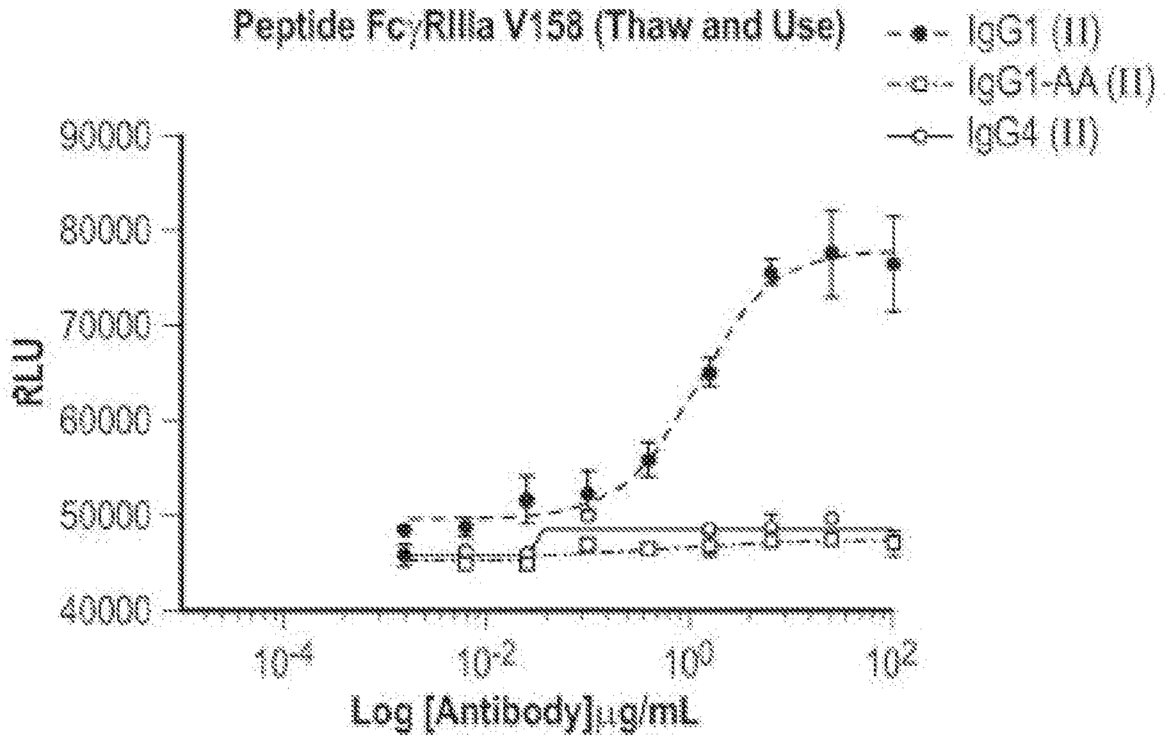

FIG. 44B is a graph showing the activation of the FcγRIIIa V158 in Jurkat cells treated with HuPT-113D IgG1 (II) (IgG1), HuPT-113D IgG-AA (II) (IgG-AA), or HuPT-113D IgG4 (II) (IgG4). The wells were coated with a native pThr-Dmp peptide IC in TFE at 1 μg/ml coat. Thawed and use cells were used.

Figure 45A:
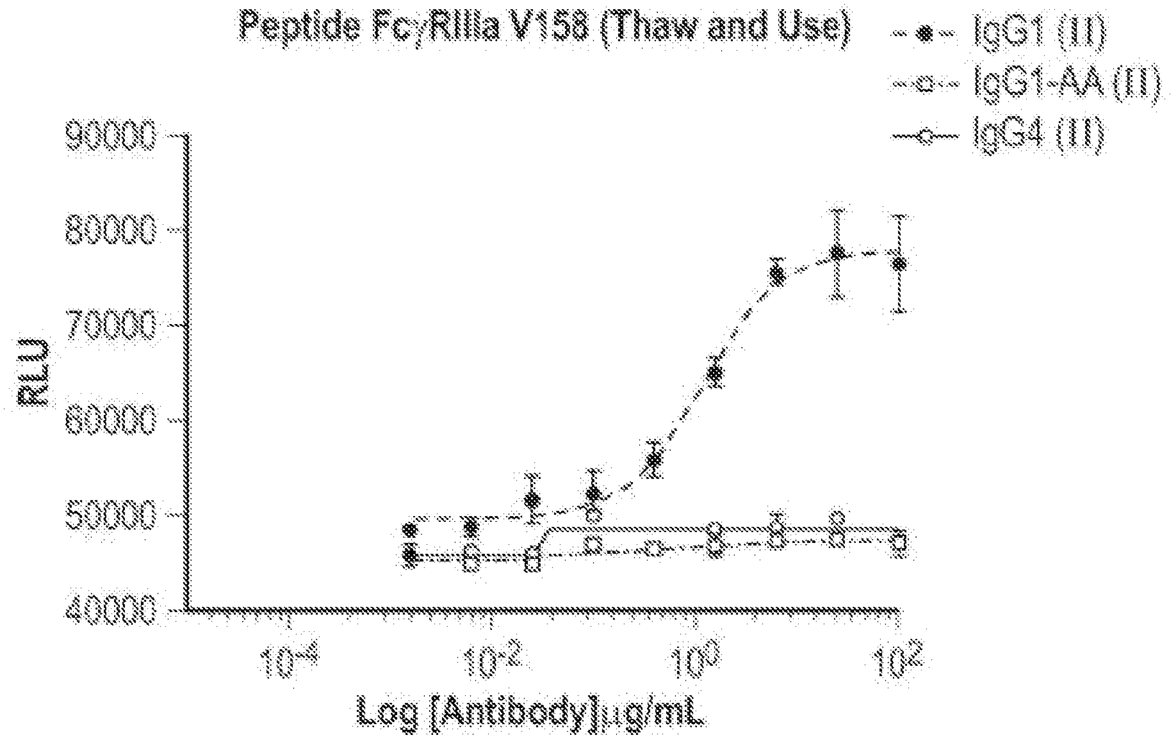

FIG. 45A is a graph showing the activation of the FcγRIIIa V158 in Jurkat cells treated with HuPT-113D IgG1 (II) (IgG1), HuPT-113D IgG-AA (II) (IgG-AA), or HuPT-113D IgG4 (II) (IgG4). The wells were coated with a native pThr-Dmp peptide IC in TFE at 1 μg/ml coat. Thawed and use cells were used.

Figure 45B:
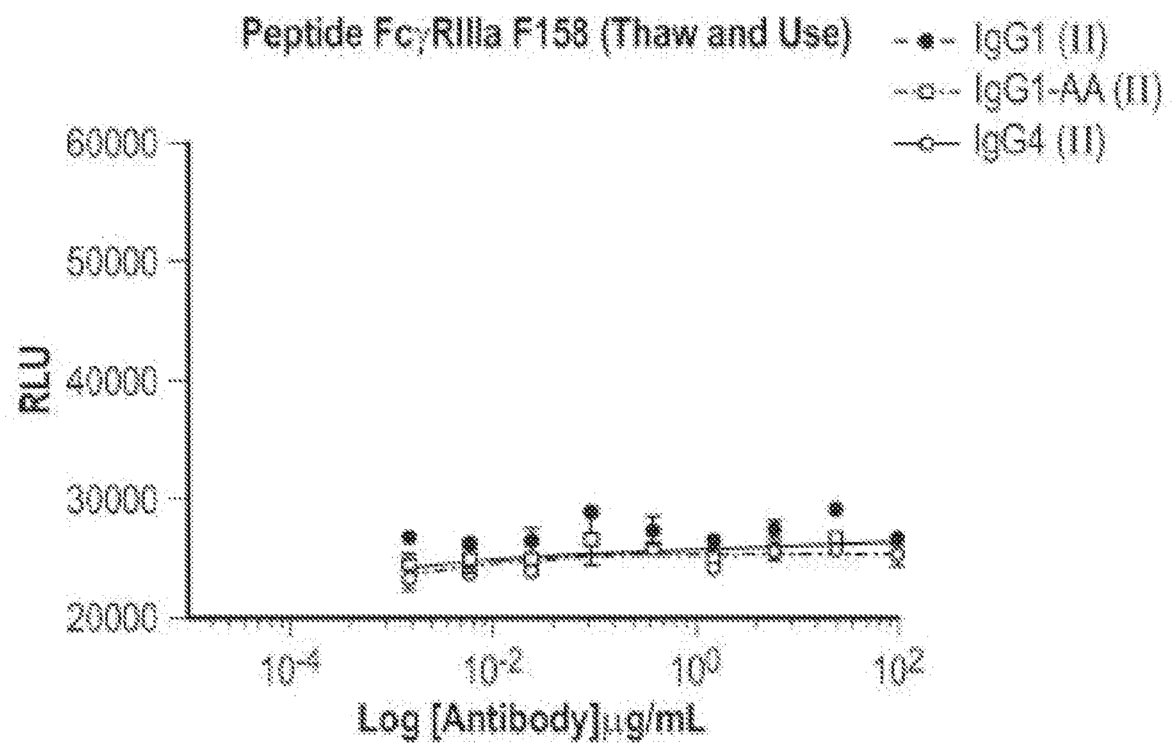

FIG. 45B is a graph showing the activation of the FcγRIIIa F158 in Jurkat cells treated with HuPT-113D IgG1 (II) (IgG1), HuPT-113D IgG-AA (II) (IgG-AA), or HuPT-113D IgG4 (II) (IgG4). The wells were coated with a native pThr-Dmp peptide IC in TFE at 1 μg/ml coat. Thawed and use cells were used.

Figure 45C:
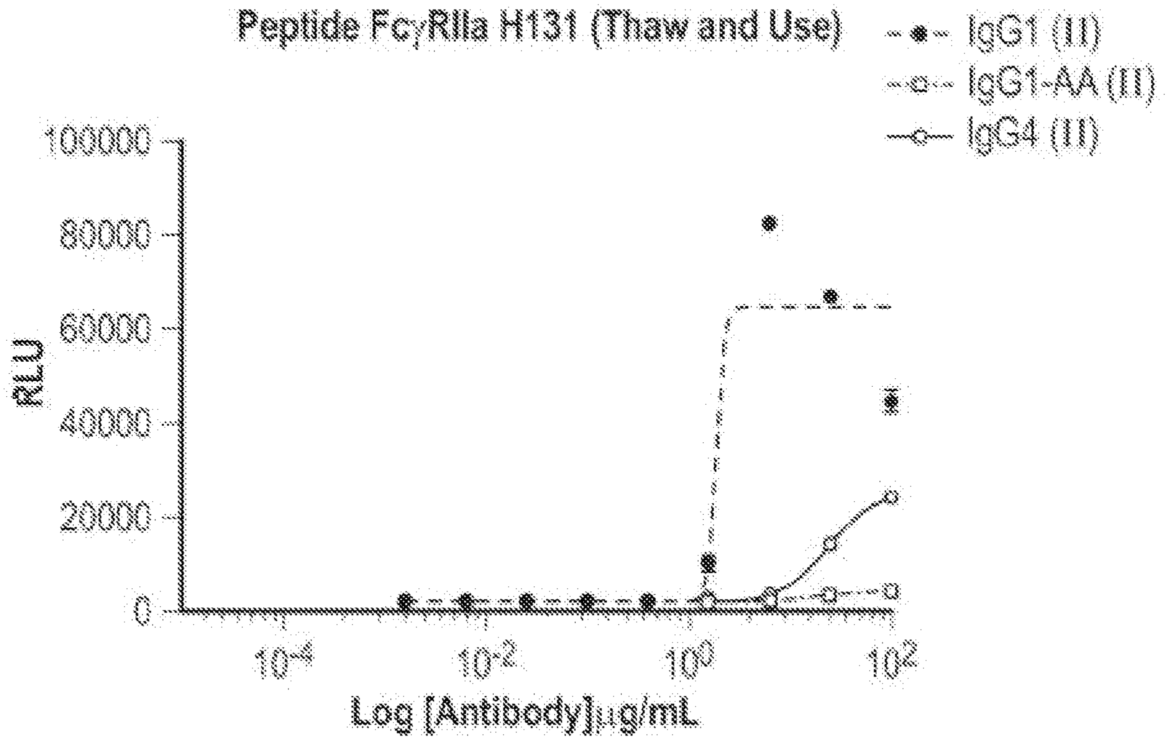

FIG. 45C is a graph showing the activation of the FcγRIIa H131 in Jurkat cells treated with HuPT-113D IgG1 (II) (IgG1), HuPT-113D IgG-AA (II) (IgG-AA), or HuPT-113D IgG4 (II) (IgG4). The wells were coated with a native pThr-Dmp peptide IC in TFE at 1 μg/ml coat. Thawed and use cells were used.

Figure 46:
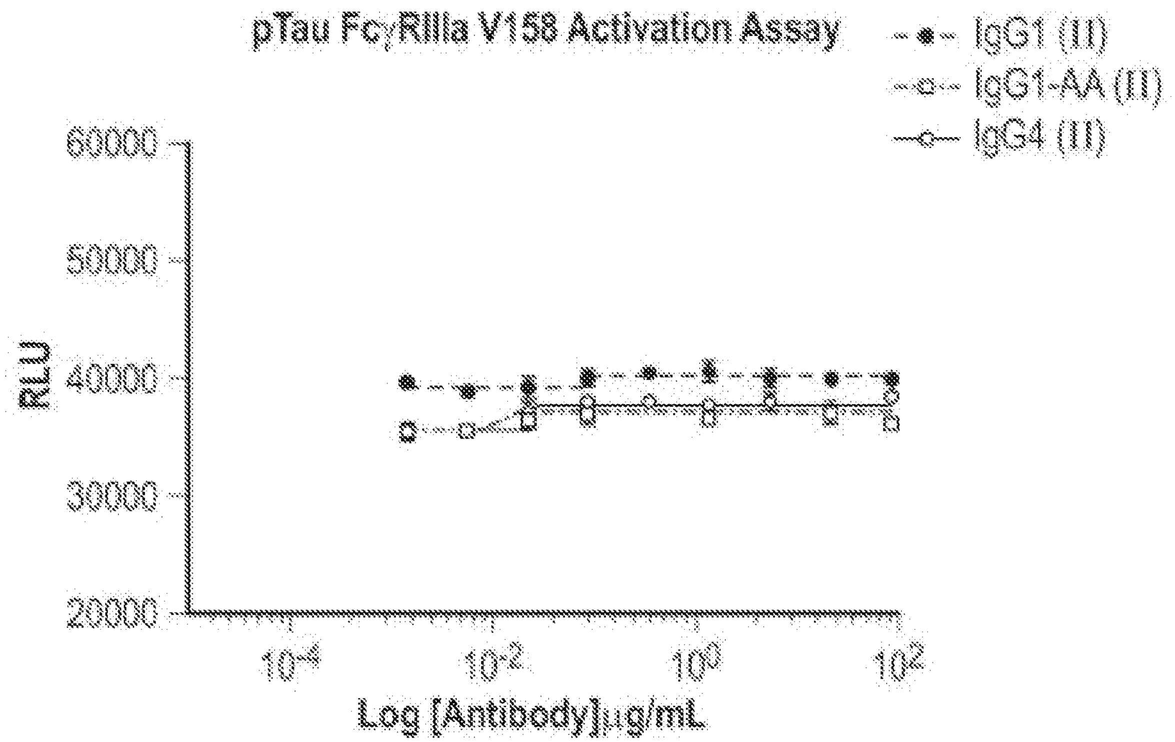

FIG. 46 is a graph showing the activation of FcγRIIIa V158 in Jurkat cells treated with HuPT-113D IgG1 (II) (IgG1), HuPT-113D IgG-AA (II) (IgG-AA), or HuPT-113D IgG4 (II) (IgG4). The wells were coated with pTau in DBPS at 10 μg/ml coat.

Figure 47:
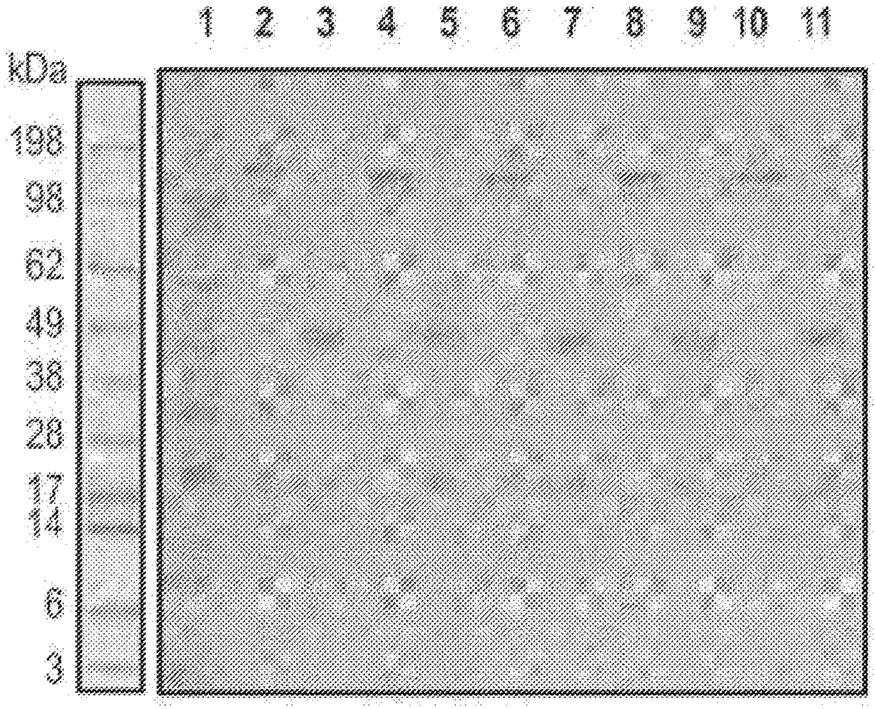

FIG. 47 is the SDS-PAGE analysis of purified HuPT-113D IgG-AA (II) (IgG-AA).

DETAILED DESCRIPTION

It is to be appreciated that certain aspects, modes, embodiments, variations and features of the present methods are described below in various levels of detail in order to provide a substantial understanding of the present technology.

The present disclosure generally provides conformation-specific antibodies, which can specifically bind to and neutralize the activity of phosphorylated-Threonine 231-tau protein (pT231-tau). The antibodies of the present technology are useful in methods for treating neurological disorders associated with elevated cis-pT231-tau protein expression in a subject in need thereof. Accordingly, the various aspects of the present methods relate to the preparation, characterization, and manipulation of anti-cis-pT231-tau antibodies. Antibodies of the present technology are useful alone or in combination with additional therapeutic agents for treating tauopathies. In some embodiments, the antibody is a humanized antibody.

In some embodiments, the antibody is coupled to a detectable label. In other embodiments, the kit comprises a secondary antibody coupled to a detectable label.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) PCR 1*: A Practical Approach* (IRL Press at Oxford University Press); MacPherson et al. (1995) PCR 2*: A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*. Methods to detect and measure levels of polypeptide gene expression products (i.e., gene translation level) are well-known in the art and include the use of polypeptide detection methods such as antibody detection and quantification techniques. (See also, Strachan & Read, *Human Molecular Genetics*, Second Edition. (John Wiley and Sons, Inc., NY, 1999)).

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art. All references cited herein are incorporated herein by reference in their entireties and for all purposes to the same extent as if each individual publication, patent, or patent application was specifically and individually incorporated by reference in its entirety for all purposes.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another.

An "adjuvant" refers to one or more substances that cause stimulation of the immune system. In this context, an adjuvant is used to enhance an immune response to one or more vaccine antigens or antibodies. An adjuvant may be administered to a subject before, in combination with, or after administration of the vaccine. Examples of chemical compounds used as adjuvants include aluminum compounds, oils, block polymers, immune stimulating complexes, vitamins and minerals (e.g., vitamin E, vitamin A, selenium, and vitamin B12), Quil A (saponins), bacterial and fungal cell wall components (e.g., lipopolysaccarides, lipoproteins, and glycoproteins), hormones, cytokines, and co-stimulatory factors.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. The term "antibody" includes intact immunoglobulins and "antibody fragments" or "antigen binding fragments" that specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4$ $M^{-1}$ greater or at least $10^5$ $M^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., *Immunology,* 3rd Ed., W. H. Freeman & Co., New York, 1997.

More particularly, antibody refers to a polypeptide ligand comprising at least a light chain immunoglobulin variable region or heavy chain immunoglobulin variable region, which specifically recognizes and binds an epitope of an antigen. Antibodies are composed of a heavy and a light chain, each of which has a variable region, termed the variable heavy ($V_H$) region and the variable light ($V_L$) region. Together, the VH region and the VL region are responsible for binding the antigen recognized by the antibody. Typically, an immunoglobulin has heavy (H) chains and light (L) chains interconnected by disulfide bonds. There are two types of light chain, lambda (λ) and kappa (κ). There are five main heavy chain classes (or isotypes), which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found. An antibody that binds cis-pT231-tau protein will have a specific VH region and VL region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

Examples of antibodies include monoclonal antibodies, polyclonal antibodies, humanized antibodies, chimeric antibodies, recombinant antibodies, multispecific antibodies, and antibody fragments. The antibody may be, for example, a conformation-specific antibody (e.g., an antibody that binds to the cis or trans conformation of a Xaa-Pro motif, wherein Xaa is an amino acid). An antibody specifically binds to an antigen.

As used herein, the term "antibody-related polypeptide" means antigen-binding antibody fragments, including single-chain antibodies that can comprise the variable region alone, or in combination, with all or part of the following polypeptide elements: hinge region, CH1, CH2, and CH3 domains of an antibody molecule. Also included in the technology are any combinations of variable region(s) and hinge region, CH1, CH2, and CH3 domains. Antibody-related molecules useful in the present methods, e.g., but are not limited to, Fab, Fab' and $F(ab')_2$, Fd, single-chain Fvs (scFv), single-chain antibodies, disulfide-linked Fvs (sdFv) and fragments comprising either a VL or VH domain. Examples include: (i) a Fab fragment, a monovalent fragment consisting of the $V_L$, $V_H$, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., *Nature* 341:544-546, 1989), which consists of a VH domain; and (vi) an isolated complementarity determining region (CDR). As such, "antibody fragments" can comprise a portion of a full length antibody, generally the antigen binding or variable region thereof. Examples of "antibody fragments" include Fab, Fab', $F(ab')_2$, and Fv fragments; diabodies; linear antibodies; single-chain antibody molecules; and multispecific antibodies formed from antibody fragments.

As used herein, the term "diabodies" refers to small antibody fragments with two antigen-binding sites, which fragments comprise a heavy-chain variable domain ($V_H$) connected to a light-chain variable domain ($V_L$) in the same polypeptide chain (VH $V_L$). By using a linker that is too short to allow pairing between the two domains on the same chain, the domains are forced to pair with the complementary domains of another chain and create two antigen binding sites. Diabodies are described more fully in, e.g., EP 404,097; WO 93/11161; and 30 Hollinger et al., *Proc. Natl. Acad. Sci. USA,* 90:6444-6448 (1993).

As used herein, the terms "single-chain antibodies" or "single-chain Fv (scFv)" refer to an antibody fusion molecule of the two domains of the Fv fragment, VL and $V_H$. Single-chain antibody molecules may comprise a polymer with a number of individual molecules, for example, dimer, trimer or other polymers. Furthermore, although the two domains of the Fv fragment, VL and $V_H$, are coded for by separate genes, they can be joined, using recombinant methods, by a synthetic linker that enables them to be made as a single protein chain in which the VL and VH regions pair to form monovalent molecules (known as single-chain Fv (scFv)). Bird et al. (1988) *Science* 242:423-426 and Huston et al. (1988) *Proc. Natl. Acad Sci.* USA 85:5879-5883. Such single-chain antibodies can be prepared by recombinant techniques or enzymatic or chemical cleavage of intact antibodies.

Any of the above-noted antibody fragments are obtained using conventional techniques known to those of skill in the art, and the fragments are screened for binding specificity and neutralization activity in the same manner as are intact antibodies.

As used herein, an "antigen" refers to a molecule to which an antibody can selectively bind. The target antigen may be a protein (e.g., an antigenic peptide), carbohydrate, nucleic acid, lipid, hapten, or other naturally occurring or synthetic compound. The target antigen may be a polypeptide (e.g., a polypeptide containing a Xaa-Pro motif (e.g., a phosphorylated or nonphosphorylated Ser/Thr-Pro motif)) or peptide mimics (e.g., a polypeptide containing a Xaa-homoproline motif (e.g., a phosphorylated or nonphosphorylated Ser/Thr-homoproline motif)). An antigen may also be administered to an animal to generate an immune response in the animal.

By "binding affinity" is meant the strength of the total noncovalent interactions between a single binding site of a molecule (e.g., an antibody) and its binding partner (e.g., an antigen or antigenic peptide). The affinity of a molecule X for its partner Y can generally be represented by the dissociation constant ($K_d$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

As used herein, the term "biological sample" means sample material derived from living cells. Biological samples may include tissues, cells, protein or membrane extracts of cells, and biological fluids (e.g., ascites fluid or cerebrospinal fluid (CSF)) isolated from a subject, as well as tissues, cells and fluids present within a subject. Biological samples of the present technology include, but are not limited to, samples taken from breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, thymus, blood, hair, buccal, skin, serum, plasma, CSF, semen, prostate fluid, seminal fluid, urine, feces, sweat, saliva, sputum, mucus, bone marrow, lymph, and tears. Biological samples can also be obtained from biopsies of internal organs or from cancers. Biological samples can be obtained from subjects for diagnosis or research or can be obtained from non-diseased individuals, as controls or for basic research. Samples may be obtained by standard methods including, e.g., venous puncture and surgical biopsy. In certain embodiments, the biological sample is a breast, lung, colon, or prostate tissue sample obtained by needle biopsy.

As used herein, the term "CDR-grafted antibody" means an antibody in which at least one CDR of an "acceptor" antibody is replaced by a CDR "graft" from a "donor" antibody possessing a desirable antigen specificity.

As used herein, the term "chimeric antibody" means an antibody in which the Fc constant region of a monoclonal antibody from one species (e.g., a mouse Fc constant region) is replaced, using recombinant DNA techniques, with an Fc constant region from an antibody of another species (e.g., a human Fc constant region). See generally, Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 125,023; Better et al., *Science* 240:1041-1043, 1988; Liu et al., *Proc. Natl. Acad. Sci. USA* 84:3439-3443, 1987; Liu et al., *J. Immunol* 139:3521-3526, 1987; Sun et al., *Proc. Natl. Acad. Sci. USA* 84:214-218, 1987; Nishimura et al., *Cancer Res* 47:999-1005, 1987; Wood et al., *Nature* 314:446-449, 1885; and Shaw et al., *J. Natl. Cancer Inst.* 80:1553-1559, 1988.

By "conformation-specific antibody" is an antibody or fragment thereof that recognizes and specifically binds to a particular conformation (e.g., a conformational isomer or conformer) of its complementary antigen. For example, as described herein, the conformation-specific antibody may specifically bind to the cis conformation of a Xaa-Pro motif (e.g., cis pT231-tau), but will not specifically bind to the trans conformation of the Xaa-Pro motif (e.g., trans pT231-tau), where Xaa is serine or threonine. In certain embodiments, the Ser/Thr-Pro motif may be phosphorylated (i.e., pSer/Thr-Pro). In this case, the conformation-specific antibody will have, for example, at least 10-to 100-fold greater affinity to the cis conformation than to the trans conformation of a Xaa-Pro motif.

As used herein, the term "consensus FR" means a framework (FR) antibody region in a consensus immunoglobulin sequence. The FR regions of an antibody do not contact the antigen.

As used herein, the term "effective amount" or "therapeutically effective amount" of a composition, is a quantity sufficient to achieve a desired therapeutic effect, e.g., an amount which results in the decrease in the symptoms associated with a disease that is being treated, e.g., the diseases or medical conditions associated with target polypeptide (e.g., tauopathy, traumatic brain injury (TBI), stroke). The amount of a composition of the present technology administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present technology can also be administered in combination with one or more additional therapeutic compounds. In some embodiments, effective amount refers to the quantity of anti-cis-pT231-tau antibody of the present technology that is partially or fully effective in neutralizing the activity of cis-pT231-tau protein.

As used herein, the term "effector cell" means an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fc receptors and carry out specific immune functions. An effector cell can induce antibody-dependent cell-mediated cytotoxicity (ADCC), e.g., a neutrophil capable of inducing ADCC. For example, monocytes, macrophages, neutrophils, eosinophils, and lymphocytes that express FcaR are involved in specific killing of target cells and presenting antigens to other components of the immune system, or binding to cells that present antigens.

As used herein, the term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. In some embodiments, an "epitope" of the cis-conformation of pT231-tau protein is a region of the protein to which the anti-cis-pT231-tau antibodies of the present technology specifically bind.

To screen for anti-cis-pT231-tau antibodies, which bind to an epitope, a routine cross-blocking assay such as that described in Antibodies, A Laboratory Manual, Cold Spring Harbor Laboratory, Ed Harlow and David Lane (1988), can be performed. This assay can be used to determine if an anti-tau antibody binds the same site or epitope as an anti-cis-pT231-tau antibody of the present technology. Alternatively, or additionally, epitope mapping can be performed by methods known in the art. For example, the antibody sequence can be mutagenized such as by alanine scanning, to identify contact residues. In a different method, peptides corresponding to different regions of pT231-tau protein can be used in competition assays with the test antibodies or with a test antibody and an antibody with a characterized or known epitope.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, "elevated expression" refers to an increase in gene expression or protein expression, as compared to a control or a reference sample (e.g., an increase of at least 2-fold, from about 2-fold to about 150-fold, from 5-fold to 150-fold, from 5-fold to 100-fold, from 10-fold to 150-fold, from 10-fold to 100-fold, from 50-fold to 150-fold, from 50-fold to 100-fold, from 75-fold to 150-fold, or from 75-fold to 100-fold, as compared to a control or a normal reference sample). By "decreased expression" refers to an overall reduction in gene expression or protein expression, as compared to a control or a reference sample (e.g., 20% or greater, of 50% or greater, or of 75%, 80%, 85%, 90%, 95%, or greater. An increase or decrease in gene expression or protein expression can be determined using any useful methods known in the art or described herein (e.g., ELISA).For therapeutic applications, to "decrease" can refer to the reduction in the level of polypeptides or proteins associated with the disorder (e.g., a tauopathy, TBI, or stroke). For diagnostic or monitoring applications, to "decrease" can refer to a decrease in the level of protein or nucleic acid detected by the diagnostic or monitoring assays.

As used herein, the term "gene" means a segment of DNA that contains all the information for the regulated biosynthesis of an RNA product, including promoters, exons, introns, and other untranslated regions that control expression.

As used herein, the term "humanized" forms of non-human (e.g., murine) antibodies are chimeric antibodies which contain minimal sequence derived from non-human immunoglobulin. For the most part, humanized antibodies are human immunoglobulins in which hypervariable region residues of the recipient are replaced by hypervariable region residues from a non-human species (donor antibody) such as mouse, rat, rabbit or nonhuman primate having the desired specificity, affinity, and capacity. In some embodiments, Fv framework region (FR) residues of the human immunoglobulin are replaced by corresponding non-human residues. Furthermore, humanized antibodies may comprise residues, which are not found in the recipient antibody or in the donor antibody. These modifications are made to further refine antibody performance such as binding affinity. Generally, the humanized antibody will comprise substantially all of at least one, and typically two, variable domains (e.g., Fab, Fab', $F(ab')_2$, or Fv), in which all or substantially all of the hypervariable loops correspond to those of a non-human immunoglobulin and all or substantially all of the FR regions are those of a human immunoglobulin consensus FR sequence although the FR regions may include one or more amino acid substitutions that improve binding affinity. The number of these amino acid substitutions in the FR are typically no more than 6 in the H chain, and in the L chain, no more than 3. The humanized antibody optionally may also comprise at least a portion of an immunoglobulin constant region (Fc), typically that of a human immunoglobulin. For further details, see Jones et al., *Nature* 321: 522-525 (1986); Reichmann et al., *Nature* 332:323-329 (1988); and Presta, *Curr. Op. Struct. Biol.* 2:593-596 (1992).

As used herein, the term "hypervariable region" refers to the amino acid residues of an antibody, which are responsible for antigen-binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the VH (Kabat et al., *Sequences of Proteins of Immunological Interest,* 5th Ed. Public Health Service, National Institutes of Health, Bethesda, MD. (1991)) and/or those residues from a "hypervariable loop" (e.g., residues 26-32 (L1), 50-52 (L2) and 91-96 (L3) in the $V_L$, and 26-32 (H1), 52A-55 (H2) and 96-101 (H3) in the VH (Chothia and Lesk *J. Mol. Biol.* 196:901-917 (1987)).

As used herein, the terms "identical" or percent "identity", when used in the context of two or more nucleic acids or polypeptide sequences, refer to two or more sequences or subsequences that are the same or have a specified percentage of amino acid residues or nucleotides that are the same (i.e., about 60%, 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein), when compared and aligned for maximum correspondence over a comparison window or designated region) as measured using a BLAST or BLAST 2.0 sequence comparison algorithms with default parameters described below, or by manual alignment and visual inspection, e.g., NCBI web site). Such sequences are then said to be "substantially identical." This term also refers to, or can be applied to, the complement of a test sequence. The term also includes sequences that have deletions and/or additions, as well as those that have substitutions. In some embodiments, identity exists over a region that is at least about 25 amino acids or nucleotides in length, or 50-100 amino acids or nucleotides in length.

As used herein, the term "immunologically cross-reactive" means an antigen that reacts with an antibody, which was generated using a different antigen.

As used herein, the term "intact antibody" means an antibody that has at least two heavy (H) chain polypeptides and two light (L) chain polypeptides interconnected by disulfide bonds. Each heavy chain is comprised of a heavy chain variable region (abbreviated herein as HCVR or $V_H$) and a heavy chain constant region. The heavy chain constant region is comprised of three domains, CH1, CH2 and CH3. Each light chain is comprised of a light chain variable region (abbreviated herein as LCVR or $V_L$) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The term "mimetic" with respect to an antigenic peptide refers to a synthetic chemical compound that has substantially the same structural and/or functional characteristics of the antigenic peptide KVAVVRTPPKSPS (SEQ ID NO: 56). The mimetic can be either entirely composed of synthetic, non-natural analogs of amino acids or may be a chimeric molecule of natural amino acids and non-natural analogs of amino acids. The mimetic can also incorporate any amount of conservative substitutions, as long as such substitutions do not substantially alter the mimetic's structure or activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. For example, a monoclonal antibody can be an antibody that is derived from a single clone, including any eukaryotic, prokaryotic, or phage clone, and not the method by which it is produced. A monoclonal antibody composition displays a single binding specificity and affinity for a particular epitope. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. Monoclonal antibodies can be prepared using a wide variety of techniques known in the art including, e.g., but not limited to, hybridoma, recombinant, and phage display technologies. For example, the monoclonal antibodies to be used in accordance with the present methods may be made by the hybridoma method first described by Kohler et al., *Nature* 256:495 (1975), or may be made by recombinant DNA methods (See, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

As used herein, "neurological disorder" refers to a disturbance in the structure or function of the nervous system resulting from a developmental abnormality, disorder, injury, or toxin such as mild cognitive impairment (MCI), Parkinson's disease (PD), traumatic brain injury, progressive supranuclear palsy, chronic traumatic encephalopathy (CTE), frontotemporal dementia, frontotemporal lobar degeneration, Lytico-Bodig disease, tangle-predominant dementia, meningioangiomatosis, subacute sclerosing panencephalitis, Pick's disease, corticobasal degeneration, and Alzheimer's disease.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences ($20^{th}$ edition, ed. A. Gennaro, 2000, Lippincott, Williams & Wilkins, Philadelphia, Pa.).

As used herein, the term "polyclonal antibody" means a preparation of antibodies derived from at least two (2) different antibody-producing cell lines. The use of this term includes preparations of at least two (2) antibodies that contain antibodies that specifically bind to different epitopes or regions of an antigen.

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single-and double-stranded regions, single- and double-stranded RNA, RNA that is mixture of single-and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature.

A polypeptide or peptide may be said to be "isolated" or "substantially pure" when physical, mechanical, or chemical methods have been employed to remove the polypeptide from cellular constituents. An "isolated polypeptide" (e.g., an isolated antibody), "substantially pure polypeptide," or "substantially pure and isolated polypeptide" is typically considered removed from cellular constituents and substantially pure when it is at least 60% by weight free from the proteins and naturally occurring organic molecules with which it is naturally associated. The polypeptide may be at least 75%, 80%, 85%, 90%, 95%, or 99% by weight pure. A substantially pure polypeptide (e.g., a substantially pure antibody or fragment thereof) may be obtained by standard techniques, for example, by expression of a recombinant nucleic acid encoding the polypeptide, or by chemically synthesizing the polypeptide. Purity can be measured by any appropriate method, e.g., by column chromatography, polyacrylamide gel electrophoresis, or HPLC analysis.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, the terms "subject", "individual" and "patient" are used interchangeably and refer to a human or non-human animal, e.g., domestic animals (e.g., dogs, cats and the like), farm animals (e.g., cows, sheep, pigs, horses and the like), wild animals, (bats, raccoons, foxes, skunks, squirrels, chipmunks, mice, rabbits, and the like), and laboratory animals (e.g., monkey, rats, mice, rabbits, guinea pigs and the like).

As used herein, the term "therapeutic agent" is intended to mean a compound that, when present in an effective amount, produces a desired therapeutic effect on a subject in need thereof.

Amino acid sequence modification(s) of the anti-cis-pT231-tau antibodies described herein are contemplated. For example, it may be desirable to improve the binding affinity and/or other biological properties of the antibody. Amino acid sequence variants of an anti-cis-pT231-tau antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to obtain the antibody of interest, as long as the obtained antibody possesses the desired properties. The modification also includes the change of the pattern of glycosylation of the protein. The sites of greatest interest for substitutional mutagenesis include the hypervariable regions, but FR alterations are also contemplated. "Conservative substitutions" are shown in the Table below.

TABLE 1

Amino Acid Substitutions

| Original Residue | Exemplary Substitutions | Conservative Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | Tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

One type of substitutional variant involves substituting one or more hypervariable region residues of a parent antibody. A convenient way for generating such substitutional variants involves affinity maturation using phage display. Specifically, several hypervariable region sites (e.g., 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Once such variants are generated, the panel of variants is subjected to screening as described herein and antibodies with similar or superior properties in one or more relevant assays may be selected for further development.

As used herein, a "reference sample" refers to any sample that is used for comparison purposes. A "normal reference sample" can be a prior sample taken from the same subject prior to the onset of a disorder (e.g., a tauopathy, traumatic brain injury (TBI), or stroke), a sample from a subject not having the disorder, a subject that has been successfully treated for the disorder, or a sample of a purified reference polypeptide at a known normal concentration. The terms "reference standard" or "reference level" refer to a value, number or expression pattern of one or more genes or proteins derived from a reference sample. A normal reference standard or level can be a value, number or expression pattern derived from a normal subject that is matched to a sample of a subject by at least one of the following criteria: age, weight, disease stage, and overall health. In one example, a normal reference level of, for example, a polypeptide indicative of a disorder or a conformation of a polypeptide indicative of a disorder, is less than 5 ng/ml in a serum sample, less than 4 ng/ml, less than 3 ng/ml, less than 2 ng/ml, or less than 1 ng/ml in a serum sample. A "positive reference" sample, standard, or value is a sample, standard, value, or number derived from a subject that is known to have a disorder (e.g., a tauopathy, TBI, or stroke) that is matched to a sample of a subject by at least one of the following criteria: age, weight, disease stage, and overall health. For example, a positive reference value for, e.g., a polypeptide indicative of a disorder, is greater than 5 ng/ml serum, greater than 10 ng/ml serum, greater than 20 ng/ml, greater than 30 ng/ml, greater than 40 ng/ml, or greater than 50 ng/ml serum.

As used herein, "specifically binds" refers to a molecule (e.g., an antibody) which recognizes and binds another molecule (e.g., an antigen), but that does not substantially recognize and bind other molecules. In one example, an antibody that specifically binds the cis conformation of pT231-tau does not specifically bind the trans conformation of pT231-tau. The terms "specific binding," "specifically binds to," or is "specific for" a particular molecule (e.g., a polypeptide, an epitope on a polypeptide, or a conformation of a polypeptide), as used herein, can be exhibited, for example, by a molecule having a $K_d$ for the molecule to which it binds to of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, or greater. The term "specifically binds" may also refer to binding where a molecule (e.g., an antibody) binds to a particular polypeptide (e.g., a polypeptide containing a Xaa-Pro motif, where Xaa is a serine or threonine), an epitope on a particular polypeptide, or a conformation of a particular polypeptide (e.g., a cis conformation of a Xaa-Pro motif, e.g., cis pT231-tau) without substantially binding to any other polypeptide, polypeptide epitope, or polypeptide conformation (e.g., the trans conformation of a Xaa-Pro motif, e.g., trans pT231-tau). For example, the conformation-specific antibody may have, for example, at least 10-to 100-fold greater affinity (e.g., $10^1$-, $10^2$-, $10^3$-, $10^4$-, $10^5$-, $10^6$-, $10^7$-, $10^8$-, $10^9$-, or $10^{10}$-fold greater affinity) to one conformation (e.g., the cis conformation) than to another conformation (e.g., the trans conformation) of, for example, a Ser/Thr-Pro motif.

As used herein, a "test sample" means a biological sample obtained from a subject of interest. For example, a test sample can be a biological fluid (e.g., serum), cell or tissue sample, sample from culture or growth media, or isolated nucleic acid or polypeptide derived therefrom.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. By "treating a tauopathy, TBI, or stroke" is meant that the symptoms associated with the tauopathy, TBI, or stroke are, e.g., alleviated, reduced, cured, or placed in a state of remission.

It is also to be appreciated that the various modes of treatment of neurological disorders as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

I. Compositions of the Present Technology

The present technology describes methods and compositions for the generation and use of conformation-specific antibodies or fragments thereof. Conformation-specific antibodies may, for example, specifically bind to the cis- or trans-conformation of a particular polypeptide. In some embodiments, a conformation-specific antibody of the present technology binds to the cis-conformation of a phosphorylated Ser/Thr-Pro motif of a polypeptide (e.g., cis pT231-tau). The binding of a conformation-specific antibody to its antigen (e.g., pT231-tau) may be useful in the treatment, diagnosis, or monitoring of the progression of a neurological disorder associated with elevated cis-pT231-tau protein expression.

The conformation-specific antibodies of the present technology may be generated using immunogenic antigens containing, for example, a phosphorylated Xaa-Pro motif, where Xaa is serine or threonine fixed in a particular conformation (e.g., the cis- or trans-conformation) or in mixed cis- and trans-conformations.

For example, the cis or trans content of phosphorylated Ser/Thr-Pro-containing antigenic peptides of the present technology may be fixed by stereoselective synthesis of (Z)-and (E)-alkene mimics by Still-Wittig and Ireland-Claisen rearrangements (*J. Org. Chem.* 68:2343-2349 (2003), hereby incorporated by reference). Alternatively, the cis or trans content of phosphorylated Ser/Thr-Pro-containing antigenic peptides of the present technology may be increased or fixed by substituting a proline amino acid residue with a proline analog. Proline analogs include, without limitation, homoproline, pipecolic acid (Pip), dimethyl proline (Dmp), azetidine-2-carboxylic acid (Aze), tert-butyl-L-proline (TBP), trans-4-fluoro-L-proline (t-4F-Pro), and cis-4-fluoro-L-proline (c-4F-Pro). The cis or trans content of a given antigen may be analyzed by, for example, nuclear magnetic resonance (NMR) analysis.

Antigenic peptides of the present technology may contain a phosphorylated or nonphosphorylated Xaa-Pro motif, wherein Xaa is serine or threonine, which is capable of cis/trans isomerization. In some embodiments, the antigenic peptide may contain the amino acid residues of a Ser/Thr-Pro motif of the tau protein, with the proline residue substituted for a proline analog. The antigenic peptide may also contain the amino acid residues of the Ser/Thr-Pro motif of a full-length tau polypeptide. The antigenic peptide may further include additional residues surrounding the Ser/Thr-Pro motif of the full-length tau polypeptide. For example, the antigenic peptide may include the 3-10 amino acid residues N-terminal to the Ser/Thr residue of a full-length tau polypeptide and the 3-10 amino acid residues C-terminal to the proline of a full-length tau polypeptide. The antigenic peptide of the present technology may be, for example, at least 4, 5, 6, 7, or 8 amino acid residues in length. The antigenic peptide may be between 8 and 20 amino acid residues in length (e.g., 8, 9, 10, 11, 12, 13, 14, 15, 16, 17, 18, 19, or 20 amino acids residues in length) or may be over 20 amino acid residues in length.

Such antigens may be produced and purified by any of a variety of methods known to one of skill in the art. Antigenic peptides may be produced and purified by, e.g., solid-phase chemical synthesis, in vitro transcription/translation, or by recombinant technology. The antigenic peptides may optionally be chemically coupled to a carrier protein or the peptides may be generated as fusion proteins to increase antigenicity. Antigenic peptides may be screened based upon their ability to induce the production of conformation-specific antibodies. In this respect, such screening techniques may include, but are not limited to, enzyme-linked immunosorbant assays (ELISA), immunoprecipitation, or other immunoassays.

Exemplary antigens useful in the production of conformation-specific antibodies include antigens containing a phosphorylated or nonphosphorylated Ser/Thr-homoproline, Ser/Thr-Pip, Ser/Thr-Dmp, Ser/Thr-Aze, Ser/Thr-TBP, Ser/Thr-t-4F-Pro, or Ser/Thr-c-4F-Pro motif. Specific examples of such antigens include, e.g., pT231-Pip tau peptide, and pT231-Dmp tau peptide (KVAVVR-pT231-Pro-PKSPS). Such peptides may be used as antigens for generating, e.g., polyclonal or monoclonal antibodies (e.g., rabbit or mouse monoclonal antibodies).

In one aspect, the present disclosure provides an isolated antibody comprising a heavy chain immunoglobulin variable domain, wherein the heavy chain immunoglobulin variable domain has an amino acid sequence of:

```
                                  (SEQ ID NO: 1)
QVQLVQSGAEVKKPGASVKVSCKASGYT

FTSYWIHWVRQAPGQGLEWIGVIDPSDS

YTRYNQKFKGRATLTVDTSTSTAYMELR

SLRSDDTAVYYCTTWEVDYWGQGTTVTV

SS

                                  (SEQ ID NO: 2)
QVQLVQSGAEVKKPGASVKVSCKASGYT

FTSYWIHWVRQAPGQGLEWIGVIDPSDS

YTRYNQKFKGRVTLTVDTSTSTAYMELR

SLRSDDTAVYYCTTWEVDYWGQGTTVTV

SS

                                  (SEQ ID NO: 3)
QVQLVQSGAEVKKPGASVKVSCKASGYT

FTSYWIHWVRQAPGQGLEWIGVIDPSDS

YTRYNQKFKGRATMTVDTSTSTAYMELR

SLRSDDTAVYYCTTWEVDYWGQGTTVTV

SS;

                                  (SEQ ID NO: 4)
QVQLVQSGAEVKKPGASVKVSCKASGYT

FTSYWIHWVRQAPGQGLEWIGVIDPSDS

YTRYNQKFKGRVTMTVDTSTSTAYMELR

SLRSDDTAVYYCTTWEVDYWGQGTTVTV

SS;
```

or a variant thereof having one or more conservative amino acid substitutions.

In another aspect, the present disclosure provides an isolated antibody comprising a heavy chain immunoglobulin variable domain, wherein the heavy chain immunoglobulin variable domain includes a signal sequence and a heavy chain immunoglobulin variable domain amino acid sequence described herein. By way of example, but not by way of limitation, in some embodiments, the signal sequence is MRWSCIILFLVATATGVNS (SEQ ID NO: 5) or MEWSWVFLFFLSVTTGVHS (SEQ ID NO: 6).

By way of example, but not by way of limitation, in some embodiments, the isolated antibody comprises a heavy chain immunoglobulin variable domain that includes a signal sequence (underlined) and has an amino acid sequence selected from:

(SEQ ID NO: 7)
MRWSCIILFLVATATGVNSQVQLVQSGA
EVKKPGASVKVSCKASGYTFTSYWIHWV
RQAPGQGLEWIGVIDPSDSYTRYNQKFK
GRATLTVDTSTSTAYMELRSLRSDDTAV
YYCTTWEVDYWGQGTTVTVSS;

(SEQ ID NO: 8)
MRWSCIILFLVATATGVNSQVQLVQSGA
EVKKPGASVKVSCKASGYTFTSYWIHWV
RQAPGQGLEWIGVIDPSDSYTRYNQKFK
GRVTLTVDTSTSTAYMELRSLRSDDTAV
YYCTTWEVDYWGQGTTVTVSS;

(SEQ ID NO: 9)
MRWSCIILFLVATATGVNSQVQLVQSGA
EVKKPGASVKVSCKASGYTFTSYWIHWV
RQAPGQGLEWIGVIDPSDSYTRYNQKFK
GRATMTVDTSTSTAYMELRSLRSDDTAV
YYCTTWEVDYWGQGTTVTVSS;

(SEQ ID NO: 10)
MRWSCIILFLVATATGVNSQVQLVQSGA
EVKKPGASVKVSCKASGYTFTSYWIHWV
RQAPGQGLEWIGVIDPSDSYTRYNQKFK
GRVTMTVDTSTSTAYMELRSLRSDDTAV
YYCTTWEVDYWGQGTTVTVSS;

(SEQ ID NO: 11)
MEWSWVFLFFLSVTTGVHSQVQLVQSGA
EVKKPGASVKVSCKASGYTFTSYWIHWV
RQAPGQGLEWIGVIDPSDSYTRYNQKFK
GRATLTVDTSTSTAYMELRSLRSDDTAV
YYCTTWEVDYWGQGTTVTVSS;

(SEQ ID NO: 12)
MEWSWVFLFFLSVTTGVHSQVQLVQSGA
EVKKPGASVKVSCKASGYTFTSYWIHWV
RQAPGQGLEWIGVIDPSDSYTRYNQKFK
GRVTLTVDTSTSTAYMELRSLRSDDTAV
YYCTTWEVDYWGQGTTVTVSS;

(SEQ ID NO: 13)
MEWSWVFLFFLSVTTGVHSQVQLVQSGA
EVKKPGASVKVSCKASGYTFTSYWIHWV
RQAPGQGLEWIGVIDPSDSYTRYNQKFK

-continued

GRATMTVDTSTSTAYMELRSLRSDDTA
VYYCTTWEVDYWGQGTTVTVSS;

(SEQ ID NO: 14)
MEWSWVFLFFLSVTTGVHSQVQLVQSGA
EVKKPGASVKVSCKASGYTFTSYWIHWV
RQAPGQGLEWIGVIDPSDSYTRYNQKFK
GRVTMTVDTSTSTAYMELRSLRSDDTA
VYYCTTWEVDYWGQGTTVTVSS;

or a variant thereof having one or more conservative amino acid substitutions.

In another aspect, the present disclosure provides an isolated antibody comprising a heavy chain immunoglobulin variable domain amino acid sequence described herein and a heavy chain immunoglobulin constant domain. By way of example, but not by way of limitation, in some embodiments, the heavy chain immunoglobulin constant domain has an amino acid sequence selected from the group consisting of:

(SEQ ID NO: 15)
PSVFPLAPSSKSTSGGTAALGCLVKDYFPEPVTVS
WNSGALTSGVHTFPAVLQSSGLYSLSSVVTVPSSS
LGTQTYICNVNHKPSNTKVDKKVEPKSCDKTHTCP
PCPAPEAAGGPSVFLFPPKPKDTLMISRTPEVTCV
VVDVSHEDPEVKFNWYVDGVEVHNAKTKPREEQYN
STYRVVSVLTVLHQDWLNGKEYKCKVSNKALPAPI
EKTISKAKGQPREPQVYTLPPSRDELTKNQVSLTC
LVKGFYPSDIAVEWESNGQPENNYKTTPPVLDSDG
SFFLYSKLTVDKSRWQQGNVFSCSVMHEALHNHYT
QKSLSLSPGK;
and (SEQ ID NO: 16)
PSVFPLAPCSRSTSESTAALGCLVKDYFPEPVTVS
WNSGALTSGVHTFPAVLQSSGLYSLSSVVTVPSSS
LGTKTYTCNVDHKPSNTKVDKRVESKYGPPCPPCP
APEFLGGPSVFLFPPKPKDTLMISRTPEVTCVVVD
VSQEDPEVQFNWYVDGVEVHNAKTKPREEQFNSTY
RVVSVLTVLHQDWLNGKEYKCKVSNKGLPSSIEKT
ISKAKGQPREPQVYTLPPSQEEMTKNQVSLTCLVK
GFYPSDIAVEWESNGQPENNYKTTPPVLDSDGSFF
LYSRLTVDKSRWQEGNVFSCSVMHEALHNHYTQKS
LSLSLG.

By way of example, but not by way of limitation, in some embodiments, the isolated antibody comprising a heavy chain immunoglobulin variable domain and a heavy chain immunoglobulin constant domain (boldface font) has an amino acid sequence selected from:

-continued (SEQ ID NO: 17)
QVQLVQSGAEVKKPGASVKVSCKASGYTFTSYWIHWVRQAPGQGLEWIGVIDPSDSYTRYNQKFKGRATLTVDTSTSTAYMELRSLRSDDTAVYYCTTWEVDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK;

(SEQ ID NO: 18)
QVQLVQSGAEVKKPGASVKVSCKASGYTFTSYWIHWVRQAPGQGLEWIGVIDPSDSYTRYNQKFKGRATLTVDTSTSTAYMELRSLRSDDTAVYYCTTWEVDYWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG;

(SEQ ID NO: 19)
QVQLVQSGAEVKKPGASVKVSCKASGYTFTSYWIHWVRQAPGQGLEWIGVIDPSDSYTRYNQKFKGRVTLTVDTSTSTAYMELRSLRSDDTAVYYCTTWEVDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK;

(SEQ ID NO: 20)
QVQLVQSGAEVKKPGASVKVSCKASGYTFTSYWIHWVRQAPGQGLEWIGVIDPSDSYTRYNQKFKGRVTLTVDTSTSTAYMELRSLRSDDTAVYYCTTWEVDYWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG;

(SEQ ID NO: 21)
QVQLVQSGAEVKKPGASVKVSCKASGYTFTSYWIHWVRQAPGQGLEWIGVIDPSDSYTRYNQKFKGRATMTVDTSTSTAYMELRSLRSDDTAVYYCTTWEVDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK;

(SEQ ID NO: 22)
QVQLVQSGAEVKKPGASVKVSCKASGYTFTSYWIHWVRQAPGQGLEWIGVIDPSDSYTRYNQKFKGRATMTVDTSTSTAYMELRSLRSDDTAVYYCTTWEVDYWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG;

-continued (SEQ ID NO: 23)
QVQLVQSGAEVKKPGASVKVSCKASGYTFTSYWIH
WVRQAPGQGLEWIGVIDPSDSYTRYNQKFKGRVTM
TVDTSTSTAYMELRSLRSDDTAVYYCTTWEVDYWG
QGTTVTVSSASTKGPSVFPLAPSSKSTSGGTAALG
CLVKDYFPEPVTVSWNSGALTSGVHTFPAVLQSSG
LYSLSSVVTVPSSSLGTQTYICNVNHKPSNTKVDK
KVEPKSCDKTHTCPPCPAPEAAGGPSVFLFPPKPK
DTLMISRTPEVTCVVVDVSHEDPEVKFNWYVDGVE
VHNAKTKPREEQYNSTYRVVSVLTVLHQDWLNGKE
YKCKVSNKALPAPIEKTISKAKGQPREPQVYTLPP
SRDELTKNQVSLTCLVKGFYPSDIAVEWESNGQPE
NNYKTTPPVLDSDGSFFLYSKLTVDKSRWQQGNVF
SCSVMHEALHNHYTQKSLSLSPGK;

(SEQ ID NO: 24)
QVQLVQSGAEVKKPGASVKVSCKASGYTFTSYWIH
WVRQAPGQGLEWIGVIDPSDSYTRYNQKFKGRVTM
TVDTSTSTAYMELRSLRSDDTAVYYCTTWEVDYWG
QGTTVTVSSASTKGPSVFPLAPCSRSTSESTAALG
CLVKDYFPEPVTVSWNSGALTSGVHTFPAVLQSSG
LYSLSSVVTVPSSSLGTKTYTCNVDHKPSNTKVDK
RVESKYGPPCPPCPAPEFLGGPSVFLFPPKPKDTL
MISRTPEVTCVVVDVSQEDPEVQFNWYVDGVEVHN
AKTKPREEQFNSTYRVVSVLTVLHQDWLNGKEYKC
KVSNKGLPSSIEKTISKAKGQPREPQVYTLPPSQE
EMTKNQVSLTCLVKGFYPSDIAVEWESNGQPENNY
KTTPPVLDSDGSFFLYSRLTVDKSRWQEGNVFSCS
VMHEALHNHYTQKSLSLSLG;

or a variant thereof having one or more conservative amino acid substitutions.

In another aspect, the present disclosure provides an isolated antibody comprising a heavy chain immunoglobulin variable domain, wherein the heavy chain immunoglobulin variable domain includes a signal sequence and a heavy chain immunoglobulin variable domain amino acid sequence, and a heavy chain immunoglobulin constant domain. By way of example, but not by way of limitation, in some embodiments, the isolated antibody comprising a heavy chain immunoglobulin variable domain, wherein the heavy chain immunoglobulin variable domain includes a signal sequence and a heavy chain immunoglobulin variable domain amino acid sequence, and a heavy chain immunoglobulin constant domain has an amino acid sequence selected from (the signal sequence is underlined and the heavy chain immunoglobulin constant domain is boldface):

(SEQ ID NO: 25)
MRWSCIILFLVATATGVNSQVQLVQSGAEVKKPGA
SVKVSCKASGYTFTSYWIHWVRQAPGQGLEWIGVI
DPSDSYTRYNQKFKGRATLTVDTSTSTAYMELRSL
RSDDTAVYYCTTWEVDYWGQGTTVTVSSASTKGPS
VFPLAPSSKSTSGGTAALGCLVKDYFPEPVTVSWN
SGALTSGVHTFPAVLQSSGLYSLSSVVTVPSSSLG
TQTYICNVNHKPSNTKVDKKVEPKSCDKTHTCPPC
PAPEAAGGPSVFLFPPKPKDTLMISRTPEVTCVVV
DVSHEDPEVKFNWYVDGVEVHNAKTKPREEQYNST
YRVVSVLTVLHQDWLNGKEYKCKVSNKALPAPIEK
TISKAKGQPREPQVYTLPPSRDELTKNQVSLTCLV
KGFYPSDIAVEWESNGQPENNYKTTPPVLDSDGSF
FLYSKLTVDKSRWQQGNVFSCSVMHEALHNHYTQK
SLSLSPGK;

(SEQ ID NO: 26)
MRWSCIILFLVATATGVNSQVQLVQSGAEVKKPGA
SVKVSCKASGYTFTSYWIHWVRQAPGQGLEWIGVI
DPSDSYTRYNQKFKGRATLTVDTSTSTAYMELRSL
RSDDTAVYYCTTWEVDYWGQGTTVTVSSASTKGPS
VFPLAPCSRSTSESTAALGCLVKDYFPEPVTVSWN
SGALTSGVHTFPAVLQSSGLYSLSSVVTVPSSSLG
TKTYTCNVDHKPSNTKVDKRVESKYGPPCPPCPAP
EFLGGPSVFLFPPKPKDTLMISRTPEVTCVVVDVS
QEDPEVQFNWYVDGVEVHNAKTKPREEQFNSTYRV
VSVLTVLHQDWLNGKEYKCKVSNKGLPSSIEKTIS
KAKGQPREPQVYTLPPSQEEMTKNQVSLTCLVKGF
YPSDIAVEWESNGQPENNYKTTPPVLDSDGSFFLY
SRLTVDKSRWQEGNVFSCSVMHEALHNHYTQKSLS
LSLG;

(SEQ ID NO: 27)
MRWSCIILFLVATATGVNSQVQLVQSGAEVKKPGA
SVKVSCKASGYTFTSYWIHWVRQAPGQGLEWIGVI
DPSDSYTRYNQKFKGRVTLTVDTSTSTAYMELRSL
RSDDTAVYYCTTWEVDYWGQGTTVTVSSASTKGPS
VFPLAPSSKSTSGGTAALGCLVKDYFPEPVTVSWN
SGALTSGVHTFPAVLQSSGLYSLSSVVTVPSSSLG
TQTYICNVNHKPSNTKVDKKVEPKSCDKTHTCPPC
PAPEAAGGPSVFLFPPKPKDTLMISRTPEVTCVVV
DVSHEDPEVKFNWYVDGVEVHNAKTKPREEQYNST
YRVVSVLTVLHQDWLNGKEYKCKVSNKALPAPIEK
TISKAKGQPREPQVYTLPPSRDELTKNQVSLTCLV

-continued

KGFYPSDIAVEWESNGQPENNYKTTPPVLDSDGSF
FLYSKLTVDKSRWQQGNVFSCSVMHEALHNHYTQK
SLSLSPGK;

(SEQ ID NO: 28)
MRWSCIILFLVATATGVNSQVQLVQSGAEVKKPGA
SVKVSCKASGYTFTSYWIHWVRQAPGQGLEWIGVI
DPSDSYTRYNQKFKGRVTLTVDTSTSTAYMELRSL
RSDDTAVYYCTTWEVDYWGQGTTVTVSSASTKGPS
VFPLAPCSRSTSESTAALGCLVKDYFPEPVTVSWN
SGALTSGVHTFPAVLQSSGLYSLSSVVTVPSSSLG
TKTYTCNVDHKPSNTKVDKRVESKYGPPCPPCPAP
EFLGGPSVFLFPPKPKDTLMISRTPEVTCVVVDVS
QEDPEVQFNWYVDGVEVHNAKTKPREEQFNSTYRV
VSVLTVLHQDWLNGKEYKCKVSNKGLPSSIEKTIS
KAKGQPREPQVYTLPPSQEEMTKNQVSLTCLVKGF
YPSDIAVEWESNGQPENNYKTTPPVLDSDGSFFLY
SRLTVDKSRWQEGNVFSCSVMHEALHNHYTQKSLS
LSLG;

(SEQ ID NO: 29)
MRWSCIILFLVATATGVNSQVQLVQSGAEVKKPGA
SVKVSCKASGYTFTSYWIHWVRQAPGQGLEWIGVI
DPSDSYTRYNQKFKGRATMTVDTSTSTAYMELRSL
RSDDTAVYYCTTWEVDYWGQGTTVTVSSASTKGPS
VFPLAPSSKSTSGGTAALGCLVKDYFPEPVTVSWN
SGALTSGVHTFPAVLQSSGLYSLSSVVTVPSSSLG
TQTYICNVNHKPSNTKVDKKVEPKSCDKTHTCPPC
PAPEAAGGPSVFLFPPKPKDTLMISRTPEVTCVVV
DVSHEDPEVKFNWYVDGVEVHNAKTKPREEQYNST
YRVVSVLTVLHQDWLNGKEYKCKVSNKALPAPIEK
TISKAKGQPREPQVYTLPPSRDELTKNQVSLTCLV
KGFYPSDIAVEWESNGQPENNYKTTPPVLDSDGSF
FLYSKLTVDKSRWQQGNVFSCSVMHEALHNHYTQK
SLSLSPGK;

(SEQ ID NO: 30)
MRWSCIILFLVATATGVNSQVQLVQSGAEVKKPGA
SVKVSCKASGYTFTSYWIHWVRQAPGQGLEWIGVI
DPSDSYTRYNQKFKGRATMTVDTSTSTAYMELRSL
RSDDTAVYYCTTWEVDYWGQGTTVTVSSASTKGPS
VFPLAPCSRSTSESTAALGCLVKDYFPEPVTVSWN
SGALTSGVHTFPAVLQSSGLYSLSSVVTVPSSSLG
TKTYTCNVDHKPSNTKVDKRVESKYGPPCPPCPAP
EFLGGPSVFLFPPKPKDTLMISRTPEVTCVVVDVS

-continued

QEDPEVQFNWYVDGVEVHNAKTKPREEQFNSTYRV
VSVLTVLHQDWLNGKEYKCKVSNKGLPSSIEKTIS
KAKGQPREPQVYTLPPSQEEMTKNQVSLTCLVKGF
YPSDIAVEWESNGQPENNYKTTPPVLDSDGSFFLY
SRLTVDKSRWQEGNVFSCSVMHEALHNHYTQKSLS
LSLG;

(SEQ ID NO: 31)
MRWSCIILFLVATATGVNSQVQLVQSGAEVKKPGA
SVKVSCKASGYTFTSYWIHWVRQAPGQGLEWIGVI
DPSDSYTRYNQKFKGRVTMTVDTSTSTAYMELRSL
RSDDTAVYYCTTWEVDYWGQGTTVTVSSASTKGPS
VFPLAPSSKSTSGGTAALGCLVKDYFPEPVTVSWN
SGALTSGVHTFPAVLQSSGLYSLSSVVTVPSSSLG
TQTYICNVNHKPSNTKVDKKVEPKSCDKTHTCPPC
PAPEAAGGPSVFLFPPKPKDTLMISRTPEVTCVVV
DVSHEDPEVKFNWYVDGVEVHNAKTKPREEQYNST
YRVVSVLTVLHQDWLNGKEYKCKVSNKALPAPIEK
TISKAKGQPREPQVYTLPPSRDELTKNQVSLTCLV
KGFYPSDIAVEWESNGQPENNYKTTPPVLDSDGSF
FLYSKLTVDKSRWQQGNVFSCSVMHEALHNHYTQK
SLSLSPGK;

(SEQ ID NO: 32)
MRWSCIILFLVATATGVNSQVQLVQSGAEVKKPGA
SVKVSCKASGYTFTSYWIHWVRQAPGQGLEWIGVI
DPSDSYTRYNQKFKGRVTMTVDTSTSTAYMELRSL
RSDDTAVYYCTTWEVDYWGQGTTVTVSSASTKGPS
VFPLAPCSRSTSESTAALGCLVKDYFPEPVTVSWN
SGALTSGVHTFPAVLQSSGLYSLSSVVTVPSSSLG
TKTYTCNVDHKPSNTKVDKRVESKYGPPCPPCPAP
EFLGGPSVFLFPPKPKDTLMISRTPEVTCVVVDVS
QEDPEVQFNWYVDGVEVHNAKTKPREEQFNSTYRV
VSVLTVLHQDWLNGKEYKCKVSNKGLPSSIEKTIS
KAKGQPREPQVYTLPPSQEEMTKNQVSLTCLVKGF
YPSDIAVEWESNGQPENNYKTTPPVLDSDGSFFLY
SRLTVDKSRWQEGNVFSCSVMHEALHNHYTQKSLS
LSLG;

(SEQ ID NO: 33)
MEWSWVFLFFLSVTTGVHSQVQLVQSGAEVKKPGA
SVKVSCKASGYTFTSYWIHWVRQAPGQGLEWIGVI
DPSDSYTRYNQKFKGRATLTVDTSTSTAYMELRSL
RSDDTAVYYCTTWEVDYWGQGTTVTVSSASTKGPS
VFPLAPSSKSTSGGTAALGCLVKDYFPEPVTVSWN

-continued

SGALTSGVHTFPAVLQSSGLYSLSSVVTVPSSSLG
TQTYICNVNHKPSNTKVDKKVEPKSCDKTHTCPPC
PAPEAAGGPSVFLFPPKPKDTLMISRTPEVTCVVV
DVSHEDPEVKFNWYVDGVEVHNAKTKPREEQYNST
YRVVSVLTVLHQDWLNGKEYKCKVSNKALPAPIEK
TISKAKGQPREPQVYTLPPSRDELTKNQVSLTCLV
KGFYPSDIAVEWESNGQPENNYKTTPPVLDSDGSF
FLYSKLTVDKSRWQQGNVFSCSVMHEALHNHYTQK
SLSLSPGK;

(SEQ ID NO: 34)
MEWSWVFLFFLSVTTGVHSQVQLVQSGAEVKKPGA
SVKVSCKASGYTFTSYWIHWVRQAPGQGLEWIGVI
DPSDSYTRYNQKFKGRATLTVDTSTSTAYMELRSL
RSDDTAVYYCTTWEVDYWGQGTTVTVSSASTKGPS
VFPLAPCSRSTSESTAALGCLVKDYFPEPVTVSWN
SGALTSGVHTFPAVLQSSGLYSLSSVVTVPSSSLG
TKTYTCNVDHKPSNTKVDKRVESKYGPPCPPCPAP
EFLGGPSVFLFPPKPKDTLMISRTPEVTCVVVDVS
QEDPEVQFNWYVDGVEVHNAKTKPREEQFNSTYRV
VSVLTVLHQDWLNGKEYKCKVSNKGLPSSIEKTIS
KAKGQPREPQVYTLPPSQEEMTKNQVSLTCLVKGF
YPSDIAVEWESNGQPENNYKTTPPVLDSDGSFFLY
SRLTVDKSRWQEGNVFSCSVMHEALHNHYTQKSLS
LSLG;

(SEQ ID NO: 35)
MEWSWVFLFFLSVTTGVHSQVQLVQSGAEVKKPGA
SVKVSCKASGYTFTSYWIHWVRQAPGQGLEWIGVI
DPSDSYTRYNQKFKGRVTLTVDTSTSTAYMELRSL
RSDDTAVYYCTTWEVDYWGQGTTVTVSSASTKGPS
VFPLAPSSKSTSGGTAALGCLVKDYFPEPVTVSWN
SGALTSGVHTFPAVLQSSGLYSLSSVVTVPSSSLG
TQTYICNVNHKPSNTKVDKKVEPKSCDKTHTCPPC
PAPEAAGGPSVFLFPPKPKDTLMISRTPEVTCVVV
DVSHEDPEVKFNWYVDGVEVHNAKTKPREEQYNST
YRVVSVLTVLHQDWLNGKEYKCKVSNKALPAPIEK
TISKAKGQPREPQVYTLPPSRDELTKNQVSLTCLV
KGFYPSDIAVEWESNGQPENNYKTTPPVLDSDGSF
FLYSKLTVDKSRWQQGNVFSCSVMHEALHNHYTQK
SLSLSPGK;

(SEQ ID NO: 36)
MEWSWVFLFFLSVTTGVHSQVQLVQSGAEVKKPGA
SVKVSCKASGYTFTSYWIHWVRQAPGQGLEWIGVI
DPSDSYTRYNQKFKGRVTLTVDTSTSTAYMELRSL
RSDDTAVYYCTTWEVDYWGQGTTVTVSSASTKGPS
VFPLAPCSRSTSESTAALGCLVKDYFPEPVTVSWN
SGALTSGVHTFPAVLQSSGLYSLSSVVTVPSSSLG
TKTYTCNVDHKPSNTKVDKRVESKYGPPCPPCPAP
EFLGGPSVFLFPPKPKDTLMISRTPEVTCVVVDVS
QEDPEVQFNWYVDGVEVHNAKTKPREEQFNSTYRV
VSVLTVLHQDWLNGKEYKCKVSNKGLPSSIEKTIS
KAKGQPREPQVYTLPPSQEEMTKNQVSLTCLVKGF
YPSDIAVEWESNGQPENNYKTTPPVLDSDGSFFLY
SRLTVDKSRWQEGNVFSCSVMHEALHNHYTQKSLS
LSLG;

(SEQ ID NO: 37)
MEWSWVFLFFLSVTTGVHSQVQLVQSGAEVKKPGA
SVKVSCKASGYTFTSYWIHWVRQAPGQGLEWIGVI
DPSDSYTRYNQKFKGRATMTVDTSTSTAYMELRSL
RSDDTAVYYCTTWEVDYWGQGTTVTVSSASTKGPS
VFPLAPSSKSTSGGTAALGCLVKDYFPEPVTVSWN
SGALTSGVHTFPAVLQSSGLYSLSSVVTVPSSSLG
TQTYICNVNHKPSNTKVDKKVEPKSCDKTHTCPPC
PAPEAAGGPSVFLFPPKPKDTLMISRTPEVTCVVV
DVSHEDPEVKFNWYVDGVEVHNAKTKPREEQYNST
YRVVSVLTVLHQDWLNGKEYKCKVSNKALPAPIEK
TISKAKGQPREPQVYTLPPSRDELTKNQVSLTCLV
KGFYPSDIAVEWESNGQPENNYKTTPPVLDSDGSF
FLYSKLTVDKSRWQQGNVFSCSVMHEALHNHYTQK
SLSLSPGK;

(SEQ ID NO: 38)
MEWSWVFLFFLSVTTGVHSQVQLVQSGAEVKKPGA
SVKVSCKASGYTFTSYWIHWVRQAPGQGLEWIGVI
DPSDSYTRYNQKFKGRATMTVDTSTSTAYMELRSL
RSDDTAVYYCTTWEVDYWGQGTTVTVSSASTKGPS
VFPLAPCSRSTSESTAALGCLVKDYFPEPVTVSWN
SGALTSGVHTFPAVLQSSGLYSLSSVVTVPSSSLG
TKTYTCNVDHKPSNTKVDKRVESKYGPPCPPCPAP
EFLGGPSVFLFPPKPKDTLMISRTPEVTCVVVDVS
QEDPEVQFNWYVDGVEVHNAKTKPREEQFNSTYRV
VSVLTVLHQDWLNGKEYKCKVSNKGLPSSIEKTIS
KAKGQPREPQVYTLPPSQEEMTKNQVSLTCLVKGF
YPSDIAVEWESNGQPENNYKTTPPVLDSDGSFFLY
SRLTVDKSRWQEGNVFSCSVMHEALHNHYTQKSLS
LSLG;

-continued (SEQ ID NO: 39)
MEWSWVFLFFLSVTTGVHSQVQLVQSGAEVKKPGA
SVKVSCKASGYTFTSYWIHWVRQAPGQGLEWIGVI
DPSDSYTRYNQKFKGRVTMTVDTSTSTAYMELRSL
RSDDTAVYYCTTWEVDYWGQGTTVTVSSASTKGPS
VFPLAPSSKSTSGGTAALGCLVKDYFPEPVTVSWN
SGALTSGVHTFPAVLQSSGLYSLSSVVTVPSSSLG
TQTYICNVNHKPSNTKVDKKVEPKSCDKTHTCPPC
PAPEAAGGPSVFLFPPKPKDTLMISRTPEVTCVVV
DVSHEDPEVKFNWYVDGVEVHNAKTKPREEQYNST
YRVVSVLTVLHQDWLNGKEYKCKVSNKALPAPIEK
TISKAKGQPREPQVYTLPPSRDELTKNQVSLTCLV
KGFYPSDIAVEWESNGQPENNYKTTPPVLDSDGSF
FLYSKLTVDKSRWQQGNVFSCSVMHEALHNHYTQK
SLSLSPGK;

(SEQ ID NO: 40)
MEWSWVFLFFLSVTTGVHSQVQLVQSGAEVKKPGA
SVKVSCKASGYTFTSYWIHWVRQAPGQGLEWIGVI
DPSDSYTRYNQKFKGRVTMTVDTSTSTAYMELRSL
RSDDTAVYYCTTWEVDYWGQGTTVTVSSASTKGPS
VFPLAPCSRSTSESTAALGCLVKDYFPEPVTVSWN
SGALTSGVHTFPAVLQSSGLYSLSSVVTVPSSSLG
TKTYTCNVDHKPSNTKVDKRVESKYGPPCPPCPAP
EFLGGPSVFLFPPKPKDTLMISRTPEVTCVVVDVS
QEDPEVQFNWYVDGVEVHNAKTKPREEQFNSTYRV
VSVLTVLHQDWLNGKEYKCKVSNKGLPSSIEKTIS
KAKGQPREPQVYTLPPSQEEMTKNQVSLTCLVKGF
YPSDIAVEWESNGQPENNYKTTPPVLDSDGSFFLY
SRLTVDKSRWQEGNVFSCSVMHEALHNHYTQKSLS
LSLG;

(SEQ ID NO: 132)
MRWSCIILFLVATATGVNSQVQLVQSGAEVKKPGA
SVKVSCKASGYTFTSYWIHWVRQAPGQGLEWIGVI
DPSDSYTRYNQKFKGRVTMTVDTSTSTAYMELRSL
RSDDTAVYYCTTWEVDYWGQGTTVTVSSASTKGPS
VFPLAPSSKSTSGGTAALGCLVKDYFPEPVTVSWN
SGALTSGVHTFPAVLQSSGLYSLSSVVTVPSSSLG
TQTYICNVNHKPSNTKVDKKVEPKSCDKTHTCPPC
PAPELLGGPSVFLFPPKPKDTLMISRTPEVTCVVV
DVSHEDPEVKFNWYVDGVEVHNAKTKPREEQYNST
YRVVSVLTVLHQDWLNGKEYKCKVSNKALPAPIEK
TISKAKGQPREPQVYTLPPSRDELTKNQVSLTCLV
KGFYPSDIAVEWESNGQPENNYKTTPPVLDSDGSF
FLYSKLTVDKSRWQQGNVFSCSVMHEALHNHYTQK
SLSLSPG (SEQ ID NO: 133)
MEWSWVFLFFLSVTTGVHSQVQLVQSGAEVKKPGA
SVKVSCKASGYTFTSYWIHWVRQAPGQGLEWIGVI
DPSDSYTRYNQKFKGRVTMTVDTSTSTAYMELRSL
RSDDTAVYYCTTWEVDYWGQGTTVTVSSASTKGPS
VFPLAPSSKSTSGGTAALGCLVKDYFPEPVTVSWN
SGALTSGVHTFPAVLQSSGLYSLSSVVTVPSSSLG
TQTYICNVNHKPSNTKVDKKVEPKSCDKTHTCPPC
PAPELLGGPSVFLFPPKPKDTLMISRTPEVTCVVV
DVSHEDPEVKFNWYVDGVEVHNAKTKPREEQYNST
YRVVSVLTVLHQDWLNGKEYKCKVSNKALPAPIEK
TISKAKGQPREPQVYTLPPSRDELTKNQVSLTCLV
KGFYPSDIAVEWESNGQPENNYKTTPPVLDSDGSF
FLYSKLTVDKSRWQQGNVFSCSVMHEALHNHYTQK
SLSLSPG or a variant thereof having one or more conservative amino acid substitutions.

Additionally or alternatively, in some embodiments, the isolated antibodies of the present technology comprise a light chain immunoglobulin variable domain, wherein the light chain immunoglobulin variable domain has an amino acid sequence of:

(SEQ ID NO: 41)
DVVMTQTPLSLPVSLGDQASISCRSSQSLVHSDGNTYLHWYLQKPG
QSPKLLIYKVSNRFSGVPDRFSGSGSGTDFTLKISRLEAEDLGVYF
CSQSTHVPWTFGGGTKLEIK;

(SEQ ID NO: 42)
DIVMTQSPLSLPVTPGEPASISCRSSQSLVHSDGNTYLHWYLQKPG
QSPQLLIYKVSNRFSGVPDRFSGSGSGTDFTLKISRVEAEDVGVYY
CSQSTHVPWTFGGGTKVEIKRT;

or a variant thereof having one or more conservative amino acid substitutions.

Additionally or alternatively, in another aspect, the present disclosure provides an isolated antibody comprising a light chain immunoglobulin variable domain, wherein the light chain immunoglobulin variable domain includes a signal sequence and a light chain immunoglobulin variable domain amino acid sequence. By way of example, but not by way of limitation, in some embodiments, the signal sequence is MKLPVRLLVLMFWIPASNS (SEQ ID NO: 43) or MSVPTQVLGLLLLWLTDARC (SEQ ID NO: 44).

By way of example, but not by way of limitation, in some embodiments, the isolated antibody comprises a light chain immunoglobulin variable domain that includes a signal sequence and has an amino acid sequence (the signal sequence is underlined) selected from:

(SEQ ID NO: 45)
MKLPVRLLVLMFWIPASNSDVVMTQTPLSLPVSLGDQASISCRSSQ
SLVHSDGNTYLHWYLQKPGQSPKLLIYKVSNRFSGVPDRFSGSGSG
TDFTLKISRLEAEDLGVYFCSQSTHVPWTFGGGTKLEIK;

(SEQ ID NO: 46)
MSVPTQVLGLLLLWLTDARCDVVMTQTPLSLPVSLGDQASISCRSS
QSLVHSDGNTYLHWYLQKPGQSPKLLIYKVSNRFSGVPDRFSGSGS
GTDFTLKISRLEAEDLGVYFCSQSTHVPWTFGGGTKLEIK;

(SEQ ID NO: 47)
MKLPVRLLVLMFWIPASNSDIVMTQSPLSLPVTPGEPASISCRSSQ
SLVHSDGNTYLHWYLQKPGQSPQLLIYKVSNRFSGVPDRFSGSGSG
TDFTLKISRVEAEDVGVYYCSQSTHVPWTFGGGTKVEIKRT;

(SEQ ID NO: 48)
MSVPTQVLGLLLLWLTDARCDIVMTQSPLSLPVTPGEPASISCRSS
QSLVHSDGNTYLHWYLQKPGQSPQLLIYKVSNRFSGVPDRFSGSGS
GTDFTLKISRVEAEDVGVYYCSQSTHVPWTFGGGTKVEIKRT;

or a variant thereof having one or more conservative amino acid substitutions.

Additionally or alternatively, in another aspect, the present disclosure provides an isolated antibody comprising a light chain immunoglobulin variable domain and a light chain immunoglobulin constant domain. By way of example, but not by way of limitation, in some embodiments, the light chain immunoglobulin constant domain has an amino acid sequence of:

(SEQ ID NO: 49)
VAAPSVFIFPPSDEQLKSGTASVVCLLNNFYPREAKVQWKVDNA
LQSGNSQESVTEQDSKDSTYSLSSTLTLSKADYEKHKVYACEVT
HQGLSSPVTKSFNRGEC.

By way of example, but not by way of limitation, in some embodiments, the isolated antibody comprising a light chain immunoglobulin variable domain and a light chain immunoglobulin constant domain has an amino acid sequence selected from (the light chain immunoglobulin constant domain is bold):

(SEQ ID NO: 50)
DVVMTQTPLSLPVSLGDQASISCRSSQSLVHSDGNTYLHWYLQK
PGQSPKLLIYKVSNRFSGVPDRFSGSGSGTDFTLKISRLEAEDL
GVYFCSQSTHVPWTFGGGTKLEIKVAAPSVFIFPPSDEQLKSGT
ASVVCLLNNFYPREAKVQWKVDNALQSGNSQESVTEQDSKDSTY
SLSSTLTLSKADYEKHKVYACEVTHQGLSSPVTKSFNRGEC.

(SEQ ID NO: 51)
DIVMTQSPLSLPVTPGEPASISCRSSQSLVHSDGNTYLHWYLQ
KPGQSPQLLIYKVSNRFSGVPDRFSGSGSGTDFTLKISRVEAE
DVGVYYCSQSTHVPWTFGGGTKVEIKRTVAAPSVFIFPPSDEQ

-continued

LKSGTASVVCLLNNFYPREAKVQWKVDNALQSGNSQESVTEQD
SKDSTYSLSSTLTLSKADYEKHKVYACEVTHQGLSSPVTKSFN
RGEC;

or a variant thereof having one or more conservative amino acid substitutions.

Additionally or alternatively, in another aspect, the present disclosure provides an isolated antibody comprising a light chain immunoglobulin variable domain, wherein the light chain immunoglobulin variable domain includes a signal sequence and a light chain immunoglobulin variable domain amino acid sequence, and a light chain immunoglobulin constant domain. By way of example, but not by way of limitation, in some embodiments, the isolated antibody comprising a light chain immunoglobulin variable domain, wherein the light chain immunoglobulin variable domain includes a signal sequence and a light chain immunoglobulin variable domain amino acid sequence, and a light chain immunoglobulin constant domain has an amino acid sequence selected from (the signal sequence is underlined and the light chain immunoglobulin constant domain is bold):

(SEQ ID NO: 52)
MKLPVRLLVLMFWIPASNSDVVMTQTPLSLPVSLGDQASISCR
SSQSLVHSDGNTYLHWYLQKPGQSPKLLIYKVSNRFSGVPDRF
SGSGSGTDFTLKISRLEAEDLGVYFCSQSTHVPWTFGGGTKLE
IKVAAPSVFIFPPSDEQLKSGTASVVCLLNNFYPREAKVQWKV
DNALQSGNSQESVTEQDSKDSTYSLSSTLTLSKADYEKHKVYA
CEVTHQGLSSPVTKSFNRGEC;

(SEQ ID NO: 53)
MSVPTQVLGLLLLWLTDARCDVVMTQTPLSLPVSLGDQASISC
RSSQSLVHSDGNTYLHWYLQKPGQSPKLLIYKVSNRFSGVPDR
FSGSGSGTDFTLKISRLEAEDLGVYFCSQSTHVPWTFGGGTKL
EIKVAAPSVFIFPPSDEQLKSGTASVVCLLNNFYPREAKVQWK
VDNALQSGNSQESVTEQDSKDSTYSLSSTLTLSKADYEKHKVY
ACEVTHQGLSSPVTKSFNRGEC;

(SEQ ID NO: 54)
MKLPVRLLVLMFWIPASNSDIVMTQSPLSLPVTPGEPASISCRS
SQSLVHSDGNTYLHWYLQKPGQSPQLLIYKVSNRFSGVPDRFSG
SGSGTDFTLKISRVEAEDVGVYYCSQSTHVPWTFGGGTKVEIKR
TVAAPSVFIFPPSDEQLKSGTASVVCLLNNFYPREAKVQWKVDN
ALQSGNSQESVTEQDSKDSTYSLSSTLTLSKADYEKHKVYACEV
THQGLSSPVTKSFNRGEC;

(SEQ ID NO: 55)
MSVPTQVLGLLLLWLTDARCDIVMTQSPLSLPVTPGEPASISCR
HSSQSLVHSDGNTYLWYLQKPGQSPQLLIYKVSNRFSGVPDRFS
GSGSGTDFTLKISRVEAEDVGVYYCSQSTHVPWTFGGGTKVEIK

-continued

RTVAAPSVFIFPPSDEQLKSGTASVVCLLNNFYPREAKVQWKVD

NALQSGNSQESVTEQDSKDSTYSLSSTLTLSKADYEKHKVYACE

VTHQGLSSPVTKSFNRGEC;

or a variant thereof having one or more conservative amino acid substitutions.

In some embodiments, the isolated antibodies of the present technology comprise at least one heavy chain that comprises an amino acid sequence selected from the group consisting of SEQ ID NOs: 1-4, 7-14, 17-40 and 132-133. In some embodiments, the isolated antibodies of the present technology comprise at least one light chain that comprises an amino acid sequence selected from the group consisting of SEQ ID NOs: 41-42, 45-48, 50-54, and 55. In some embodiments, the isolated antibodies of the present technology comprise at least one heavy chain that comprises an amino acid sequence selected from the group consisting of SEQ ID NOs: 1-4, 7-14, 17-40 and 132-133 and at least one light chain that comprises an amino acid sequence selected from the group consisting of SEQ ID NOs: 41-42, 45-48, 50-54, and 55.

In some embodiments, the heavy chain and light chain immunoglobulin variable domain sequences form an antigen binding site that binds to an epitope of human cis-pT231-tau protein comprising the amino acid sequence KVAVVRTPPKSPS (SEQ ID NO: 56) or a mimetic thereof.

In some embodiments of the antibodies, the heavy chain and light chain immunoglobulin variable domain sequences are components of the same polypeptide chain. In some embodiments of the antibodies, the heavy chain and light chain immunoglobulin variable domain sequences are components of different polypeptide chains. In certain embodiments, the antibody is a full-length antibody.

In another aspect, the present disclosure provides an antigen binding fragment of the antibodies disclosed herein, wherein the antigen binding fragment is selected from the group consisting of Fab, F (ab)'2, Fab', scFv, and Fv.

In some embodiments, the anti-cis-pT231-tau antibodies of the present technology bind specifically to cis-pT231-tau protein. In some embodiments, the antibodies of the present technology bind cis-pT231-tau protein with a dissociation constant ($K_D$) of less than $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M. In certain embodiments, the antibodies are monoclonal antibodies, chimeric antibodies, or humanized antibodies. In some embodiments, the antibodies comprise a human antibody framework region.

Anti-cis-pT231-tau antibodies within the scope of the present technology include, e.g., but are not limited to, monoclonal, chimeric, humanized, and diabodies that specifically bind the target polypeptide, a homolog, derivative or a fragment thereof. Antibodies useful for the methods disclosed herein may comprise an Fc domain of any isotype, e.g., but are not limited to, IgG (including IgG1, IgG2, IgG3, and IgG4), IgA (including IgA1 and IgA2), IgD, IgE, or IgM, and IgY. Non-limiting examples of constant region sequences include:

Human IgD constant region,
Uniprot: P01880

SEQ ID NO: 134

APTKAPDVFPIISGCRHPKDNSPVVLACLITGYHP

TSVTVTWYMGTQSQPQRTFPEIQRRDSYYMTSSQL

-continued

STPLQQWRQGEYKCVVQHTASKSKKEIFRWPESPK

AQASSVPTAQPQAEGSLAKATTAPATTRNTGRGGE

EKKKEKEKEEQEERETKTPECPSHTQPLGVYLLTP

AVQDLWLRDKATFTCFVVGSDLKDAHLTWEVAGKV

PTGGVEEGLLERHSNGSQSQHSRLTLPRSLWNAGT

SVTCTLNHPSLPPQRLMALREPAAQAPVKLSLNLL

ASSDPPEAASWLLCEVSGFSPPNILLMWLEDQREV

NTSGFAPARPPPQPGSTTFWAWSVLRVPAPPSPQP

ATYTCVVSHEDSRTLLNASRSLEVSYVTDHGPMK

Human IgG1 constant region,
Uniprot: P01857

SEQ ID NO: 135

ASTKGPSVFPLAPSSKSTSGGTAALGCLVKDYFPE

PVTVSWNSGALTSGVHTFPAVLQSSGLYSLSSVVT

VPSSSLGTQTYICNVNHKPSNTKVDKKVEPKSCDK

THTCPPCPAPELLGGPSVFLFPPKPKDTLMISRTP

EVTCVVVDVSHEDPEVKFNWYVDGVEVHNAKTKPR

EEQYNSTYRVVSVLTVLHQDWLNGKEYKCKVSNKA

LPAPIEKTISKAKGQPREPQVYTLPPSRDELTKNQ

VSLTCLVKGFYPSDIAVEWESNGQPENNYKTTPPV

LDSDGSFFLYSKLTVDKSRWQQGNVFSCSVMHEAL

HNHYTQKSLSLSPGK

Human IgG2 constant region,
Uniprot: P01859

SEQ ID NO: 136

ASTKGPSVFPLAPCSRSTSESTAALGCLVKDYFPE

PVTVSWNSGALTSGVHTFPAVLQSSGLYSLSSVVT

VPSSNFGTQTYTCNVDHKPSNTKVDKTVERKCCVE

CPPCPAPPVAGPSVFLFPPKPKDTLMISRTPEVTC

VVVDVSHEDPEVQFNWYVDGVEVHNAKTKPREEQF

NSTFRVVSVLTVVHQDWLNGKEYKCKVSNKGLPAP

IEKTISKTKGQPREPQVYTLPPSREEMTKNQVSLT

CLVKGFYPSDISVEWESNGQPENNYKTTPPMLDSD

GSFFLYSKLTVDKSRWQQGNVFSCSVMHEALHNHY

TQKSLSLSPGK

Human IgG3 constant region,
Uniprot: P01860

SEQ ID NO: 137

ASTKGPSVFPLAPCSRSTSGGTAALGCLVKDYFPE

PVTVSWNSGALTSGVHTFPAVLQSSGLYSLSSVVT

VPSSSLGTQTYTCNVNHKPSNTKVDKRVELKTPLG

DTTHTCPRCPEPKSCDTPPPCPRCPEPKSCDTPPP

CPRCPEPKSCDTPPPCPRCPAPELLGGPSVFLFPP

KPKDTLMISRTPEVTCVVVDVSHEDPEVQFKWYVD

GVEVHNAKTKPREEQYNSTFRVVSVLTVLHQDWLN

-continued

GKEYKCKVSNKALPAPIEKTISKTKGQPREPQVYT

LPPSREEMTKNQVSLTCLVKGFYPSDIAVEWESSG

QPENNYNTTPPMLDSDGSFFLYSKLTVDKSRWQQG

NIFSCSVMHEALHNRFTQKSLSLSPGK

Human IgM constant region,
Uniprot: P01871

SEQ ID NO: 138

GSASAPTLFPLVSCENSPSDTSSVAVGCLAQDFLP

DSITLSWKYKNNSDISSTRGFPSVLRGGKYAATSQ

VLLPSKDVMQGTDEHVVCKVQHPNGNKEKNVPLPV

IAELPPKVSVFVPPRDGFFGNPRKSKLICQATGFS

PRQIQVSWLREGKQVGSGVTTDQVQAEAKESGPTT

YKVTSTLTIKESDWLGQSMFTCRVDHRGLTFQQNA

SSMCVPDQDTAIRVFAIPPSFASIFLTKSTKLTCL

VTDLTTYDSVTISWTRQNGEAVKTHTNISESHPNA

TFSAVGEASICEDDWNSGERFTCTVTHTDLPSPLK

QTISRPKGVALHRPDVYLLPPAREQLNLRESATIT

CLVTGFSPADVFVQWMQRGQPLSPEKYVTSAPMPE

PQAPGRYFAHSILTVSEEEWNTGETYTCVAHEALP

NRVTERTVDKSTGKPTLYNVSLVMSDTAGTCY

Human IgG4 constant region,
Uniprot: P01861

SEQ ID NO: 139

ASTKGPSVFPLAPCSRSTSESTAALGCLVKDYFPE

PVTVSWNSGALTSGVHTFPAVLQSSGLYSLSSVVT

VPSSSLGTKTYTCNVDHKPSNTKVDKRVESKYGPP

CPSCPAPEFLGGPSVFLFPPKPKDTLMISRTPEVT

CVVVDVSQEDPEVQFNWYVDGVEVHNAKTKPREEQ

FNSTYRVVSVLTVLHQDWLNGKEYKCKVSNKGLPS

SIEKTISKAKGQPREPQVYTLPPSQEEMTKNQVSL

TCLVKGFYPSDIAVEWESNGQPENNYKTTPPVLDS

DGSFFLYSRLTVDKSRWQEGNVFSCSVMHEALHNH

YTQKSLSLSLGK

Human IgA1 constant region,
Uniprot: P01876

SEQ ID NO: 140

ASPTSPKVFPLSLCSTQPDGNVVIACLVQGFFPQE

PLSVTWSESGQGVTARNFPPSQDASGDLYTTSSQL

TLPATQCLAGKSVTCHVKHYTNPSQDVTVPCPVPS

TPPTPSPSTPPTPSPSCCHPRLSLHRPALEDLLLG

SEANLTCTLTGLRDASGVTFTWTPSSGKSAVQGPP

ERDLCGCYSVSSVLPGCAEPWNHGKTFTCTAAYPE

SKTPLTATLSKSGNTFRPEVHLLPPPSEELALNEL

VTLTCLARGFSPKDVLVRWLQGSQELPREKYLTWA

SRQEPSQGTTTFAVTSILRVAAEDWKKGDTFSCMV

-continued

GHEALPLAFTQKTIDRLAGKPTHVNVSVVMAEVDG

TCY

Human IgA2 constant region,
Uniprot: P01877

SEQ ID NO: 141

ASPTSPKVFPLSLDSTPQDGNVVVACLVQGFFPQE

PLSVTWSESGQNVTARNFPPSQDASGDLYTTSSQL

TLPATQCPDGKSVTCHVKHYTNPSQDVTVPCPVPP

PPPCCHPRLSLHRPALEDLLLGSEANLTCTLTGLR

DASGATFTWTPSSGKSAVQGPPERDLCGCYSVSSV

LPGCAQPWNHGETFTCTAAHPELKTPLTANITKSG

NTFRPEVHLLPPPSEELALNELVTLTCLARGFSPK

DVLVRWLQGSQELPREKYLTWASRQEPSQGTTTFA

VTSILRVAAEDWKKGDTFSCMVGHEALPLAFTQKT

IDRMAGKPTHVNVSVVMAEVDGTCY

Human Ig kappa constant region,
Uniprot: P01834

SEQ ID NO: 142

TVAAPSVFIFPPSDEQLKSGTASVVCLLNNFYPRE

AKVQWKVDNALQSGNSQESVTEQDSKDSTYSLSST

LTLSKADYEKHKVYACEVTHQGLSSPVTKSFNRGE

C

In some embodiments, the anti-cis-pT231-tau antibodies of the present technology comprise a heavy chain constant region that is at least 80%, at least 85%, at least 90%, at least 95%, at least 99%, or is 100% identical to SEQ ID NOS: 134-140 or 141. Additionally or alternatively, in some embodiments, the anti-cis-pT231-tau antibodies of the present technology comprise a light chain constant region that is at least 80%, at least 85%, at least 90%, at least 95%, at least 99%, or is 100% identical to SEQ ID NO: 142.

The heavy chain (HC) and light chain (LC) immunoglobulin variable domain sequences of the HuPT-113A, HuPT-113B, HuPT-113C and HuPT-113D antibodies (including leader sequences) are provided below:

| Antibody | HC variable domain | LC variable domain |
|---|---|---|
| HuPT-113A | SEQ ID NO: 7 | SEQ ID NO: 45 |
| HuPT-113B | SEQ ID NO: 8 | SEQ ID NO: 45 |
| HuPT-113C | SEQ ID NO: 9 | SEQ ID NO: 45 |
| HuPT-113D | SEQ ID NO: 10 | SEQ ID NO: 45 |

The heavy chain (HC) and light chain (LC) immunoglobulin sequences of the HuPT-113D IgG1-AA (II), HuPT-113D IgG4 (II), and HuPT-113D IgG1 (II) antibodies are provided below:

| Antibody | HC | LC |
|---|---|---|
| HuPT-113D IgG1-AA (II) | SEQ ID NO: 39 | SEQ ID NO: 55 |
| HuPT-113D IgG4 (II) | SEQ ID NO: 40 | SEQ ID NO: 55 |
| HuPT-113D IgG1 (II) | SEQ ID NO: 132 | SEQ ID NO: 55 |

In some embodiments of the antibodies, the HC variable domain sequence comprises a variable domain sequence of HuPT-113A and the LC variable domain sequence comprises a variable domain sequence of HuPT-113A. In certain embodiments, the antibodies further comprise a HC constant region selected from the group consisting of IgG1, IgG2, IgG3, IgG4, IgA1, IgA2, IgD, IgE, and IgM. In certain embodiments, the antibodies contain an IgG1 constant region that comprises amino acid substitutions from Leu to Ala at positions 234 and 235.

In some embodiments of the antibodies, the HC variable domain sequence comprises a variable domain sequence of HuPT-113B and the LC variable domain sequence comprises a variable domain sequence of HuPT-113B. In certain embodiments, the antibodies further comprise a HC constant region selected from the group consisting of IgG1, IgG2, IgG3, IgG4, IgA1, IgA2, IgD, IgE, and IgM. In certain embodiments, the antibodies contain an IgG1 constant region that comprises amino acid substitutions from Leu to Ala at positions 234 and 235.

In some embodiments of the antibodies, the HC variable domain sequence comprises a variable domain sequence of HuPT-113C and the LC variable domain sequence comprises a variable domain sequence of HuPT-113C. In certain embodiments, the antibodies further comprise a HC constant region selected from the group consisting of IgG1, IgG2, IgG3, IgG4, IgA1, IgA2, IgD, IgE, and IgM. In certain embodiments, the antibodies contain an IgG1 constant region that comprises amino acid substitutions from Leu to Ala at positions 234 and 235.

In some embodiments of the antibodies, the HC variable domain sequence comprises a variable domain sequence of HuPT-113D and the LC variable domain sequence comprises a variable domain sequence of HuPT-113D. In certain embodiments, the antibodies further comprise a HC constant region selected from the group consisting of IgG1, IgG2, IgG3, IgG4, IgA1, IgA2, IgD, IgE, and IgM. In certain embodiments, the antibodies contain an IgG1 constant region that comprises amino acid substitutions from Leu to Ala at positions 234 and 235.

In certain embodiments, the isolated antibody includes one or more of the following characteristics: (a) the light chain immunoglobulin variable domain sequence is at least 85% identical to SEQ ID NO: 45; and/or (b) the heavy chain immunoglobulin variable domain sequence is at least 85% identical to any one of SEQ ID NOs: 7-10. In another aspect, one or more amino acid residues in the antibodies provided herein are substituted with another amino acid. The substitution may be a "conservative substitution" as defined herein.

In some aspects of the antibodies provided herein, the antibody contains structural modifications to facilitate rapid binding and cell uptake and/or slow release. In some aspects, the cis-pT231-tau antibody contains a deletion in the CH2 constant heavy chain region of the antibody to facilitate rapid binding and cell uptake and/or slow release. In some aspects, a Fab fragment is used to facilitate rapid binding and cell uptake and/or slow release. In some aspects, a F (ab)'2 fragment is used to facilitate rapid binding and cell uptake and/or slow release.

In some embodiments, the present technology provides a nucleic acid sequence encoding a cis-pT231-tau neutralizing antibody of the present technology or a fragment thereof. In some embodiments, the present technology provides a host cell expressing a nucleic acid sequence encoding a cis-pT231-tau neutralizing antibody of the present technology.

The antibodies of the present technology can be monospecific, bispecific, trispecific or of greater multispecificity. Multispecific antibodies can be specific for different epitopes of the cis-pT231-tau protein of the present technology or can be specific for both the cis-pT231-tau protein as well as for heterologous compositions, such as a heterologous polypeptide or solid support material. See, e.g., WO 93/17715; WO 92/08802; WO 91/00360; WO 92/05793; Tutt et al., *J. Immunol.* 147:60-69 (1991); U.S. Pat. Nos. 5,573,920, 4,474,893, 5,601,819, 4,714,681, 4,925,648; 6,106,835; Kostelny et al., *J. Immunol.* 148:1547-1553 (1992). In some embodiments, the antibodies are chimeric. In certain embodiments, the antibodies are humanized.

The antibodies of the present technology can further be recombinantly fused to a heterologous polypeptide at the N- or C-terminus or chemically conjugated (including covalently and non-covalently conjugations) to polypeptides or other compositions. For example, the antibodies of the present technology can be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

A. Methods of Preparing Anti-cis-pT231-tau Antibodies of the Present Technology

General Overview. Initially, a target polypeptide is chosen to which an antibody of the present technology can be raised. For example, an antibody may be raised against the full-length tau protein, or to a portion of the tau protein containing phosphorylated Threonine at position 231 (pT231). Techniques for generating antibodies directed to such target polypeptides are well known to those skilled in the art. Examples of such techniques include, for example, but are not limited to, those involving display libraries, xeno or human mice, hybridomas, and the like. Target polypeptides within the scope of the present technology include any polypeptide derived from tau protein containing pT231, which is capable of eliciting an immune response. The preparation of antibodies specific for cis-pT231-tau protein is illustrated in Examples 2-8.

It should be understood that recombinantly engineered antibodies and antibody fragments, e.g., antibody-related polypeptides, which are directed to cis-pT231-tau protein and fragments thereof are suitable for use in accordance with the present disclosure.

Anti-cis-pT231-tau antibodies that can be subjected to the techniques set forth herein include monoclonal and polyclonal antibodies, and antibody fragments such as Fab, Fab', $F(ab')_2$, Fd, scFv, diabodies, antibody light chains, antibody heavy chains and/or antibody fragments. Methods useful for the high yield production of antibody Fv-containing polypeptides, e.g., Fab' and $F(ab')_2$ antibody fragments have been described. See U.S. Pat. No. 5,648,237.

Generally, an antibody is obtained from an originating species. More particularly, the nucleic acid or amino acid sequence of the variable portion of the light chain, heavy chain or both, of an originating species antibody having specificity for a target polypeptide antigen is obtained. An originating species is any species, which was useful to generate the antibody of the present technology or library of antibodies, e.g., rat, mouse, rabbit, chicken, monkey, human, and the like.

Phage or phagemid display technologies are useful techniques to derive the antibodies of the present technology. Techniques for generating and cloning monoclonal antibodies are well known to those skilled in the art. Expression of sequences encoding antibodies of the present technology, can be carried out in *E. coli.*

Due to the degeneracy of nucleic acid coding sequences, other sequences which encode substantially the same amino acid sequences as those of the naturally occurring proteins may be used in the practice of the present technology These include, but are not limited to, nucleic acid sequences including all or portions of the nucleic acid sequences encoding the above polypeptides, which are altered by the substitution of different codons that encode a functionally equivalent amino acid residue within the sequence, thus producing a silent change. It is appreciated that the nucleotide sequence of an immunoglobulin according to the present technology tolerates sequence homology variations of up to 25% as calculated by standard methods ("Current Methods in Sequence Comparison and Analysis," Macromolecule Sequencing and Synthesis, Selected Methods and Applications, pp. 127-149, 1998, Alan R. Liss, Inc.) so long as such a variant forms an operative antibody which recognizes cis-pT231-tau proteins. For example, one or more amino acid residues within a polypeptide sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the present technology are proteins or fragments or derivatives thereof which are differentially modified during or after translation, e.g., by glycosylation, proteolytic cleavage, linkage to an antibody molecule or other cellular ligands, etc. Additionally, an immunoglobulin encoding nucleic acid sequence can be mutated in vitro or in vivo to create and/or destroy translation, initiation, and/or termination sequences or to create variations in coding regions and/or form new restriction endonuclease sites or destroy pre-existing ones, to facilitate further in vitro modification. Any technique for mutagenesis known in the art can be used, including but not limited to in vitro site directed mutagenesis, *J. Biol. Chem.* 253:6551, use of Tab linkers (Pharmacia), and the like.

Preparation of Polyclonal Antisera and Immunogens. Methods of generating antibodies or antibody fragments of the present technology typically include immunizing a subject (generally a non-human subject such as a mouse or rabbit) with a purified cis-pT231-tau protein or fragment thereof or with a cell expressing the cis-pT231-tau protein or fragment thereof. An appropriate immunogenic preparation can contain, e.g., a recombinantly-expressed cis-pT231-tau protein or a chemically-synthesized cis-pT231-tau peptide. The cis-conformation of pT231-tau protein, or a portion or fragment thereof, can be used as an immunogen to generate an anti-cis-pT231-tau antibody that binds to the cis-pT231-tau protein, or a portion or fragment thereof using standard techniques for polyclonal and monoclonal antibody preparation.

The full-length pT231-tau protein or fragments thereof, are useful as fragments as immunogens. In some embodiments, a pT231-tau fragment comprises at least eight amino acid residues of the amino acid sequence KVAVVRTPPK-SPS (SEQ ID NO: 56) or a mimetic thereof, and encompasses an epitope of the pT231-tau protein such that an antibody raised against the peptide forms a specific immune complex with cis-pT231-tau protein.

In some embodiments, the antigenic tau peptide containing pT231 comprises at least 5, 8, 10, 15, 20, or 30 amino acid residues. Longer antigenic peptides are sometimes desirable over shorter antigenic peptides, depending on use and according to methods well known to those skilled in the art. Multimers of a given epitope are sometimes more effective than a monomer.

If needed, the immunogenicity of the cis-pT231-tau protein (or fragment thereof) can be increased by fusion or conjugation to a hapten such as keyhole limpet hemocyanin (KLH) or ovalbumin (OVA). Many such haptens are known in the art. One can also combine the cis-pT231-tau protein with a conventional adjuvant such as Freund's complete or incomplete adjuvant to increase the subject's immune reaction to the polypeptide. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory compounds. These techniques are standard in the art.

In describing the present technology, immune responses may be described as either "primary" or "secondary" immune responses. A primary immune response, which is also described as a "protective" immune response, refers to an immune response produced in an individual as a result of some initial exposure (e.g., the initial "immunization") to a particular antigen, e.g., cis-pT231-tau protein. In some embodiments, the immunization can occur as a result of vaccinating the individual with a vaccine containing the antigen. For example, the vaccine can be a cis-pT231-tau vaccine comprising one or more cis-pT231-tau protein-derived antigens. A primary immune response can become weakened or attenuated over time and can even disappear or at least become so attenuated that it cannot be detected. Accordingly, the present technology also relates to a "secondary" immune response, which is also described here as a "memory immune response." The term secondary immune response refers to an immune response elicited in an individual after a primary immune response has already been produced.

Thus, a secondary immune response can be elicited, e.g., to enhance an existing immune response that has become weakened or attenuated, or to recreate a previous immune response that has either disappeared or can no longer be detected. The secondary or memory immune response can be either a humoral (antibody) response or a cellular response. A secondary or memory humoral response occurs upon stimulation of memory B cells that were generated at the first presentation of the antigen. Delayed type hypersensitivity (DTH) reactions are a type of cellular secondary or memory immune response that are mediated by $CD4^+$ T cells. A first exposure to an antigen primes the immune system and additional exposure(s) results in a DTH.

Following appropriate immunization, the anti-cis-pT231-tau antibody can be prepared from the subject's serum. If desired, the antibody molecules directed against the cis-pT231-tau protein can be isolated from the mammal (e.g., from the blood) and further purified by well-known techniques, such as polypeptide A chromatography to obtain the IgG fraction.

Monoclonal Antibody. In one embodiment of the present technology, the antibody is an anti-cis-pT231-tau monoclonal antibody. For example, in some embodiments, the anti-cis-pT231-tau monoclonal antibody may be a human or a mouse anti-cis-pT231-tau monoclonal antibody. For preparation of monoclonal antibodies directed towards the cis-conformation of pT231-tau protein, or derivatives, fragments, analogs or homologs thereof, any technique that provides for the production of antibody molecules by continuous cell line culture can be utilized. Such techniques include, but are not limited to, the hybridoma technique (See, e.g., Kohler & Milstein, 1975. *Nature* 256:495-497); the trioma technique; the human B-cell hybridoma technique (See, e.g., Kozbor, et al., 1983. *Immunol. Today* 4:72) and the EBV hybridoma technique to produce human monoclonal antibodies (See, e.g., Cole, et al., 1985. In: MONOCLONAL ANTIBODIES AND CANCER THERAPY, Alan R. Liss, Inc., pp. 77-96). Human monoclonal antibodies can be utilized in the practice of the present technology and can be produced by using human hybridomas (See, e.g., Cote, et al., 1983. *Proc. Natl. Acad. Sci*. USA 80:2026-2030) or by transforming human B-cells with Epstein Barr Virus in vitro (See, e.g., Cole, et al., 1985. In: MONOCLONAL ANTIBODIES AND CANCER THERAPY, Alan R. Liss, Inc., pp. 77-96). For example, a population of nucleic acids that encode regions of antibodies can be isolated. PCR utilizing primers derived from sequences encoding conserved regions of antibodies is used to amplify sequences encoding portions of antibodies from the population and then DNAs encoding antibodies or fragments thereof, such as variable domains, are reconstructed from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for an antigen or epitope present on the cis-conformation of the pT231-tau protein. Alternatively, hybridomas expressing anti-cis-pT231-tau monoclonal antibodies can be prepared by immunizing a subject and then isolating hybridomas from the subject's spleen using routine methods. See, e.g., Milstein et al., (Galfre and Milstein, *Methods Enzymol* (1981) 73:3-46). Screening the hybridomas using standard methods will produce monoclonal antibodies of varying specificity (i.e., for different epitopes) and affinity. A selected monoclonal antibody with the desired properties, e.g., cis-pT231-tau binding, can be used as expressed by the hybridoma, it can be bound to a molecule such as polyethylene glycol (PEG) to alter its properties, or a cDNA encoding it can be isolated, sequenced and manipulated in various ways. Synthetic dendromeric trees can be added to reactive amino acid side chains, e.g., lysine, to enhance the immunogenic properties of cis-pT231-tau protein. Also, CPG-dinucleotide techniques can be used to enhance the immunogenic properties of the cis-pT231-tau protein. Other manipulations include substituting or deleting particular amino acyl residues that contribute to instability of the antibody during storage or after administration to a subject, and affinity maturation techniques to improve affinity of the antibody of the cis-pT231-tau protein.

Hybridoma Technique. In some embodiments, the antibody of the present technology is an anti-cis-pT231-tau monoclonal antibody produced by a hybridoma, which includes a B cell obtained from a transgenic non-human animal, e.g., a transgenic mouse, having a genome comprising a human heavy chain transgene and a light chain transgene fused to an immortalized cell. Hybridoma techniques include those known in the art and taught in Harlow et al., *Antibodies: A Laboratory Manual* Cold Spring Harbor Laboratory, Cold Spring Harbor, NY, 349 (1988); Hammerling et al., *Monoclonal Antibodies And T-Cell Hybridomas,* 563-681 (1981). Other methods for producing hybridomas and monoclonal antibodies are well known to those of skill in the art.

Phage Display Technique. As noted above, the antibodies of the present technology can be produced through the application of recombinant DNA and phage display technology. For example, anti-cis-pT231-tau antibodies, can be prepared using various phage display methods known in the art. In phage display methods, functional antibody domains are displayed on the surface of a phage particle, which carries polynucleotide sequences encoding them. Phages with a desired binding property are selected from a repertoire or combinatorial antibody library (e.g., human or murine) by selecting directly with an antigen, typically an antigen bound or captured to a solid surface or bead. Phages used in these methods are typically filamentous phage including fd and M13 with Fab, Fv or disulfide stabilized Fv antibody domains that are recombinantly fused to either the phage gene III or gene VIII protein. In addition, methods can be adapted for the construction of Fab expression libraries (See, e.g., Huse, et al.,. *Science* 246:1275-1281, 1989) to allow rapid and effective identification of monoclonal Fab fragments with the desired specificity for a cis-pT231-tau polypeptide, e.g., a polypeptide or derivatives, fragments, analogs or homologs thereof. Other examples of phage display methods that can be used to make the antibodies of the present technology include those disclosed in Huston et al., *Proc. Natl. Acad. Sci U.S.A.,* 85:5879-5883, 1988; Chaudhary et al., *Proc. Natl. Acad. Sci U.S.A.,* 87:1066-1070, 1990; Brinkman et al., *J. Immunol. Methods* 182:41-50, 1995; Ames et al., *J. Immunol. Methods* 184:177-186, 1995; Kettleborough et al., *Eur. J. Immunol.* 24:952-958, 1994; Persic et al., *Gene* 187:9-18, 1997; Burton et al., *Advances in Immunology* 57:191-280, 1994; PCT/GB91/01134; WO 90/02809; WO 91/10737; WO 92/01047; WO 92/18619; WO 93/11236; WO 95/15982; WO 95/20401; WO 96/06213; WO 92/01047 (Medical Research Council et al.); WO 97/08320 (Morphosys); WO 92/01047 (CAT/MRC); WO 91/17271 (Affymax); and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743. Methods useful for displaying polypeptides on the surface of bacteriophage particles by attaching the polypeptides via disulfide bonds have been described by Lohning, U.S. Pat. No. 6,753,136. As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and $F(ab')_2$ fragments can also be employed using methods known in the art such as those disclosed in WO 92/22324; Mullinax et al., *BioTechniques* 12:864-869, 1992; and Sawai et al., *AJRI* 34:26-34, 1995; and Better et al., *Science* 240:1041-1043, 1988.

Generally, hybrid antibodies or hybrid antibody fragments that are cloned into a display vector can be selected against the appropriate antigen in order to identify variants that maintain good binding activity, because the antibody or antibody fragment will be present on the surface of the phage or phagemid particle. See, e.g., Barbas III et al., *Phage Display, A Laboratory Manual* (Cold Spring Harbor Laboratory Press, Cold Spring Harbor, N.Y., 2001). However, other vector formats could be used for this process, such as cloning the antibody fragment library into a lytic phage vector (modified T7 or Lambda Zap systems) for selection and/or screening.

Expression of Recombinant Anti-cis-pT231-tau antibodies. As noted above, the antibodies of the present technology can be produced through the application of recombinant DNA technology. Recombinant polynucleotide constructs encoding an anti-cis-pT231-tau antibody of the present technology typically include an expression control sequence operably-linked to the coding sequences of anti-cis-pT231-tau antibody chains, including naturally-associated or heterologous promoter regions. As such, another aspect of the technology includes vectors containing one or more nucleic acid sequences encoding an anti-cis-pT231-tau antibody of the present technology. For recombinant expression of one or more of the polypeptides of the present technology, the nucleic acid containing all or a portion of the nucleotide sequence encoding the anti-cis-pT231-tau antibody is inserted into an appropriate cloning vector, or an expression vector (i.e., a vector that contains the necessary elements for the transcription and translation of the inserted polypeptide coding sequence) by recombinant DNA techniques well known in the art and as detailed below. Methods for producing diverse populations of vectors have been described by Lerner et al., U.S. Pat. Nos. 6,291,160 and 6,680,192.

In general, expression vectors useful in recombinant DNA techniques are often in the form of plasmids. In the present disclosure, "plasmid" and "vector" can be used interchangeably as the plasmid is the most commonly used form of vector. However, the present technology is intended to include such other forms of expression vectors that are not technically plasmids, such as viral vectors (e.g., replication defective retroviruses, adenoviruses and adeno-associated viruses), which serve equivalent functions. Such viral vectors permit infection of a subject and expression of a construct in that subject. In some embodiments, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences encoding the anti-cis-pT231-tau antibody, and the collection and purification of the anti-cis-pT231-tau antibody, e.g., cross-reacting anti-cis-pT231-tau antibodies. See generally, U.S. 2002/0199213. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. Vectors can also encode signal peptide, e.g., pectate lyase, useful to direct the secretion of extracellular antibody fragments. See U.S. Pat. No. 5,576,195.

The recombinant expression vectors of the present technology comprise a nucleic acid encoding a protein with cis-pT231-tau binding properties in a form suitable for expression of the nucleic acid in a host cell, which means that the recombinant expression vectors include one or more regulatory sequences, selected on the basis of the host cells to be used for expression that is operably-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, e.g., in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc. Typical regulatory sequences useful as promoters of recombinant polypeptide expression (e.g., anti-cis-pT231-tau antibody), include, e.g., but are not limited to, promoters of 3-phosphoglycerate kinase and other glycolytic enzymes. Inducible yeast promoters include, among others, promoters from alcohol dehydrogenase, isocytochrome C, and enzymes responsible for maltose and galactose utilization. In one embodiment, a polynucleotide encoding an anti-cis-pT231-tau antibody of the present technology is operably-linked to an ara B promoter and expressible in a host cell. See U.S. Pat. No. 5,028,530. The expression vectors of the present technology can be introduced into host cells to thereby produce polypeptides or peptides, including fusion polypeptides, encoded by nucleic acids as described herein (e.g., anti-cis-pT231-tau antibody, etc.).

Another aspect of the present technology pertains to anti-cis-pT231-tau antibody-expressing host cells, which contain a nucleic acid encoding one or more anti-cis-pT231-tau antibodies. The recombinant expression vectors of the present technology can be designed for expression of an anti-cis-pT231-tau antibody in prokaryotic or eukaryotic cells. For example, an anti-cis-pT231-tau antibody can be expressed in bacterial cells such as *Escherichia coli*, insect cells (using baculovirus expression vectors), fungal cells, e.g., yeast, yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, e.g., using T7 promoter regulatory sequences and T7 polymerase. Methods useful for the preparation and screening of polypeptides having a predetermined property, e.g., anti-cis-pT231-tau antibody, via expression of stochastically generated polynucleotide sequences has been previously described. See U.S. Pat. Nos. 5,763,192; 5,723,323; 5,814,476; 5,817,483; 5,824,514; 5,976,862; 6,492,107; 6,569,641.

Expression of polypeptides in prokaryotes is most often carried out in *E. coli* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (i) to increase expression of recombinant polypeptide; (ii) to increase the solubility of the recombinant polypeptide; and (iii) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67:31-40), pMAL (New England Biolabs, Beverly, Mass.) and pRIT5 (Pharmacia, Piscataway, N.J.) that fuse glutathione S-transferase (GST), maltose E binding polypeptide, or polypeptide A, respectively, to the target recombinant polypeptide.

Examples of suitable inducible non-fusion *E. coli* expression vectors include pTrc (Amrann et al., (1988) *Gene* 69:301-315) and pET 11d (Studier et al., GENE EXPRESSION TECHNOLOGY: METHODS IN ENZYMOLOGY 185, Academic Press, San Diego, Calif. (1990)60-89). Methods for targeted assembly of distinct active peptide or protein domains to yield multifunctional polypeptides via polypeptide fusion has been described by Pack et al., U.S. Pat. Nos. 6,294,353; 6,692,935. One strategy to maximize recombinant polypeptide expression, e.g., an anti-cis-pT231-tau antibody, in *E. coli* is to express the polypeptide in host bacteria with an impaired capacity to proteolytically cleave the recombinant polypeptide. See, e.g., Gottesman, GENE EXPRESSION TECHNOLOGY: METHODS IN ENZYMOLOGY 185, Academic Press, San Diego, Calif. $(1990)_{119}$-128. Another strategy is to alter the nucleic acid sequence of the nucleic acid to be inserted into an expression vector so that the individual codons for each amino acid are those preferentially utilized in the expression host, e.g., *E. coli* (See, e.g., Wada, et al., 1992. *Nucl. Acids Res.* 20:2111-2118). Such alteration of nucleic acid sequences of the present technology can be carried out by standard DNA synthesis techniques.

In another embodiment, the anti-cis-pT231-tau antibody expression vector is a yeast expression vector. Examples of vectors for expression in yeast *Saccharomyces cerevisiae* include pYepSec1 (Baldari, et al., 1987. *EMBO J.* 6:229-234), pMFa (Kurjan and Herskowitz, *Cell* 30:933-943, 1982), pJRY88 (Schultz et al., *Gene* 54:113-123, 1987), pYES2 (Invitrogen Corporation, San Diego, Calif.), and picZ (Invitrogen Corp, San Diego, Calif.). Alternatively, an anti-cis-pT231-tau antibody can be expressed in insect cells using baculovirus expression vectors. Baculovirus vectors available for expression of polypeptides, e.g., anti-cis-pT231-tau antibody, in cultured insect cells (e.g., SF9 cells) include the pAc series (Smith, et al., *Mol. Cell. Biol.* 3:2156-2165, 1983) and the pVL series (Lucklow and Summers, 1989. *Virology* 170:31-39).

In yet another embodiment, a nucleic acid encoding an anti-cis-pT231-tau antibody of the present technology is expressed in mammalian cells using a mammalian expression vector. Examples of mammalian expression vectors include, e.g., but are not limited to, pCDM8 (Seed, *Nature* 329:840, 1987) and pMT2PC (Kaufman, et al., *EMBO J.* 6:187-195, 1987). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells that are useful for expression of the anti-cis-pT231-tau antibody of the present technology, see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid in a particular cell type (e.g., tissue-specific regulatory elements). Tissue-specific regulatory elements are known in the art. Non-limiting examples of suitable tissue-specific promoters include the albumin promoter (liver-specific; Pinkert, et al., *Genes Dev.* 1:268-277, 1987), lymphoid-specific promoters (Calame and Eaton, *Adv. Immunol.* 43:235-275, 1988), promoters of T cell receptors (Winoto and Baltimore, *EMBO J.* 8:729-733, 1989) and immunoglobulins (Banerji, et al., 1983. *Cell* 33:729-740; Queen and Baltimore, *Cell* 33:741-748, 1983.), neuron-specific promoters (e.g., the neurofilament promoter; Byrne and Ruddle, *Proc. Natl. Acad. Sci. USA* 86:5473-5477, 1989), pancreas-specific promoters (Edlund, et al., 1985. Science 230:912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, *Science* 249: 374-379, 1990) and the α-fetoprotein promoter (Campes and Tilghman, *Genes Dev.* 3:537-546, 1989).

Another aspect of the present methods pertains to host cells into which a recombinant expression vector of the present technology has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an anti-cis-pT231-tau antibody can be expressed in bacterial cells such as *E. coli*, insect cells, yeast or mammalian cells. Mammalian cells are a suitable host for expressing nucleotide segments encoding immunoglobulins or fragments thereof. See Winnacker, *From Genes To Clones*, (VCH Publishers, NY, 1987). A number of suitable host cell lines capable of secreting intact heterologous proteins have been developed in the art, and include Chinese hamster ovary (CHO) cell lines, various COS cell lines, HeLa cells, L cells and myeloma cell lines. In some embodiments, the cells are non-human. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Queen et al., *Immunol. Rev.* 89:49, 1986. Illustrative expression control sequences are promoters derived from endogenous genes, cytomegalovirus, SV40, adenovirus, bovine papillomavirus, and the like. Co et al., *J Immunol.* 148:1149, 1992. Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, electroporation, biolistics or viral-based transfection. Other methods used to transform mammalian cells include the use of polybrene, protoplast fusion, liposomes, electroporation, and microinjection (See generally, Sambrook et al., *Molecular Cloning*). Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N. Y., 1989), and other laboratory manuals. The vectors containing the DNA segments of interest can be transferred into the host cell by well-known methods, depending on the type of cellular host.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the anti-cis-pT231-tau antibody or can be introduced on a separate vector. Cells stably transfected with the introduced nucleic acid can be identified by drug selection (e.g., cells that have incorporated the selectable marker gene will survive, while the other cells die).

A host cell that includes an anti-cis-pT231-tau antibody of the present technology, such as a prokaryotic or eukaryotic host cell in culture, can be used to produce (i.e., express) recombinant anti-cis-pT231-tau antibody. In one embodiment, the method comprises culturing the host cell (into which a recombinant expression vector encoding the anti-cis-pT231-tau antibody has been introduced) in a suitable medium such that the anti-cis-pT231-tau antibody is produced. In another embodiment, the method further comprises the step of isolating the anti-cis-pT231-tau antibody from the medium or the host cell. Once expressed, collections of the anti-cis-pT231-tau antibody, e.g., the anti-cis-pT231-tau antibodies or the anti-cis-pT231-tau antibody-related polypeptides are purified from culture media and host cells. The anti-cis-pT231-tau antibody can be purified according to standard procedures of the art, including HPLC purification, column chromatography, gel electrophoresis and the like. In one embodiment, the anti-cis-pT231-tau antibody is produced in a host organism by the method of Boss et al., U.S. Pat. No. 4,816,397. Usually, anti-cis-pT231-tau antibody chains are expressed with signal sequences and are thus released to the culture media. However, if the anti-cis-pT231-tau antibody chains are not naturally secreted by host cells, the anti-cis-pT231-tau antibody chains can be released by treatment with mild detergent. Purification of recombinant polypeptides is well known in the art and includes ammonium sulfate precipitation, affinity chromatography purification technique, column chromatography, ion exchange purification technique, gel electrophoresis and the like (See generally Scopes, Protein Purification (Springer-Verlag, N.Y., 1982).

Polynucleotides encoding anti-cis-pT231-tau antibodies, e.g., the anti-cis-pT231-tau antibody coding sequences, can be incorporated in transgenes for introduction into the genome of a transgenic animal and subsequent expression in the milk of the transgenic animal. See, e.g., U.S. Pat. Nos. 5,741,957, 5,304,489, and 5,849,992. Suitable transgenes include coding sequences for light and/or heavy chains in operable linkage with a promoter and enhancer from a mammary gland specific gene, such as casein or β-lactoglobulin. For production of transgenic animals, transgenes can be microinjected into fertilized oocytes, or can be incorporated into the genome of embryonic stem cells, and the nuclei of such cells transferred into enucleated oocytes.

Single-Chain Antibodies. In one embodiment, the anti-cis-pT231-tau antibody of the present technology is a single-chain anti-cis-pT231-tau antibody. According to the present technology, techniques can be adapted for the production of single-chain antibodies specific to a cis-pT231-tau protein (See, e.g., U.S. Pat. No. 4,946,778). Examples of techniques, which can be used to produce single-chain Fvs, and antibodies of the present technology include those described in U.S. Pat. Nos. 4,946,778 and 5,258,498; Huston et al., *Methods in Enzymology,* 203:46-88, 1991; Shu, L. et al., *Proc. Natl. Acad. Sci. USA,* 90:7995-7999, 1993; and Skerra et al., *Science* 240:1038-1040, 1988.

Chimeric and Humanized Antibodies. In one embodiment, the anti-cis-pT231-tau antibody of the present technology is a chimeric anti-cis-pT231-tau antibody. In one embodiment, the anti-cis-pT231-tau antibody of the present technology is a humanized anti-cis-pT231-tau antibody. In one embodiment of the present technology, the donor and acceptor antibodies are monoclonal antibodies from different species. For example, the acceptor antibody is a human antibody (to minimize its antigenicity in a human), in which case the resulting CDR-grafted antibody is termed a "humanized" antibody.

Recombinant anti-cis-pT231-tau antibodies, such as chimeric and humanized monoclonal antibodies, comprising both human and non-human portions, can be made using standard recombinant DNA techniques, and are within the scope of the present technology. For some uses, including in vivo use of the anti-cis-pT231-tau antibody of the present technology in humans as well as use of these agents in in vitro detection assays, it is possible to use chimeric or humanized anti-cis-pT231-tau antibodies. Such chimeric and humanized monoclonal antibodies can be produced by recombinant DNA techniques known in the art. Such useful methods include, e.g., but are not limited to, methods described in International Application No. PCT/US86/02269; U.S. Pat. No. 5,225,539; European Patent No. 184187; European Patent No. 171496; European Patent No. 173494; PCT International Publication No. WO 86/01533; U.S. Pat. Nos. 4,816,567; 5,225,539; European Patent No. 125023; Better, et al., 1988. *Science* 240:1041-1043; Liu, et al., 1987. *Proc. Natl. Acad. Sci. USA* 84:3439-3443; Liu, et al., 1987. *J. Immunol.* 139:3521-3526; Sun, et al., 1987. *Proc. Natl. Acad. Sci. USA* 84:214-218; Nishimura, et al., 1987. *Cancer Res.* 47:999-1005; Wood, et al., 1985. *Nature* 314:446-449; Shaw, et al., 1988. *J. Natl. Cancer Inst.* 80:1553-1559; Morrison (1985) *Science* 229:1202-1207; Oi, et al. (1986) *BioTechniques* 4:214; Jones, et al., 1986. *Nature* 321:552-525; Verhoeyan, et al., 1988. *Science* 239:1534; Morrison, *Science* 229:1202, 1985; Oi et al., *BioTechniques* 4:214, 1986; Gillies et al., *J. Immunol. Methods,* 125:191-202, 1989; U.S. Pat. No. 5,807,715; and Beidler, et al., 1988. *J. Immunol.* 141:4053-4060. For example, antibodies can be humanized using a variety of techniques including CDR-grafting (EP 0 239 400; WO 91/09967; U.S. Pat. Nos. 5,530,101; 5,585,089; 5,859,205; 6,248,516; EP460167), veneering or resurfacing (EP 0 592 106; EP 0 519 596; Padlan E. A., *Molecular Immunology,* 28:489-498, 1991; Studnicka et al., *Protein Engineering* 7:805-814, 1994; Roguska et al., PNAS 91:969-973, 1994), and chain shuffling (U.S. Pat. No. 5,565,332). In one embodiment, a cDNA encoding a murine anti-cis-pT231-tau monoclonal antibody is digested with a restriction enzyme selected specifically to remove the sequence encoding the Fc constant region, and the equivalent portion of a cDNA encoding a human Fc constant region is substituted (See Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 125,023; Better et al. (1988) *Science* 240:1041-1043; Liu et al. (1987) *Proc. Natl. Acad. Sci. USA* 84:3439-3443; Liu et al. (1987) *J Immunol* 139:3521-3526; Sun et al. (1987) *Proc. Natl. Acad. Sci. USA* 84:214-218; Nishimura et al. (1987) *Cancer Res* 47:999-1005; Wood et al. (1985) *Nature* 314:446-449; and Shaw et al. (1988) *J. Natl. Cancer Inst.* 80:1553-1559; U.S. Pat. Nos. 6,180,370; 6,300,064; 6,696,248; 6,706,484; 6,828,422.

In one embodiment, the present technology provides the construction of humanized anti-cis-pT231-tau antibodies that are unlikely to induce a human anti-mouse antibody (hereinafter referred to as "HAMA") response, while still having an effective antibody effector function. As used herein, the terms "human" and "humanized", in relation to antibodies, relate to any antibody, which is expected to elicit a therapeutically tolerable weak immunogenic response in a human subject. In one embodiment, the present technology provides for a humanized anti-cis-pT231-tau antibodies, heavy and light chain immunoglobulins.

CDR Antibodies. In some embodiments, the anti-cis-pT231-tau antibody of the present technology is an anti-cis-pT231-tau CDR antibody. Generally the donor and acceptor antibodies used to generate the anti-cis-pT231-tau CDR antibody are monoclonal antibodies from different species; typically the acceptor antibody is a human antibody (to minimize its antigenicity in a human), in which case the resulting CDR-grafted antibody is termed a "humanized" antibody. The graft may be of a single CDR (or even a portion of a single CDR) within a single VH or VL of the acceptor antibody, or can be of multiple CDRs (or portions thereof) within one or both of the VH and $V_L$. Frequently, all three CDRs in all variable domains of the acceptor antibody will be replaced with the corresponding donor CDRs, though one need replace only as many as necessary to permit adequate binding of the resulting CDR-grafted antibody to cis-pT231-tau protein. Methods for generating CDR-grafted and humanized antibodies are taught by Queen et al. U.S. Pat. Nos. 5,585,089; 5,693,761; 5,693,762; and Winter U.S. Pat. No. 5,225,539; and EP 0682040. Methods useful to prepare VH and VL polypeptides are taught by Winter et al., U.S. Pat. Nos. 4,816,397; 6,291,158; 6,291,159; 6,291,161; 6,545,142; EP 0368684; EP0451216; and EP0120694.

After selecting suitable framework region candidates from the same family and/or the same family member, either or both the heavy and light chain variable regions are produced by grafting the CDRs from the originating species into the hybrid framework regions. Assembly of hybrid antibodies or hybrid antibody fragments having hybrid variable chain regions with regard to either of the above aspects can be accomplished using conventional methods known to those skilled in the art. For example, DNA sequences encoding the hybrid variable domains described herein (i.e., frameworks based on the target species and CDRs from the originating species) can be produced by oligonucleotide synthesis and/or PCR. The nucleic acid encoding CDR regions can also be isolated from the originating species antibodies using suitable restriction enzymes and ligated into the target species framework by ligating with suitable ligation enzymes. Alternatively, the framework regions of the variable chains of the originating species antibody can be changed by site-directed mutagenesis.

Since the hybrids are constructed from choices among multiple candidates corresponding to each framework region, there exist many combinations of sequences, which are amenable to construction in accordance with the principles described herein. Accordingly, libraries of hybrids can be assembled having members with different combinations of individual framework regions. Such libraries can be electronic database collections of sequences or physical collections of hybrids.

This process typically does not alter the acceptor antibody's FRs flanking the grafted CDRs. However, one skilled in the art can sometimes improve antigen binding affinity of the resulting anti-cis-pT231-tau CDR-grafted antibody by replacing certain residues of a given FR to make the FR more similar to the corresponding FR of the donor antibody. Suitable locations of the substitutions include amino acid residues adjacent to the CDR, or which are capable of interacting with a CDR (See, e.g., U.S. Pat. No. 5,585,089, especially columns 12-16). Or one skilled in the art can start with the donor FR and modify it to be more similar to the acceptor FR or a human consensus FR. Techniques for making these modifications are known in the art. Particularly if the resulting FR fits a human consensus FR for that position, or is at least 90% or more identical to such a consensus FR, doing so may not increase the antigenicity of the resulting modified anti-cis-pT231-tau CDR-grafted antibody significantly compared to the same antibody with a fully human FR.

Fusion Proteins. In one embodiment, the anti-cis-pT231-tau antibody of the present technology is a fusion protein. The anti-cis-pT231-tau antibodies of the present technology, when fused to a second protein, can be used as an antigenic tag. Examples of domains that can be fused to polypeptides include not only heterologous signal sequences, but also other heterologous functional regions. The fusion does not necessarily need to be direct, but can occur through linker sequences. Moreover, fusion proteins of the present technology can also be engineered to improve characteristics of the anti-cis-pT231-tau antibodies. For instance, a region of additional amino acids, particularly charged amino acids, can be added to the N-terminus of the anti-cis-pT231-tau antibody to improve stability and persistence during purification from the host cell or subsequent handling and storage. Also, peptide moieties can be added to an anti-cis-pT231-tau antibody to facilitate purification. Such regions can be removed prior to final preparation of the anti-cis-pT231-tau antibody. The addition of peptide moieties to facilitate handling of polypeptides are familiar and routine techniques in the art. The anti-cis-pT231-tau antibody of the present technology can be fused to marker sequences, such as a peptide, which facilitates purification of the fused polypeptide. In select embodiments, the marker amino acid sequence is a hexa-histidine peptide, such as the tag provided in a pQE vector (QIAGEN, Inc., Chatsworth, Calif), among others, many of which are commercially available. As described in Gentz et al., *Proc. Natl. Acad. Sci. USA* 86:821-824, 1989, for instance, hexa-histidine provides for convenient purification of the fusion protein. Another peptide tag useful for purification, the "HA" tag, corresponds to an epitope derived from the influenza hemagglutinin protein. Wilson et al., *Cell* 37:767, 1984.

Thus, any of these above fusion proteins can be engineered using the polynucleotides or the polypeptides of the present technology. Also, in some embodiments, the fusion proteins described herein show an increased half-life in vivo.

Fusion proteins having disulfide-linked dimeric structures (due to the IgG) can be more efficient in binding and neutralizing other molecules compared to the monomeric secreted protein or protein fragment alone. Fountoulakis et al., J. Biochem. 270:3958-3964, 1995.

Similarly, EP-A-O 464 533 (Canadian counterpart 2045869) discloses fusion proteins comprising various portions of constant region of immunoglobulin molecules together with another human protein or a fragment thereof. In many cases, the Fc part in a fusion protein is beneficial in therapy and diagnosis, and thus can result in, e.g., improved pharmacokinetic properties. See EP-A 0232 262. Alternatively, deleting the Fc part after the fusion protein has been expressed, detected, and purified, may be desired. For example, the Fc portion can hinder therapy and diagnosis if the fusion protein is used as an antigen for immunizations. In drug discovery, e.g., human proteins, such as hIL-5, have been fused with Fc portions for the purpose of high-throughput screening assays to identify antagonists of hIL-5. Bennett et al., *J. Molecular Recognition* 8:52-58, 1995; Johanson et al., *J. Biol. Chem.,* 270:9459-9471, 1995.

Labeled Anti-cis-pT231-tau antibodies. In one embodiment, the anti-cis-pT231-tau antibody of the present technology is coupled with a label moiety, i.e., detectable group. The particular label or detectable group conjugated to the anti-cis-pT231-tau antibody is not a critical aspect of the technology, so long as it does not significantly interfere with the specific binding of the anti-cis-pT231-tau antibody of the present technology to the cis-pT231-tau protein. The detectable group can be any material having a detectable physical or chemical property. Such detectable labels have been well-developed in the field of immunoassays and imaging. In general, almost any label useful in such methods can be applied to the present technology. Thus, a label is any composition detectable by spectroscopic, photochemical, biochemical, immunochemical, electrical, optical or chemical means. Labels useful in the practice of the present technology include magnetic beads (e.g., Dynabeads™), fluorescent dyes (e.g., fluorescein isothiocyanate, Texas red, rhodamine, and the like), radiolabels (e.g., $^{3}H$, $^{14}C$, $^{35}S$, $^{125}I$, $^{121}I$, $^{131}I$, $^{112}In$, $^{99}mTc$), other imaging agents such as microbubbles (for ultrasound imaging), $^{18}F$, $^{11}C$, $^{15}O$, (for Positron emission tomography), $^{99}mTC$, $^{111}In$ (for Single photon emission tomography), enzymes (e.g., horse radish peroxidase, alkaline phosphatase and others commonly used in an ELISA), and calorimetric labels such as colloidal gold or colored glass or plastic (e.g., polystyrene, polypropylene, latex, and the like) beads. Patents that describe the use of such labels include U.S. Pat. Nos. 3,817,837; 3,850,752; 3,939,350; 3,996,345; 4,277,437; 4,275,149; and 4,366,241, each incorporated herein by reference in their entirety and for all purposes. See also Handbook of Fluorescent Probes and Research Chemicals ($6^{th}$ Ed., Molecular Probes, Inc., Eugene OR.).

The label can be coupled directly or indirectly to the desired component of an assay according to methods well known in the art. As indicated above, a wide variety of labels can be used, with the choice of label depending on factors such as required sensitivity, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule, which is either inherently detectable or covalently bound to a signal system, such as a detectable enzyme, a fluorescent compound, or a chemiluminescent compound. A number of ligands and anti-ligands can be used. Where a ligand has a natural anti-ligand, e.g., biotin, thyroxine, and cortisol, it can be used in conjunction with the labeled, naturally-occurring anti-ligands. Alternatively, any haptenic or antigenic compound can be used in combination with an antibody, e.g., an anti-cis-pT231-tau antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds useful as labeling moieties, include, but are not limited to, e.g., fluorescein and its derivatives, rhodamine and its derivatives, dansyl, umbelliferone, and the like. Chemiluminescent compounds useful as labeling moieties, include, but are not limited to, e.g., luciferin, and 2,3-dihydrophthalazinediones, e.g., luminol. For a review of various labeling or signal-producing systems, which can be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally simple colorimetric labels can be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies, e.g., the anti-cis-pT231-tau antibodies. In this case, antigen-coated particles are agglutinated by samples comprising the target antibodies. In this format, none of the components need be labeled and the presence of the target antibody is detected by simple visual inspection.

B. Identifying and Characterizing the Anti-cis-pT231-tau Antibodies of the Present Technology Methods for identifying and/or screening the anti-cis-pT231-tau antibodies of the present technology. Methods useful to identify and screen antibodies against cis-pT231-tau polypeptides for those that possess the desired specificity to cis-pT231-tau protein include any immunologically-mediated techniques known within the art. Components of an immune response can be detected in vitro by various methods that are well known to those of ordinary skill in the art. For example, (1) cytotoxic T lymphocytes can be incubated with radioactively labeled target cells and the lysis of these target cells detected by the release of radioactivity; (2) helper T lymphocytes can be incubated with antigens and antigen presenting cells and the synthesis and secretion of cytokines measured by standard methods (Windhagen A et al., Immunity, 2:373-80, 1995); (3) antigen presenting cells can be incubated with whole protein antigen and the presentation of that antigen on MHC detected by either T lymphocyte activation assays or biophysical methods (Harding et al., Proc. Natl. Acad. Sci., 86:4230-4, 1989); (4) mast cells can be incubated with reagents that cross-link their Fc-epsilon receptors and histamine release measured by enzyme immunoassay (Siraganian et al., TIPS, 4:432-437, 1983); and (5) enzyme-linked immunosorbent assay (ELISA).

Similarly, products of an immune response in either a model organism (e.g., mouse) or a human subject can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., *Blood,* 72:1310-5, 1988); (3) the proliferation of peripheral blood mononuclear cells (PBMCs) in response to mitogens or mixed lymphocyte reaction can be measured using $^{3}$H-thymidine; (4) the phagocytic capacity of granulocytes, macrophages, and other phagocytes in PBMCs can be measured by placing PBMCs in wells together with labeled particles (Peters et al., *Blood,* 72:1310-5, 1988); and (5) the differentiation of immune system cells can be measured by labeling PBMCs with antibodies to CD molecules such as CD4 and CD8 and measuring the fraction of the PBMCs expressing these markers.

In one embodiment, anti-cis-pT231-tau antibodies of the present technology are selected using display of cis-pT231-tau peptides on the surface of replicable genetic packages. See, e.g., U.S. Pat. Nos. 5,514,548; 5,837,500; 5,871,907; 5,885,793; 5,969,108; 6,225,447; 6,291,650; 6,492,160; EP 585 287; EP 605522; EP 616640; EP 1024191; EP 589 877; EP 774 511; EP 844 306. Methods useful for producing/selecting a filamentous bacteriophage particle containing a phagemid genome encoding for a binding molecule with a desired specificity has been described. See, e.g., EP 774 511; U.S. Pat. Nos. 5,871,907; 5,969,108; 6,225,447; 6,291,650; 6,492,160.

In some embodiments, anti-cis-pT231-tau antibodies of the present technology are selected using display of cis-pT231-tau peptides on the surface of a yeast host cell. Methods useful for the isolation of scFv polypeptides by yeast surface display have been described by Kieke et al., *Protein Eng.* 1997 November; 10 (11): 1303-10.

In some embodiments, anti-cis-pT231-tau antibodies of the present technology are selected using ribosome display. Methods useful for identifying ligands in peptide libraries using ribosome display have been described by Mattheakis et al., *Proc. Natl. Acad. Sci. USA* 91:9022-26, 1994; and Hanes et al., *Proc. Natl. Acad. Sci. USA* 94:4937-42, 1997.

In certain embodiments, anti-cis-pT231-tau antibodies of the present technology are selected using tRNA display of cis-pT231-tau peptides. Methods useful for in vitro selection of ligands using tRNA display have been described by Merryman et al., *Chem. Biol.,* 9:741-46, 2002.

In one embodiment, anti-cis-pT231-tau antibodies of the present technology are selected using RNA display. Methods useful for selecting peptides and proteins using RNA display libraries have been described by Roberts et al. *Proc. Natl. Acad. Sci. USA,* 94:12297-302, 1997; and Nemoto et al., *FEBS Lett.,* 414:405-8, 1997. Methods useful for selecting peptides and proteins using unnatural RNA display libraries have been described by Frankel et al., *Curr. Opin. Struct. Biol.,* 13:506-12, 2003.

In some embodiments, anti-cis-pT231-tau antibodies of the present technology are expressed in the periplasm of gram negative bacteria and mixed with labeled cis-pT231-tau protein. See WO 02/34886. In clones expressing recombinant polypeptides with affinity for cis-pT231-tau protein, the concentration of the labeled cis-pT231-tau protein bound to the anti-cis-pT231-tau antibodies is increased and allows the cells to be isolated from the rest of the library as described in Harvey et al., *Proc. Natl. Acad. Sci.* 22:9193-98 2004 and U.S. Pat. Publication No. 2004/0058403.

After selection of the desired anti-cis-pT231-tau antibodies, it is contemplated that said antibodies can be produced in large volume by any technique known to those skilled in the art, e.g., prokaryotic or eukaryotic cell expression and the like. The anti-cis-pT231-tau antibodies which are, e.g., but not limited to, anti-cis-pT231-tau hybrid antibodies or fragments can be produced by using conventional techniques to construct an expression vector that encodes an antibody heavy chain in which the CDRs and, if necessary, a minimal portion of the variable region framework, that are required to retain original species antibody binding specificity (as engineered according to the techniques described herein) are derived from the originating species antibody and the remainder of the antibody is derived from a target species immunoglobulin which can be manipulated as described herein, thereby producing a vector for the expression of a hybrid antibody heavy chain.

Measurement of cis-pT231-tau Binding. In some embodiments, a cis-pT231-tau binding assay refers to an assay format wherein cis-pT231-tau protein and an anti-cis-pT231-tau antibody are mixed under conditions suitable for binding between the cis-pT231-tau protein and the anti-cis-pT231-tau antibody and assessing the amount of binding between the cis-pT231-tau protein and the anti-cis-pT231-tau antibody. The amount of binding is compared with a suitable control, which can be the amount of binding in the absence of the cis-pT231-tau protein, the amount of the binding in the presence of non-specific immunoglobulin composition, or both. The amount of binding can be assessed by any suitable method. Binding assay methods include, e.g., ELISA, radioimmnoassays, scintillation proximity assays, fluorescence energy transfer assays, liquid chromatography, membrane filtration assays, and the like. Biophysical assays for the direct measurement of cis-pT231-tau protein binding to anti-cis-pT231-tau antibody are, e.g., nuclear magnetic resonance, fluorescence, fluorescence polarization, surface plasmon resonance (BIACORE chips) and the like. Specific binding is determined by standard assays known in the art, e.g., radioligand binding assays, ELISA, FRET, immunoprecipitation, SPR, NMR (2D-NMR), mass spectroscopy and the like. If the specific binding of a candidate anti-cis-pT231-tau antibody is at least 1 percent greater than the binding observed in the absence of the candidate anti-cis-pT231-tau antibody, the candidate anti-cis-pT231-tau antibody is useful as an anti-cis-pT231-tau antibody of the present technology.

Measurement of cis-pT231-tau Neutralization. As used here, "cis-pT231-tau neutralization" refers to reduction of the activity and/or expression of cis-pT231-tau protein through the binding of an anti-cis-pT231-tau antibody. The capacity of anti-cis-pT231-tau antibodies of the present technology to neutralize cis-pT231-tau activity/expression may be assessed in vitro or in vivo using methods known in the art. See, e.g., WO 2014152157; Yanamandra et al., *Ann Clin Transl Neurol.* 2 (3): 278-288 (2015).

II. Uses of the Anti-Cis-pT231-Tau Antibodies of the Present Technology

General. The anti-cis-pT231-tau antibodies of the present technology are useful in methods known in the art relating to the localization and/or quantitation of a cis-pT231-tau protein (e.g., for use in measuring levels of the cis-pT231-tau protein within appropriate the like). Antibodies of the present technology are useful to isolate a cis-pT231-tau protein by standard techniques, such as affinity chromatography or immunoprecipitation. An anti-cis-pT231-tau antibody of the present technology can facilitate the purification of natural immunoreactive cis-pT231-tau proteins from biological samples, e.g., mammalian sera or cells as well as recombinantly-produced immunoreactive cis-pT231-tau proteins expressed in a host system. Moreover, anti-cis-pT231-tau antibodies can be used to detect an immunoreactive cis-pT231-tau protein (e.g., in plasma, a cellular lysate or cell supernatant) in order to evaluate the abundance and pattern of expression of the immunoreactive polypeptide. The anti-cis-pT231-tau antibodies of the present technology can be used diagnostically to monitor immunoreactive cis-pT231-tau protein levels in tissue as part of a clinical testing procedure, e.g., to determine the efficacy of a given treatment regimen. As noted above, the detection can be facilitated by coupling (i.e., physically linking) the anti-cis-pT231-tau antibodies of the present technology to a detectable substance.

Detection of Cis-pT231-tau protein. An exemplary method for detecting the presence or absence of an immunoreactive cis-pT231-tau protein in a biological sample involves obtaining a biological sample from a test subject and contacting the biological sample with an anti-cis-pT231-tau antibody of the present technology capable of detecting an immunoreactive cis-pT231-tau protein such that the presence of an immunoreactive cis-pT231-tau protein is detected in the biological sample. Detection may be accomplished by means of a detectable label attached to the antibody.

The term "labeled" with regard to the anti-cis-pT231-tau antibody is intended to encompass direct labeling of the antibody by coupling (i.e., physically linking) a detectable substance to the antibody, as well as indirect labeling of the antibody by reactivity with another compound that is directly labeled, such as a secondary antibody. Examples of indirect labeling include detection of a primary antibody using a fluorescently-labeled secondary antibody and end-labeling of a DNA probe with biotin such that it can be detected with fluorescently-labeled streptavidin.

The detection method of the present technology can be used to detect an immunoreactive cis-pT231-tau protein in a biological sample in vitro as well as in vivo. In vitro techniques for detection of an immunoreactive cis-pT231-tau protein include enzyme linked immunosorbent assays (ELISAs), Western blots, immunoprecipitations, radioimmunoassay, and immunofluorescence. Furthermore, in vivo techniques for detection of an immunoreactive cis-pT231-tau protein include introducing into a subject a labeled anti-cis-pT231-tau antibody. For example, the anti-cis-pT231-tau antibody can be labeled with a radioactive marker whose presence and location in a subject can be detected by standard imaging techniques. In one embodiment, the biological sample contains cis-pT231-tau protein molecules from the test subject.

Immunoassay and Imaging. An anti-cis-pT231-tau antibody of the present technology can be used to assay immunoreactive cis-pT231-tau protein levels in a biological sample (e.g., human plasma) using antibody-based techniques. For example, protein expression in tissues can be studied with classical immunohistological methods. Jalkanen, M. et al., *J. Cell. Biol.* 101:976-985, 1985; Jalkanen, M. et al., *J. Cell. Biol.* 105:3087-3096, 1987. Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes or other radioactive agent, such as iodine ($^{125}I$, $^{121}I$, $^{131}I$), carbon ($^{14}C$), sulfur ($^{35}S$), tritium ($^{3}H$), indium ($^{112}In$), and technetium ($^{99}mTc$), and fluorescent labels, such as fluorescein, rhodamine, and green fluorescent protein (GFP), as well as biotin.

In addition to assaying immunoreactive cis-pT231-tau protein levels in a biological sample, anti-cis-pT231-tau antibodies of the present technology may be used for in vivo imaging of cis-pT231-tau. Antibodies useful for this method include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the anti-cis-pT231-tau antibodies by labeling of nutrients for the relevant scFv clone.

An anti-cis-pT231-tau antibody which has been labeled with an appropriate detectable imaging moiety, such as a radioisotope (e.g., $^{131}I$, $^{112}In$, $^{99}mTc$), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}mTc$. The labeled anti-cis-pT231-tau antibody will then accumulate at the location of cells, which contain the specific target polypeptide. For example, labeled anti-cis-pT231-tau antibodies of the present technology will accumulate within the subject in cells and tissues in which the cis-pT231-tau protein has localized.

Thus, the present technology provides a diagnostic method of a medical condition, which involves: (a) assaying the expression of immunoreactive cis-pT231-tau protein by measuring binding of an anti-cis-pT231-tau antibody of the present technology in cells or body fluid of an individual; (b) comparing the amount of immunoreactive cis-pT231-tau protein present in the sample with a standard reference, wherein an increase or decrease in immunoreactive cis-pT231-tau protein levels compared to the standard is indicative of a medical condition.

Affinity Purification. The anti-cis-pT231-tau antibodies of the present technology may be used to purify immunoreactive cis-pT231-tau protein from a sample. In some embodiments, the antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10 (1986); Jacoby et al., *Meth. Enzym.* 34 Academic Press, N.Y. (1974)).

The simplest method to bind the antigen to the antibody-support matrix is to collect the beads in a column and pass the antigen solution down the column. The efficiency of this method depends on the contact time between the immobilized antibody and the antigen, which can be extended by using low flow rates. The immobilized antibody captures the antigen as it flows past. Alternatively, an antigen can be contacted with the antibody-support matrix by mixing the antigen solution with the support (e.g., beads) and rotating or rocking the slurry, allowing maximum contact between the antigen and the immobilized antibody. After the binding reaction has been completed, the slurry is passed into a column for collection of the beads. The beads are washed using a suitable washing buffer and then the pure or substantially pure antigen is eluted.

An antibody or polypeptide of interest can be conjugated to a solid support, such as a bead. In addition, a first solid support such as a bead can also be conjugated, if desired, to a second solid support, which can be a second bead or other support, by any suitable means, including those disclosed herein for conjugation of a polypeptide to a support. Accordingly, any of the conjugation methods and means disclosed herein with reference to conjugation of a polypeptide to a solid support can also be applied for conjugation of a first support to a second support, where the first and second solid support can be the same or different.

Appropriate linkers, which can be cross-linking agents, for use for conjugating a polypeptide to a solid support include a variety of agents that can react with a functional group present on a surface of the support, or with the polypeptide, or both. Reagents useful as cross-linking agents include homo-bi-functional and, in particular, hetero-bi-functional reagents. Useful bi-functional cross-linking agents include, but are not limited to, N-SIAB, dimaleimide, DTNB, N-SATA, N-SPDP, SMCC and 6-HYNIC. A cross-linking agent can be selected to provide a selectively cleavable bond between a polypeptide and the solid support. For example, a photolabile cross-linker, such as 3-amino-(2-nitrophenyl) propionic acid can be employed as a means for cleaving a polypeptide from a solid support. (Brown et al., *Mol. Divers*, pp, 4-12 (1995); Rothschild et al., *Nucl. Acids Res.,* 24:351-66 (1996); and U.S. Pat. No. 5,643,722). Other cross-linking reagents are well-known in the art. (See, e.g., Wong (1991), supra; and Hermanson (1996), supra).

An antibody or polypeptide can be immobilized on a solid support, such as a bead, through a covalent amide bond formed between a carboxyl group functionalized bead and the amino terminus of the polypeptide or, conversely, through a covalent amide bond formed between an amino group functionalized bead and the carboxyl terminus of the polypeptide. In addition, a bi-functional trityl linker can be attached to the support, e.g, to the 4-nitrophenyl active ester on a resin, such as a Wang resin, through an amino group or a carboxyl group on the resin via an amino resin. Using a bi-functional trityl approach, the solid support can require treatment with a volatile acid, such as formic acid or trifluoracetic acid to ensure that the polypeptide is cleaved and can be removed. In such a case, the polypeptide can be deposited as a beadless patch at the bottom of a well of a solid support or on the flat surface of a solid support. After addition of a matrix solution, the polypeptide can be desorbed into a MS.

Hydrophobic trityl linkers can also be exploited as acid-labile linkers by using a volatile acid or an appropriate matrix solution, e.g., a matrix solution containing 3-HPA, to cleave an amino linked trityl group from the polypeptide. Acid lability can also be changed. For example, trityl, monomethoxytrityl, dimethoxytrityl or trimethoxytrityl can be changed to the appropriate p-substituted, or more acid-labile tritylamine derivatives, of the polypeptide, i.e., trityl ether and tritylamine bonds can be made to the polypeptide. Accordingly, a polypeptide can be removed from a hydrophobic linker, e.g., by disrupting the hydrophobic attraction or by cleaving tritylether or tritylamine bonds under acidic conditions, including, if desired, under typical MS conditions, where a matrix, such as 3-HPA acts as an acid.

Orthogonally cleavable linkers can also be useful for binding a first solid support, e.g., a bead to a second solid support, or for binding a polypeptide of interest to a solid support. Using such linkers, a first solid support, e.g., a bead, can be selectively cleaved from a second solid support, without cleaving the polypeptide from the support; the polypeptide then can be cleaved from the bead at a later time. For example, a disulfide linker, which can be cleaved using a reducing agent, such as DTT, can be employed to bind a bead to a second solid support, and an acid cleavable bi-functional trityl group could be used to immobilize a polypeptide to the support. As desired, the linkage of the polypeptide to the solid support can be cleaved first, e.g., leaving the linkage between the first and second support intact. Trityl linkers can provide a covalent or hydrophobic conjugation and, regardless of the nature of the conjugation, the trityl group is readily cleaved in acidic conditions.

For example, a bead can be bound to a second support through a linking group which can be selected to have a length and a chemical nature such that high density binding of the beads to the solid support, or high density binding of the polypeptides to the beads, is promoted. Such a linking group can have, e.g., "tree-like" structure, thereby providing a multiplicity of functional groups per attachment site on a solid support. Examples of such linking group; include polylysine, polyglutamic acid, penta-erythrole and tris-hydroxy-aminomethane.

Noncovalent Binding Association. An antibody or polypeptide can be conjugated to a solid support, or a first solid support can also be conjugated to a second solid support, through a noncovalent interaction. For example, a magnetic bead made of a ferromagnetic material, which is capable of being magnetized, can be attracted to a magnetic solid support, and can be released from the support by removal of the magnetic field. Alternatively, the solid support can be provided with an ionic or hydrophobic moiety, which can allow the interaction of an ionic or hydrophobic moiety, respectively, with a polypeptide, e.g., a polypeptide containing an attached trityl group or with a second solid support having hydrophobic character.

A solid support can also be provided with a member of a specific binding pair and, therefore, can be conjugated to a polypeptide or a second solid support containing a complementary binding moiety. For example, a bead coated with avidin or with streptavidin can be bound to a polypeptide having a biotin moiety incorporated therein, or to a second solid support coated with biotin or derivative of biotin, such as iminobiotin.

It should be recognized that any of the binding members disclosed herein or otherwise known in the art can be reversed. Thus, biotin, e.g., can be incorporated into either a polypeptide or a solid support and, conversely, avidin or other biotin binding moiety would be incorporated into the support or the polypeptide, respectively. Other specific binding pairs contemplated for use herein include, but are not limited to, hormones and their receptors, enzyme, and their substrates, a nucleotide sequence and its complementary sequence, an antibody and the antigen to which it interacts specifically, and other such pairs knows to those skilled in the art.

A. Diagnostic Uses of Anti-cis-pT231-tau Antibodies of the Present Technology

General. The anti-cis-pT231-tau antibodies of the present technology are useful in diagnostic methods. As such, the present technology provides methods using the antibodies in the diagnosis of cis-pT231-tau activity in a subject. Anti-cis-pT231-tau antibodies of the present technology may be selected such that they have any level of epitope binding specificity and very high binding affinity to a cis-pT231-tau protein. In general, the higher the binding affinity of an antibody the more stringent wash conditions can be performed in an immunoassay to remove nonspecifically bound material without removing target polypeptide. Accordingly, anti-cis-pT231-tau antibodies of the present technology useful in diagnostic assays usually have binding affinities of at least $10^8$, $10^9$, $10^{10}$, $10^{11}$ or $10^{12}$ $M^{-1}$. Further, it is desirable that anti-cis-pT231-tau antibodies used as diagnostic reagents have a sufficient kinetic on-rate to reach equilibrium under standard conditions in at least 12 h, at least five (5) h, or at least one (1) hour.

Anti-cis-pT231-tau antibodies can be used to detect an immunoreactive cis-pT231-tau protein in a variety of standard assay formats. Such formats include immunoprecipitation, Western blotting, ELISA, radioimmunoassay, and immunometric assays. See Harlow & Lane, *Antibodies, A Laboratory Manual* (Cold Spring Harbor Publications, New York, 1988); U.S. Pat. Nos. 3,791,932; 3,839,153; 3,850,752; 3,879,262; 4,034,074, 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Biological samples can be obtained from any tissue or body fluid of a subject. In certain embodiments, the subject is at an early stage of said tauopathy. In one embodiment, the early stage of said tauopathy is determined by an elevated level of cis pT231-tau or an increase in cis:trans pT231-tau ratio in a sample obtained from the subject. In some embodiments, the method further comprises determining the levels of CSF t-tau, pT181-tau, Aβ42, or ApoE4 levels in the sample obtained from the subject. In certain embodiments, the sample is selected from the group consisting of urine, blood, serum, plasma, saliva, amniotic fluid, and cerebrospinal fluid (CSF). In some embodiments, the subject has a history of repeated brain trauma.

Immunometric or sandwich assays are one format for the diagnostic methods of the present technology. See U.S. Pat. Nos. 4,376,110, 4,486,530, 5,914,241, and 5,965,375. Such assays use one antibody, e.g., an anti-cis-pT231-tau antibody or a population of anti-cis-pT231-tau antibodies immobilized to a solid phase, and another anti-cis-pT231-tau antibody or a population of anti-cis-pT231-tau antibodies in solution. Typically, the solution anti-cis-pT231-tau antibody or population of anti-cis-pT231-tau antibodies is labeled. If an antibody population is used, the population can contain antibodies binding to different epitope specificities within the target polypeptide. Accordingly, the same population can be used for both solid phase and solution antibody. If anti-cis-pT231-tau monoclonal antibodies are used, first and second cis-pT231-tau monoclonal antibodies having different binding specificities are used for the solid and solution phase. Solid phase (also referred to as "capture") and solution (also referred to as "detection") antibodies can be contacted with target antigen in either order or simultaneously. If the solid phase antibody is contacted first, the assay is referred to as being a forward assay. Conversely, if the solution antibody is contacted first, the assay is referred to as being a reverse assay. If the target is contacted with both antibodies simultaneously, the assay is referred to as a simultaneous assay. After contacting the cis-pT231-tau protein with the anti-cis-pT231-tau antibody, a sample is incubated for a period that usually varies from about 10 min to about 24 hr and is usually about 1 hr. A wash step is then performed to remove components of the sample not specifically bound to the anti-cis-pT231-tau antibody being used as a diagnostic reagent. When solid phase and solution antibodies are bound in separate steps, a wash can be performed after either or both binding steps. After washing, binding is quantified, typically by detecting a label linked to the solid phase through binding of labeled solution antibody. Usually for a given pair of antibodies or populations of antibodies and given reaction conditions, a calibration curve is prepared from samples containing known concentrations of target antigen. Concentrations of the immunoreactive cis-pT231-tau protein in samples being tested are then read by interpolation from the calibration curve (i.e., standard curve). Analyte can be measured either from the amount of labeled solution antibody bound at equilibrium or by kinetic measurements of bound labeled solution antibody at a series of time points before equilibrium is reached. The slope of such a curve is a measure of the concentration of the cis-pT231-tau protein in a sample.

Suitable supports for use in the above methods include, e.g., nitrocellulose membranes, nylon membranes, and derivatized nylon membranes, and also particles, such as agarose, a dextran-based gel, dipsticks, particulates, microspheres, magnetic particles, test tubes, microtiter wells, SEPHADEX™ (Amersham Pharmacia Biotech, Piscataway N.J.), and the like. Immobilization can be by absorption or by covalent attachment. Optionally, anti-cis-pT231-tau antibodies can be joined to a linker molecule, such as biotin for attachment to a surface bound linker, such as avidin.

B. Therapeutic Use of Anti-cis-pT231-tau Antibodies of the Present Technology

The antibodies of the present technology are useful for the treatment of neurological disorders characterized by pathologically high levels of the cis-conformation of phosphorylated tau protein. Such treatment can be used in patients identified as having pathologically high levels of the cis-conformation of phosphorylated tau (e.g., those diagnosed by the methods described herein) or in patients diagnosed with a disease known to be associated with such pathological levels. Examples of neurological disorders that can be treated by the antibodies of the present technology include: Alzheimer's disease (AD), mild cognitive impairment (MCI), Parkinson's disease (PD), corticobasal degeneration, Pick's disease, stroke, traumatic brain injury (TBI), chronic traumatic encephalopathy (CTE), progressive supranuclear palsy, frontotemporal lobar degeneration, Lytico-Bodig disease, tangle-predominant dementia, meningioangiomatosis, and subacute sclerosing panencephalitis.

The compositions of the present technology may be employed in conjunction with other therapeutic agents useful in the treatment of neurological disorders associated with elevated cis-pT231-tau protein expression. For example, the antibodies of the present technology may be separately, sequentially or simultaneously administered with at least one additional therapeutic agent-selected from the group consisting of donepezil, rivastigmine, galantamine, memantine, and lithium chloride.

The compositions of the present technology may optionally be administered as a single bolus to a subject in need thereof. Alternatively, the dosing regimen may comprise multiple administrations performed at various times after the appearance of tau NFTs.

Administration can be carried out by any suitable route, including orally, intranasally, parenterally (intravenously, intramuscularly, intraperitoneally, or subcutaneously), rectally, intracranially, intrathecally, or topically. Administration includes self-administration and the administration by another. It is also to be appreciated that the various modes of treatment of medical conditions as described are intended to mean "substantial", which includes total but also less than total treatment, and wherein some biologically or medically relevant result is achieved.

In some embodiments, the antibodies of the present technology comprise pharmaceutical formulations, which may be administered to subjects in need thereof in one or more doses. Dosage regimens can be adjusted to provide the desired response (e.g., a therapeutic response).

Typically, an effective amount of the antibody compositions of the present technology, sufficient for achieving a therapeutic effect, range from about 0.000001 mg per kilogram body weight per day to about 10,000 mg per kilogram body weight per day. Typically, the dosage ranges are from about 0.0001 mg per kilogram body weight per day to about 100 mg per kilogram body weight per day. For administration of anti-cis-pT231-tau antibodies, the dosage ranges from about 0.0001 to 100 mg/kg, and more usually 0.01 to 5 mg/kg every week, every two weeks or every three weeks, of the subject body weight. For example, dosages can be 1 mg/kg body weight or 10 mg/kg body weight every week, every two weeks or every three weeks or within the range of 1-10 mg/kg every week, every two weeks or every three weeks. In one embodiment, a single dosage of antibody ranges from 0.1-10,000 micrograms per kg body weight. In one embodiment, antibody concentrations in a carrier range from 0.2 to 2000 micrograms per delivered milliliter. An exemplary treatment regime entails administration once per every two weeks or once a month or once every 3 to 6 months. Anti-cis-pT231-tau antibodies may be administered on multiple occasions. Intervals between single dosages can be hourly, daily, weekly, monthly or yearly. Intervals can also be irregular as indicated by measuring blood levels of the antibody in the subject. In some methods, dosage is adjusted to achieve a serum antibody concentration in the subject of from about 75 μg/mL to about 125 μg/mL, 100 μg/mL to about 150 μg/mL, from about 125 μg/mL to about 175 μg/mL, or from about 150 μg/mL to about 200 μg/mL. Alternatively, anti-cis-pT231-tau antibodies can be administered as a sustained release formulation, in which case less frequent administration is required. Dosage and frequency vary depending on the half-life of the antibody in the subject. The dosage and frequency of administration can vary depending on whether the treatment is prophylactic or therapeutic. In prophylactic applications, a relatively low dosage is administered at relatively infrequent intervals over a long period of time. In therapeutic applications, a relatively high dosage at relatively short intervals is sometimes required until progression of the disease is reduced or terminated, or until the subject shows partial or complete amelioration of symptoms of disease. Thereafter, the patent can be administered a prophylactic regime.

Toxicity. Optimally, an effective amount (e.g., dose) of anti-cis-pT231-tau antibody described herein will provide therapeutic benefit without causing substantial toxicity to the subject. Toxicity of the anti-cis-pT231-tau antibody described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the anti-cis-pT231-tau antibody described herein lies within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics*, Ch. 1 (1975).

Formulations of Pharmaceutical Compositions. According to the methods of the present technology, the anti-cis-pT231-tau antibody can be incorporated into pharmaceutical compositions suitable for administration. The pharmaceutical compositions generally comprise recombinant or substantially purified native antibody and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (See, e.g., *Remington's Pharmaceutical Sciences*, Mack Publishing Co., Easton, PA $18^{th}$ ed., 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. "Pharmaceutically-acceptable salts and esters" means salts and esters that are pharmaceutically-acceptable and have the desired pharmacological properties. Such salts include salts that can be formed where acidic protons present in the composition are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically-acceptable esters include esters formed from carboxy, sulfonyloxy, and phosphonoxy groups present in the anti-cis-pT231-tau antibody, e.g., $C_{1-6}$ alkyl esters. When there are two acidic groups present, a pharmaceutically-acceptable salt or ester can be a mono-acid-mono-salt or ester or a di-salt or ester; and similarly where there are more than two acidic groups present, some or all of such groups can be salified or esterified. The anti-cis-pT231-tau antibody named in this technology can be present in unsalified or unesterified form, or in salified and/or esterified form, and the naming of such anti-cis-pT231-tau antibody is intended to include both the original (unsalified and unesterified) compound and its pharmaceutically-acceptable salts and esters. Also, certain embodiments of the present technology can be present in more than one stereoisomeric form, and the naming of such anti-cis-pT231-tau antibody is intended to include all single stereoisomers and all mixtures (whether racemic or otherwise) of such stereoisomers. A person of ordinary skill in the art, would have no difficulty determining the appropriate timing, sequence and dosages of administration for particular drugs and compositions of the present technology.

Examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the anti-cis-pT231-tau antibody, use thereof in the compositions is contemplated. Supplementary active compounds can also be incorporated into the compositions.

A pharmaceutical composition of the present technology is formulated to be compatible with its intended route of administration. The anti-cis-pT231-tau antibody compositions of the present technology can be administered by parenteral, topical, intravenous, oral, subcutaneous, intraarterial, intradermal, transdermal, rectal, intracranial, intrathecal, intraperitoneal, intranasal; or intramuscular routes, or as inhalants. The anti-cis-pT231-tau antibody can optionally be administered in combination with other agents that are at least partly effective in treating various diseases including various actin- or microfilament-related diseases.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be desirable to include isotonic compounds, e.g., sugars, polyalcohols such as manitol, sorbitol, sodium chloride in the composition. Prolonged absorption of the injectable compositions can be brought about by including in the composition a compound, which delays absorption, e.g., aluminum monostearate and gelatin.

Sterile injectable solutions can be prepared by incorporating the anti-cis-pT231-tau antibody in the required amount in an appropriate solvent with one or a combination of ingredients enumerated above, as required, followed by filtered sterilization. Generally, dispersions are prepared by incorporating the anti-cis-pT231-tau antibody into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The antibodies of the present technology can be administered in the form of a depot injection or implant preparation, which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the anti-cis-pT231-tau antibody can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the anti-cis-pT231-tau antibody is delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the anti-cis-pT231-tau antibody is formulated into ointments, salves, gels, or creams as generally known in the art.

The anti-cis-pT231-tau antibody can also be prepared as pharmaceutical compositions in the form of suppositories (e.g., with conventional suppository bases such as cocoa butter and other glycerides) or retention enemas for rectal delivery.

In one embodiment, the anti-cis-pT231-tau antibody is prepared with carriers that will protect the anti-cis-pT231-tau antibody against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

1. C. Kits

The present technology provides kits for the diagnosis and/or treatment of neurological disorders associated with elevated cis-pT231-tau protein expression, comprising at least one antibody of the present technology, or a functional variant (e.g., substitutional variant) thereof. Optionally, the above described components of the kits of the present technology are packed in suitable containers and labeled for diagnosis and/or treatment of neurological disorders associated with elevated cis-pT231-tau protein expression. The above-mentioned components may be stored in unit or multi-dose containers, for example, sealed ampoules, vials, bottles, syringes, and test tubes, as an aqueous, optionally sterile, solution or as a lyophilized, optionally sterile, formulation for reconstitution. The kit may further comprise a second container, which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper, which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic or diagnostic products, that contain information about, for example, the indications, usage, dosage, manufacture, administration, contraindications and/or warnings concerning the use of such therapeutic or diagnostic products.

The kits are useful for detecting the presence of an immunoreactive cis-pT231-tau protein in a biological sample, e.g., any body fluid including, but not limited to, e.g., serum, plasma, lymph, cystic fluid, urine, stool, cerebrospinal fluid, ascitic fluid or blood and including biopsy samples of body tissue. For example, the kit can comprise: one or more anti-cis-pT231-tau antibodies of the present technology (or antigen-binding fragments thereof) capable of binding a cis-pT231-tau protein in a biological sample; means for determining the amount of the cis-pT231-tau protein in the sample; and means for comparing the amount of the immunoreactive cis-pT231-tau protein in the sample with a standard. One or more of the anti-cis-pT231-tau antibodies may be labeled. The kit components, (e.g., reagents) can be packaged in a suitable container. The kit can further comprise instructions for using the kit to detect the immunoreactive cis-pT231-tau protein.

For antibody-based kits, the kit can comprise, e.g., 1) a first antibody, e.g. a cis-pT231-tau antibody of the present technology, attached to a solid support, which binds to a cis-pT231-tau protein; and, optionally; 2) a second, different antibody which binds to either the cis-pT231-tau protein or to the first antibody, and is conjugated to a detectable label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit, e.g., for detection of a cis-pT231-tau protein in vitro or in vivo, or for treatment of neurological disorders associated with elevated cis-pT231-tau protein expression in a subject in need thereof. In certain embodiments, the use of the reagents can be according to the methods of the present technology.

EXAMPLES

The present technology is further illustrated by the following Examples, which should not be construed as limiting in any way. The following Examples demonstrate the preparation, characterization, and use of illustrative conformation-specific phosphorylated Tau (pT231-tau) antibodies of the present technology. Examples 1-12 demonstrate the production of chimeric and humanized antibodies of the present technology, and characterization of their binding specificities.

Example 1—Sequence of the Variable Regions of Mouse PT-113 Monoclonal Antibody Total RNA was extracted from approximately 106 mouse PT-113 hybridoma cells (see WO 2014152157) using TRIzol reagents (Invitrogen, Carlsbad, CA) according to the supplier's protocol. Oligo dT-primed cDNA for 5'-RACE was synthesized using the SMARTer RACE cDNA Amplification Kit (Clontech, Mountain View, CA) following the supplier's protocol. The variable domain cDNAs for the heavy and light chains were amplified by polymerase chain reaction (PCR) with Phusion DNA polymerase (Thermo Fisher Scientific, Waltham, MA) using 3' primers that anneal specifically to the mouse heavy and light chain constant regions, and the 5'-RACE primer provided in the SMARTer RACE cDNA Amplification Kit. MCG2b (5'-GCCAGTGGATAGACTGATGG-3') (SEQ ID NO. 145) was used as a gene specific 3' primer for amplification of VH. For VL amplification, MCK (5'-GATGGATACAGTTGGTGCAGC-3') (SEQ ID NO. 146) was used.

The amplified VH and VL cDNAs were subcloned into the pJet1.2 vector (Thermo Fisher Scientific) for sequence determination. DNA sequencing was carried out at Eurofins Genomics (Louisville, KY) with JetRev (5'-AAGAACATCGATTTTCCATGGCAG-3') (SEQ ID NO. 147) as a primer. Several heavy and light chain clones were sequenced and unique sequences homologous to typical mouse heavy and light chain variable regions were identified. The nucleotide sequences of the heavy and light variable regions (VH and VL, respectively) of mouse PT-113 IgG2b/kappa monoclonal antibody are shown alongside their deduced amino acid sequences in FIGS. 1 and 2, respectively.

FIG. 3 shows the position of each amino acid residue and the locations of the complementarity determining regions (CDRs) of the mouse PT-113 VH domain based on the Kabat definition. FIG. 3 also shows the alignment of the amino acid sequences between the PT-113 VH domain and its predicted mouse parental germline V segment IGHV1S127*01 and its JH2 segment. Asterisks indicate the differences between the PT-113VH and IGHVIS127*01 amino acid sequences, which are most likely due to somatic hypermutation.

FIG. 4 shows the position of each amino acid residue and the location of the CDRs of the mouse PT-113 VL domain based on the Kabat definition. FIG. 4 also shows the alignment of the amino acid sequences between the PT-113 VL domain and its predicted mouse parental germline V segment IGKV1-110*02 (2) and its JK1 segment. Asterisks indicate the differences between the PT-113 VL and IGKV1-110*02 amino acid sequences, which are most likely due to somatic hypermutation.

Example 2: Construction of Chimeric PT-113 IgG1 Antibody

A gene encoding the VH domain of the mouse PT-113 antibody was designed as an exon including a splice donor signal after the coding region, a SpeI site at the 5' end and a HindIII site at the 3' end (FIG. 5). Likewise, a gene encoding the VL domain of the mouse PT-113 antibody was designed as an exon including a splice donor signal after the coding region, a NheI site at the 5' end and an EcoRI site at the 3' end (FIG. 6). Codons infrequently used in mammals were replaced by the frequently used corresponding codons in the PT-113 VH and VL exons.

The PT-113 VH and VL genes were synthesized by Eurofins MWG Operon (Huntsville, AL). After digestion with SpeI and HindIII (for the VH gene) or NheI and EcoRI (for the VL gene), the resulting PT-113 VH and VL fragments were cloned into a mammalian expression vector carrying human gamma-1 and kappa constant regions for production of chimeric PT-113 (ChPT-113) IgG1/kappa antibody. The schematic structure of the resulting expression vector, pChPT-113, is shown in FIG. 7.

Example 3: Design of Humanized PT-113 VH and VL Genes

Designing of humanized PT-113 VH and VL amino acid sequences was carried out as described below.

Human VH sequences homologous to the murine PT-113 VH framework were queried within the GenBank database, and the VH sequence encoded by the human AF174092 cDNA (GenBank accession number: AF174092, described in Wang & Stollar, Clin. Immunol. 93:132-142 (1999)) was chosen as an acceptor for humanization. The CDR sequences of PT-113 VH were first transferred to the corresponding positions of AF174092 VH. Next, at framework positions 48, 67, 69, 71, 93 and 94, where three-dimensional models of the PT-113 variable domains indicated significant contact with the CDRs, amino acid residues of AF174092 VH were replaced by the corresponding residues of mouse PT-113 VH. The amino acid sequence of the resulting humanized VH domain, HuPT-113 VH1, along with the mouse PT-113 and human AF174092 VH sequences are shown in FIG. 8.

While A1a at position 67 and Leu at position 69 in mouse PT-113 VH are located closely to the CDRs and were predicted to be important for the formation of the CDR structure, detailed analysis of the structure of the PT-113 CDR suggested a possibility that either one, or possibly both, of the two amino acid residues at positions 67 and 69 in HuPT-113 VH1 may be replaced by the corresponding residue(s) of the human acceptor AF174092 VH sequence. In order to further reduce potential immunogenicity, three additional humanized VH domains (HuPT-113 VH2, HuPT-113 VH3 and HuPT-113 VH4) were designed. In HuPT-113 VH2, Ala at position 67 in HuPT-113 VH1 was changed to Val. In HuPT-113 VH3, Leu at position 69 in HuPT-113 VH1 was changed to Met. In HuPT-113 VH4, Ala at position 67 and Leu at position 69 in HuPT-113 VH1 were changed to Val and Met, respectively. The amino acid sequences of HuPT-113 VH2, VH3 and VH4 are shown in FIG. 8.

Based on the homology search with the murine PT-113 VL framework sequences, the human Vκ region encoded by the M99608 cDNA (GenBank accession number: M99608, described in Weng et al. J. Immuno. 149:2518-2529 (1992)) was chosen as an acceptor for humanization. The CDR sequences of PT-113 VL were first transferred to the corresponding positions of M99608 VL. No amino acid substitutions with mouse residues were needed in the framework regions. The amino acid sequence of the resulting humanized VL, HuPT-113 VL1, is shown alongside the mouse PT-113 and human M99608 VL sequences in FIG. 9.

Example 4: Construction of Humanized PT-113 VH and VL Genes

A gene encoding HuPT-113 VH1 was designed as an exon including a signal peptide, a splice donor signal, a SpeI site at the 5' end, and a HindIII site at the 3' end (FIG. 10). The signal peptide sequence and splice donor signal in the mouse PT-113 VH exon (FIG. 5) were used for HuPT-113 VH1.

A gene encoding HuPT-113 VL1 was likewise designed as an exon including a signal peptide, a splice donor signal, a NheI site at the 5' end, and an EcoRI site at the 3' end (FIG. 14). The signal peptide sequence and splice donor signal in the mouse PT-113 VL exon (FIG. 6) were used for HuPT-113 VL1.

The HuPT-113 VH1 and VL1 genes were synthesized by Eurofins MWG Operon. After digestion with SpeI and HindIII (for VH) or NheI and EcoRI (for VL), HuPT-113 VH1 and HuPT-113 VL1 genes were subcloned into corresponding sites in a mammalian expression vector for production in the human IgG1/kappa form. The resulting expression vector pHuPT-113A expresses the humanized PT-113 IgG1/kappa antibody containing HuPT-113 VH1 and VL1 (HuPT-113A).

Genes encoding the HuPT-113 VH2, VH3 and VH4 exons (FIG. 8) were generated by site-directed mutagenesis of the HuPT-113 VH1 gene using the overlap-extension PCR method described in Higuchi, R., *Using PCR to Engineer DNA. In PCR Technology: Principles and Applications for DNA Amplification.* 61-67 (H. A. Erlich, ed., New York, NY (1989)). The nucleotide sequences of HuPT-113 VH2, VH3 and VH4 along with their deduced amino acid sequences are shown in FIGS. 11, 12 and 13, respectively. The HuPT-113 VH1 gene in the pHuPT-113A expression vector was replaced by HuPT-113 VH2, VH3 and VH4 to generate pHuPT-113B, pHuPT-113C and pHuPT-113D, respectively. HuPT-113B, HuPT-113C and HuPT-113D IgG1 (I) antibodies are expressed from the pHuPT-113B, pHuPT-113C and pHuPT-113D vectors, respectively.

Example 5: Characterization of ChPT-113, HuPT-113A, HuPT-113B, HuPT-113C and HuPT-113D IgG1 (I) Antibodies for Antigen Binding Binding of ChPT-113, HuPT-113A, HuPT-113B, HuPT-113C and HuPT-113D IgG1 (I) antibodies to the pThr-Dmp peptide (H-KVAVVRT($PO_3H_2$)XPKSPS—OH, X=5,5-dimethyl-L-proline) was characterized by ELISA. For production of these five antibodies, pChPT-113, pHuPT-113A, pHuPT-113B, pHuPT-113C, and pHuPT-113D vectors were individually transfected into the human embryonic kidney cell line, HEK293, using Lipofectamine 2000 reagent (Invitrogen, Carlsbad, CA) following the supplier's protocol. HEK293 cells were grown in DME media containing 10% fetal bovine serum (FBS; HyClone, Logan, UT) at 37° C. in a 7.5% $CO_2$ incubator.

Antibody expression in culture supernatants of transiently transfected HEK293 cells was analyzed by ELISA. An ELISA plate was coated overnight at 4° C. with 100 μl/well of 1/2,000-diluted goat anti-human IgG, Fcγ-specific polyclonal antibody (Sigma-Aldrich, St. Louis, MO) in PBS, washed with Washing Buffer (PBS containing 0.05% Tween 20), and blocked with 300 μl/well of Block Buffer (PBS containing 2% skim milk and 0.05% Tween 20). After washing with Washing Buffer, 100 μl/well of test samples appropriately diluted in Binding Buffer (PBS containing 1% Skim Milk and 0.025% Tween 20) were applied to the ELISA plate. An appropriate humanized IgG1/kappa antibody was used as a standard. After incubating the ELISA plate for 1 hr at room temperature and washing with Washing Buffer, bound antibodies were detected using 100 μl/well of 1/2,000-diluted HRP-conjugated goat anti-human kappa chain polyclonal antibody (SouthernBiotech, Birmingham, AL). After incubating for 0.5 hr at room temperature and washing with Washing Buffer, color development was initiated by adding 100 μl/well of ABTS substrate (Sigma-Aldrich) and stopped with 100 μl/well of 2% oxalic acid. Absorbance was read at 405 nm.

Binding of ChPT-113, HuPT-113A, HuPT-113B, HuPT-113C, and HuPT-113D IgG1 (I) antibodies to pThr-Dmp was tested by ELISA. For coating of a MaxiSorp ELISA plate (Thermo Fisher Scientific, Waltham, MA), 50 μl of 1 μg/ml pThr-Dmp (Lot #1556880, AnaSpec, Fremont, CA) in 2,2,2-trifluoroethanol was applied to each well. After drying up the peptide solution at 37° C. overnight, the wells were blocked with ELISA Buffer (10 mM TrisHCl (pH 7.6) containing 150 mM NaCl, 5% skim milk, 0.4% bovine serum albumin, and 0.05% Tween 20). A test antibody at various concentrations in ELISA Buffer (50 μl/well) was loaded and incubated at room temperature for 2 hrs. After washing the wells with Wash Buffer (10 mM TrisHCl (pH 7.6) containing 150 mM NaCl, 0.4% bovine serum albumin and 0.05% Tween 20), 50 μl/well of HRP-conjugated goat anti-human kappa chain antibody (1/2,000-diluted in ELISA Buffer) was applied to each well. After 1 hr incubation at room temperature, the wells were washed with Wash Buffer. Color development was initiated with 50 μl/well of TMB substrate (1-Step Ultra TMB-ELISA, Cat #34028, Thermo Fisher Scientific) and stopped with 50 μl/well of 2N $H_2SO_4$. Absorbance was measured at 450 nm.

The binding patterns of ChPT-113, HuPT-113A, HuPT-113B, HuPT-113C, and HuPT-113D IgG1 (I) antibodies to the pThr-Dmp peptide are shown in FIG. 15. No significant differences in the pThr-Dmp binding patterns were observed among these five antibodies. HuPT-113D IgG1 (I), which carries the least number of mouse framework residues among the four humanized PT-113 antibodies, was selected for further analysis.

Example 6: Construction of HuPT-113D IgG1-AA (I) Antibody

To eliminate the potential cytocidal activity of HuPT-113D IgG1 (I) antibody, amino acid substitutions from Leu to Ala at positions 234 and 235 (Eu numbering of Kabat), which are known to eliminate the effector function of IgG antibodies (Xu et al., *Cell. Immunol.* 200:16-26 (2000); Hezareh et al., *J. Virol.* 75:12161-12168 (2001)), were introduced into the CH2 constant region in pHuPT-113D by site-directed mutagenesis using the overlap-extension PCR method (see Higuchi, R (1989), supra). The resulting plasmid pHuPT-113D-AA expresses the HuPT-113D IgG1-AA (I) antibody.

Example 7: Generation of CHO-K1 Stable Transfectants Producing ChPT-113 IgG1, HuPT-113D IgG1 (I) and HuPT-113D IgG1-AA (I) Antibodies To obtain cell lines stably producing ChPT-113 IgG1, HuPT-113D IgG1 (I), and HuPT-113D IgG1-AA (I) antibodies, the expression vectors pChPT-113, pHuPT-113D, and pHuPT-113D-AA, respectively, were introduced into the chromosome of a Chinese hamster ovary cell line CHO-K1 (ATCC, Manassas, VA). CHO-K1 cells were grown in SFM4CHO media (HyClone, Logan, UT) at 37° C. in a 7.5% $CO_2$ incubator. Stable transfection into CHO-K1 was carried out by electroporation. Before transfection, each expression vector was linearized using FspI. Approximately $2.5\times10^6$ cells were transfected with 20 μg of linearized plasmid, suspended in SFM4CHO media, and plated into several 96-well plates after appropriate dilutions of cells. After 48 hrs, 10 μg/ml of puromycin was added for isolation of stable transfectants. Approximately ten days after the initiation of selection, culture supernatants of transfectants were assayed for antibody production by sandwich ELISA as described above.

CHO-K1 stable transfectants producing a high level of ChPT-113 IgG1, HuPT-113D IgG1 (I), and HuPT-113D-AA (I) antibodies (CHO-K1-ChPT-113 1D11, CHO-K1-HuPT-113D 1D6 and CHO-K1-HuPT-113D-AA 1D2, respectively) were tested with the PCR Mycoplasma Detection Set (Takara Bio USA, Madison, WI) and found negative for the presence of mycoplasma.

Example 8: Purification of ChPT-113 and HuPT-113D IgG1/kappa (I) Antibodies

Each of CHO-K1-ChPT-113 1D11, CHO-K1-HuPT-113D 1D6, and CHO-K1-HuPT-113D-AA 1D2 cells were grown in SFM4CHO in a roller bottle to the density of about $10^6$/ml, fed with $1/10^{th}$ volume of 35 mg/ml of Cell Boost 4 (HyClone, Logan, UT), and grown further until the cell viability became less than 50%. After centrifugation and filtration, culture supernatant was loaded onto a protein-A Sepharose column (HiTrap MabSelect SuRe, GE Healthcare, Piscataway, NJ). The column was washed with PBS before the antibody was eluted with 0.1 M glycine-HCl (pH 3.0). After neutralization with 1 M Tris-HCl (pH 8), the buffer of eluted antibody was changed to PBS by dialysis. Antibody concentration was determined by measuring absorbance at 280 nm (1.4 OD=1 mg/ml). The yield from 500 ml culture supernatants was 20 mg for ChPT-113 IgG1, 38 mg for HuPT-113D IgG1 (I), and 16 mg for HuPT-113D IgG1-AA (I).

Purified ChPT-113 IgG1, HuPT-113D IgG1 (I), and HuPT-113D IgG1-AA (I) antibodies were characterized by SDS-PAGE according to standard procedures. Analysis under reducing conditions indicated that each of these antibodies is comprised of a heavy chain with a molecular weight of approximately 50 kDa and a light chain with a molecular weight of approximately 25 kDa (FIG. 16). The purity of each antibody appeared to be more than 95%.

Example 9: cDNA Analysis of Heavy and Light Chain mRNA Sequences Isolated from CHO-K1-ChPT-113 1D11, CHO-K1-HuPT-113D 1D6, and CHO-K1-HuPT-113D-AA 1D2 Cells The authenticity of the heavy and light chains produced by CHO-K1-ChPT-113 1D11, CHO-K1-HuPT-113D 1D6, and CHO-K1-HuPT-113D-AA 1D2 cells was confirmed by cDNA sequencing. Total RNA was extracted from these cells using TRIzol reagent, and oligo dT-primed cDNA was synthesized using the ProtoScript M-MuL V First Strand cDNA Synthesis Kit (New England Biolabs, Ipswich, MA) following supplier's protocols. The coding region of gamma heavy chain was amplified by PCR using CMV2 and JNT098 as primers (FIG. 17) and Phusion DNA polymerase (Thermo Fisher Scientific). PCR fragments were gel-purified and subjected to sequencing with CMV2 and JNT098 as primers. Similarly, the coding region of kappa light chain was amplified using CMV2 and JNT026 (FIG. 17). Gel-purified DNA fragments were subjected to sequencing with CMV2 and JNT026 as primers.

The obtained nucleotide sequences of the coding region for ChPT-113 IgG1 heavy chain, ChPT-113 IgG1 light chain, HuPT-113D IgG1 (I) heavy chain, HuPT-113D IgG1 (I) light chain, HuPT-113D IgG1-AA (I) heavy chain, and HuPT-113D IgG1-AA (I) light chain all matched perfectly with the corresponding sequences in the pChPT-113, pHuPT-113D and pHuPT-113D-AA vectors (FIGS. 18 to 22).

Example 10: Antigen Binding of Mouse PT-113 19G2b and ChPT-113 IgG1 Antibodies

Binding of purified mouse PT-113 IgG2b and ChPT-113 IgG1 antibodies to the following four Thr231-tau peptides (synthesized by AnaSpec (Fremont, CA)), was analyzed by ELISA:

pThr-Dmp (Lot #1556880)
pThr-Pro (Lot #1556878)
pThr-Ala (Lot #1556881)
np-Thr-Pro (Lot #1556879)

Wells of MaxiSorp plates were coated with 50 μl/well of each peptide dissolved at 1 μg/ml in 2,2,2-trifluoroethanol. The subsequent procedure of ELISA is described in Example 5, with exception that the detection of mouse PT-113 IgG2b was carried out with HRP-conjugated goat anti-mouse kappa chain antibody (SouthernBiotech, Birmingham, AL).

The binding patterns of mouse PT-113 IgG2b and ChPT-113 IgG1 to the four peptides are shown in FIGS. 23 and 24, respectively. The general trend of the binding to the four tested T231-tau peptides was similar between these two antibodies. Particularly, both mouse PT-113 IgG2b and ChPT-113 IgG1 bound strongly to the pThr-Dmp tau peptide (locked in cis-conformation) and poorly to the pThr-Ala tau peptide (locked in trans-conformation). Further, FIGS. 23 and 24 show that the binding of ChPT-113 IgG1 to the np-Thr-Pro tau peptide (i.e., non-phosphorylated-T231-tau peptide) was weaker than that of mouse PT-113. This result demonstrates that the ChPT-113 IgG1 antibody shows less immunological cross-reactivity with non-phosphorylated-T231-tau peptides compared to that observed with the mouse PT-113 antibody.

Example 11: Competitive Binding Assays with Mouse PT-113 IgG2b and ChPT-113 IgG1 Antibodies The affinities of the mouse and chimeric PT-113 antibodies were assessed via a competitive binding assay. Wells of a MaxiSorp plate were coated with the pThr-Dmp tau peptide and blocked with ELISA Buffer as described in Example 5. After washing the wells, 50 μl of a mixture of 2 μg/ml of biotinylated mouse PT-113 IgG2b antibody and various concentrations of a competitor antibody (10 μg/ml and serial three-fold dilutions) in ELISA Buffer were applied to each well. After incubation for 2 hrs at room temperature and washing with Wash Buffer, 50 μl of HRP-conjugated streptavidin (1/2,000-diluted in ELISA Buffer; SouthernBiotech, Birmingham, AL) was applied to each well for incubation at room temperature for 1 hr. After washing with Wash Buffer, color development was initiated with 50 μl/well of TMB substrate and stopped with 50 μl/well of 2N $H_2SO_4$. Absorbance was read at 450 nm.

The result of the competitive binding ELISA is shown in FIG. 25. The competition pattern with mouse PT-113 IgG2b was similar to that with ChPT-113 IgG1, indicating that the affinity for binding to the pThr-Dmp tau peptide (locked in cis-conformation) is very similar between these two antibodies; however, no complete blocking of the binding of biotinylated PT-113 was observed even at the highest concentration used (10 μg/ml).

Example 12: Analysis of HuPT-113D IgG1 (I) and HuPT-113D IgG1-AA (I) Antibodies for Antigen Binding Antigen binding of purified HuPT-113D IgG1 (I) and HuPT-113D IgG1-AA (I) antibodies to each of the four T231-tau peptides, pThr-Dmp, pThr-Pro, pThr-Ala, and np-Thr-Pro, was compared to that of ChPT-113 IgG1 by ELISA following the procedures described in Examples 5 and 10. As shown in FIG. 26, these three antibodies showed similar binding patterns with each of the four T231-tau peptides. Particularly, the binding to the pThr-Dmp tau peptide (locked in cis-conformation) was nearly indistinguishable among the ChPT-113 IgG1, HuPT-113D IgG1 (I), and HuPT-113D IgG1-AA (I) antibodies.

These results show that the antibodies of the present technology specifically bind to the cis-conformation of phosphorylated-Threonine 231-tau protein (cis-pT231-tau), and are thus useful in methods for treating a neurological disorder associated with elevated cis-pT231-tau protein expression in a subject in need thereof.

Example 13: HuPT-113D (II) Antibodies

Transient Transfection. 12 mg of purified double gene vector was used to transfect $2\times10^9$ GS-KO CHO cells. Transfected cells were seeded at $3\times10^6$ cells/ml in medium supplemented with (II)'s proprietary feeds and 1 mM Glutamine and cultured in 5 L (Generon, 931116) shake flasks at 31° C., 5% $CO_2$, 85% humidity, and 140 rpm.

Primary Recovery. The 2 L culture was harvested by centrifugation at 8000 rpm and filter sterilized by 0.22 μm filtration before Protein A purification.

Protein A assay by Octet QKe. Samples of clarified cell culture supernatant were analyzed on an Octet QKe using Protein A Biosensors (ForteBio, 18-5010). 200 μL aliquots of supernatant samples, filtered with 0.22 μm filter, were loaded into a 96-well plate and quantified against an eight-point standard curve. Samples with concentrations outside the range of the standard curve were re-analyzed following dilution.

Protein A Affinity Chromatography. For the transient cultures, clarified supernatant was purified using one or four 5 mL HiTrap MabSelect SuRE columns on an AKT A purifier (run at 10 mL/min). In all cases, the column was equilibrated with 50 mM sodium phosphate, 125 mM sodium chloride, pH 7.0, washed with 50 mM sodium phosphate and 1 M sodium chloride pH 7.0 followed by re-introduction of equilibration prior to elution. The molecule was eluted with 10 mM sodium formate, pH 3.5. Eluted fractions were immediately pH adjusted by neutralizing with 2×PBS buffer, pH 7.4, and titrated to approximately pH 7.2 by the addition of dilute sodium hydroxide solution.

SE-HPLC. Duplicate samples were analyzed by SE-HPLC on an Agilent 1200 series HPLC system using a Zorbax GF-250 9.4 mm ID×25 cm column (Agilent). 80 μl aliquots of 1 mg/ml samples (or stock concentration if samples are <1 mg/mL) were injected and run in50 mM sodium phosphate, 150 mM sodium chloride, 500 mM arginine, pH 6.0 at 1 mL/min for 15 minutes. Soluble aggregate levels were analyzed using Chemstation software. Signals arising from buffer constituents were analyzed by blank buffer injection and are omitted in the data analysis unless indicated otherwise.

SDS-PAGE Analysis. Reduced samples were prepared for analysis by mixing with NuPage 4× LOS sample buffer (Life Technologies, NP0007) and NuPage 10× sample reducing agent (Life Technologies, NP0009), and incubated at 70° C., 10 min. For non-reduced samples, the reducing agent and heat incubation were omitted. Samples were electrophoresed on 1.5 mm NuPage 4-12% Bis-Tris Novex pre-cast gels (Life Technologies, NP0315/6) with NuPage MES SOS running buffer under denaturing conditions. 10 μl aliquot of SeeBlue Plus 2 pre-stained molecular weight standards (Life Technologies, LC5925) and of a control antibody at 1 mg/ml were included on the gel. 1 μg of each sample was loaded onto the gel. Once electrophoresed, gels were stained with InstantBlue (TripleRed, ISBO 1L) for 30 min at room temperature. Images of the stained gels were analyzed on a BioSpectrum Imaging System (UVP).

Protein A Purification Results. Initial purification was performed using a single 5 mL column. This resulted in recovery of 60.8 mg of material corresponding to approximately 25% according to the Octet measurement and a binding capacity of approximately 12 mg of antibody per gram of resin.

Subsequent purifications were performed using four tandem 5 mL MabSelect SURE columns, which gives a binding capacity in excess of the product titers for all three antibodies (i.e., HuPT-113D IgG1-AA (II), HuPT-113D IgG4 (II), and HuPT-113D IgG1 (II)). Purification of all three antibody products resulted in the elution of a single well defined peak. Octet analysis of the unbound fraction indicated that all of the product was recovered.

FIG. 47 confirms the presence of antibody products with good levels of purity. The antibody products compare well with the control IgG1 antibody (lanes 10 and 11). For all products two bands were observed under reducing conditions consistent with the sizes of heavy (>49 kDa) and light chain (<28 kDa) (lanes, 5, 7 and 9) and comparable with the bands found for the control antibody (lane 11). The results for the inter assay control IgG1 antibody (lanes 10 and 11) were as expected. Under non-reducing conditions a protein species band between 98 kDa and 198 kDa is seen for all products (lanes 2, 4, 6 and 8) comparable with the control IgG1 antibody run under the same conditions (lane 10) and consistent with the expected molecular weight for a full length antibody. For batch 455-030417-01 of HuPT-113D IgG1-AA (II), a band at approximately 198 kDa can be seen in the non-reduced sample indicating the presence of aggregate and consistent with the results of the SE-HPLC.

Example 14: FcR Activation by HuPT-113D Antibodies

This study shows that the HuPT-113D IgG1-AA (II) and HuPT-113D IgG4 (II) do not activate FcR (i.e., the antibodies of the present technology do not induce activation of immune cells expressing different Fc receptors).

Methods and Materials

Ovalbumin was purchased from Sigma-Aldrich and stored at +2-8° C. until use. Anti-Ovalbumin (rabbit polyclonal) was purchased from Sigma-Aldrich and stored at −20° C. until use. Anti-Ovalbumin (mouse monoclonal IgG2a) was purchased from Biolegend and stored at +2-8° C. until use.

The following HuPT-113D antibodies: HuPT-113D IgG1-AA (II), HuPT-113D IgG4 (II), and HuPT-113D IgG1 (II), were used.

The following peptides from the human Tau protein were used:

1) WT-pThr-Pro, a 10 amino acid sequence from human Tau.
2) pThr-Dmp, a 10 amino acid "cislocked" sequence analogous to the WT peptide.

Both peptides (≥10 mg per peptide) were lyophilised and stored at −80° C. until reconstitution. The peptides were reconstituted in 2,2,2-Trifluoroethanol (Fisher Scientific) at a concentration of 1 mg/mL and stored at −80° C. in multiple aliquots to minimize the number of freeze-thaw cycles. The pThr-Dmp peptide was also biotinylated using the Lightening-Link® Rapid Biotin Kit (Innova Biosciences) and stored at −20° C. until use.

Cell lines. THP-1 cells (DSMZ) were cultured in THP-1 Culture Medium (RPMI 1640 ((II))+10% heat-inactivated (hi) FBS ((II))) and passaged 3 times per week. Jurkat cells expressing FcγRIIIa V158 variant and the Luciferase gene (Promega) were cultured in Jurkat Culture Medium (RPMI 1640 ((II)), 10% hiFBS ((II)), 100 μg/mL Hygromycin (LifeTechnologies), 250 μg/mL G-418 Sulfate Solution (Promega), 1 mM Sodium Pyruvate (Life Technologies), 0.1 mM MEM Nonessential Amino Acids (Life Technologies)) and passaged three times per week.

Cell line FcR expression. THP-1 or Jurkat cells were harvested, washed in cold CellWASH Solution (BD) and stained for cell surface expression of CD16 (FcγRIII), CD32 (FcγRII) and CD64 (FcγR1). An FcR blocking step (Biolegend) was also included prior to the addition of the staining antibodies to minimize non-specific binding. FcR expression was determined by flow cytometry using anti-CD16 A647, anti-CD32 PE and anti-CD64 A488 (Biolegend) and analyzed on the Guava® easyCyte 8HT system (Merck Millipore).

HuPT-113D Enzyme-Linked Immunosorbent Assay. Wells of MaxiSorp plates (Fisher Scientific) were coated overnight at +4° C. with 1, 10 or100 μL/well of pThr-Dmp peptide dissolved in 2,2,2-trifluoroethanol or DPBS ((II)). Wells were then washed with Wash Buffer (DPBS+0.05% Tween-20 (Sigma-Aldrich)) and blocked with DPBS+1% BSA (Miltenyi Biotec) for 60 min at RT. Wells were washed with wash buffer and 100 μl/well of one of the HuPT-113D antibodies (e.g., HuPT-113D IgG1-AA (II), HuPT-113D IgG4 (II), or HuPT-113D IgG1 (II)) was added in duplicate for 60 min at RT. After washing the wells with wash buffer, bound antibody was detected with biotinylated anti-human Fc antibody and streptavidin-HRP and signal detected with 100 μL TMB substrate (Sigma-Aldrich). The reaction was stopped by adding 50 μL TMB Stop Solution (Sigma-Aldrich) and Absorbance was measured at 450 nm.

THP-1 cytokine assay. Assay plates (Lumitrac 600, Greiner Bio-One) were coated overnight at +4° C. with 100 μL/well of Ovalbumin in DPBS or pThr-Dmp peptide dissolved in 2,2,2-trifluoroethanol or DPBS. Wells were then washed with DPBS and blocked with 200 μL Blocking Medium (RPMI+5% super low IgG serum (GE Life Sciences)) for 60 min at RT. After blocking, 100 μl of antibody (anti-Ovalbumin or HuPT-113D antibodies (e.g., HuPT-113D IgG1-AA (II), HuPT-113D IgG4 (II), or HuPT-113D IgG1 (II))) was added per well for 60 min at RT. In some assays unbound antibody was removed by washing in wash buffer and THP-1 cells were added in 100 μl Assay Medium (RPMI+0.5% super low IgG serum) per well and incubated for 24 hours at 37° C., 5% $CO_2$ in a humidified atmosphere. Supernatant samples were harvested and centrifuged for 10 min at 300×G to remove any cells before being stored at −80° C. for cytokine analysis. Cytokine levels (TNFα, IL-1β and IL-6) in the supernatant were assessed by Milliplex® assay (Merck Millipore) on the MAGPIX® multiplexing platform (Luminex).

Jurkat FcRIIIa activation assay. Assay plates were coated overnight at +4° C. with 100 μL/well of Ovalbumin in DPBS or pThr-Dmp peptide dissolved in 2,2,2-trifluoroethanol or DPBS. Wells were then washed with DPBS and blocked with 200 μL Blocking Medium (RPMI+5% super low IgG serum (GE Life Sciences)) for 60 min at RT. After blocking, 100 μL of antibody (anti-Ovalbumin or HuPT-113D antibodies (e.g., HuPT-113D IgG1-AA (II), HuPT-113D IgG4 (II), or HuPT-113D IgG1 (II))) was added per well for 60 min at RT. In some assays unbound antibody was removed by washing in wash buffer and Jurkat cells were added in 100 μL Assay Medium (RPMI+0.5% super low IgG serum) per well and incubated for 24 hours at 37° C., 5% $CO_2$ in a humidified atmosphere. FcγRIIIa activation was assessed by adding BioGlo™ reagent for 10 min and RLU measured by a GloMax® luminometer (Promega).

Results

THP-1 cells Fc receptor expression. THP-1 cells were stained with antibodies against the 3 major Fc receptors (CD16, CD32 and CD64) to assess cell surface expression. FIGS. 30A-C shows the histogram plots for each FcR, with unstained cells in red and anti-FcR antibody stained cells in blue. THP-1 cells appear to express high levels of CD32 (FCγRII) and CD64 (FCγRI) but little or no CD16 (FCγRIII). This shows that the THP-1 assays assessed HuPT-113D IgG1-AA (II), HuPT-113D IgG4 (II), and HuPT-113D IgG1 (II) binding and activation of primarily CD32 and CD64 and the Jurkat assays assessed HuPT-113D IgG1-AA (II), HuPT-113D IgG4 (II), and HuPT-113D IgG1 (II) binding and activation via CD16 only.

Jurkat FcγRIIIa (CD16) V158 cells were also assessed by flow cytometry but no FcR expression was detected (data not shown). This was to be expected since CD16 levels are very low in the Jurkats and signaling is typically detected by the Luciferase reporter gene assay. The manufacturer provides data showing inhibition of signaling when an anti-CD16blocking antibody is added, showing that the Luciferase signal is CD16-dependent.

Positive control induced activation of THP-1 cells by immune complex (IC). The IC was immobilized (by coating the plate with antigen) to increase the cross-linking and subsequent activation of the FcR. The IC contains the Ovalbumin protein and an anti-Ovalbumin antibody. Two different anti-Ovalbumin antibodies were used separately to generate the IC; one murine monoclonal antibody and one rabbit polyclonal antibody. The rabbit polyclonal is known to stimulate immune cells but the murine monoclonal was untested in these assays. The murine monoclonal antibody was included to mimic the monoclonal nature of the HuPT-113D antibodies.

FIGS. 31A-D show the impact of the Ovalbumin IC coating density and cell number on the activation of THP-1 cells. The Ovalbumin IC was generated with Ovalbumin-coated wells and rabbit polyclonal anti-Ovalbumin antibody (after the addition of antibody to the wells coated with Ovalbumin the wells were not washed so there is likely to be some free antibody present in some conditions). The top two plots show the TNFα secretion and the bottom two plots the IL-6 secretion in response to increasing amounts of IC (0.1, 1 and 10 μg/mL Ovalbumin coating with a fixed amount of rabbit antibody at 50 g/mL) and THP-1 cells (5,000 and 50,000 cells/well). Increasing the amount of Ovalbumin IC and number of THP-1 cells led to an increase in the levels of TNFα and IL-6 secreted during the assay.

FIGS. 32A-D (TNFα release) and FIGS. 33A-D (IL-6 release) show the further optimization of the IC concentration and THP-1 cell number using the murine monoclonal antibody to generate the Ovalbumin IC. FIGS. 32A-B and 33A-B used 50,000 THP-1 cells/well and FIGS. 32C-D and 33C-D used 150,000 THP-1 cells/well. FIGS. 32A and C and 33A and C show the data when 0.1 μg/mL Ovalbumin was used to coat the wells. FIGS. 32B and D and 33B and D show the data when 10 μg/mL Ovalbumin was used to coat the wells. FIGS. 32A-D and 33A-D show that using 150,000 THP-1 cells/well with Ovalbumin coated at 10 μg/mL gave the highest levels of cytokine release and the THP-1 cell activation was antibody dose dependent.

The data shows that the THP-1 cytokine assay can be used to assess the ability of antibodies to bind and subsequently activate the cells after binding to immobilized protein antigen.

Positive control-induced activation of Jurkat cells. This study showed the FcR activation in Jurkat cells by a well-characterized immune complex (IC). The IC was immobilized (by coating the plate with antigen) to increase the cross-linking and subsequent activation of the FcR. The IC contains the Ovalbumin protein and an anti-Ovalbumin antibody. Two different anti-Ovalbumin antibodies were used separately to generate the IC; one murine monoclonal antibody and one rabbit polyclonal antibody. Neither antibody has been tested in these assays previously. The murine monoclonal antibody was included to mimic the monoclonal nature of the HuPT-113D antibodies (e.g., HuPT-113D IgG1-AA (II), HuPT-113D IgG4 (II), and HuPT-113D IgG1 (II)) used in this study.

FIGS. 34A-B show the impact of the Ovalbumin IC concentration and number of Jurkat cells on the activation of the FcR. The Ovalbumin IC was generated with Ovalbumin-coated wells (10 μg/mL) and a range of concentrations of both rabbit polyclonal and murine monoclonal anti-Ovalbumin antibodies (after the addition of antibody to the wells coated with Ovalbumin the wells were not washed so there is likely to be some free antibody present in some conditions). FIG. 34A shows the FcR activation using 50,000 Jurkat cells/well and FIG. 34B shows the activation using 100,000 Jurkat cells/well. Both plots show FcR activation by the rabbit polyclonal antibody but not with the murine monoclonal antibody with 100,000 Jurkats generating a stronger response than 50,000 Jurkat cells/well.

The data shows that the Jurkat FcR activation assay can be used to assess the ability of antibodies to bind and subsequently activate the FcγRIIIa after binding to immobilized protein antigens. The data also suggests that the murine antibody is less potent than the rabbit antibody at activating the FcγRIIIa.

HuPT-113D Peptides binding ELISA. To show that all three HuPT-113D antibodies (HuPT-113D IgG1-AA (II), HuPT-113D IgG4 (II), and HuPT-113D IgG1 (II)) were able to successfully form an IC, a binding ELISA was used to assess HuPT-113D antibody binding to the pThr-Dmp peptide. A dose response for each HuPT-113D antibody was generated with the ELISA plates coated with 1, 10 and 100 μg/mL of the pThr-Dmp peptide in 2,2,2-Trifluoroethanol.

FIG. 35 shows the binding curves for each antibody at each pThr-Dmp peptide coating concentration. All three HuPT-113D antibodies gave very similar binding curves and there was no impact of increasing the pThr-Dmp peptide coating concentration, suggesting that the 1 μg/mL concentration was already saturating the wells. EC50 values for all conditions were around 21 ng/ml (140 μM).

HuPT-113D pThr-Dmp peptide coating optimization in THP-1 cytokine assay. This study was performed to determine if there was any impact of 2,2,2-trifluoroethanol on the THP-1 cells. The pThr-Dmp peptide was diluted in either 2,2,2-trifluoroethanol or DPBS to 1 μg/mL and used to coat the wells of an assay plate. After coating, the wells were washed with DPBS and a range of concentrations of the HuPT-113D IgG1 (II) was added and allowed to form an IC before the THP-1 cells were added (150,1000 cells/well). After 24 hours the levels of TNFα and IL-6 were assessed.

FIG. 36A shows the levels of TNFα secretion and FIG. 36B shows the levels of IL-6 secretion. The data shows that the secretion of both cytokines was increased in a dose-dependent manner and there was no significant difference between the 2,2,2-trifluoroethanol and DPBS peptide coating conditions.

HuPT-113D pThr-Dmp peptide coating optimization in Jurkat FcR activation Assay. This study was performed to determine if there was any impact of 2,2,2-trifluoroethanol on the Jurkat cells. The pThr-Dmp peptide was diluted in either 2,2,2-trifluoroethanol or DPBS to 1 μg/mL and used to coat the wells of an assay plate. After coating, the wells were washed with DPBS and a range of concentrations of the HuPT-113D IgG1 (II) was added and allowed to form an IC before the Jurkat cells were added (100,000 cells/well). After 24 hours the activation of the FcγRIIIa was assessed with BioGlo® reagent.

FIG. 37 shows the levels of FcγRIIIa activation with each peptide coating condition. There was no significant difference between the 2,2,2-trifluoroethanol and DPBS peptide coating conditions and neither appeared to be able to activate the FcγRIIIa.

HuPT-113D THP-1 cytokine assay 1. To compare the ability of each HuPT-113D antibody (e.g., HuPT-113D IgG1-AA (II), HuPT-113D IgG4 (II), and HuPT-113D IgG1 (II)) to induce cytokine secretion in the THP-1 cell assay, both native and biotinylated pThr-Dmp peptide were used to generate the IC. The native peptide (pThr-Dmp peptide) was used to coat the wells of an assay plate at 1 μg/mL and the biotinylated peptide was used to coat the wells of a streptavidin pre-coated plate (Greiner Bio-one). After coating overnight with peptide, both plates were washed and a serial dilution of HuPT-113D IgG1-AA (II), HuPT-113D IgG4 (II), or HuPT-113D IgG1 (II) was added to the plate in triplicate. An additional wash step was included after the HuPT-113D antibody was added to ensure that only IC was present when the THP-1 cells were added. This additional wash step removed any free HuPT-113D antibody that might act as a blocking antibody and prevent the IC immobilized on the plate crosslinking the FcR.

FIGS. 38A-C show the induction of cytokine release (TNFα, IL-1B and IL-6) by each HuPT-113D antibody (e.g., HuPT-113D IgG1-AA (II), HuPT-113D IgG4 (II), and HuPT-113D IgG1 (II)) with native pThr-Dmp peptide. FIGS. 38D-F show the induction of cytokine release (TNFα, IL-1β and IL-6) by each HuPT-113D antibody with biotinylated pThr-Dmp peptide. HuPT-113D IgG1 (II) is shown in blue, HuPT-113D IgG1-AA (II) in red and HuPT-113D IgG4 (II) in green. All three HuPT-113D antibodies induced cytokine release in a dose dependent manner although each antibody tended to generate a different curve with the IgG1 antibody in particular producing a lower maximum level of cytokine release.

However, when the native peptide was used to generate the IC a similar pattern was seen in all three cytokines with the IgG1 antibody showing the highest and the IgG1-AA the lowest potency for cytokine induction. The biotinylated peptide plots showed a similar pattern with the IgG1-AA the least potent stimulator of cytokine release.

Directly comparing the results of the native and biotinylated peptides showed that the biotinylated peptide increased the background levels of cytokine release. This is likely due to the streptavidin used to coat the plates rather than the biotinylated peptide itself. To keep background levels of THP-1 cell activation as low as possible, subsequent assays used the native pThr-Dmp peptide to coat the plates and generate the IC.

FIG. 39 shows the EC50 values calculated for the three HuPT-113D antibodies (native peptide). The IgG1 antibody had the lowest EC50 value for all three cytokines and the IgG1-AA the highest suggesting that the IgG1-AA antibody has the lowest capacity for inducing the release of cytokine from THP-1 cells.

HuPT-113D Jurkat FcR activation assay 1.To compare the ability of each HuPT-113D antibody (e.g., HuPT-113D IgG1-AA (II), HuPT-113D IgG4 (II), and HuPT-113D IgG1 (II)) to activate the FcγRIIIa in the Jurkat cell assay, the native pThr-Dmp peptide was used to generate the IC (the native peptide was used to coat the wells of an assay plate at 1, 10 or 100 μg/mL). The plates were then washed and a serial dilution of HuPT-113D IgG1-AA (II), HuPT-113D IgG4 (II), and HuPT-113D IgG1 (II) was added to the plate in triplicate. An additional wash step was included after the HuPT-113D antibody was added to ensure that only IC was present when the Jurkat cells were added. This additional wash step removed any free HuPT-113D antibody that might act as a blocking antibody and prevent the IC immobilized on the plate crosslinking the FcγRIIIa.

FIG. 39 shows the activation of the FcγRIIIa by each of the HuPT-113D antibodies. The IgG1 antibody was able to activate the Jurkat cells in a dose-dependent manner with a similar curve generated for each of the peptide coating concentrations. The IgG1-AA and IgG4 antibodies did not show any activation of the Jurkat cells.

HuPT-113D THP-1 cytokine assay 2. The THP-1 cytokine assay was repeated to verify that the HuPT-113D IgG1-AA (II) and HuPT-113D IgG4 (II) antibodies were indeed less potent inducers of cytokine release. Plates were coated with 1 μg/mL native peptide and a larger dose range of each antibody included. Any unbound antibody was washed away prior to addition of the THP-1 cells to ensure only IC was present.

FIG. 41A-C shows the plots for each HuPT-113D antibody for each of the three cytokines. The plots are similar to those seen above in FIGS. 38A-F, with IgG1 the most and IgG1-AA the least potent inducer of cytokine release in the THP-1 cells.

FIG. 42 shows the EC50 values calculated for the three HuPT-113D antibodies. The IgG1 antibody had a lower EC50 value for all three cytokines than the IgG1-AA and IgG4 antibodies suggesting the IgG1-AA and IgG4 antibodies have a lower capacity for inducing the release of cytokines from THP-1 cells.

HuPT-113D Jurkat FcR activation assay. The Jurkat FcR activation assay was repeated to verify that the IgG1-AA and IgG4 antibodies were indeed less potent inducers of FcR activation. Plates were coated with 1μg/mL native peptide and a larger dose range of each antibody included. Any unbound antibody was washed away prior to addition of the Jurkat cells to ensure only IC was present.

FIG. 43 shows the plots for each HuPT-113D antibody. The plots are similar to those seen above in FIG. 40, with only the IgG1 antibody able to activate the FcγRIIIa.

The results also show that HuPT-113D IgG1 (II) induced a dose-dependent response in all three cytokines (TNFα, IL-1β and IL-6) in the THP-1 cytokine assay.

The results also show that the IgG1-AA and IgG4 versions were less potent inducers of the cytokines with EC50 values up to 30 times higher than that of the IgG1.

The results show that HuPT-113D IgG1 (II) induced a dose-dependent response in the Jurkat FcγRIIIa activation assay. No activation was seen for the HuPT-113D IgG1-AA (II) and HuPT-113D IgG4 (II) antibodies.

The results indicate that the HuPT-113D IgG1-AA (II) and HuPT-113D IgG4 (II) show a lower ability to bind and activate immune cells via their FcRs and should be considered as lower risk of inducing an unwanted immune response in a subject.

These results show that the HuPT-113D antibodies of the present technology (e.g., HuPT-113D IgG1-AA (II) and HuPT-113D IgG4 (II)) do not activate FcγRIIIa, which indicates that the antibodies of the present technology would not induce a cytotoxic response in the a subject.

Example 15: Jurkat FcγRIIIa V158 Activation Assay-Thaw and Use Kits Versus Propagation Cell Line This study assessed the ability of the antibodies of the present technology to activate FcRIIIa V158 cells.

Methods. Wells were coated with pThr-Dmp peptide in TFE at 1 μg/ml. HuPT-113D IgG1-AA (II), HuPT-113D IgG4 (II), or HuPT-113D IgG1 (II) was added for 60 min. Jurkat cells were added for 24 hrs. BioGlo® reagent was added after 24 hrs and luminescence was read on GloMax®.

Results. Only the HuPT-113D IgG1 (II) antibody was able to activate the cells. See FIGS. 44A-B. The results show that there was no activation by HuPT-113D IgG1-AA (II) and HuPT-113D IgG4 (II) antibodies. See FIGS. 44A-B. The propagation and thaw and use cells had similar results.

These results show that the HuPT-113D antibodies of the present technology (e.g., HuPT-113D IgG1-AA (II) and HuPT-113D IgG4 (II)) do not activate FcγRIIIa, which indicates that the antibodies of the present technology would not induce a cytotoxic response in the a subject.

Example 16: Jurkat FcγRIIIa and FcγRIIa Activation Using HuPT-113D Antibodies This study assessed the ability of the antibodies of the present technology to activate FcγRIIIa V158, FcγRIIIa F158, and FcγRIIa H131.

Methods.

Wells were coated with pThr-Dmp peptide in TFE at 1 μg/ml. HuPT-113D IgG1-AA (II), HuPT-113D IgG4 (II), or HuPT-113D IgG1 (II) was added for 60 min. Jurkat cells were added for 24 hrs. BioGlo® reagent was added after 24 hrs and luminescence was read on GloMax®.

Results

HuPT-113D IgG1 (II) activated FcγRIIIa V158 and FcγRIIa H131 cells. See FIGS. 45A and C. HuPT-113D IgG4 (II) showed low level activation in the FcγRIIa H131 cells and no activation in the FcγRIIIa V158. See FIGS. 45A and C. HuPT-113D IgG1-AA (II) did not activate FcγRIIIa V158 cells and FcγRIIa H131 cells. See FIGS. 45A and C. None of the antibodies activated FcγRIIIa F158. See FIG. 45B.

These results show that the HuPT-113D antibodies of the present technology (e.g., HuPT-113D IgG1-AA (II) and HuPT-113D IgG4 (II)) do not activate FcγRIIIa, which indicates that the antibodies of the present technology would not induce a cytotoxic response in the a subject.

Example 17: Jurkat FcγRIIIa V158 Activation Assays—Propagation Cells

This study assessed HuPT-113D activation of FcγRIIIa V158 cells.

Methods

Wells were coated with pTau in DPBS at 10 μg/ml. HuPT-113D IgG1-AA (II), HuPT-113D IgG4 (II), or HuPT-113D IgG1 (II) was added for 60 min. Jurkat cells were added for 24 hrs. BioGlo® reagent was added after 24 hrs and luminescence was read on GloMax®

Results

None of the antibodies induced activation of FcγRIIIa V158 cells. See FIG. 46.

These results show that the HuPT-113D antibodies of the present technology (e.g., HuPT-113D IgG1-AA (II) and HuPT-113D IgG4 (II)) do not activate FcγRIIIa, which indicates that the antibodies of the present technology would not induce a cytotoxic response in the a subject.

Example 18: Prevention of Traumatic Brain Injury (TBI) Using HuPT-113D Antibodies This study will show that the antibodies of the present technology (e.g., HuPT-113A, HuPT-113B, HuPT-113C, HuPT-113D, HuPT-113D IgG1-AA (II), and HuPT-113D IgG4 (II)) are useful to prevent TBI.

Methods wt C57/B16 mice are treated with a single dose of HuPT-113D antibody or control antibody (200 μg ip=~8 mg/kg)$_3$ days prior to TBI. TBI model is selected from: Single severe TBI (blast; ssTBI), Repetitive mild TBI (impact; rmTBI), or Single mild TBI (impact; smTBI). 15 minutes prior to injury all mice are treated with a single dose of HuPT-113D antibody or control antibody (20 μg/5 μl) via intracerebroventricular dosing. In some embodiments, the mice are treated at 3 dose levels, e.g., 3, 10 and 30 mg/kg.

In some embodiments, a sham group of mice (i.e., no TBI) is used a control.

A first cohort (mice pre-treated with 8 mg/kg ip q4 days for 12 days (3 doses total)) are sacrificed 14 days post injury for ELISA/Western blot analysis (e.g., to assess cis tau and total (mid domain) tau in brain and CSF) and fEPSP.

A second cohort (mice treated as above but continued on treatment, 8 mg/kg ip weekly, for 6 further weeks) are sacrificed 2 months post-injury. Behavioral endpoints are assessed prior to sacrifice (e.g., EPM, MWM, and locomotor test (rotorod).

A third cohort (mice continued to receive 8 mg/kg ip weekly until 6 months following injury) are sacrificed and tau aggregation (e.g., cis tau and total tau) and neuronal atrophy are assessed. Other endpoint includes assaying for IHC and assays using ALZ50, MC1, and/or AT8.

Results

It is anticipated that mice treated with the antibodies of the present technology will show one or more of reduced cistauosis, reduced tauopathy development and spread, reduced neurodegeneration, and improved histopathological and functional outcomes as compared to untreated control mice.

These results will show that the antibodies of the present technology (e.g., HuPT-113A, HuPT-113B, HuPT-113C, HuPT-113D, HuPT-113D IgG1-AA (II), and HuPT-113D IgG4 (II)) are useful to prevent a neurological disorder associated with elevated cis-pT231-tau protein expression, such as TBI.

Example 19: Prevention of Neurodegenerative Conditions Using HuPT-113D Antibodies in the TMHT Mouse Model of Alzheimer's Disease This study will show that the antibodies of the present technology (e.g., HuPT-113A, HuPT-113B, HuPT-113C, HuPT-113D, HuPT-113D IgG1-AA (II), and HuPT-113D IgG4 (II)) are useful in preventing neurodegenerative conditions such as Alzheimer's disease.

Methods

TMHT (Thy-1 mutated human tau) transgenic mice (Flunkert et al., 2013) are treated with HuPT-113D antibody or control antibody (between 1-100 mg/kg) beginning at 1 month of age. The mice are treated with HuPT-113D antibody or control antibody weekly by intra-peritoneal (IP) injection, sub-cutaneous (SC) injection, or intra-venous (IV) administration. In alternative assays, different dose frequencies can include, but are not limited to, daily, every 2 days, every 3 days, every 4 days, bi-weekly, every 3 weeks and monthly. WT mice are used as a control.

A first cohort (mice treated with 1-100 mg/kg IP weekly for 2 months) are sacrificed at 3 months of age for ELISA/Western blot analysis (e.g., to assess cis tau and total (mid domain) tau in brain and CSF).

A second cohort (mice treated with 1-100 mg/kg IP weekly for 4 months) are sacrificed at 5 months of age. Behavioral endpoints are assessed prior to sacrifice (e.g., MWM, elevated plus maze, novel object recognition, general measures of locomotor activity including rotorod performance, olfaction).

A third cohort (mice treated with 1-100 mg/kg IP weekly for 8 months until 9 months of age) are sacrificed and tau aggregation (e.g., cis tau and total tau) and neuronal atrophy are assessed. Other endpoints may include assaying for IHC and assays using ALZ50, MC1, and/or AT8.

Results

It is anticipated that mice treated with the antibodies of the present technology will exhibit one or more of reduced cistauosis, overall reduced tauopathy development and spread, reduced neurodegeneration, and improved histopathological and functional outcomes as compared to untreated control mice or mice treated with a control antibody that does not recognize cis tau.

These results will show that the antibodies of the present technology (e.g., HuPT-113A, HuPT-113B, HuPT-113C, HuPT-113D, HuPT-113D IgG1-AA (II), and HuPT-113D IgG4 (II)) are useful in preventing a neurological disorder associated with elevated cis-pT231-tau protein expression, such as Alzheimer's disease.

Example 20: Treatment of Neurodegenerative Conditions Using HuPT-113D Antibodies in the THMT Mouse Model of Alzheimer's Disease This study will show that the antibodies of the present technology (e.g., HuPT-113A, HuPT-113B, HuPT-113C, HuPT-113D, HuPT-113D IgG1-AA (II), and HuPT-113D IgG4 (II)) are useful to treat neurodegenerative conditions such as Alzheimer's disease.

Methods

TMHT (Thy-1 mutated human tau) transgenic mice (Flunkert et al., 2013) are treated with HuPT-113D antibody or control antibody (200 μg ip=~8 mg/kg) beginning at 5 months of age. WT mice are used as a control.

Mice are treated with 8 mg/kg ip every 4 days for 12 days (3 total treatments). Behavioral endpoints are assessed prior to sacrifice (e.g., MWM, olfaction). Mice are then sacrificed for ELISA/Western blot analysis (e.g., to assess cis tau and total (mid domain) tau in brain and CSF). In an alternative assay, the mice that are treated with 3 different increasing dose levels for each treatment, e.g., 3, 10 and 30 mg/kg.

Results

It is anticipated that mice treated with the antibodies of the present technology will show one or more of reduced cistauosis, reduced tauopathy development and spread, reduced neurodegeneration, and improved histopathological and functional outcomes as compared to control antibody treated mice and untreated control mice.

These results will show that the antibodies of the present technology (e.g., HuPT-113A, HuPT-113B, HuPT-113C, HuPT-113D, HuPT-113D IgG1-AA (II), and HuPT-113D IgG4 (II)) are useful to treat a neurological disorder associated with elevated cis-pT231-tau protein expression, such as Alzheimer's disease.

Example 21: Prevention of Neurodegenerative Conditions Using HuPT-113D Antibodies in the hTau Mouse Model of Alzheimer's Disease This study will show that the antibodies of the present technology (e.g., HuPT-113A, HuPT-113B, HuPT-113C, HuPT-113D, HuPT-113D IgG1-AA (II), and HuPT-113D IgG4 (II)) are useful to prevent neurodegenerative conditions such as Alzheimer's disease.

Methods hTau transgenic mice (Andorfer et al., 2003) are treated with HuPT-113D antibody or control antibody (200 μg ip=~8 mg/kg) beginning at 1 month of age. WT mice are used as a control.

A first cohort (mice treated with 8 mg/kg ip every 4 days for 5 months) are sacrificed at 6 months of age for ELISA/Western blot analysis (e.g., to assess cis tau and total (mid domain) tau in brain and CSF).

A second cohort (mice continued to receive 8 mg/kg ip weekly for 11 months until 12 months of age). Behavioral endpoints are assessed prior to sacrifice (e.g., MWM, novel object recognition). Tau aggregation (e.g., cis tau and total tau) and neuronal atrophy are assessed. Other endpoints may include assaying for IHC and assays using ALZ50, MC1, and/or AT8.

Results

It is anticipated that mice treated with the antibodies of the present technology will show one or more of reduced cistauosis, reduced tauopathy development and spread, reduced neurodegeneration, and improved histopathological and functional outcomes as compared to control antibody treated mice and untreated control mice.

These results will show that the antibodies of the present technology (e.g., HuPT-113A, HuPT-113B, HuPT-113C, HuPT-113D, HuPT-113D IgG1-AA (II), and HuPT-113D IgG4 (II)) are useful to prevent a neurological disorder associated with elevated cis-pT231-tau protein expression, such as Alzheimer's disease.

Example 22: Treatment of Neurodegenerative Conditions Using HuPT-113D Antibodies in the hTau Mouse Model of Alzheimer's Disease This study will show that the antibodies of the present technology (e.g., HuPT-113A, HuPT-113B, HuPT-113C, HuPT-113D, HuPT-113D IgG1-AA (II), and HuPT-113D IgG4 (II)) are useful to treat neurodegenerative conditions such as Alzheimer's Disease.

Methods hTau transgenic mice (Andorfer et al., 2003) are treated with HuPT-113D antibody or control antibody (200 μg ip=~8 mg/kg) beginning at 12 months of age. WT mice are used as a control.

Mice are treated with 8 mg/kg ip every 4 days for 12 days (3 doses total). Behavioral endpoints are assessed prior to sacrifice (e.g., MWM, novel object recognition). Mice are sacrificed at 3 months of age for ELISA/Western blot analysis (e.g., to assess cis tau and total (mid domain) tau in brain and CSF). In an alternative assay, the mice that are treated with 3 different increasing dose levels for each treatment, e.g., 3, 10 and 30 mg/kg.

Results

It is anticipated that mice treated with the antibodies of the present technology will show one or more of reduced cistauosis, reduced tauopathy development and spread, reduced neurodegeneration, and improved histopathological and functional outcomes as compared to control antibody treated mice and untreated control mice.

These results will show that the antibodies of the present technology (e.g., HuPT-113A, HuPT-113B, HuPT-113C, HuPT-113D, HuPT-113D IgG1-AA (II), and HuPT-113D IgG4 (II)) are useful to treat a neurological disorder associated with elevated cis-pT231-tau protein expression, such as Alzheimer's disease.

Example 23: Treatment of Traumatic Brain Injury (TBI) Using HuPT-113D Antibodies This study will show that the antibodies of the present technology (e.g., HuPT-113A, HuPT-113B, HuPT-113C, HuPT-113D, HuPT-113D IgG1-AA (II), and HuPT-113D IgG4 (II)) are useful to treat TBI.

Methods wt C57/B16 mice are treated with a single dose of HuPT-113D antibody or control antibody (200 μg ip=~8 mg/kg) immediately after TBI. TBI model is selected from: Single severe TBI (blast; ssTBI), Repetitive mild TBI (impact; rmTBI), or Single mild TBI (impact; smTBI). 15 minutes post injury all mice are treated with a single dose of HuPT-113D antibody or control antibody (20 μg/5 μl) via intracerebroventricular dosing. In some embodiments, the mice are treated at 3 dose levels, e.g., 3, 10 and 30 mg/kg.

In some embodiments, a sham group of mice (i.e., no TBI) is used a control.

A first cohort (mice treated with 8 mg/kg ip q4 days for 12 days (3 doses total)) are sacrificed 14 days post injury for ELISA/Western blot analysis (e.g., to assess cis tau and total (mid domain) tau in brain and CSF) and fEPSP.

A second cohort (mice treated as above but continued on treatment, 8 mg/kg ip weekly, for 6 further weeks) are sacrificed 2 months post-injury. Behavioral endpoints are assessed prior to sacrifice (e.g., EPM, MWM, and locomotor test (rotorod).

A third cohort (mice continued to receive 8 mg/kg ip weekly until 6 months following injury) are sacrificed and tau aggregation (e.g., cis tau and total tau) and neuronal atrophy are assessed. Other endpoint includes assaying for IHC and assays using ALZ50, MC1, and/or AT8.

Results

It is anticipated that mice treated with the antibodies of the present technology will show one or more of reduced cistauosis, reduced tauopathy development and spread, reduced neurodegeneration, and improved histopathological and functional outcomes as compared to untreated control mice.

These results will show that the antibodies of the present technology (e.g., HuPT-113A, HuPT-113B, HuPT-113C, HuPT-113D, HuPT-113D IgG1-AA (II), and HuPT-113D IgG4 (II)) are useful to treat a neurological disorder associated with elevated cis-pT231-tau protein expression, such as TBI.

EQUIVALENTS

The present technology is not to be limited in terms of the particular embodiments described in this application, which are intended as single illustrations of individual aspects of the present technology. Many modifications and variations of this technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled.It is to be understood that this technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for treating a neurological disorder associated with elevated cis-pT231-tau protein expression in a subject in need thereof, comprising administering to the subject an effective amount of an antibody comprising a heavy chain sequence as set forth in SEQ ID NO: 24 and a light chain sequence as set forth in SEQ ID NO: 51.

2. The method of claim 1, wherein the neurological disorder is a tauopathy, traumatic brain injury (TBI), or stroke.

3. The method of claim 2, wherein said tauopathy is selected from the group consisting of: progressive supranuclear palsy (PSP), chronic traumatic encephalopathy (CTE), frontotemporal dementia (FTD), frontotemporal lobar degeneration, Lytico-Bodig disease, tangle-predominant dementia, meningioangiomatosis, subacute sclerosing panencephalitis, Pick's disease, corticobasal degeneration, and Alzheimer's disease AD).

4. The method of claim 3, wherein the subject is at an early stage of said tauopathy.

5. The method of claim 4, wherein the early stage of said tauopathy is determined by an elevated level of cis pT231-tau or an increase in cis:trans pT231-tau ratio in a sample obtained from the subject.

6. The method of claim 5, further comprising determining the levels of CSF t-tau, pT181-tau, Aβ42, or ApoE4 levels in the sample obtained from the subject.

7. The method of claim 6, wherein said sample is selected from the group consisting of: urine, blood, serum, plasma, saliva, amniotic fluid, and cerebrospinal fluid (CSF).

8. The method of claim 1, wherein said subject has a history of repeated brain trauma.

9. The method of claim 1, wherein the antibody is administered to the subject separately, sequentially or simultaneously with an additional therapeutic agent.

10. The method of claim 9, wherein the additional therapeutic agent is one or more of donepezil, rivastigmine, galantamine, memantine, and lithium chloride.

* * * * *

SEQUENCE LISTING

```
Sequence total quantity: 164
SEQ ID NO: 1            moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 1
QVQLVQSGAE VKKPGASVKV SCKASGYTFT SYWIHWVRQA PGQGLEWIGV IDPSDSYTRY  60
NQKFKGRATL TVDTSTSTAY MELRSLRSDD TAVYYCTTWE VDYWGQGTTV TVSS        114

SEQ ID NO: 2            moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 2
QVQLVQSGAE VKKPGASVKV SCKASGYTFT SYWIHWVRQA PGQGLEWIGV IDPSDSYTRY  60
NQKFKGRVTL TVDTSTSTAY MELRSLRSDD TAVYYCTTWE VDYWGQGTTV TVSS        114

SEQ ID NO: 3            moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 3
QVQLVQSGAE VKKPGASVKV SCKASGYTFT SYWIHWVRQA PGQGLEWIGV IDPSDSYTRY  60
NQKFKGRATM TVDTSTSTAY MELRSLRSDD TAVYYCTTWE VDYWGQGTTV TVSS        114

SEQ ID NO: 4            moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 4
QVQLVQSGAE VKKPGASVKV SCKASGYTFT SYWIHWVRQA PGQGLEWIGV IDPSDSYTRY  60
NQKFKGRVTM TVDTSTSTAY MELRSLRSDD TAVYYCTTWE VDYWGQGTTV TVSS        114

SEQ ID NO: 5            moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 5
MRWSCIILFL VATATGVNS                                               19

SEQ ID NO: 6            moltype = AA  length = 19
```

```
FEATURE                Location/Qualifiers
REGION                 1..19
                       note = Description of Artificial Sequence: Synthetic peptide
source                 1..19
                       mol_type = protein
                       organism = synthetic construct
SEQUENCE: 6
MEWSWVFLFF LSVTTGVHS                                               19

SEQ ID NO: 7           moltype = AA  length = 133
FEATURE                Location/Qualifiers
REGION                 1..133
                       note = Description of Artificial Sequence: Synthetic
                        polypeptide
source                 1..133
                       mol_type = protein
                       organism = synthetic construct
SEQUENCE: 7
MRWSCIILFL VATATGVNSQ VQLVQSGAEV KKPGASVKVS CKASGYTFTS YWIHWVRQAP  60
GQGLEWIGVI DPSDSYTRYN QKFKGRATLT VDTSTSTAYM ELRSLRSDDT AVYYCTTWEV  120
DYWGQGTTVT VSS                                                     133

SEQ ID NO: 8           moltype = AA  length = 133
FEATURE                Location/Qualifiers
REGION                 1..133
                       note = Description of Artificial Sequence: Synthetic
                        polypeptide
source                 1..133
                       mol_type = protein
                       organism = synthetic construct
SEQUENCE: 8
MRWSCIILFL VATATGVNSQ VQLVQSGAEV KKPGASVKVS CKASGYTFTS YWIHWVRQAP  60
GQGLEWIGVI DPSDSYTRYN QKFKGRVTLT VDTSTSTAYM ELRSLRSDDT AVYYCTTWEV  120
DYWGQGTTVT VSS                                                     133

SEQ ID NO: 9           moltype = AA  length = 133
FEATURE                Location/Qualifiers
REGION                 1..133
                       note = Description of Artificial Sequence: Synthetic
                        polypeptide
source                 1..133
                       mol_type = protein
                       organism = synthetic construct
SEQUENCE: 9
MRWSCIILFL VATATGVNSQ VQLVQSGAEV KKPGASVKVS CKASGYTFTS YWIHWVRQAP  60
GQGLEWIGVI DPSDSYTRYN QKFKGRATMT VDTSTSTAYM ELRSLRSDDT AVYYCTTWEV  120
DYWGQGTTVT VSS                                                     133

SEQ ID NO: 10          moltype = AA  length = 133
FEATURE                Location/Qualifiers
REGION                 1..133
                       note = Description of Artificial Sequence: Synthetic
                        polypeptide
source                 1..133
                       mol_type = protein
                       organism = synthetic construct
SEQUENCE: 10
MRWSCIILFL VATATGVNSQ VQLVQSGAEV KKPGASVKVS CKASGYTFTS YWIHWVRQAP  60
GQGLEWIGVI DPSDSYTRYN QKFKGRVTMT VDTSTSTAYM ELRSLRSDDT AVYYCTTWEV  120
DYWGQGTTVT VSS                                                     133

SEQ ID NO: 11          moltype = AA  length = 133
FEATURE                Location/Qualifiers
REGION                 1..133
                       note = Description of Artificial Sequence: Synthetic
                        polypeptide
source                 1..133
                       mol_type = protein
                       organism = synthetic construct
SEQUENCE: 11
MEWSWVFLFF LSVTTGVHSQ VQLVQSGAEV KKPGASVKVS CKASGYTFTS YWIHWVRQAP  60
GQGLEWIGVI DPSDSYTRYN QKFKGRATLT VDTSTSTAYM ELRSLRSDDT AVYYCTTWEV  120
DYWGQGTTVT VSS                                                     133

SEQ ID NO: 12          moltype = AA  length = 133
FEATURE                Location/Qualifiers
REGION                 1..133
                       note = Description of Artificial Sequence: Synthetic
                        polypeptide
```

```
source                  1..133
                        mol_type = protein
                        organism = synthetic construct
SEQUENCE: 12
MEWSWVFLFF LSVTTGVHSQ VQLVQSGAEV KKPGASVKVS CKASGYTFTS YWIHWVRQAP  60
GQGLEWIGVI DPSDSYTRYN QKFKGRVTLT VDTSTSTAYM ELRSLRSDDT AVYYCTTWEV  120
DYWGQGTTVT VSS                                                     133

SEQ ID NO: 13           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 13
MEWSWVFLFF LSVTTGVHSQ VQLVQSGAEV KKPGASVKVS CKASGYTFTS YWIHWVRQAP  60
GQGLEWIGVI DPSDSYTRYN QKFKGRATMT VDTSTSTAYM ELRSLRSDDT AVYYCTTWEV  120
DYWGQGTTVT VSS                                                     133

SEQ ID NO: 14           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 14
MEWSWVFLFF LSVTTGVHSQ VQLVQSGAEV KKPGASVKVS CKASGYTFTS YWIHWVRQAP  60
GQGLEWIGVI DPSDSYTRYN QKFKGRVTMT VDTSTSTAYM ELRSLRSDDT AVYYCTTWEV  120
DYWGQGTTVT VSS                                                     133

SEQ ID NO: 15           moltype = AA  length = 325
FEATURE                 Location/Qualifiers
REGION                  1..325
                        note = Description of Artificial Sequence: Synthetic
                         polypeptide
source                  1..325
                        mol_type = protein
                        organism = synthetic construct
SEQUENCE: 15
PSVFPLAPSS KSTSGGTAAL GCLVKDYFPE PVTVSWNSGA LTSGVHTFPA VLQSSGLYSL  60
SSVVTVPSSS LGTQTYICNV NHKPSNTKVD KKVEPKSCDK THTCPPCPAP EAAGGPSVFL  120
FPPKPKDTLM ISRTPEVTCV VVDVSHEDPE VKFNWYVDGV EVHNAKTKPR EEQYNSTYRV  180
VSVLTVLHQD WLNGKEYKCK VSNKALPAPI EKTISKAKGQ PREPQVYTLP PSRDELTKNQ  240
VSLTCLVKGF YPSDIAVEWE SNGQPENNYK TTPPVLDSDG SFFLYSKLTV DKSRWQQGNV  300
FSCSVMHEAL HNHYTQKSLS LSPGK                                        325

SEQ ID NO: 16           moltype = AA  length = 321
FEATURE                 Location/Qualifiers
REGION                  1..321
                        note = Description of Artificial Sequence: Synthetic
                         polypeptide
source                  1..321
                        mol_type = protein
                        organism = synthetic construct
SEQUENCE: 16
PSVFPLAPCS RSTSESTAAL GCLVKDYFPE PVTVSWNSGA LTSGVHTFPA VLQSSGLYSL  60
SSVVTVPSSS LGTKTYTCNV DHKPSNTKVD KRVESKYGPP CPPCPAPEFL GGPSVFLFPP  120
KPKDTLMISR TPEVTCVVVD VSQEDPEVQF NWYVDGVEVH NAKTKPREEQ FNSTYRVVSV  180
LTVLHQDWLN GKEYKCKVSN KGLPSSIEKT ISKAKGQPRE PQVYTLPPSQ EEMTKNQVSL  240
TCLVKGFYPS DIAVEWESNG QPENNYKTTP PVLDSDGSFF LYSRLTVDKS RWQEGNVFSC  300
SVMHEALHNH YTQKSLSLSL G                                            321

SEQ ID NO: 17           moltype = AA  length = 444
FEATURE                 Location/Qualifiers
REGION                  1..444
                        note = Description of Artificial Sequence: Synthetic
                         polypeptide
source                  1..444
                        mol_type = protein
                        organism = synthetic construct
SEQUENCE: 17
QVQLVQSGAE VKKPGASVKV SCKASGYTFT SYWIHWVRQA PGQGLEWIGV IDPSDSYTRY  60
NQKFKGRATL TVDTSTSTAY MELRSLRSDD TAVYYCTTWE VDYWGQGTTV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE AAGGPSVFLF  240
```

```
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGK                                        444

SEQ ID NO: 18          moltype = AA  length = 440
FEATURE                Location/Qualifiers
REGION                 1..440
                       note = Description of Artificial Sequence: Synthetic
                        polypeptide
source                 1..440
                       mol_type = protein
                       organism = synthetic construct
SEQUENCE: 18
QVQLVQSGAE VKKPGASVKV SCKASGYTFT SYWIHWVRQA PGQGLEWIGV IDPSDSYTRY  60
NQKFKGRATL TVDTSTSTAY MELRSLRSDD TAVYYCTTWE VDYWGQGTTV TVSSASTKGP  120
SVFPLAPCSR STSESTAALG CLVKDYFPEP VTVSWNSGAL TSGVHTFPAV LQSSGLYSLS  180
SVVTVPSSSL GTKTYTCNVD HKPSNTKVDK RVESKYGPPC PPCPAPEFLG GPSVFLFPPK  240
PKDTLMISRT PEVTCVVVDV SQEDPEVQFN WYVDGVEVHN AKTKPREEQF NSTYRVVSVL  300
TVLHQDWLNG KEYKCKVSNK GLPSSIEKTI SKAKGQPREP QVYTLPPSQE EMTKNQVSLT  360
CLVKGFYPSD IAVEWESNGQ PENNYKTTPP VLDSDGSFFL YSRLTVDKSR WQEGNVFSCS  420
VMHEALHNHY TQKSLSLSLG                                             440

SEQ ID NO: 19          moltype = AA  length = 444
FEATURE                Location/Qualifiers
REGION                 1..444
                       note = Description of Artificial Sequence: Synthetic
                        polypeptide
source                 1..444
                       mol_type = protein
                       organism = synthetic construct
SEQUENCE: 19
QVQLVQSGAE VKKPGASVKV SCKASGYTFT SYWIHWVRQA PGQGLEWIGV IDPSDSYTRY  60
NQKFKGRVTL TVDTSTSTAY MELRSLRSDD TAVYYCTTWE VDYWGQGTTV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE AAGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGK                                        444

SEQ ID NO: 20          moltype = AA  length = 440
FEATURE                Location/Qualifiers
REGION                 1..440
                       note = Description of Artificial Sequence: Synthetic
                        polypeptide
source                 1..440
                       mol_type = protein
                       organism = synthetic construct
SEQUENCE: 20
QVQLVQSGAE VKKPGASVKV SCKASGYTFT SYWIHWVRQA PGQGLEWIGV IDPSDSYTRY  60
NQKFKGRVTL TVDTSTSTAY MELRSLRSDD TAVYYCTTWE VDYWGQGTTV TVSSASTKGP  120
SVFPLAPCSR STSESTAALG CLVKDYFPEP VTVSWNSGAL TSGVHTFPAV LQSSGLYSLS  180
SVVTVPSSSL GTKTYTCNVD HKPSNTKVDK RVESKYGPPC PPCPAPEFLG GPSVFLFPPK  240
PKDTLMISRT PEVTCVVVDV SQEDPEVQFN WYVDGVEVHN AKTKPREEQF NSTYRVVSVL  300
TVLHQDWLNG KEYKCKVSNK GLPSSIEKTI SKAKGQPREP QVYTLPPSQE EMTKNQVSLT  360
CLVKGFYPSD IAVEWESNGQ PENNYKTTPP VLDSDGSFFL YSRLTVDKSR WQEGNVFSCS  420
VMHEALHNHY TQKSLSLSLG                                             440

SEQ ID NO: 21          moltype = AA  length = 444
FEATURE                Location/Qualifiers
REGION                 1..444
                       note = Description of Artificial Sequence: Synthetic
                        polypeptide
source                 1..444
                       mol_type = protein
                       organism = synthetic construct
SEQUENCE: 21
QVQLVQSGAE VKKPGASVKV SCKASGYTFT SYWIHWVRQA PGQGLEWIGV IDPSDSYTRY  60
NQKFKGRATM TVDTSTSTAY MELRSLRSDD TAVYYCTTWE VDYWGQGTTV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE AAGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGK                                        444

SEQ ID NO: 22          moltype = AA  length = 440
FEATURE                Location/Qualifiers
```

```
REGION                1..440
                      note = Description of Artificial Sequence: Synthetic
                       polypeptide
source                1..440
                      mol_type = protein
                      organism = synthetic construct
SEQUENCE: 22
QVQLVQSGAE VKKPGASVKV SCKASGYTFT SYWIHWVRQA PGQGLEWIGV IDPSDSYTRY  60
NQKFKGRATM TVDTSTSTAY MELRSLRSDD TAVYYCTTWE VDYWGQGTTV TVSSASTKGP  120
SVFPLAPCSR STSESTAALG CLVKDYFPEP VTVSWNSGAL TSGVHTFPAV LQSSGLYSLS  180
SVVTVPSSSL GTKTYTCNVD HKPSNTKVDK RVESKYGPPC PPCPAPEFLG GPSVFLFPPK  240
PKDTLMISRT PEVTCVVVDV SQEDPEVQFN WYVDGVEVHN AKTKPREEQF NSTYRVVSVL  300
TVLHQDWLNG KEYKCKVSNK GLPSSIEKTI SKAKGQPREP QVYTLPPSQE EMTKNQVSLT  360
CLVKGFYPSD IAVEWESNGQ PENNYKTTPP VLDSDGSFFL YSRLTVDKSR WQEGNVFSCS  420
VMHEALHNHY TQKSLSLSLG                                            440

SEQ ID NO: 23         moltype = AA  length = 444
FEATURE               Location/Qualifiers
REGION                1..444
                      note = Description of Artificial Sequence: Synthetic
                       polypeptide
source                1..444
                      mol_type = protein
                      organism = synthetic construct
SEQUENCE: 23
QVQLVQSGAE VKKPGASVKV SCKASGYTFT SYWIHWVRQA PGQGLEWIGV IDPSDSYTRY  60
NQKFKGRVTM TVDTSTSTAY MELRSLRSDD TAVYYCTTWE VDYWGQGTTV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE AAGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGK                                       444

SEQ ID NO: 24         moltype = AA  length = 440
FEATURE               Location/Qualifiers
REGION                1..440
                      note = Description of Artificial Sequence: Synthetic
                       polypeptide
source                1..440
                      mol_type = protein
                      organism = synthetic construct
SEQUENCE: 24
QVQLVQSGAE VKKPGASVKV SCKASGYTFT SYWIHWVRQA PGQGLEWIGV IDPSDSYTRY  60
NQKFKGRVTM TVDTSTSTAY MELRSLRSDD TAVYYCTTWE VDYWGQGTTV TVSSASTKGP  120
SVFPLAPCSR STSESTAALG CLVKDYFPEP VTVSWNSGAL TSGVHTFPAV LQSSGLYSLS  180
SVVTVPSSSL GTKTYTCNVD HKPSNTKVDK RVESKYGPPC PPCPAPEFLG GPSVFLFPPK  240
PKDTLMISRT PEVTCVVVDV SQEDPEVQFN WYVDGVEVHN AKTKPREEQF NSTYRVVSVL  300
TVLHQDWLNG KEYKCKVSNK GLPSSIEKTI SKAKGQPREP QVYTLPPSQE EMTKNQVSLT  360
CLVKGFYPSD IAVEWESNGQ PENNYKTTPP VLDSDGSFFL YSRLTVDKSR WQEGNVFSCS  420
VMHEALHNHY TQKSLSLSLG                                            440

SEQ ID NO: 25         moltype = AA  length = 463
FEATURE               Location/Qualifiers
REGION                1..463
                      note = Description of Artificial Sequence: Synthetic
                       polypeptide
source                1..463
                      mol_type = protein
                      organism = synthetic construct
SEQUENCE: 25
MRWSCIILFL VATATGVNSQ VQLVQSGAEV KKPGASVKVS CKASGYTFTS YWIHWVRQAP  60
GQGLEWIGVI DPSDSYTRYN QKFKGRATLT VDTSTSTAYM ELRSLRSDDT AVYYCTTWEV  120
DYWGQGTTVT VSSASTKGPS VFPLAPSSKS TSGGTAALGC LVKDYFPEPV TVSWNSGALT  180
SGVHTFPAVL QSSGLYSLSS VVTVPSSSLG TQTYICNVNH KPSNTKVDKK VEPKSCDKTH  240
TCPPCPAPEA AGGPSVFLFP PKPKDTLMIS RTPEVTCVVV DVSHEDPEVK FNWYVDGVEV  300
HNAKTKPREE QYNSTYRVVS VLTVLHQDWL NGKEYKCKVS NKALPAPIEK TISKAKGQPR  360
EPQVYTLPPS RDELTKNQVS LTCLVKGFYP SDIAVEWESN GQPENNYKTT PPVLDSDGSF  420
FLYSKLTVDK SRWQQGNVFS CSVMHEALHN HYTQKSLSLS PGK                  463

SEQ ID NO: 26         moltype = AA  length = 459
FEATURE               Location/Qualifiers
REGION                1..459
                      note = Description of Artificial Sequence: Synthetic
                       polypeptide
source                1..459
                      mol_type = protein
                      organism = synthetic construct
SEQUENCE: 26
```

```
MRWSCIILFL VATATGVNSQ VQLVQSGAEV KKPGASVKVS CKASGYTFTS YWIHWVRQAP  60
GQGLEWIGVI DPSDSYTRYN QKFKGRATLT VDTSTSTAYM ELRSLRSDDT AVYYCTTWEV  120
DYWGQGTTVT VSSASTKGPS VFPLAPCSRS TSESTAALGC LVKDYFPEPV TVSWNSGALT  180
SGVHTFPAVL QSSGLYSLSS VVTVPSSSLG TKTYTCNVDH KPSNTKVDKR VESKYGPPCP  240
PCPAPEFLGG PSVFLFPPKP KDTLMISRTP EVTCVVVDVS QEDPEVQFNW YVDGVEVHNA  300
KTKPREEQFN STYRVVSVLT VLHQDWLNGK EYKCKVSNKG LPSSIEKTIS KAKGQPREPQ  360
VYTLPPSQEE MTKNQVSLTC LVKGFYPSDI AVEWESNGQP ENNYKTTPPV LDSDGSFFLY  420
SRLTVDKSRW QEGNVFSCSV MHEALHNHYT QKSLSLSLG                         459

SEQ ID NO: 27          moltype = AA  length = 463
FEATURE                Location/Qualifiers
REGION                 1..463
                       note = Description of Artificial Sequence: Synthetic
                        polypeptide
source                 1..463
                       mol_type = protein
                       organism = synthetic construct
SEQUENCE: 27
MRWSCIILFL VATATGVNSQ VQLVQSGAEV KKPGASVKVS CKASGYTFTS YWIHWVRQAP  60
GQGLEWIGVI DPSDSYTRYN QKFKGRVTLT VDTSTSTAYM ELRSLRSDDT AVYYCTTWEV  120
DYWGQGTTVT VSSASTKGPS VFPLAPSSKS TSGGTAALGC LVKDYFPEPV TVSWNSGALT  180
SGVHTFPAVL QSSGLYSLSS VVTVPSSSLG TQTYICNVNH KPSNTKVDKK VEPKSCDKTH  240
TCPPCPAPEA AGGPSVFLFP PKPKDTLMIS RTPEVTCVVV DVSHEDPEVK FNWYVDGVEV  300
HNAKTKPREE QYNSTYRVVS VLTVLHQDWL NGKEYKCKVS NKALPAPIEK TISKAKGQPR  360
EPQVYTLPPS RDELTKNQVS LTCLVKGFYP SDIAVEWESN GQPENNYKTT PPVLDSDGSF  420
FLYSKLTVDK SRWQQGNVFS CSVMHEALHN HYTQKSLSLS PGK                    463

SEQ ID NO: 28          moltype = AA  length = 459
FEATURE                Location/Qualifiers
REGION                 1..459
                       note = Description of Artificial Sequence: Synthetic
                        polypeptide
source                 1..459
                       mol_type = protein
                       organism = synthetic construct
SEQUENCE: 28
MRWSCIILFL VATATGVNSQ VQLVQSGAEV KKPGASVKVS CKASGYTFTS YWIHWVRQAP  60
GQGLEWIGVI DPSDSYTRYN QKFKGRVTLT VDTSTSTAYM ELRSLRSDDT AVYYCTTWEV  120
DYWGQGTTVT VSSASTKGPS VFPLAPCSRS TSESTAALGC LVKDYFPEPV TVSWNSGALT  180
SGVHTFPAVL QSSGLYSLSS VVTVPSSSLG TKTYTCNVDH KPSNTKVDKR VESKYGPPCP  240
PCPAPEFLGG PSVFLFPPKP KDTLMISRTP EVTCVVVDVS QEDPEVQFNW YVDGVEVHNA  300
KTKPREEQFN STYRVVSVLT VLHQDWLNGK EYKCKVSNKG LPSSIEKTIS KAKGQPREPQ  360
VYTLPPSQEE MTKNQVSLTC LVKGFYPSDI AVEWESNGQP ENNYKTTPPV LDSDGSFFLY  420
SRLTVDKSRW QEGNVFSCSV MHEALHNHYT QKSLSLSLG                         459

SEQ ID NO: 29          moltype = AA  length = 463
FEATURE                Location/Qualifiers
REGION                 1..463
                       note = Description of Artificial Sequence: Synthetic
                        polypeptide
source                 1..463
                       mol_type = protein
                       organism = synthetic construct
SEQUENCE: 29
MRWSCIILFL VATATGVNSQ VQLVQSGAEV KKPGASVKVS CKASGYTFTS YWIHWVRQAP  60
GQGLEWIGVI DPSDSYTRYN QKFKGRATMT VDTSTSTAYM ELRSLRSDDT AVYYCTTWEV  120
DYWGQGTTVT VSSASTKGPS VFPLAPSSKS TSGGTAALGC LVKDYFPEPV TVSWNSGALT  180
SGVHTFPAVL QSSGLYSLSS VVTVPSSSLG TQTYICNVNH KPSNTKVDKK VEPKSCDKTH  240
TCPPCPAPEA AGGPSVFLFP PKPKDTLMIS RTPEVTCVVV DVSHEDPEVK FNWYVDGVEV  300
HNAKTKPREE QYNSTYRVVS VLTVLHQDWL NGKEYKCKVS NKALPAPIEK TISKAKGQPR  360
EPQVYTLPPS RDELTKNQVS LTCLVKGFYP SDIAVEWESN GQPENNYKTT PPVLDSDGSF  420
FLYSKLTVDK SRWQQGNVFS CSVMHEALHN HYTQKSLSLS PGK                    463

SEQ ID NO: 30          moltype = AA  length = 459
FEATURE                Location/Qualifiers
REGION                 1..459
                       note = Description of Artificial Sequence: Synthetic
                        polypeptide
source                 1..459
                       mol_type = protein
                       organism = synthetic construct
SEQUENCE: 30
MRWSCIILFL VATATGVNSQ VQLVQSGAEV KKPGASVKVS CKASGYTFTS YWIHWVRQAP  60
GQGLEWIGVI DPSDSYTRYN QKFKGRATMT VDTSTSTAYM ELRSLRSDDT AVYYCTTWEV  120
DYWGQGTTVT VSSASTKGPS VFPLAPCSRS TSESTAALGC LVKDYFPEPV TVSWNSGALT  180
SGVHTFPAVL QSSGLYSLSS VVTVPSSSLG TKTYTCNVDH KPSNTKVDKR VESKYGPPCP  240
PCPAPEFLGG PSVFLFPPKP KDTLMISRTP EVTCVVVDVS QEDPEVQFNW YVDGVEVHNA  300
KTKPREEQFN STYRVVSVLT VLHQDWLNGK EYKCKVSNKG LPSSIEKTIS KAKGQPREPQ  360
VYTLPPSQEE MTKNQVSLTC LVKGFYPSDI AVEWESNGQP ENNYKTTPPV LDSDGSFFLY  420
```

```
SRLTVDKSRW QEGNVFSCSV MHEALHNHYT QKSLSLSLG                    459

SEQ ID NO: 31          moltype = AA  length = 463
FEATURE                Location/Qualifiers
REGION                 1..463
                       note = Description of Artificial Sequence: Synthetic
                        polypeptide
source                 1..463
                       mol_type = protein
                       organism = synthetic construct
SEQUENCE: 31
MRWSCIILFL VATATGVNSQ VQLVQSGAEV KKPGASVKVS CKASGYTFTS YWIHWVRQAP  60
GQGLEWIGVI DPSDSYTRYN QKFKGRVTMT VDTSTSTAYM ELRSLRSDDT AVYYCTTWEV  120
DYWGQGTTVT VSSASTKGPS VFPLAPSSKS TSGGTAALGC LVKDYFPEPV TVSWNSGALT  180
SGVHTFPAVL QSSGLYSLSS VVTVPSSSLG TQTYICNVNH KPSNTKVDKK VEPKSCDKTH  240
TCPPCPAPEA AGGPSVFLFP PKPKDTLMIS RTPEVTCVVV DVSHEDPEVK FNWYVDGVEV  300
HNAKTKPREE QYNSTYRVVS VLTVLHQDWL NGKEYKCKVS NKALPAPIEK TISKAKGQPR  360
EPQVYTLPPS RDELTKNQVS LTCLVKGFYP SDIAVEWESN GQPENNYKTT PPVLDSDGSF  420
FLYSKLTVDK SRWQQGNVFS CSVMHEALHN HYTQKSLSLS PGK                463

SEQ ID NO: 32          moltype = AA  length = 459
FEATURE                Location/Qualifiers
REGION                 1..459
                       note = Description of Artificial Sequence: Synthetic
                        polypeptide
source                 1..459
                       mol_type = protein
                       organism = synthetic construct
SEQUENCE: 32
MRWSCIILFL VATATGVNSQ VQLVQSGAEV KKPGASVKVS CKASGYTFTS YWIHWVRQAP  60
GQGLEWIGVI DPSDSYTRYN QKFKGRVTMT VDTSTSTAYM ELRSLRSDDT AVYYCTTWEV  120
DYWGQGTTVT VSSASTKGPS VFPLAPCSRS TSESTAALGC LVKDYFPEPV TVSWNSGALT  180
SGVHTFPAVL QSSGLYSLSS VVTVPSSSLG TKTYTCNVDH KPSNTKVDKR VESKYGPPCP  240
PCPAPEFLGG PSVFLFPPKP KDTLMISRTP EVTCVVVDVS QEDPEVQFNW YVDGVEVHNA  300
KTKPREEQFN STYRVVSVLT VLHQDWLNGK EYKCKVSNKG LPSSIEKTIS KAKGQPREPQ  360
VYTLPPSQEE MTKNQVSLTC LVKGFYPSDI AVEWESNGQP ENNYKTTPPV LDSDGSFFLY  420
SRLTVDKSRW QEGNVFSCSV MHEALHNHYT QKSLSLSLG                    459

SEQ ID NO: 33          moltype = AA  length = 463
FEATURE                Location/Qualifiers
REGION                 1..463
                       note = Description of Artificial Sequence: Synthetic
                        polypeptide
source                 1..463
                       mol_type = protein
                       organism = synthetic construct
SEQUENCE: 33
MEWSWVFLFF LSVTTGVHSQ VQLVQSGAEV KKPGASVKVS CKASGYTFTS YWIHWVRQAP  60
GQGLEWIGVI DPSDSYTRYN QKFKGRATLT VDTSTSTAYM ELRSLRSDDT AVYYCTTWEV  120
DYWGQGTTVT VSSASTKGPS VFPLAPSSKS TSGGTAALGC LVKDYFPEPV TVSWNSGALT  180
SGVHTFPAVL QSSGLYSLSS VVTVPSSSLG TQTYICNVNH KPSNTKVDKK VEPKSCDKTH  240
TCPPCPAPEA AGGPSVFLFP PKPKDTLMIS RTPEVTCVVV DVSHEDPEVK FNWYVDGVEV  300
HNAKTKPREE QYNSTYRVVS VLTVLHQDWL NGKEYKCKVS NKALPAPIEK TISKAKGQPR  360
EPQVYTLPPS RDELTKNQVS LTCLVKGFYP SDIAVEWESN GQPENNYKTT PPVLDSDGSF  420
FLYSKLTVDK SRWQQGNVFS CSVMHEALHN HYTQKSLSLS PGK                463

SEQ ID NO: 34          moltype = AA  length = 459
FEATURE                Location/Qualifiers
REGION                 1..459
                       note = Description of Artificial Sequence: Synthetic
                        polypeptide
source                 1..459
                       mol_type = protein
                       organism = synthetic construct
SEQUENCE: 34
MEWSWVFLFF LSVTTGVHSQ VQLVQSGAEV KKPGASVKVS CKASGYTFTS YWIHWVRQAP  60
GQGLEWIGVI DPSDSYTRYN QKFKGRATLT VDTSTSTAYM ELRSLRSDDT AVYYCTTWEV  120
DYWGQGTTVT VSSASTKGPS VFPLAPCSRS TSESTAALGC LVKDYFPEPV TVSWNSGALT  180
SGVHTFPAVL QSSGLYSLSS VVTVPSSSLG TKTYTCNVDH KPSNTKVDKR VESKYGPPCP  240
PCPAPEFLGG PSVFLFPPKP KDTLMISRTP EVTCVVVDVS QEDPEVQFNW YVDGVEVHNA  300
KTKPREEQFN STYRVVSVLT VLHQDWLNGK EYKCKVSNKG LPSSIEKTIS KAKGQPREPQ  360
VYTLPPSQEE MTKNQVSLTC LVKGFYPSDI AVEWESNGQP ENNYKTTPPV LDSDGSFFLY  420
SRLTVDKSRW QEGNVFSCSV MHEALHNHYT QKSLSLSLG                    459

SEQ ID NO: 35          moltype = AA  length = 463
FEATURE                Location/Qualifiers
REGION                 1..463
                       note = Description of Artificial Sequence: Synthetic
                        polypeptide
```

```
source                  1..463
                        mol_type = protein
                        organism = synthetic construct
SEQUENCE: 35
MEWSWVFLFF LSVTTGVHSQ VQLVQSGAEV KKPGASVKVS CKASGYTFTS YWIHWVRQAP  60
GQGLEWIGVI DPSDSYTRYN QKFKGRVTLT VDTSTSTAYM ELRSLRSDDT AVYYCTTWEV  120
DYWGQGTTVT VSSASTKGPS VFPLAPSSKS TSGGTAALGC LVKDYFPEPV TVSWNSGALT  180
SGVHTFPAVL QSSGLYSLSS VVTVPSSSLG TQTYICNVNH KPSNTKVDKK VEPKSCDKTH  240
TCPPCPAPEA AGGPSVFLFP PKPKDTLMIS RTPEVTCVVV DVSHEDPEVK FNWYVDGVEV  300
HNAKTKPREE QYNSTYRVVS VLTVLHQDWL NGKEYKCKVS NKALPAPIEK TISKAKGQPR  360
EPQVYTLPPS RDELTKNQVS LTCLVKGFYP SDIAVEWESN GQPENNYKTT PPVLDSDGSF  420
FLYSKLTVDK SRWQQGNVFS CSVMHEALHN HYTQKSLSLS PGK                  463

SEQ ID NO: 36           moltype = AA  length = 459
FEATURE                 Location/Qualifiers
REGION                  1..459
                        note = Description of Artificial Sequence: Synthetic
                         polypeptide
source                  1..459
                        mol_type = protein
                        organism = synthetic construct
SEQUENCE: 36
MEWSWVFLFF LSVTTGVHSQ VQLVQSGAEV KKPGASVKVS CKASGYTFTS YWIHWVRQAP  60
GQGLEWIGVI DPSDSYTRYN QKFKGRVTLT VDTSTSTAYM ELRSLRSDDT AVYYCTTWEV  120
DYWGQGTTVT VSSASTKGPS VFPLAPCSRS TSESTAALGC LVKDYFPEPV TVSWNSGALT  180
SGVHTFPAVL QSSGLYSLSS VVTVPSSSLG TKTYTCNVDH KPSNTKVDKR VESKYGPPCP  240
PCPAPEFLGG PSVFLFPPKP KDTLMISRTP EVTCVVVDVS QEDPEVQFNW YVDGVEVHNA  300
KTKPREEQFN STYRVVSVLT VLHQDWLNGK EYKCKVSNKG LPSSIEKTIS KAKGQPREPQ  360
VYTLPPSQEE MTKNQVSLTC LVKGFYPSDI AVEWESNGQP ENNYKTTPPV LDSDGSFFLY  420
SRLTVDKSRW QEGNVFSCSV MHEALHNHYT QKSLSLSLG                        459

SEQ ID NO: 37           moltype = AA  length = 463
FEATURE                 Location/Qualifiers
REGION                  1..463
                        note = Description of Artificial Sequence: Synthetic
                         polypeptide
source                  1..463
                        mol_type = protein
                        organism = synthetic construct
SEQUENCE: 37
MEWSWVFLFF LSVTTGVHSQ VQLVQSGAEV KKPGASVKVS CKASGYTFTS YWIHWVRQAP  60
GQGLEWIGVI DPSDSYTRYN QKFKGRATMT VDTSTSTAYM ELRSLRSDDT AVYYCTTWEV  120
DYWGQGTTVT VSSASTKGPS VFPLAPSSKS TSGGTAALGC LVKDYFPEPV TVSWNSGALT  180
SGVHTFPAVL QSSGLYSLSS VVTVPSSSLG TQTYICNVNH KPSNTKVDKK VEPKSCDKTH  240
TCPPCPAPEA AGGPSVFLFP PKPKDTLMIS RTPEVTCVVV DVSHEDPEVK FNWYVDGVEV  300
HNAKTKPREE QYNSTYRVVS VLTVLHQDWL NGKEYKCKVS NKALPAPIEK TISKAKGQPR  360
EPQVYTLPPS RDELTKNQVS LTCLVKGFYP SDIAVEWESN GQPENNYKTT PPVLDSDGSF  420
FLYSKLTVDK SRWQQGNVFS CSVMHEALHN HYTQKSLSLS PGK                  463

SEQ ID NO: 38           moltype = AA  length = 459
FEATURE                 Location/Qualifiers
REGION                  1..459
                        note = Description of Artificial Sequence: Synthetic
                         polypeptide
source                  1..459
                        mol_type = protein
                        organism = synthetic construct
SEQUENCE: 38
MEWSWVFLFF LSVTTGVHSQ VQLVQSGAEV KKPGASVKVS CKASGYTFTS YWIHWVRQAP  60
GQGLEWIGVI DPSDSYTRYN QKFKGRATMT VDTSTSTAYM ELRSLRSDDT AVYYCTTWEV  120
DYWGQGTTVT VSSASTKGPS VFPLAPCSRS TSESTAALGC LVKDYFPEPV TVSWNSGALT  180
SGVHTFPAVL QSSGLYSLSS VVTVPSSSLG TKTYTCNVDH KPSNTKVDKR VESKYGPPCP  240
PCPAPEFLGG PSVFLFPPKP KDTLMISRTP EVTCVVVDVS QEDPEVQFNW YVDGVEVHNA  300
KTKPREEQFN STYRVVSVLT VLHQDWLNGK EYKCKVSNKG LPSSIEKTIS KAKGQPREPQ  360
VYTLPPSQEE MTKNQVSLTC LVKGFYPSDI AVEWESNGQP ENNYKTTPPV LDSDGSFFLY  420
SRLTVDKSRW QEGNVFSCSV MHEALHNHYT QKSLSLSLG                        459

SEQ ID NO: 39           moltype = AA  length = 463
FEATURE                 Location/Qualifiers
REGION                  1..463
                        note = Description of Artificial Sequence: Synthetic
                         polypeptide
source                  1..463
                        mol_type = protein
                        organism = synthetic construct
SEQUENCE: 39
MEWSWVFLFF LSVTTGVHSQ VQLVQSGAEV KKPGASVKVS CKASGYTFTS YWIHWVRQAP  60
GQGLEWIGVI DPSDSYTRYN QKFKGRVTMT VDTSTSTAYM ELRSLRSDDT AVYYCTTWEV  120
DYWGQGTTVT VSSASTKGPS VFPLAPSSKS TSGGTAALGC LVKDYFPEPV TVSWNSGALT  180
```

-continued

```
SGVHTFPAVL QSSGLYSLSS VVTVPSSSLG TQTYICNVNH KPSNTKVDKK VEPKSCDKTH  240
TCPPCPAPEA AGGPSVFLFP PKPKDTLMIS RTPEVTCVVV DVSHEDPEVK FNWYVDGVEV  300
HNAKTKPREE QYNSTYRVVS VLTVLHQDWL NGKEYKCKVS NKALPAPIEK TISKAKGQPR  360
EPQVYTLPPS RDELTKNQVS LTCLVKGFYP SDIAVEWESN GQPENNYKTT PPVLDSDGSF  420
FLYSKLTVDK SRWQQGNVFS CSVMHEALHN HYTQKSLSLS PGK                  463

SEQ ID NO: 40          moltype = AA  length = 459
FEATURE                Location/Qualifiers
REGION                 1..459
                       note = Description of Artificial Sequence: Synthetic
                        polypeptide
source                 1..459
                       mol_type = protein
                       organism = synthetic construct
SEQUENCE: 40
MEWSWVFLFF LSVTTGVHSQ VQLVQSGAEV KKPGASVKVS CKASGYTFTS YWIHWVRQAP  60
GQGLEWIGVI DPSDSYTRYN QKFKGRVTMT VDTSTSTAYM ELRSLRSDDT AVYYCTTWEV  120
DYWGQGTTVT VSSASTKGPS VFPLAPCSRS TSESTAALGC LVKDYFPEPV TVSWNSGALT  180
SGVHTFPAVL QSSGLYSLSS VVTVPSSSLG TKTYTCNVDH KPSNTKVDKR VESKYGPPCP  240
PCPAPEFLGG PSVFLFPPKP KDTLMISRTP EVTCVVVDVS QEDPEVQFNW YVDGVEVHNA  300
KTKPREEQFN STYRVVSVLT VLHQDWLNGK EYKCKVSNKG LPSSIEKTIS KAKGQPREPQ  360
VYTLPPSQEE MTKNQVSLTC LVKGFYPSDI AVEWESNGQP ENNYKTTPPV LDSDGSFFLY  420
SRLTVDKSRW QEGNVFSCSV MHEALHNHYT QKSLSLSLG                       459

SEQ ID NO: 41          moltype = AA  length = 112
FEATURE                Location/Qualifiers
REGION                 1..112
                       note = Description of Artificial Sequence: Synthetic
                        polypeptide
source                 1..112
                       mol_type = protein
                       organism = synthetic construct
SEQUENCE: 41
DVVMTQTPLS LPVSLGDQAS ISCRSSQSLV HSDGNTYLHW YLQKPGQSPK LLIYKVSNRF  60
SGVPDRFSGS GSGTDFTLKI SRLEAEDLGV YFCSQSTHVP WTFGGGTKLE IK          112

SEQ ID NO: 42          moltype = AA  length = 114
FEATURE                Location/Qualifiers
REGION                 1..114
                       note = Description of Artificial Sequence: Synthetic
                        polypeptide
source                 1..114
                       mol_type = protein
                       organism = synthetic construct
SEQUENCE: 42
DIVMTQSPLS LPVTPGEPAS ISCRSSQSLV HSDGNTYLHW YLQKPGQSPQ LLIYKVSNRF  60
SGVPDRFSGS GSGTDFTLKI SRVEAEDVGV YYCSQSTHVP WTFGGGTKVE IKRT        114

SEQ ID NO: 43          moltype = AA  length = 19
FEATURE                Location/Qualifiers
REGION                 1..19
                       note = Description of Artificial Sequence: Synthetic peptide
source                 1..19
                       mol_type = protein
                       organism = synthetic construct
SEQUENCE: 43
MKLPVRLLVL MFWIPASNS                                              19

SEQ ID NO: 44          moltype = AA  length = 20
FEATURE                Location/Qualifiers
REGION                 1..20
                       note = Description of Artificial Sequence: Synthetic peptide
source                 1..20
                       mol_type = protein
                       organism = synthetic construct
SEQUENCE: 44
MSVPTQVLGL LLLWLTDARC                                             20

SEQ ID NO: 45          moltype = AA  length = 131
FEATURE                Location/Qualifiers
REGION                 1..131
                       note = Description of Artificial Sequence: Synthetic
                        polypeptide
source                 1..131
                       mol_type = protein
                       organism = synthetic construct
SEQUENCE: 45
MKLPVRLLVL MFWIPASNSD VVMTQTPLSL PVSLGDQASI SCRSSQSLVH SDGNTYLHWY  60
LQKPGQSPKL LIYKVSNRFS GVPDRFSGSG SGTDFTLKIS RLEAEDLGVY FCSQSTHVPW  120
```

-continued

```
TFGGGTKLEI K                                                    131

SEQ ID NO: 46          moltype = AA  length = 132
FEATURE                Location/Qualifiers
REGION                 1..132
                       note = Description of Artificial Sequence: Synthetic
                        polypeptide
source                 1..132
                       mol_type = protein
                       organism = synthetic construct
SEQUENCE: 46
MSVPTQVLGL LLLWLTDARC DVVMTQTPLS LPVSLGDQAS ISCRSSQSLV HSDGNTYLHW  60
YLQKPGQSPK LLIYKVSNRF SGVPDRFSGS GSGTDFTLKI SRLEAEDLGV YFCSQSTHVP  120
WTFGGGTKLE IK                                                   132

SEQ ID NO: 47          moltype = AA  length = 133
FEATURE                Location/Qualifiers
REGION                 1..133
                       note = Description of Artificial Sequence: Synthetic
                        polypeptide
source                 1..133
                       mol_type = protein
                       organism = synthetic construct
SEQUENCE: 47
MKLPVRLLVL MFWIPASNSD IVMTQSPLSL PVTPGEPASI SCRSSQSLVH SDGNTYLHWY  60
LQKPGQSPQL LIYKVSNRFS GVPDRFSGSG SGTDFTLKIS RVEAEDVGVY YCSQSTHVPW  120
TFGGGTKVEI KRT                                                  133

SEQ ID NO: 48          moltype = AA  length = 134
FEATURE                Location/Qualifiers
REGION                 1..134
                       note = Description of Artificial Sequence: Synthetic
                        polypeptide
source                 1..134
                       mol_type = protein
                       organism = synthetic construct
SEQUENCE: 48
MSVPTQVLGL LLLWLTDARC DIVMTQSPLS LPVTPGEPAS ISCRSSQSLV HSDGNTYLHW  60
YLQKPGQSPQ LLIYKVSNRF SGVPDRFSGS GSGTDFTLKI SRVEAEDVGV YYCSQSTHVP  120
WTFGGGTKVE IKRT                                                 134

SEQ ID NO: 49          moltype = AA  length = 105
FEATURE                Location/Qualifiers
REGION                 1..105
                       note = Description of Artificial Sequence: Synthetic
                        polypeptide
source                 1..105
                       mol_type = protein
                       organism = synthetic construct
SEQUENCE: 49
VAAPSVFIFP PSDEQLKSGT ASVVCLLNNF YPREAKVQWK VDNALQSGNS QESVTEQDSK  60
DSTYSLSSTL TLSKADYEKH KVYACEVTHQ GLSSPVTKSF NRGEC                105

SEQ ID NO: 50          moltype = AA  length = 217
FEATURE                Location/Qualifiers
REGION                 1..217
                       note = Description of Artificial Sequence: Synthetic
                        polypeptide
source                 1..217
                       mol_type = protein
                       organism = synthetic construct
SEQUENCE: 50
DVVMTQTPLS LPVSLGDQAS ISCRSSQSLV HSDGNTYLHW YLQKPGQSPK LLIYKVSNRF  60
SGVPDRFSGS GSGTDFTLKI SRLEAEDLGV YFCSQSTHVP WTFGGGTKLE IKVAAPSVFI  120
FPPSDEQLKS GTASVVCLLN NFYPREAKVQ WKVDNALQSG NSQESVTEQD SKDSTYSLSS  180
TLTLSKADYE KHKVYACEVT HQGLSSPVTK SFNRGEC                        217

SEQ ID NO: 51          moltype = AA  length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 51
DIVMTQSPLS LPVTPGEPAS ISCRSSQSLV HSDGNTYLHW YLQKPGQSPQ LLIYKVSNRF  60
SGVPDRFSGS GSGTDFTLKI SRVEAEDVGV YYCSQSTHVP WTFGGGTKVE IKRTVAAPSV  120
FIFPPSDEQL KSGTASVVCL LNNFYPREAK VQWKVDNALQ SGNSQESVTE QDSKDSTYSL  180
```

```
SSTLTLSKAD YEKHKVYACE VTHQGLSSPV TKSFNRGEC                          219

SEQ ID NO: 52           moltype = AA  length = 236
FEATURE                 Location/Qualifiers
REGION                  1..236
                        note = Description of Artificial Sequence: Synthetic
                         polypeptide
source                  1..236
                        mol_type = protein
                        organism = synthetic construct
SEQUENCE: 52
MKLPVRLLVL MFWIPASNSD VVMTQTPLSL PVSLGDQASI SCRSSQSLVH SDGNTYLHWY  60
LQKPGQSPKL LIYKVSNRFS GVPDRFSGSG SGTDFTLKIS RLEAEDLGVY FCSQSTHVPW  120
TFGGGTKLEI KVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 53           moltype = AA  length = 237
FEATURE                 Location/Qualifiers
REGION                  1..237
                        note = Description of Artificial Sequence: Synthetic
                         polypeptide
source                  1..237
                        mol_type = protein
                        organism = synthetic construct
SEQUENCE: 53
MSVPTQVLGL LLLWLTDARC DVVMTQTPLS LPVSLGDQAS ISCRSSQSLV HSDGNTYLHW  60
YLQKPGQSPK LLIYKVSNRF SGVPDRFSGS GSGTDFTLKI SRLEAEDLGV YFCSQSTHVP  120
WTFGGGTKLE IKVAAPSVFI FPPSDEQLKS GTASVVCLLN NFYPREAKVQ WKVDNALQSG  180
NSQESVTEQD SKDSTYSLSS TLTLSKADYE KHKVYACEVT HQGLSSPVTK SFNRGEC     237

SEQ ID NO: 54           moltype = AA  length = 238
FEATURE                 Location/Qualifiers
REGION                  1..238
                        note = Description of Artificial Sequence: Synthetic
                         polypeptide
source                  1..238
                        mol_type = protein
                        organism = synthetic construct
SEQUENCE: 54
MKLPVRLLVL MFWIPASNSD IVMTQSPLSL PVTPGEPASI SCRSSQSLVH SDGNTYLHWY  60
LQKPGQSPQL LIYKVSNRFS GVPDRFSGSG SGTDFTLKIS RVEAEDVGVY YCSQSTHVPW  120
TFGGGTKVEI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGEC    238

SEQ ID NO: 55           moltype = AA  length = 239
FEATURE                 Location/Qualifiers
REGION                  1..239
                        note = Description of Artificial Sequence: Synthetic
                         polypeptide
source                  1..239
                        mol_type = protein
                        organism = synthetic construct
SEQUENCE: 55
MSVPTQVLGL LLLWLTDARC DIVMTQSPLS LPVTPGEPAS ISCRSSQSLV HSDGNTYLHW  60
YLQKPGQSPQ LLIYKVSNRF SGVPDRFSGS GSGTDFTLKI SRVEAEDVGV YYCSQSTHVP  120
WTFGGGTKVE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 56           moltype = AA  length = 13
FEATURE                 Location/Qualifiers
source                  1..13
                        mol_type = protein
                        organism = Homo sapiens
SEQUENCE: 56
KVAVVRTPPK SPS                                                      13

SEQ ID NO: 57           moltype = DNA  length = 438
FEATURE                 Location/Qualifiers
misc_feature            1..438
                        note = Description of Artificial Sequence: Synthetic
                         polynucleotide
source                  1..438
                        mol_type = other DNA
                        organism = synthetic construct
CDS                     1..438
SEQUENCE: 57
atgagatgga gctgtatcat cctcttcttg gtagcaacag ctacaggtgt caactcccag  60
gtccaactgc agcagcctgg ggctgagctg gtgaagcctg gggcttcagt gaagatgtcc  120
tgcaaggctt ctggctacac cttcaccagc tactggatac actgggtgaa gcagaggcct  180
```

```
ggacaaggcc ttgagtggat cggagtgatt gatccttctg atagttatac taggtacaat  240
caaaagttca agggcaaggc cacgttgact gtagacacat cctccagcac agcctacatg  300
caactcagca gcctgacatc tgaggactct gcggtctatt actgtacaac atgggaggtt  360
gactactggg gccaaggcac cactctcaca gtctcctcag ccaaaacaac acccccatca  420
gtctatcccc tggcccct                                                 438

SEQ ID NO: 58          moltype = AA  length = 146
FEATURE                Location/Qualifiers
REGION                 1..146
                       note = Description of Artificial Sequence: Synthetic
                        polypeptide
source                 1..146
                       mol_type = protein
                       organism = synthetic construct
SEQUENCE: 58
MRWSCIILFL VATATGVNSQ VQLQQPGAEL VKPGASVKMS CKASGYTFTS YWIHWVKQRP  60
GQGLEWIGVI DPSDSYTRYN QKFKGKATLT VDTSSSTAYM QLSSLTSEDS AVYYCTTWEV  120
DYWGQGTTLT VSSAKTTPPS VYPLAP                                        146

SEQ ID NO: 59          moltype = DNA  length = 438
FEATURE                Location/Qualifiers
misc_feature           1..438
                       note = Description of Artificial Sequence: Synthetic
                        polynucleotide
source                 1..438
                       mol_type = other DNA
                       organism = synthetic construct
CDS                    1..438
SEQUENCE: 59
atgaagttgc ctgttaggct gttggtgctg atgttctgga ttcctgcttc caacagtgat  60
gttgtgatga cccaaactcc actctccctg cctgtcagtc ttggagatca agcctccatc  120
tcttgcagat ctagtcagag ccttgtccac agtgatggaa acacctattt acattggtac  180
ctgcagaagc caggccagtc tccaaagctc ctgatctaca aagtttccaa ccgattttct  240
ggggtcccag acaggttcag tggcagtgga tcagggacag atttcacact caagatcagc  300
agactggagg ctgaggatct gggagtttat ttctgctctc aaagtacaca tgttccgtgg  360
acgttcggtg gaggcaccaa gctggaaatc aaacgggctg atgctgcacc aactgtatcc  420
atcttcccac catccagt                                                 438

SEQ ID NO: 60          moltype = AA  length = 146
FEATURE                Location/Qualifiers
REGION                 1..146
                       note = Description of Artificial Sequence: Synthetic
                        polypeptide
source                 1..146
                       mol_type = protein
                       organism = synthetic construct
SEQUENCE: 60
MKLPVRLLVL MFWIPASNSD VVMTQTPLSL PVSLGDQASI SCRSSQSLVH SDGNTYLHWY  60
LQKPGQSPKL LIYKVSNRFS GVPDRFSGSG SGTDFTLKIS RLEAEDLGVY FCSQSTHVPW  120
TFGGGTKLEI KRADAAPTVS IFPPSS                                        146

SEQ ID NO: 61          moltype = AA  length = 39
FEATURE                Location/Qualifiers
REGION                 1..39
                       note = Description of Artificial Sequence: Synthetic
                        polypeptide
source                 1..39
                       mol_type = protein
                       organism = synthetic construct
SEQUENCE: 61
QVQLQQPGAE LVKPGASVKM SCKASGYTFT SYWIHWVKQ                         39

SEQ ID NO: 62          moltype = AA  length = 39
FEATURE                Location/Qualifiers
source                 1..39
                       mol_type = protein
                       organism = Mus sp.
SEQUENCE: 62
QVQLQQPGAE LVKPGASVKM SCKASGYTFT SYWMHWVKQ                         39

SEQ ID NO: 63          moltype = AA  length = 41
FEATURE                Location/Qualifiers
REGION                 1..41
                       note = Description of Artificial Sequence: Synthetic
                        polypeptide
source                 1..41
                       mol_type = protein
                       organism = synthetic construct
SEQUENCE: 63
```

```
RPGQGLEWIG VIDPSDSYTR YNQKFKGKAT LTVDTSSSTA Y                    41

SEQ ID NO: 64          moltype = AA  length = 41
FEATURE                Location/Qualifiers
source                 1..41
                       mol_type = protein
                       organism = Mus sp.
SEQUENCE: 64
RPGQGLEWIG TIDPSDSYTS YNQKFKGKAT LTVDTSSSTA Y                    41

SEQ ID NO: 65          moltype = AA  length = 34
FEATURE                Location/Qualifiers
REGION                 1..34
                       note = Description of Artificial Sequence: Synthetic
                        polypeptide
source                 1..34
                       mol_type = protein
                       organism = synthetic construct
SEQUENCE: 65
MQLSSLTSED SAVYYCTTWE VDYWGQGTTL TVSS                            34

SEQ ID NO: 66          moltype = AA  length = 18
FEATURE                Location/Qualifiers
source                 1..18
                       mol_type = protein
                       organism = Mus sp.
SEQUENCE: 66
MQLSSLTSED SAVYYCTR                                              18

SEQ ID NO: 67          moltype = AA  length = 11
FEATURE                Location/Qualifiers
source                 1..11
                       mol_type = protein
                       organism = Mus sp.
SEQUENCE: 67
WGQGTTVTVS S                                                     11

SEQ ID NO: 68          moltype = AA  length = 44
FEATURE                Location/Qualifiers
REGION                 1..44
                       note = Description of Artificial Sequence: Synthetic
                        polypeptide
source                 1..44
                       mol_type = protein
                       organism = synthetic construct
SEQUENCE: 68
DVVMTQTPLS LPVSLGDQAS ISCRSSQSLV HSDGNTYLHW YLQK                 44

SEQ ID NO: 69          moltype = AA  length = 44
FEATURE                Location/Qualifiers
source                 1..44
                       mol_type = protein
                       organism = Mus sp.
SEQUENCE: 69
DVVMTQTPLS LPVSLGDQAS ISCRSSQSLV HSNGNTYLHW YLQK                 44

SEQ ID NO: 70          moltype = AA  length = 40
FEATURE                Location/Qualifiers
REGION                 1..40
                       note = Description of Artificial Sequence: Synthetic
                        polypeptide
source                 1..40
                       mol_type = protein
                       organism = synthetic construct
SEQUENCE: 70
PGQSPKLLIY KVSNRFSGVP DRFSGSGSGT DFTLKISRLE                      40

SEQ ID NO: 71          moltype = AA  length = 40
FEATURE                Location/Qualifiers
source                 1..40
                       mol_type = protein
                       organism = Mus sp.
SEQUENCE: 71
PGQSPKLLIY KVSNRFSGVP DRFSGSGSGT DFTLKISRVE                      40

SEQ ID NO: 72          moltype = AA  length = 28
FEATURE                Location/Qualifiers
REGION                 1..28
                       note = Description of Artificial Sequence: Synthetic peptide
```

```
source                 1..28
                       mol_type = protein
                       organism = synthetic construct
SEQUENCE: 72
AEDLGVYFCS QSTHVPWTFG GGTKLEIK                                   28

SEQ ID NO: 73          moltype = AA  length = 9
FEATURE                Location/Qualifiers
source                 1..9
                       mol_type = protein
                       organism = Mus sp.
SEQUENCE: 73
AEDLGVYFC                                                        9

SEQ ID NO: 74          moltype = AA  length = 10
FEATURE                Location/Qualifiers
source                 1..10
                       mol_type = protein
                       organism = Mus sp.
SEQUENCE: 74
FGGGTKLEIK                                                       10

SEQ ID NO: 75          moltype = AA  length = 133
FEATURE                Location/Qualifiers
REGION                 1..133
                       note = Description of Artificial Sequence: Synthetic
                        polypeptide
source                 1..133
                       mol_type = protein
                       organism = synthetic construct
SEQUENCE: 75
MRWSCIILFL VATATGVNSQ VQLQQPGAEL VKPGASVKMS CKASGYTFTS YWIHWVKQRP  60
GQGLEWIGVI DPSDSYTRYN QKFKGKATLT VDTSSSTAYM QLSSLTSEDS AVYYCTTWEV  120
DYWGQGTTLT VSS                                                   133

SEQ ID NO: 76          moltype = DNA  length = 435
FEATURE                Location/Qualifiers
misc_feature           1..435
                       note = Description of Artificial Sequence: Synthetic
                        polynucleotide
source                 1..435
                       mol_type = other DNA
                       organism = synthetic construct
CDS                    13..411
SEQUENCE: 76
actagtacca ccatgagatg gagctgtatc atcctcttct tggtggcaac agctacaggt  60
gtcaactccc aggtccaact gcagcagcct ggggctgagc tggtgaagcc tggggcttca  120
gtgaagatgt cctgcaaggc ttctggctac accttcacca gctactggat tcactgggtc  180
aagcagaggc ctggacaagg ccttgagtgg atcggagtga ttgatccttc agatagttat  240
actagataca atcaaaagtt caagggcaag gccacattga ctgtggacac atcctccagc  300
acagcctaca tgcagctcag cagcctgaca tctgaagact ctgccgtcta ttactgtaca  360
acctgggaag tcgactactg gggccaaggc accactctca cagtctcctc aggtgagtcc  420
ttaaaaccta agctt                                                 435

SEQ ID NO: 77          moltype = AA  length = 131
FEATURE                Location/Qualifiers
REGION                 1..131
                       note = Description of Artificial Sequence: Synthetic
                        polypeptide
source                 1..131
                       mol_type = protein
                       organism = synthetic construct
SEQUENCE: 77
MKLPVRLLVL MFWIPASNSD VVMTQTPLSL PVSLGDQASI SCRSSQSLVH SDGNTYLHWY  60
LQKPGQSPKL LIYKVSNRFS GVPDRFSGSG SGTDFTLKIS RLEAEDLGVY FCSQSTHVPW  120
TFGGGTKLEI K                                                     131

SEQ ID NO: 78          moltype = DNA  length = 431
FEATURE                Location/Qualifiers
misc_feature           1..431
                       note = Description of Artificial Sequence: Synthetic
                        polynucleotide
source                 1..431
                       mol_type = other DNA
                       organism = synthetic construct
CDS                    13..405
SEQUENCE: 78
gctagcacca ccatgaagtt gcctgttagg ctgttggtgc tgatgttctg gattcctgct  60
tccaacagtg atgttgtgat gacccaaact ccactctccc tgcctgtcag tcttggagat  120
```

```
caagcctcca tctcttgcag atctagtcag agccttgtgc acagtgatgg aaacacctat  180
ctgcattggt acctgcagaa gccaggccag tctccaaagc tcctgatcta caaagtttcc  240
aaccgatttt ctggggtccc agacaggttc agtggcagtg gatcagggac agatttcaca  300
ctcaagatca gcagactgga ggctgaggat ctgggagttt atttctgctc tcaaagtaca  360
catgttcctt ggaccttcgg tggaggcacc aagctggaaa tcaaacgtaa gtagaatcca  420
aagtcgaatt c                                                       431

SEQ ID NO: 79          moltype = AA  length = 39
FEATURE                Location/Qualifiers
REGION                 1..39
                       note = Description of Artificial Sequence: Synthetic
                        polypeptide
source                 1..39
                       mol_type = protein
                       organism = synthetic construct
SEQUENCE: 79
QVQLQQPGAE LVKPGASVKM SCKASGYTFT SYWIHWVKQ                         39

SEQ ID NO: 80          moltype = AA  length = 39
FEATURE                Location/Qualifiers
REGION                 1..39
                       note = Description of Artificial Sequence: Synthetic
                        polypeptide
source                 1..39
                       mol_type = protein
                       organism = synthetic construct
SEQUENCE: 80
QVQLVQSGAE VKKPGASVKV SCKASGYTFT SYWIHWVRQ                         39

SEQ ID NO: 81          moltype = AA  length = 39
FEATURE                Location/Qualifiers
REGION                 1..39
                       note = Description of Artificial Sequence: Synthetic
                        polypeptide
source                 1..39
                       mol_type = protein
                       organism = synthetic construct
SEQUENCE: 81
QVQLVQSGAE VKKPGASVKV SCKASGYTFT SYWIHWVRQ                         39

SEQ ID NO: 82          moltype = AA  length = 39
FEATURE                Location/Qualifiers
REGION                 1..39
                       note = Description of Artificial Sequence: Synthetic
                        polypeptide
source                 1..39
                       mol_type = protein
                       organism = synthetic construct
SEQUENCE: 82
QVQLVQSGAE VKKPGASVKV SCKASGYTFT SYWIHWVRQ                         39

SEQ ID NO: 83          moltype = AA  length = 39
FEATURE                Location/Qualifiers
REGION                 1..39
                       note = Description of Artificial Sequence: Synthetic
                        polypeptide
source                 1..39
                       mol_type = protein
                       organism = synthetic construct
SEQUENCE: 83
QVQLVQSGAE VKKPGASVKV SCKASGYTFT SYWIHWVRQ                         39

SEQ ID NO: 84          moltype = AA  length = 34
FEATURE                Location/Qualifiers
source                 1..34
                       mol_type = protein
                       organism = Homo sapiens
SEQUENCE: 84
QVQLVQSGAE VKKPGASVKV SCKASGYTFT WVRQ                              34

SEQ ID NO: 85          moltype = AA  length = 41
FEATURE                Location/Qualifiers
REGION                 1..41
                       note = Description of Artificial Sequence: Synthetic
                        polypeptide
source                 1..41
                       mol_type = protein
                       organism = synthetic construct
SEQUENCE: 85
```

```
RPGQGLEWIG VIDPSDSYTR YNQKFKGKAT LTVDTSSSTA Y                41

SEQ ID NO: 86          moltype = AA  length = 41
FEATURE                Location/Qualifiers
REGION                 1..41
                       note = Description of Artificial Sequence: Synthetic
                        polypeptide
source                 1..41
                       mol_type = protein
                       organism = synthetic construct
SEQUENCE: 86
APGQGLEWIG VIDPSDSYTR YNQKFKGRAT LTVDTSTSTA Y                41

SEQ ID NO: 87          moltype = AA  length = 41
FEATURE                Location/Qualifiers
REGION                 1..41
                       note = Description of Artificial Sequence: Synthetic
                        polypeptide
source                 1..41
                       mol_type = protein
                       organism = synthetic construct
SEQUENCE: 87
APGQGLEWIG VIDPSDSYTR YNQKFKGRVT LTVDTSTSTA Y                41

SEQ ID NO: 88          moltype = AA  length = 41
FEATURE                Location/Qualifiers
REGION                 1..41
                       note = Description of Artificial Sequence: Synthetic
                        polypeptide
source                 1..41
                       mol_type = protein
                       organism = synthetic construct
SEQUENCE: 88
APGQGLEWIG VIDPSDSYTR YNQKFKGRAT MTVDTSTSTA Y                41

SEQ ID NO: 89          moltype = AA  length = 41
FEATURE                Location/Qualifiers
REGION                 1..41
                       note = Description of Artificial Sequence: Synthetic
                        polypeptide
source                 1..41
                       mol_type = protein
                       organism = synthetic construct
SEQUENCE: 89
APGQGLEWIG VIDPSDSYTR YNQKFKGRVT MTVDTSTSTA Y                41

SEQ ID NO: 90          moltype = AA  length = 24
FEATURE                Location/Qualifiers
source                 1..24
                       mol_type = protein
                       organism = Homo sapiens
SEQUENCE: 90
APGQGLEWMG RVTMTTDTST STAY                                   24

SEQ ID NO: 91          moltype = AA  length = 34
FEATURE                Location/Qualifiers
REGION                 1..34
                       note = Description of Artificial Sequence: Synthetic
                        polypeptide
source                 1..34
                       mol_type = protein
                       organism = synthetic construct
SEQUENCE: 91
MQLSSLTSED SAVYYCTTWE VDYWGQGTTL TVSS                        34

SEQ ID NO: 92          moltype = AA  length = 34
FEATURE                Location/Qualifiers
REGION                 1..34
                       note = Description of Artificial Sequence: Synthetic
                        polypeptide
source                 1..34
                       mol_type = protein
                       organism = synthetic construct
SEQUENCE: 92
MELRSLRSDD TAVYYCTTWE VDYWGQGTTV TVSS                        34

SEQ ID NO: 93          moltype = AA  length = 34
FEATURE                Location/Qualifiers
REGION                 1..34
```

```
                        note = Description of Artificial Sequence: Synthetic
                         polypeptide
source                  1..34
                        mol_type = protein
                        organism = synthetic construct
SEQUENCE: 93
MELRSLRSDD TAVYYCTTWE VDYWGQGTTV TVSS                              34

SEQ ID NO: 94           moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 94
MELRSLRSDD TAVYYCTTWE VDYWGQGTTV TVSS                              34

SEQ ID NO: 95           moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 95
MELRSLRSDD TAVYYCTTWE VDYWGQGTTV TVSS                              34

SEQ ID NO: 96           moltype = AA  length = 29
FEATURE                 Location/Qualifiers
source                  1..29
                        mol_type = protein
                        organism = Homo sapiens
SEQUENCE: 96
MELRSLRSDD TAVYYCARWG QGTTVTVSS                                    29

SEQ ID NO: 97           moltype = AA  length = 44
FEATURE                 Location/Qualifiers
REGION                  1..44
                        note = Description of Artificial Sequence: Synthetic
                         polypeptide
source                  1..44
                        mol_type = protein
                        organism = synthetic construct
SEQUENCE: 97
DVVMTQTPLS LPVSLGDQAS ISCRSSQSLV HSDGNTYLHW YLQK                   44

SEQ ID NO: 98           moltype = AA  length = 44
FEATURE                 Location/Qualifiers
REGION                  1..44
                        note = Description of Artificial Sequence: Synthetic
                         polypeptide
source                  1..44
                        mol_type = protein
                        organism = synthetic construct
SEQUENCE: 98
DIVMTQSPLS LPVTPGEPAS ISCRSSQSLV HSDGNTYLHW YLQK                   44

SEQ ID NO: 99           moltype = AA  length = 28
FEATURE                 Location/Qualifiers
source                  1..28
                        mol_type = protein
                        organism = Homo sapiens
SEQUENCE: 99
DIVMTQSPLS LPVTPGEPAS ISCWYLQK                                     28

SEQ ID NO: 100          moltype = AA  length = 40
FEATURE                 Location/Qualifiers
REGION                  1..40
                        note = Description of Artificial Sequence: Synthetic
                         polypeptide
source                  1..40
                        mol_type = protein
                        organism = synthetic construct
SEQUENCE: 100
PGQSPKLLIY KVSNRFSGVP DRFSGSGSGT DFTLKISRLE                        40
```

```
SEQ ID NO: 101         moltype = AA  length = 40
FEATURE                Location/Qualifiers
REGION                 1..40
                       note = Description of Artificial Sequence: Synthetic
                        polypeptide
source                 1..40
                       mol_type = protein
                       organism = synthetic construct
SEQUENCE: 101
PGQSPQLLIY KVSNRFSGVP DRFSGSGSGT DFTLKISRVE                        40

SEQ ID NO: 102         moltype = AA  length = 33
FEATURE                Location/Qualifiers
source                 1..33
                       mol_type = protein
                       organism = Homo sapiens
SEQUENCE: 102
PGQSPQLLIY GVPDRFSGSG SGTDFTLKIS RVE                               33

SEQ ID NO: 103         moltype = AA  length = 28
FEATURE                Location/Qualifiers
REGION                 1..28
                       note = Description of Artificial Sequence: Synthetic peptide
source                 1..28
                       mol_type = protein
                       organism = synthetic construct
SEQUENCE: 103
AEDLGVYFCS QSTHVPWTFG GGTKLEIK                                     28

SEQ ID NO: 104         moltype = AA  length = 28
FEATURE                Location/Qualifiers
REGION                 1..28
                       note = Description of Artificial Sequence: Synthetic peptide
source                 1..28
                       mol_type = protein
                       organism = synthetic construct
SEQUENCE: 104
AEDVGVYYCS QSTHVPWTFG GGTKVEIK                                     28

SEQ ID NO: 105         moltype = AA  length = 19
FEATURE                Location/Qualifiers
source                 1..19
                       mol_type = protein
                       organism = Homo sapiens
SEQUENCE: 105
AEDVGVYYCF GGGTKVEIK                                               19

SEQ ID NO: 106         moltype = AA  length = 133
FEATURE                Location/Qualifiers
REGION                 1..133
                       note = Description of Artificial Sequence: Synthetic
                        polypeptide
source                 1..133
                       mol_type = protein
                       organism = synthetic construct
SEQUENCE: 106
MRWSCIILFL VATATGVNSQ VQLVQSGAEV KKPGASVKVS CKASGYTFTS YWIHWVRQAP  60
GQGLEWIGVI DPSDSYTRYN QKFKGRATLT VDTSTSTAYM ELRSLRSDDT AVYYCTTWEV  120
DYWGQGTTVT VSS                                                     133

SEQ ID NO: 107         moltype = DNA  length = 435
FEATURE                Location/Qualifiers
misc_feature           1..435
                       note = Description of Artificial Sequence: Synthetic
                        polynucleotide
source                 1..435
                       mol_type = other DNA
                       organism = synthetic construct
CDS                    13..411
SEQUENCE: 107
actagtacca ccatgagatg gagctgtatc atcctcttct tggtggcaac agctacaggt  60
gtcaactccc aggtccaact ggtccagtct ggggctgaag tcaagaagcc tggggcttca  120
gtgaaagtgt cctgcaaggc ttctggctac accttcacca gctactggat tcactgggtc  180
aggcaggccc ctggacaagg ccttgagtgg atcggagtga ttgatccttc agatagttat  240
actagataca atcaaaagtt caagggcagg gccacattga ctgtggacac atccaccagc  300
acagcctaca tggagctcag gagcctgaga tctgatgaca ctgccgtcta ttactgtaca  360
acctgggaag tcgactactg gggccaaggc accactgtca cagtctcctc aggtgagtcc  420
ttaaaaccta agctt                                                   435
```

```
SEQ ID NO: 108         moltype = AA  length = 133
FEATURE                Location/Qualifiers
REGION                 1..133
                       note = Description of Artificial Sequence: Synthetic
                        polypeptide
source                 1..133
                       mol_type = protein
                       organism = synthetic construct
SEQUENCE: 108
MRWSCIILFL VATATGVNSQ VQLVQSGAEV KKPGASVKVS CKASGYTFTS YWIHWVRQAP  60
GQGLEWIGVI DPSDSYTRYN QKFKGRVTLT VDTSTSTAYM ELRSLRSDDT AVYYCTTWEV  120
DYWGQGTTVT VSS                                                     133

SEQ ID NO: 109         moltype = DNA  length = 435
FEATURE                Location/Qualifiers
misc_feature           1..435
                       note = Description of Artificial Sequence: Synthetic
                        polynucleotide
source                 1..435
                       mol_type = other DNA
                       organism = synthetic construct
CDS                    13..411
SEQUENCE: 109
actagtacca ccatgagatg gagctgtatc atcctcttct tggtggcaac agctacaggt  60
gtcaactccc aggtccaact ggtccagtct ggggctgaag tcaagaagcc tggggcttca  120
gtgaaagtgt cctgcaaggc ttctggctac accttcacca gctactggat tcactgggtc  180
aggcaggccc ctggacaagg ccttgagtgg atcggagtga ttgatccttc agatagttat  240
actagataca atcaaaagtt caagggcagg gtcacattga ctgtggacac atccaccagc  300
acagcctaca tggagctcag gagcctgaga tctgatgaca ctgccgtcta ttactgtaca  360
acctgggaag tcgactactg gggccaaggc accactgtca cagtctcctc aggtgagtcc  420
ttaaaaccta agctt                                                   435

SEQ ID NO: 110         moltype = AA  length = 133
FEATURE                Location/Qualifiers
REGION                 1..133
                       note = Description of Artificial Sequence: Synthetic
                        polypeptide
source                 1..133
                       mol_type = protein
                       organism = synthetic construct
SEQUENCE: 110
MRWSCIILFL VATATGVNSQ VQLVQSGAEV KKPGASVKVS CKASGYTFTS YWIHWVRQAP  60
GQGLEWIGVI DPSDSYTRYN QKFKGRATMT VDTSTSTAYM ELRSLRSDDT AVYYCTTWEV  120
DYWGQGTTVT VSS                                                     133

SEQ ID NO: 111         moltype = DNA  length = 435
FEATURE                Location/Qualifiers
misc_feature           1..435
                       note = Description of Artificial Sequence: Synthetic
                        polynucleotide
source                 1..435
                       mol_type = other DNA
                       organism = synthetic construct
CDS                    13..411
SEQUENCE: 111
actagtacca ccatgagatg gagctgtatc atcctcttct tggtggcaac agctacaggt  60
gtcaactccc aggtccaact ggtccagtct ggggctgaag tcaagaagcc tggggcttca  120
gtgaaagtgt cctgcaaggc ttctggctac accttcacca gctactggat tcactgggtc  180
aggcaggccc ctggacaagg ccttgagtgg atcggagtga ttgatccttc agatagttat  240
actagataca atcaaaagtt caagggcagg gccacaatga ctgtggacac atccaccagc  300
acagcctaca tggagctcag gagcctgaga tctgatgaca ctgccgtcta ttactgtaca  360
acctgggaag tcgactactg gggccaaggc accactgtca cagtctcctc aggtgagtcc  420
ttaaaaccta agctt                                                   435

SEQ ID NO: 112         moltype = DNA  length = 435
FEATURE                Location/Qualifiers
misc_feature           1..435
                       note = Description of Artificial Sequence: Synthetic
                        polynucleotide
source                 1..435
                       mol_type = other DNA
                       organism = synthetic construct
CDS                    13..411
SEQUENCE: 112
actagtacca ccatgagatg gagctgtatc atcctcttct tggtggcaac agctacaggt  60
gtcaactccc aggtccaact ggtccagtct ggggctgaag tcaagaagcc tggggcttca  120
gtgaaagtgt cctgcaaggc ttctggctac accttcacca gctactggat tcactgggtc  180
aggcaggccc ctggacaagg ccttgagtgg atcggagtga ttgatccttc agatagttat  240
actagataca atcaaaagtt caagggcagg gtcacaatga ctgtggacac atccaccagc  300
```

```
acagcctaca tggagctcag gagcctgaga tctgatgaca ctgccgtcta ttactgtaca  360
acctgggaag tcgactactg gggccaaggc accactgtca cagtctcctc aggtgagtcc  420
ttaaaaccta agctt                                                    435

SEQ ID NO: 113         moltype = AA  length = 131
FEATURE                Location/Qualifiers
REGION                 1..131
                       note = Description of Artificial Sequence: Synthetic
                        polypeptide
source                 1..131
                       mol_type = protein
                       organism = synthetic construct
SEQUENCE: 113
MKLPVRLLVL MFWIPASNSD IVMTQSPLSL PVTPGEPASI SCRSSQSLVH SDGNTYLHWY  60
LQKPGQSPQL LIYKVSNRFS GVPDRFSGSG SGTDFTLKIS RVEAEDVGVY YCSQSTHVPW  120
TFGGGTKVEI K                                                        131

SEQ ID NO: 114         moltype = DNA  length = 431
FEATURE                Location/Qualifiers
misc_feature           1..431
                       note = Description of Artificial Sequence: Synthetic
                        polynucleotide
source                 1..431
                       mol_type = other DNA
                       organism = synthetic construct
CDS                    13..405
SEQUENCE: 114
gctagcacca ccatgaagtt gcctgttagg ctgttggtgc tgatgttctg gattcctgct  60
tccaacagtg atattgtgat gacccaatct ccactctccc tgcctgtcac tcctggagag  120
ccagcctcca tctcttgcag atccagtcag agccttgtgc acagtgatgg aaacacctat  180
ctgcattggt acctgcagaa gccaggccag tctccacagc tcctgatcta caaagtttcc  240
aaccgatttt ctggggtccc agacaggttc agtggcagtg gatcagggac agatttcaca  300
ctcaagatca gcagagtgga ggctgaggat gtgggagttt attactgctc tcaaagtaca  360
catgttcctt ggaccttcgg tggaggcacc aaagtcgaaa tcaaacgtaa gtagaatcca  420
aagtcgaatt c                                                        431

SEQ ID NO: 115         moltype = DNA  length = 24
FEATURE                Location/Qualifiers
misc_feature           1..24
                       note = Description of Artificial Sequence: Synthetic
                        oligonucleotide
source                 1..24
                       mol_type = other DNA
                       organism = synthetic construct
SEQUENCE: 115
gaaccgtcag atcgcctgga gacg                                         24

SEQ ID NO: 116         moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 116
tgaaagatga gctggaggac                                              20

SEQ ID NO: 117         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 117
acgtgccaag catcctcg                                                18

SEQ ID NO: 118         moltype = DNA  length = 1392
FEATURE                Location/Qualifiers
misc_feature           1..1392
                       note = Description of Artificial Sequence: Synthetic
                        polynucleotide
source                 1..1392
                       mol_type = other DNA
                       organism = synthetic construct
CDS                    1..1389
SEQUENCE: 118
```

```
atgagatgga gctgtatcat cctcttcttg gtggcaacag ctacaggtgt caactcccag  60
gtccaactgc agcagcctgg ggctgagctg gtgaagcctg gggcttcagt gaagatgtcc  120
tgcaaggctt ctggctacac cttcaccagc tactggattc actgggtcaa gcagaggcct  180
ggacaaggcc ttgagtggat cggagtgatt gatccttcag atagttatac tagatacaat  240
caaaagttca agggcaaggc cacattgact gtggacacat cctccagcac agcctacatg  300
cagctcagca gcctgacatc tgaagactct gccgtctatt actgtacaac ctgggaagtc  360
gactactggg gccaaggcac cactctcaca gtctcctcag cctccaccaa gggcccatcg  420
gtcttccccc tggcaccctc ctccaagagc acctctgggg gcacagcggc cctgggctgc  480
ctggtcaagg actacttccc cgaaccggtg acggtgtcgt ggaactcagg cgccctgacc  540
agcggcgtgc acaccttccc ggctgtccta cagtcctcag gactctactc cctcagcagc  600
gtggtgaccg tgccctccag cagcttgggc acccagacct acatctgcaa cgtgaatcac  660
aagcccagca acaccaaggt ggacaagaaa gttgagccca aatcttgtga caaaactcac  720
acatgcccac cgtgcccagc acctgaactc ctggggggac cgtcagtctt cctcttcccc  780
ccaaaaccca aggacaccct catgatctcc cggacccctg aggtcacatg cgtggtggtg  840
gacgtgagcc acgaagaccc tgaggtcaag ttcaactggt acgtggacgg cgtggaggtg  900
cataatgcca agacaaagcc gcgggaggag cagtacaaca gcacgtaccg tgtggtcagc  960
gtcctcaccg tcctgcacca ggactggctg aatggcaagg agtacaagtg caaggtctcc  1020
aacaaagccc tcccagcccc catcgagaaa accatctcca aagccaaagg gcagccccga  1080
gaaccacagg tgtacaccct gcccccatcc cgggatgagc tgaccaagaa ccaggtcagc  1140
ctgacctgcc tggtcaaagg cttctatccc agcgacatcg ccgtggagtg ggagagcaat  1200
gggcagccgg agaacaacta caagaccacg cctcccgtgc tggactccga cggctccttc  1260
ttcctctaca gcaagctcac cgtggacaag agcaggtggc agcaggggaa cgtcttctca  1320
tgctccgtga tgcatgaggc tctgcacaac cactacacgc agaagagcct ctccctgtct  1380
ccgggtaaat ga                                                     1392

SEQ ID NO: 119         moltype = AA  length = 463
FEATURE                Location/Qualifiers
REGION                 1..463
                       note = Description of Artificial Sequence: Synthetic
                        polypeptide
source                 1..463
                       mol_type = protein
                       organism = synthetic construct
SEQUENCE: 119
MRWSCIILFL VATATGVNSQ VQLQQPGAEL VKPGASVKMS CKASGYTFTS YWIHWVKQRP  60
GQGLEWIGVI DPSDSYTRYN QKFKGKATLT VDTSSSTAYM QLSSLTSEDS AVYYCTTWEV  120
DYWGQGTTLT VSSASTKGPS VFPLAPSSKS TSGGTAALGC LVKDYFPEPV TVSWNSGALT  180
SGVHTFPAVL QSSGLYSLSS VVTVPSSSLG TQTYICNVNH KPSNTKVDKK VEPKSCDKTH  240
TCPPCPAPEL LGGPSVFLFP PKPKDTLMIS RTPEVTCVVV DVSHEDPEVK FNWYVDGVEV  300
HNAKTKPREE QYNSTYRVVS VLTVLHQDWL NGKEYKCKVS NKALPAPIEK TISKAKGQPR  360
EPQVYTLPPS RDELTKNQVS LTCLVKGFYP SDIAVEWESN GQPENNYKTT PPVLDSDGSF  420
FLYSKLTVDK SRWQQGNVFS CSVMHEALHN HYTQKSLSLS PGK                   463

SEQ ID NO: 120         moltype = DNA  length = 717
FEATURE                Location/Qualifiers
misc_feature           1..717
                       note = Description of Artificial Sequence: Synthetic
                        polynucleotide
source                 1..717
                       mol_type = other DNA
                       organism = synthetic construct
CDS                    1..714
SEQUENCE: 120
atgaagttgc ctgttaggct gttggtgctg atgttctgga ttcctgcttc caacagtgat  60
gttgtgatga cccaaactcc actctccctg cctgtcagtc ttggagatca agcctccatc  120
tcttgcagat ctagtcagag ccttgtgcac agtgatggaa acacctatct gcattggtac  180
ctgcagaagc caggccagtc tccaaagctc ctgatctaca aagtttccaa ccgattttct  240
ggggtcccag acaggttcag tggcagtgga tcagggacag atttcacact caagatcagc  300
agactggagg ctgaggatct gggagtttat ttctgctctc aaagtacaca tgttccttgg  360
accttcggtg gaggcaccaa gctggaaatc aaacgaactg tggctgcacc atctgtcttc  420
atcttcccgc catctgatga gcagttgaaa tctggaactg cctctgttgt gtgcctgctg  480
aataacttct atcccagaga ggccaaagta cagtggaagg tggataacgc cctccaatcg  540
ggtaactccc aggagagtgt cacagagcag gacagcaagg acagcaccta cagcctcagc  600
agcaccctga cgctgagcaa agcagactac gagaaacaca aagtctacgc ctgcgaagtc  660
acccatcagg gcctgagctc gcccgtcaca aagagcttca acaggggaga gtgttag     717

SEQ ID NO: 121         moltype = AA  length = 238
FEATURE                Location/Qualifiers
REGION                 1..238
                       note = Description of Artificial Sequence: Synthetic
                        polypeptide
source                 1..238
                       mol_type = protein
                       organism = synthetic construct
SEQUENCE: 121
MKLPVRLLVL MFWIPASNSD VVMTQTPLSL PVSLGDQASI SCRSSQSLVH SDGNTYLHWY  60
LQKPGQSPKL LIYKVSNRFS GVPDRFSGSG SGTDFTLKIS RLEAEDLGVY FCSQSTHVPW  120
TFGGGTKLEI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGEC    238
```

```
SEQ ID NO: 122          moltype = DNA  length = 1392
FEATURE                 Location/Qualifiers
misc_feature            1..1392
                        note = Description of Artificial Sequence: Synthetic
                         polynucleotide
source                  1..1392
                        mol_type = other DNA
                        organism = synthetic construct
CDS                     1..1389
SEQUENCE: 122
atgagatgga gctgtatcat cctcttcttg gtggcaacag ctacaggtgt caactcccag  60
gtccaactgg tccagtctgg ggctgaagtc aagaagcctg gggcttcagt gaaagtgtcc  120
tgcaaggctt ctggctacac cttcaccagc tactggattc actgggtcag gcaggcccct  180
ggacaaggcc ttgagtggat cggagtgatt gatccttcag atagttatac tagatacaat  240
caaaagttca agggcagggt cacaatgact gtggacacat ccaccagcac agcctacatg  300
gagctcagga gcctgagatc tgatgacact gccgtctatt actgtacaac ctgggaagtc  360
gactactggg gccaaggcac cactgtcaca gtctcctcag cctccaccaa gggcccatcg  420
gtcttccccc tggcaccctc ctccaagagc acctctgggg gcacagcggc cctgggctgc  480
ctggtcaagg actacttccc cgaaccggtg acggtgtcgt ggaactcagg cgccctgacc  540
agcggcgtgc acaccttccc ggctgtccta cagtcctcag gactctactc cctcagcagc  600
gtggtgaccg tgccctccag cagcttgggc acccagacct acatctgcaa cgtgaatcac  660
aagcccagca acaccaaggt ggacaagaaa gttgagccca aatcttgtga caaaactcac  720
acatgcccac cgtgcccagc acctgaactc ctggggggac cgtcagtctt cctcttcccc  780
ccaaaaccca aggacaccct catgatctcc cggacccctg aggtcacatg cgtggtggtg  840
gacgtgagcc acgaagaccc tgaggtcaag ttcaactggt acgtggacgg cgtggaggtg  900
cataatgcca agacaaagcc gcgggaggag cagtacaaca gcacgtaccg tgtggtcagc  960
gtcctcaccg tcctgcacca ggactggctg aatggcaagg agtacaagtg caaggtctcc  1020
aacaaagccc tcccagcccc catcgagaaa accatctcca aagccaaagg gcagccccga  1080
gaaccacagg tgtacaccct gcccccatcc cgggatgagc tgaccaagaa ccaggtcagc  1140
ctgacctgcc tggtcaaagg cttctatccc agcgacatcg ccgtggagtg ggagagcaat  1200
gggcagccgg agaacaacta caagaccacg cctcccgtgc tggactccga cggctccttc  1260
ttcctctaca gcaagctcac cgtggacaag agcaggtggc agcaggggaa cgtcttctca  1320
tgctccgtga tgcatgaggc tctgcacaac cactacacgc agaagagcct ctccctgtct  1380
ccgggtaaat ga                                                      1392

SEQ ID NO: 123          moltype = AA  length = 463
FEATURE                 Location/Qualifiers
REGION                  1..463
                        note = Description of Artificial Sequence: Synthetic
                         polypeptide
source                  1..463
                        mol_type = protein
                        organism = synthetic construct
SEQUENCE: 123
MRWSCIILFL VATATGVNSQ VQLVQSGAEV KKPGASVKVS CKASGYTFTS YWIHWVRQAP  60
GQGLEWIGVI DPSDSYTRYN QKFKGRVTMT VDTSTSTAYM ELRSLRSDDT AVYYCTTWEV  120
DYWGQGTTVT VSSASTKGPS VFPLAPSSKS TSGGTAALGC LVKDYFPEPV TVSWNSGALT  180
SGVHTFPAVL QSSGLYSLSS VVTVPSSSLG TQTYICNVNH KPSNTKVDKK VEPKSCDKTH  240
TCPPCPAPEL LGGPSVFLFP PKPKDTLMIS RTPEVTCVVV DVSHEDPEVK FNWYVDGVEV  300
HNAKTKPREE QYNSTYRVVS VLTVLHQDWL NGKEYKCKVS NKALPAPIEK TISKAKGQPR  360
EPQVYTLPPS RDELTKNQVS LTCLVKGFYP SDIAVEWESN GQPENNYKTT PPVLDSDGSF  420
FLYSKLTVDK SRWQQGNVFS CSVMHEALHN HYTQKSLSLS PGK                    463

SEQ ID NO: 124          moltype = DNA  length = 717
FEATURE                 Location/Qualifiers
misc_feature            1..717
                        note = Description of Artificial Sequence: Synthetic
                         polynucleotide
source                  1..717
                        mol_type = other DNA
                        organism = synthetic construct
CDS                     1..714
SEQUENCE: 124
atgaagttgc ctgttaggct gttggtgctg atgttctgga ttcctgcttc caacagtgat  60
attgtgatga cccaatctcc actctccctg cctgtcactc ctggagagcc agcctccatc  120
tcttgcagat ccagtcagag ccttgtgcac agtgatggaa acacctatct gcattggtac  180
ctgcagaagc caggccagtc tccacagctc ctgatctaca aagtttccaa ccgattttct  240
ggggtcccag acaggttcag tggcagtgga tcagggacag atttcacact caagatcagc  300
agagtggagg ctgaggatgt gggagtttat tactgctctc aaagtacaca tgttccttgg  360
accttcggtg gaggcaccaa agtcgaaatc aaacgaactg tggctgcacc atctgtcttc  420
atcttcccgc catctgatga gcagttgaaa tctggaactg cctctgttgt gtgcctgctg  480
aataacttct atcccagaga ggccaaagta cagtggaagg tggataacgc cctccaatcg  540
ggtaactccc aggagagtgt cacagagcag gacagcaagg acagcaccta cagcctcagc  600
agcaccctga cgctgagcaa agcagactac gagaaacaca aagtctacgc ctgcgaagtc  660
acccatcagg gcctgagctc gcccgtcaca aagagcttca acaggggaga gtgttag     717

SEQ ID NO: 125          moltype = AA  length = 238
FEATURE                 Location/Qualifiers
```

```
REGION                  1..238
                        note = Description of Artificial Sequence: Synthetic
                         polypeptide
source                  1..238
                        mol_type = protein
                        organism = synthetic construct
SEQUENCE: 125
MKLPVRLLVL MFWIPASNSD IVMTQSPLSL PVTPGEPASI SCRSSQSLVH SDGNTYLHWY  60
LQKPGQSPQL LIYKVSNRFS GVPDRFSGSG SGTDFTLKIS RVEAEDVGVY YCSQSTHVPW  120
TFGGGTKVEI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGEC    238

SEQ ID NO: 126          moltype = DNA  length = 1392
FEATURE                 Location/Qualifiers
misc_feature            1..1392
                        note = Description of Artificial Sequence: Synthetic
                         polynucleotide
source                  1..1392
                        mol_type = other DNA
                        organism = synthetic construct
CDS                     1..1389
SEQUENCE: 126
atgagatgga gctgtatcat cctcttcttg gtggcaacag ctacaggtgt caactcccag  60
gtccaactgg tccagtctgg ggctgaagtc aagaagcctg gggcttcagt gaaagtgtcc  120
tgcaaggctt ctggctacac cttcaccagc tactggattc actgggtcag gcaggcccct  180
ggacaaggcc ttgagtggat cggagtgatt gatccttcag atagttatac tagatacaat  240
caaaagttca agggcagggt cacaatgact gtggacacat ccaccagcac agcctacatg  300
gagctcagga gcctgagatc tgatgacact gccgtctatt actgtacaac ctgggaagtc  360
gactactggg gccaaggcac cactgtcaca gtctcctcag cctccaccaa gggcccatcg  420
gtcttccccc tggcaccctc ctccaagagc acctctgggg gcacagcggc cctgggctgc  480
ctggtcaagg actacttccc cgaaccggtg acggtgtcgt ggaactcagg cgccctgacc  540
agcggcgtgc acaccttccc ggctgtccta cagtcctcag gactctactc cctcagcagc  600
gtggtgaccg tgccctccag cagcttgggc acccagacct acatctgcaa cgtgaatcac  660
aagcccagca acaccaaggt ggacaagaaa gttgagccca aatcttgtga caaaactcac  720
acatgcccac cgtgcccagc acctgaagct gctggaggac cgtcagtctt cctcttcccc  780
ccaaaaccca aggacaccct catgatctcc cggacccctg aggtcacatg cgtggtggtg  840
gacgtgagcc acgaagaccc tgaggtcaag ttcaactggt acgtggacgg cgtggaggtg  900
cataatgcca agacaaagcc gcgggaggag cagtacaaca gcacgtaccg tgtggtcagc  960
gtcctcaccg tcctgcacca ggactggctg aatggcaagg agtacaagtg caaggtctcc  1020
aacaaagccc tcccagcccc catcgagaaa accatctcca aagccaaagg gcagccccga  1080
gaaccacagg tgtacaccct gcccccatcc cgggatgagc tgaccaagaa ccaggtcagc  1140
ctgacctgcc tggtcaaagg cttctatccc agcgacatcg ccgtggagtg ggagagcaat  1200
gggcagccgg agaacaacta caagaccacg cctcccgtgc tggactccga cggctccttc  1260
ttcctctaca gcaagctcac cgtggacaag agcaggtggc agcaggggaa cgtcttctca  1320
tgctccgtga tgcatgaggc tctgcacaac cactacacgc agaagagcct ctccctgtct  1380
ccgggtaaat ga                                                    1392

SEQ ID NO: 127          moltype = AA  length = 463
FEATURE                 Location/Qualifiers
REGION                  1..463
                        note = Description of Artificial Sequence: Synthetic
                         polypeptide
source                  1..463
                        mol_type = protein
                        organism = synthetic construct
SEQUENCE: 127
MRWSCIILFL VATATGVNSQ VQLVQSGAEV KKPGASVKVS CKASGYTFTS YWIHWVRQAP  60
GQGLEWIGVI DPSDSYTRYN QKFKGRVTMT VDTSTSTAYM ELRSLRSDDT AVYYCTTWEV  120
DYWGQGTTVT VSSASTKGPS VFPLAPSSKS TSGGTAALGC LVKDYFPEPV TVSWNSGALT  180
SGVHTFPAVL QSSGLYSLSS VVTVPSSSLG TQTYICNVNH KPSNTKVDKK VEPKSCDKTH  240
TCPPCPAPEA AGGPSVFLFP PKPKDTLMIS RTPEVTCVVV DVSHEDPEVK FNWYVDGVEV  300
HNAKTKPREE QYNSTYRVVS VLTVLHQDWL NGKEYKCKVS NKALPAPIEK TISKAKGQPR  360
EPQVYTLPPS RDELTKNQVS LTCLVKGFYP SDIAVEWESN GQPENNYKTT PPVLDSDGSF  420
FLYSKLTVDK SRWQQGNVFS CSVMHEALHN HYTQKSLSLS PGK                  463

SEQ ID NO: 128          moltype = DNA  length = 1414
FEATURE                 Location/Qualifiers
misc_feature            1..1414
                        note = Description of Artificial Sequence: Synthetic
                         polynucleotide
source                  1..1414
                        mol_type = other DNA
                        organism = synthetic construct
SEQUENCE: 128
aagcttgccg ccaccatgga atggtcctgg gtgttcctgt tcttcctgtc cgtgaccacc  60
ggcgtgcact ctcaggttca gttggttcag tctggcgccg aagtgaagaa acctggcgcc  120
tctgtgaagg tgtcctgcaa ggcttccggc tacaccttta ccagctactg gatccactgg  180
gtccgacagg ctccaggaca aggcctggaa tggatcggcg tgatcgaccc ctctgacagc  240
tacacccggt acaaccagaa attcaagggc agagtgacca tgaccgtgga cacctctacc  300
```

```
tccaccgcct acatggaact gcggtccctg agatctgacg acaccgccgt gtactactgc  360
accacctggg aagtcgatta ctggggccag ggcaccacag tgacagtgtc ctctgcttcc  420
accaagggac ccagcgtttt ccctctggct ccatcctcca agtctacctc tggcggaaca  480
gctgctctgg gctgcctggt caaggactac tttcctgagc ctgtgaccgt gtcctggaac  540
tctggcgctc tgacatctgg cgtgcacaca ttccctgctg tgctgcagtc ctccggcctg  600
tactctctgt cctctgtcgt gaccgtgcct tccagctctc tgggaaccca gacctacatc  660
tgcaatgtga accacaagcc ttccaacacc aaggtggaca agaaggtgga acccaagtcc  720
tgcgacaaga cccacacctg tcctccatgt cctgctccag aagctgctgg cggcccttcc  780
gtgtttctgt tccctccaaa gcctaaggac accctgatga tctctcggac ccctgaagtg  840
acctgcgtgg tggtggatgt gtctcacgag gacccagaag tgaagttcaa ttggtacgtg  900
gacggcgtgg aagtgcacaa cgccaagacc aagcctagag aggaacagta caactccacc  960
tacagagtgg tgtccgtgct gaccgtgctg caccaggatt ggctgaacgg caaagagtac  1020
aagtgcaagg tgtccaacaa ggccctgcct gctcctatcg aaaagaccat ctccaaggcc  1080
aagggccagc ctagggaacc ccaggtttac accttgcctc catctcggga cgagctgacc  1140
aagaaccagg tgtccctgac ctgtctcgtg aagggcttct acccctccga tatcgccgtg  1200
gaatgggagt ctaatggcca gcctgagaac aactacaaga caacccctcc tgtgctggac  1260
tccgacggct cattctttct gtactccaag ctgacagtgg acaagtccag atggcagcag  1320
ggcaacgtgt tctcctgcag cgtgatgcac gaggccctgc acaatcacta cacacagaag  1380
tccctgtctc tgtcccctgg caagtgatga attc                             1414
```

```
SEQ ID NO: 129          moltype = DNA  length = 742
FEATURE                 Location/Qualifiers
misc_feature            1..742
                        note = Description of Artificial Sequence: Synthetic
                         polynucleotide
source                  1..742
                        mol_type = other DNA
                        organism = synthetic construct
SEQUENCE: 129
aagcttgccg ccaccatgtc tgtgcctaca caggttctgg gactgctgct gctgtggctg  60
accgacgcca gatgcgacat cgtgatgacc cagtctccac tgagcctgcc tgtgacacct  120
ggcgagcctg cttccatctc ctgcagatcc tctcagtccc tggtgcactc tgacggcaac  180
acctacctgc actggtatct gcagaagccc ggccagtctc ctcagctgct gatctacaag  240
gtgtccaacc ggttctctgg cgtgcccgac agattttccg gctctggctc tggcaccgac  300
ttcaccctga agatctccag agtggaagcc gaggacgtgg gcgtgtacta ctgctcccag  360
tctacccatg tgccttggac ctttggcgga ggcaccaagg tggaaatcaa gcgtacggtg  420
gccgctccca gcgtgttcat cttccccccca agcgacgagc agctgaagag cggcaccgcc  480
agcgtggtgt gtctgctgaa caacttctac cccagggagg ccaaggtgca gtggaaggtg  540
gacaacgccc tgcagagcgg caacagccag gagagcgtca ccgagcagga cagcaaggac  600
tccacctaca gcctgagcag caccctgacc ctgagcaagg ccgactacga gaagcacaag  660
gtgtacgcct gtgaggtgac ccaccagggc ctgtccagcc ccgtgaccaa gagcttcaac  720
aggggcgagt gctgatgaat tc                                          742
```

```
SEQ ID NO: 130          moltype = DNA  length = 1402
FEATURE                 Location/Qualifiers
misc_feature            1..1402
                        note = Description of Artificial Sequence: Synthetic
                         polynucleotide
source                  1..1402
                        mol_type = other DNA
                        organism = synthetic construct
SEQUENCE: 130
aagcttgccg ccaccatgga atggtcctgg gtgttcctgt tcttcctgtc cgtgaccacc  60
ggcgtgcact ctcaggttca gttggttcag tctggcgccg aagtgaagaa acctggcgcc  120
tctgtgaagg tgtcctgcaa ggcttccggc tacaccttta ccagctactg gatccactgg  180
gtccgacagg ctccaggaca aggcctggaa tggatcggcg tgatcgaccc ctctgacagc  240
tacacccggt acaaccagaa attcaagggc agagtgacca tgaccgtgga cacctctacc  300
tccaccgcct acatggaact gcggtccctg agatctgacg acaccgccgt gtactactgc  360
accacctggg aagtcgatta ctggggccag ggcaccacag tgacagtgtc ctctgcttcc  420
acaaagggcc caagcgtgtt cccccctggcc ccctgctcca gaagcaccag cgagagcaca  480
gccgccctgg gctgcctggt gaaggactac ttccccgagc ccgtgaccgt gtcctggaac  540
agcggagccc tgaccagcgg cgtgcacacc ttccccgccg tgctgcagag cagcggcctg  600
tacagcctga gcagcgtggt gaccgtgccc agcagcagcc tgggcaccaa gacctacacc  660
tgtaacgtgg accacaagcc cagcaacacc aaggtggaca agagggtgga gagcaagtac  720
ggcccaccct gccccccctg cccagccccc gagttcctgg gcggacccag cgtgttcctg  780
ttccccccca agcccaagga caccctgatg atcagcagaa cccccgaggt gacctgtgtg  840
gtggtggacg tgtcccagga ggaccccgag gtccagttca actggtacgt ggacggcgtg  900
gaggtgcaca acgccaagac caagcccaga gaggagcagt ttaacagcac ctaccgggtg  960
gtgtccgtgc tgaccgtgct gcaccaggac tggctgaacg gcaaagagta caagtgtaag  1020
gtctccaaca agggcctgcc aagcagcatc gaaaagacca tcagcaaggc caagggccag  1080
cctagagagc cccaggtcta caccctgcca cccagccaag aggagatgac caagaaccag  1140
gtgtccctga cctgtctggt gaagggcttc tacccaagcg acatcgccgt ggagtgggag  1200
agcaacggcc agcccgagaa caactacaag accacccccc cagtgctgga cagcgacggc  1260
agcttcttcc tgtacagcag gctgaccgtg gacaagtcca gatggcagga gggcaacgtc  1320
tttagctgct ccgtgatgca cgaggccctg cacaaccact acacccagaa gagcctgagc  1380
ctgtccctgg gctgatgaat tc                                          1402
```

```
SEQ ID NO: 131          moltype = DNA  length = 1411
FEATURE                 Location/Qualifiers
```

```
misc_feature            1..1411
                        note = Description of Artificial Sequence: Synthetic
                         polynucleotide
source                  1..1411
                        mol_type = other DNA
                        organism = synthetic construct
SEQUENCE: 131
aagcttgccg ccaccatgga atggtcctgg gtgttcctgt tcttcctgtc cgtgaccacc  60
ggcgtgcact ctcaggttca gttggttcag tctggcgccg aagtgaagaa acctggcgcc  120
tctgtgaagg tgtcctgcaa ggcttccggc tacaccttta ccagctactg gatccactgg  180
gtccgacagg ctccaggaca aggcctggaa tggatcggcg tgatcgaccc ctctgacagc  240
tacacccggt acaaccagaa attcaagggc agagtgacca tgaccgtgga cacctctacc  300
tccaccgcct acatggaact gcggtccctg agatctgacg acaccgccgt gtactactgc  360
accacctggg aagtcgatta ctggggccag ggcaccacag tgacagtgtc ctctgcttcc  420
acaaagggcc caagcgtgtt cccctggcc cccagcagca agagcaccag cggcggcaca  480
gccgccctgg gctgcctggt gaaggactac ttccccgagc ccgtgaccgt gtcctggaac  540
agcggagccc tgacctccgg cgtgcacacc ttccccgccg tgctgcagag cagcggcctg  600
tacagcctga gcagcgtggt gaccgtgccc agcagcagcc tgggcaccca gacctacatc  660
tgtaacgtga accacaagcc cagcaacacc aaggtggaca agaaggtgga gcccaagagc  720
tgtgacaaga cccacacctg ccccccctgc ccagcccccg agctgctggg cggacccagc  780
gtgttcctgt tcccccccaa gcccaaggac accctgatga tcagcagaac ccccgaggtg  840
acctgtgtgg tggtggacgt gtcccacgag gacccagagg tgaagttcaa ctggtacgtg  900
gacggcgtgg aggtgcacaa cgccaagacc aagcccagag aggagcagta caacagcacc  960
tacagggtgg tgtccgtgct gaccgtgctg caccaggact ggctgaacgg caaggagtac  1020
aagtgtaagg tgtccaacaa ggccctgcca gccccaatcg aaaagaccat cagcaaggcc  1080
aagggccagc caagagagcc ccaggtgtac accctgccac ccagcaggga cgagctgacc  1140
aagaaccagg tgtccctgac ctgtctggtg aagggcttct acccaagcga catcgccgtg  1200
gagtgggaga gcaacggcca gcccgagaac aactacaaga ccaccccccc agtgctggac  1260
agcgacggca gcttcttcct gtacagcaag ctgaccgtgg acaagagcag atggcagcag  1320
ggcaacgtgt tcagctgctc cgtgatgcac gaggccctgc acaaccacta cacccagaag  1380
agcctgagcc tgtccccagg ctgatgaatt c                                 1411

SEQ ID NO: 132          moltype = AA  length = 462
FEATURE                 Location/Qualifiers
REGION                  1..462
                        note = Description of Artificial Sequence: Synthetic
                         polypeptide
source                  1..462
                        mol_type = protein
                        organism = synthetic construct
SEQUENCE: 132
MRWSCIILFL VATATGVNSQ VQLVQSGAEV KKPGASVKVS CKASGYTFTS YWIHWVRQAP  60
GQGLEWIGVI DPSDSYTRYN QKFKGRVTMT VDTSTSTAYM ELRSLRSDDT AVYYCTTWEV  120
DYWGQGTTVT VSSASTKGPS VFPLAPSSKS TSGGTAALGC LVKDYFPEPV TVSWNSGALT  180
SGVHTFPAVL QSSGLYSLSS VVTVPSSSLG TQTYICNVNH KPSNTKVDKK VEPKSCDKTH  240
TCPPCPAPEL LGGPSVFLFP PKPKDTLMIS RTPEVTCVVV DVSHEDPEVK FNWYVDGVEV  300
HNAKTKPREE QYNSTYRVVS VLTVLHQDWL NGKEYKCKVS NKALPAPIEK TISKAKGQPR  360
EPQVYTLPPS RDELTKNQVS LTCLVKGFYP SDIAVEWESN GQPENNYKTT PPVLDSDGSF  420
FLYSKLTVDK SRWQQGNVFS CSVMHEALHN HYTQKSLSLS PG                    462

SEQ ID NO: 133          moltype = AA  length = 462
FEATURE                 Location/Qualifiers
REGION                  1..462
                        note = Description of Artificial Sequence: Synthetic
                         polypeptide
source                  1..462
                        mol_type = protein
                        organism = synthetic construct
SEQUENCE: 133
MEWSWVFLFF LSVTTGVHSQ VQLVQSGAEV KKPGASVKVS CKASGYTFTS YWIHWVRQAP  60
GQGLEWIGVI DPSDSYTRYN QKFKGRVTMT VDTSTSTAYM ELRSLRSDDT AVYYCTTWEV  120
DYWGQGTTVT VSSASTKGPS VFPLAPSSKS TSGGTAALGC LVKDYFPEPV TVSWNSGALT  180
SGVHTFPAVL QSSGLYSLSS VVTVPSSSLG TQTYICNVNH KPSNTKVDKK VEPKSCDKTH  240
TCPPCPAPEL LGGPSVFLFP PKPKDTLMIS RTPEVTCVVV DVSHEDPEVK FNWYVDGVEV  300
HNAKTKPREE QYNSTYRVVS VLTVLHQDWL NGKEYKCKVS NKALPAPIEK TISKAKGQPR  360
EPQVYTLPPS RDELTKNQVS LTCLVKGFYP SDIAVEWESN GQPENNYKTT PPVLDSDGSF  420
FLYSKLTVDK SRWQQGNVFS CSVMHEALHN HYTQKSLSLS PG                    462

SEQ ID NO: 134          moltype = AA  length = 384
FEATURE                 Location/Qualifiers
source                  1..384
                        mol_type = protein
                        organism = Homo sapiens
SEQUENCE: 134
APTKAPDVFP IISGCRHPKD NSPVVLACLI TGYHPTSVTV TWYMGTQSQP QRTFPEIQRR  60
DSYYMTSSQL STPLQQWRQG EYKCVVQHTA SKSKKEIFRW PESPKAQASS VPTAQPQAEG  120
SLAKATTAPA TTRNTGRGGE EKKKEKEKEE QEERETKTPE CPSHTQPLGV YLLTPAVQDL  180
WLRDKATFTC FVVGSDLKDA HLTWEVAGKV PTGGVEEGLL ERHSNGSQSQ HSRLTLPRSL  240
WNAGTSVTCT LNHPSLPPQR LMALREPAAQ APVKLSLNLL ASSDPPEAAS WLLCEVSGFS  300
```

```
PPNILLMWLE DQREVNTSGF APARPPPQPG STTFWAWSVL RVPAPPSPQP ATYTCVVSHE  360
DSRTLLNASR SLEVSYVTDH GPMK                                         384

SEQ ID NO: 135          moltype = AA  length = 330
FEATURE                 Location/Qualifiers
source                  1..330
                        mol_type = protein
                        organism = Homo sapiens
SEQUENCE: 135
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 136          moltype = AA  length = 326
FEATURE                 Location/Qualifiers
source                  1..326
                        mol_type = protein
                        organism = Homo sapiens
SEQUENCE: 136
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDISVEW ESNGQPENNY KTTPPMLDSD GSFFLYSKLT VDKSRWQQGN  300
VFSCSVMHEA LHNHYTQKSL SLSPGK                                       326

SEQ ID NO: 137          moltype = AA  length = 377
FEATURE                 Location/Qualifiers
source                  1..377
                        mol_type = protein
                        organism = Homo sapiens
SEQUENCE: 137
ASTKGPSVFP LAPCSRSTSG GTAALGCLVK DYFPEPVTVS WNSGALTSGV HTFPAVLQSS  60
GLYSLSSVVT VPSSSLGTQT YTCNVNHKPS NTKVDKRVEL KTPLGDTTHT CPRCPEPKSC  120
DTPPPCPRCP EPKSCDTPPP CPRCPEPKSC DTPPPCPRCP APELLGGPSV FLFPPKPKDT  180
LMISRTPEVT CVVVDVSHED PEVQFKWYVD GVEVHNAKTK PREEQYNSTF RVVSVLTVLH  240
QDWLNGKEYK CKVSNKALPA PIEKTISKTK GQPREPQVYT LPPSREEMTK NQVSLTCLVK  300
GFYPSDIAVE WESSGQPENN YNTTPPMLDS DGSFFLYSKL TVDKSRWQQG NIFSCSVMHE  360
ALHNRFTQKS LSLSPGK                                                 377

SEQ ID NO: 138          moltype = AA  length = 452
FEATURE                 Location/Qualifiers
source                  1..452
                        mol_type = protein
                        organism = Homo sapiens
SEQUENCE: 138
GSASAPTLFP LVSCENSPSD TSSVAVGCLA QDFLPDSITL SWKYKNNSDI SSTRGFPSVL  60
RGGKYAATSQ VLLPSKDVMQ GTDEHVVCKV QHPNGNKEKN VPLPVIAELP PKVSVFVPPR  120
DGFFGNPRKS KLICQATGFS PRQIQVSWLR EGKQVGSGVT TDQVQAEAKE SGPTTYKVTS  180
TLTIKESDWL GQSMFTCRVD HRGLTFQQNA SSMCVPDQDT AIRVFAIPPS FASIFLTKST  240
KLTCLVTDLT TYDSVTISWT RQNGEAVKTH TNISESHPNA TFSAVGEASI CEDDWNSGER  300
FTCTVTHTDL PSPLKQTISR PKGVALHRPD VYLLPPAREQ LNLRESATIT CLVTGFSPAD  360
VFVQWMQRGQ PLSPEKYVTS APMPEPQAPG RYFAHSILTV SEEEWNTGET YTCVAHEALP  420
NRVTERTVDK STGKPTLYNV SLVMSDTAGT CY                                 452

SEQ ID NO: 139          moltype = AA  length = 327
FEATURE                 Location/Qualifiers
source                  1..327
                        mol_type = protein
                        organism = Homo sapiens
SEQUENCE: 139
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 140          moltype = AA  length = 353
FEATURE                 Location/Qualifiers
source                  1..353
                        mol_type = protein
                        organism = Homo sapiens
SEQUENCE: 140
ASPTSPKVFP LSLCSTQPDG NVVIACLVQG FFPQEPLSVT WSESGQGVTA RNFPPSQDAS  60
GDLYTTSSQL TLPATQCLAG KSVTCHVKHY TNPSQDVTVP CPVPSTPPTP SPSTPPTPSP  120
```

```
SCCHPRLSLH RPALEDLLLG SEANLTCTLT GLRDASGVTF TWTPSSGKSA VQGPPERDLC  180
GCYSVSSVLP GCAEPWNHGK TFTCTAAYPE SKTPLTATLS KSGNTFRPEV HLLPPPSEEL  240
ALNELVTLTC LARGFSPKDV LVRWLQGSQE LPREKYLTWA SRQEPSQGTT TFAVTSILRV  300
AAEDWKKGDT FSCMVGHEAL PLAFTQKTID RLAGKPTHVN VSVVMAEVDG TCY         353

SEQ ID NO: 141         moltype = AA  length = 340
FEATURE                Location/Qualifiers
source                 1..340
                       mol_type = protein
                       organism = Homo sapiens
SEQUENCE: 141
ASPTSPKVFP LSLDSTPQDG NVVVACLVQG FFPQEPLSVT WSESGQNVTA RNFPPSQDAS  60
GDLYTTSSQL TLPATQCPDG KSVTCHVKHY TNPSQDVTVP CPVPPPPPCC HPRLSLHRPA  120
LEDLLLGSEA NLTCTLTGLR DASGATFTWT PSSGKSAVQG PPERDLCGCY SVSSVLPGCA  180
QPWNHGETFT CTAAHPELKT PLTANITKSG NTFRPEVHLL PPPSEELALN ELVTLTCLAR  240
GFSPKDVLVR WLQGSQELPR EKYLTWASRQ EPSQGTTTFA VTSILRVAAE DWKKGDTFSC  300
MVGHEALPLA FTQKTIDRMA GKPTHVNVSV VMAEVDGTCY                        340

SEQ ID NO: 142         moltype = AA  length = 106
FEATURE                Location/Qualifiers
source                 1..106
                       mol_type = protein
                       organism = Homo sapiens
SEQUENCE: 142
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                 106

SEQ ID NO: 143         moltype = AA  length = 13
FEATURE                Location/Qualifiers
REGION                 1..13
                       note = Description of Unknown: pT231-Dmp tau peptide
MOD_RES                7
                       note = phospho-Thr
source                 1..13
                       mol_type = protein
                       organism = unidentified
SEQUENCE: 143
KVAVVRTPPK SPS                                                     13

SEQ ID NO: 144         moltype = AA  length = 6
FEATURE                Location/Qualifiers
REGION                 1..6
                       note = Description of Artificial Sequence: Synthetic 6xHis
                        tag
source                 1..6
                       mol_type = protein
                       organism = synthetic construct
SEQUENCE: 144
HHHHHH                                                             6

SEQ ID NO: 145         moltype = DNA  length = 20
FEATURE                Location/Qualifiers
misc_feature           1..20
                       note = Description of Artificial Sequence: Synthetic primer
source                 1..20
                       mol_type = other DNA
                       organism = synthetic construct
SEQUENCE: 145
gccagtggat agactgatgg                                              20

SEQ ID NO: 146         moltype = DNA  length = 21
FEATURE                Location/Qualifiers
misc_feature           1..21
                       note = Description of Artificial Sequence: Synthetic primer
source                 1..21
                       mol_type = other DNA
                       organism = synthetic construct
SEQUENCE: 146
gatggataca gttggtgcag c                                            21

SEQ ID NO: 147         moltype = DNA  length = 24
FEATURE                Location/Qualifiers
misc_feature           1..24
                       note = Description of Artificial Sequence: Synthetic primer
source                 1..24
                       mol_type = other DNA
                       organism = synthetic construct
SEQUENCE: 147
aagaacatcg attttccatg gcag                                         24
```

```
SEQ ID NO: 148          moltype = AA  length = 13
FEATURE                 Location/Qualifiers
REGION                  1..13
                        note = Description of Artificial Sequence: Synthetic peptide
MOD_RES                 7
                        note = phospho-Thr
MOD_RES                 8
                        note = 5,5-dimethyl-L-proline
source                  1..13
                        mol_type = protein
                        organism = synthetic construct
SEQUENCE: 148
KVAVVRTPPK SPS                                                             13

SEQ ID NO: 149          moltype = AA  length = 13
FEATURE                 Location/Qualifiers
REGION                  1..13
                        note = Description of Artificial Sequence: Synthetic peptide
MOD_RES                 7
                        note = phospho-Thr
source                  1..13
                        mol_type = protein
                        organism = synthetic construct
SEQUENCE: 149
KVAVVRTPPK SPS                                                             13

SEQ ID NO: 150          moltype = AA  length = 13
FEATURE                 Location/Qualifiers
REGION                  1..13
                        note = Description of Artificial Sequence: Synthetic peptide
MOD_RES                 7
                        note = phospho-Thr
source                  1..13
                        mol_type = protein
                        organism = synthetic construct
SEQUENCE: 150
KVAVVRTAPK SPS                                                             13

SEQ ID NO: 151          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 151
KVAVVRTPPK SPS                                                             13

SEQ ID NO: 152          moltype = AA  length = 13
FEATURE                 Location/Qualifiers
MOD_RES                 7
                        note = phospho-Thr
source                  1..13
                        mol_type = protein
                        organism = Homo sapiens
SEQUENCE: 152
KVAVVRTPPK SPS                                                             13

SEQ ID NO: 153          moltype = AA  length = 13
FEATURE                 Location/Qualifiers
MOD_RES                 7
                        note = phospho-Thr
MOD_RES                 8
                        note = 5,5-dimethyl-L-proline
source                  1..13
                        mol_type = protein
                        organism = Homo sapiens
SEQUENCE: 153
KVAVVRTPPK SPS                                                             13

SEQ ID NO: 154          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
```

```
SEQUENCE: 154
QVQLQQPGAE LVKPGASVKM SCKASGYTFT SYWIHWVKQR PGQGLEWIGV IDPSDSYTRY  60
NQKFKGKATL TVDTSSSTAY MQLSSLTSED SAVYYCTTWE VDYWGQGTTL TVSS        114

SEQ ID NO: 155         moltype = AA  length = 98
FEATURE                Location/Qualifiers
source                 1..98
                       mol_type = protein
                       organism = Mus sp.
SEQUENCE: 155
QVQLQQPGAE LVKPGASVKM SCKASGYTFT SYWMHWVKQR PGQGLEWIGT IDPSDSYTSY  60
NQKFKGKATL TVDTSSSTAY MQLSSLTSED SAVYYCTR                          98

SEQ ID NO: 156         moltype = AA  length = 112
FEATURE                Location/Qualifiers
REGION                 1..112
                       note = Description of Artificial Sequence: Synthetic
                        polypeptide
source                 1..112
                       mol_type = protein
                       organism = synthetic construct
SEQUENCE: 156
DVVMTQTPLS LPVSLGDQAS ISCRSSQSLV HSDGNTYLHW YLQKPGQSPK LLIYKVSNRF  60
SGVPDRFSGS GSGTDFTLKI SRLEAEDLGV YFCSQSTHVP WTFGGGTKLE IK          112

SEQ ID NO: 157         moltype = AA  length = 93
FEATURE                Location/Qualifiers
source                 1..93
                       mol_type = protein
                       organism = Mus sp.
SEQUENCE: 157
DVVMTQTPLS LPVSLGDQAS ISCRSSQSLV HSNGNTYLHW YLQKPGQSPK LLIYKVSNRF  60
SGVPDRFSGS GSGTDFTLKI SRVEAEDLGV YFC                               93

SEQ ID NO: 158         moltype = AA  length = 114
FEATURE                Location/Qualifiers
REGION                 1..114
                       note = Description of Artificial Sequence: Synthetic
                        polypeptide
source                 1..114
                       mol_type = protein
                       organism = synthetic construct
SEQUENCE: 158
QVQLVQSGAE VKKPGASVKV SCKASGYTFT SYWIHWVRQA PGQGLEWIGV IDPSDSYTRY  60
NQKFKGRATL TVDTSTSTAY MELRSLRSDD TAVYYCTTWE VDYWGQGTTV TVSS        114

SEQ ID NO: 159         moltype = AA  length = 114
FEATURE                Location/Qualifiers
REGION                 1..114
                       note = Description of Artificial Sequence: Synthetic
                        polypeptide
source                 1..114
                       mol_type = protein
                       organism = synthetic construct
SEQUENCE: 159
QVQLVQSGAE VKKPGASVKV SCKASGYTFT SYWIHWVRQA PGQGLEWIGV IDPSDSYTRY  60
NQKFKGRVTL TVDTSTSTAY MELRSLRSDD TAVYYCTTWE VDYWGQGTTV TVSS        114

SEQ ID NO: 160         moltype = AA  length = 114
FEATURE                Location/Qualifiers
REGION                 1..114
                       note = Description of Artificial Sequence: Synthetic
                        polypeptide
source                 1..114
                       mol_type = protein
                       organism = synthetic construct
SEQUENCE: 160
QVQLVQSGAE VKKPGASVKV SCKASGYTFT SYWIHWVRQA PGQGLEWIGV IDPSDSYTRY  60
NQKFKGRATM TVDTSTSTAY MELRSLRSDD TAVYYCTTWE VDYWGQGTTV TVSS        114

SEQ ID NO: 161         moltype = AA  length = 114
FEATURE                Location/Qualifiers
REGION                 1..114
                       note = Description of Artificial Sequence: Synthetic
                        polypeptide
source                 1..114
                       mol_type = protein
                       organism = synthetic construct
SEQUENCE: 161
```

-continued

```
QVQLVQSGAE VKKPGASVKV SCKASGYTFT SYWIHWVRQA PGQGLEWIGV IDPSDSYTRY  60
NQKFKGRVTM TVDTSTSTAY MELRSLRSDD TAVYYCTTWE VDYWGQGTTV TVSS        114

SEQ ID NO: 162          moltype = AA  length = 87
FEATURE                 Location/Qualifiers
source                  1..87
                        mol_type = protein
                        organism = Homo sapiens
SEQUENCE: 162
QVQLVQSGAE VKKPGASVKV SCKASGYTFT WVRQAPGQGL EWMGRVTMTT DTSTSTAYME  60
LRSLRSDDTA VYYCARWGQG TTVTVSS                                      87

SEQ ID NO: 163          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 163
DIVMTQSPLS LPVTPGEPAS ISCRSSQSLV HSDGNTYLHW YLQKPGQSPQ LLIYKVSNRF  60
SGVPDRFSGS GSGTDFTLKI SRVEAEDVGV YYCSQSTHVP WTFGGGTKVE IK          112

SEQ ID NO: 164          moltype = AA  length = 80
FEATURE                 Location/Qualifiers
source                  1..80
                        mol_type = protein
                        organism = Homo sapiens
SEQUENCE: 164
DIVMTQSPLS LPVTPGEPAS ISCWYLQKPG QSPQLLIYGV PDRFSGSGSG TDFTLKISRV  60
EAEDVGVYYC FGGGTKVEIK                                              80
```